US010174132B2

(12) United States Patent
Boons et al.

(10) Patent No.: US 10,174,132 B2
(45) Date of Patent: Jan. 8, 2019

(54) HEPARAN SULFATE SYNTHESIS

(71) Applicant: UNIVERSITY OF GEORGIA RESEARCH FOUNDATION, INC., Athens, GA (US)

(72) Inventors: Geert-Jan Boons, Athens, GA (US); Andre Venot, Boulder, CO (US); Sailaja Arungundram, Kirkland, WA (US); Kanar al-Mafraji, Nijmegen (NL)

(73) Assignee: UNIVERSITY OF GEORGIA RESEARCH FOUNDATION, INC., Athens, GA (US)

(*) Notice: Subject to any disclaimer, the term of this patent is extended or adjusted under 35 U.S.C. 154(b) by 312 days.

(21) Appl. No.: 14/754,175

(22) Filed: Jun. 29, 2015

(65) Prior Publication Data

US 2016/0060365 A1    Mar. 3, 2016

Related U.S. Application Data

(63) Continuation of application No. 13/250,651, filed on Sep. 30, 2011, now abandoned, which is a continuation-in-part of application No. PCT/US2010/029235, filed on Mar. 30, 2010.

(60) Provisional application No. 61/211,479, filed on Mar. 30, 2009, provisional application No. 61/276,627, filed on Sep. 14, 2009.

(51) Int. Cl.
*C08B 37/00* (2006.01)
*C07H 5/04* (2006.01)
*C07H 15/04* (2006.01)
*C07H 15/203* (2006.01)
*C07H 23/00* (2006.01)

(52) U.S. Cl.
CPC ........... *C08B 37/0075* (2013.01); *C07H 5/04* (2013.01); *C07H 15/04* (2013.01); *C07H 15/203* (2013.01); *C07H 23/00* (2013.01)

(58) Field of Classification Search
CPC ...... C07H 15/04; C07H 15/203; C07H 23/00; C07H 5/04; C08B 37/0075
USPC .............................. 506/19; 536/21, 54, 55.1
See application file for complete search history.

(56) References Cited

U.S. PATENT DOCUMENTS

| | | | |
|---|---|---|---|
| 6,528,497 B1 * | 3/2003 | Basten | C08B 37/0063 514/25 |
| 6,953,850 B1 | 10/2005 | Dekany et al. | |
| 7,541,445 B2 | 6/2009 | Seifert et al. | |
| 7,582,737 B2 | 9/2009 | Hung et al. | |
| 7,820,797 B2 | 10/2010 | Boons et al. | |
| 2005/0080042 A1 | 4/2005 | Seifert et al. | |
| 2006/0079483 A1 | 4/2006 | Hung | |
| 2009/0041836 A1 | 2/2009 | Boons et al. | |
| 2009/0196916 A1 | 8/2009 | Ingale et al. | |
| 2012/0142560 A1 | 6/2012 | Boons et al. | |

FOREIGN PATENT DOCUMENTS

| | | |
|---|---|---|
| FR | 2 873 377 A1 | 1/2006 |
| WO | WO 2003/022860 A1 | 3/2003 |
| WO | WO 2005/000907 A1 | 1/2005 |
| WO | WO 2007/079448 A2 | 7/2007 |
| WO | WO 2007/146070 A2 | 12/2007 |
| WO | WO 2007/079448 A3 | 1/2008 |
| WO | WO 2007/146070 A3 | 4/2008 |
| WO | WO 2010/002478 A2 | 1/2010 |
| WO | WO 2010/002478 A3 | 7/2010 |
| WO | WO 2010/002478 A4 | 8/2010 |
| WO | WO 2010/117803 A2 | 10/2010 |
| WO | WO 2010/117803 A3 | 3/2011 |

OTHER PUBLICATIONS

Lubineau et al, Chemistry—A European Journal, 2004, 10, 4265-4282.*
Poletti et al, Eur. J. Org. Chem. 2003, 2999-3024.*
Schelhaas et al, Angew. Chem. Int. Ed. Engl., 1996, 35, 2056-83.*
Zhang, Chem. Rev. 2009, 109, 749-785.*
Alper et al., "Metal catalyzed diazo transfer for the synthesis of azides from amines," *Tetrahedron Lett.* Aug. 19, 1996, 37:6029-6032.
Aly and Schmidt, "New Diacylamino Protecting Groups for Glucosamine," *Eur. J. Org. Chem.* 2005:4382-4392; available online on Aug. 26, 2005.
Arungundram, Sailaja, "Modular synthesis of heparan sulfate fragments using orthogonally protected disaccharide building blocks," Abstract No. CARB 117, presented on Aug. 19, 2009—presented in Section B General Papers: Synthetic Chemistry at the *238th American Chemical Society National Meeting, Division of Carbohydrate Chemistry*; Washington D.C.: Aug. 16-20, 2009. Abstract available online [retrieved on Nov. 14, 2012]. Retrieved from the Internet: <http://oasys2.confex.com/acs/238nm/techprogram/P1304064.HTM>; 1 page.
Arungundram et al., "Modular synthesis of heparan sulfate oligosaccharides for structure-activity relationship studies," *J. Am. Chem. Soc.* Nov. 11, 2009, 131:17394-17405.
Arungundram et al., Supplemental information for "Modular synthesis of heparan sulfate oligosaccharides for structure-activity relationship studies," *J. Am. Chem. Soc.* Nov. 11, 2009, 131:17394-17405; available on the world wide web at pubs.acs.org/doi/suppl/10.1021/ja907358k.
Arungundram, Sailaja, "A modular approach for the synthesis of heparin sulfate oligosaccharides," Doctoral Dissertation completed under Dr. Geert-Jan Boons; University of Georgia department of Chemistry. Degree date May 2010. 213 pages.

(Continued)

*Primary Examiner* — Ganapathy Krishnan
(74) *Attorney, Agent, or Firm* — Mueting, Raasch & Gebhardt, P.A.

(57) ABSTRACT

The invention provides an efficient modular chemical synthesis for heparan sulfate oligosaccharides based on orthogonal protection strategies. Modular disaccharide building blocks, themselves the product of a novel combinatorial synthesis, are combined in numerous ways to produce a range of oligosaccharides.

4 Claims, 11 Drawing Sheets

(56) References Cited

OTHER PUBLICATIONS

Asai et al., "The novel beta-secretase inhibitor KMI-429 reduces amyloid beta peptide production in amyloid precursor protein transgenic and wild-type mice," *J. Neurochem.* Jan. 2006, 96:533-540; available online on Dec. 8, 2005.

Barroca et al., "Syntheses of β-D-GalpNAc4SO$_3$-(1→4)-L-IdopA2SO$_3$, a disaccharide fragment of dermatan sulfate, and of its methyl alpha-L-glycoside derivative," *Carbohydr. Res.* Nov. 17, 2000, 329:667-679.

Basten et al., "In vitro evaluation of synthetic heparin-like conjugates comprising different thrombin binding domains," *Bioorg. Med. Chem. Lett.* May 1998, 8:1201-1206.

Belot et al., "Unexpected stereochemical outcome of activated 4,6-O-benzylidene derivatives of the 2-deoxy-2-trichloroacetamido-D-galacto series in glycosylation reactions during the synthesis of a chondroitin 6-sulfate trisaccharide methyl glycoside," 2000 *Carbohydr. Res.* 325:93-106.

Bishop et al., "Heparan sulphate proteoglycans fine-tune mammalian physiology," *Nature* Apr. 26, 2007, 446:1030-1037.

Boltje et al., "Opportunities and challenges in synthetic oligosaccharide and glycoconjugate research," *Nature Chem.* Nov. 1, 2009, 1:611-622; available online on Oct. 23, 2009.

Bongat and Demchenko, "Recent trends in the synthesis of O-glycosides of 2-amino-2-deoxysugars," *Carbohydr. Res.* Feb. 26, 2007, 342:374-406; available online on Oct. 27, 2006.

Boons, "Recent developments in chemical oligosaccharide synthesis," *Contemp. Org. Synth.* 1996, 3:173-200.

Boons et al., "New set of orthogonal protecting groups for the modular synthesis of heparan sulfate fragments" *Organic Letters*, 2003; 5(26):4975-8.

Boons, "Synthesis of Libraries of Heparan Sulfate Derivatives," slides shown with oral presentation at the *67th Harden Conference* sponsored by The Biochemical Society; held at Robinson College in Cambridge, UK; Mar. 29-Apr. 2, 2009. Meeting program (7 pages) and 27 slides included.

Boons, Geert-Jan, "Novel Click Reagents for Glycoprotein Isolation and Visualization," Grant Abstract, Grant No. RR005351-20; Sub-Project ID: 7795 [online]. National Center for Research Resources, National Institutes of Health, project dates Feb. 1, 2009 to Jan. 31, 2010 [retrieved on Feb. 18, 2013]. Retrieved from the Internet: <http://projectreporter.nih.gov/pr_Prj_info_desc_dtls.cfm?aid=7957582&icde=15329271&ddparam=&ddvalue=&ddsub=&cr=5&csb=default&cs=ASC&print=yes>; 2 pgs.

Boons, Geert-Jan, "A Fully Synthetic Carbohydrate-Based Cancer Vaccine," Grant Abstract, Grant No. CA088986 [online]. National Cancer Institute, National Institutes of Health, project dates May 1, 2011 to Mar. 31, 2016 [retrieved on Feb. 18, 2013]. Retrieved from the Internet: <http://projectreporter.nih.gov/pr_Prj_info_desc_dtls.cfm?aid=8258735&icde=15328996&ddparam=&ddvalue=&ddsub=&cr=1&csb=default&cs=ASC&print=yes>; 3 pgs.

Borman, "Giant Leap for Obstinate Targets—Sugar Chemistry: Parallel combinatorial synthesis yields 12 hard-to-make oligosaccharides," *Chemical & Engineering News*, Nov. 23, 2009, 87(47):10; available on the internet at <http://pubs.acs.org/cen/news/87/i47/8747notw7.html >; 2 pages.

Brewer and Rich, "Synthesis of a tripeptide derivative containing the Phe-Arg hydroxyethylene dipeptide isostere," *Org. Lett.* Mar. 22, 2001, 3:945-948; available online on Feb. 23, 2001.

Chang et al., "In vivo inhibition of Aβ production by memapsin 2 (β-secretase) inhibitors," *J. Neurochem.* Jun. 2004, 89:1409-1416.

Chen et al., "Using an enzymatic combinatorial approach to identify anticoagulant heparan sulfate structures," *Chem. Biol.* Sep. 21, 2007, 14:986-993.

Chen et al., "Synthesis of a tetrasaccharide substrate of heparanase," *Carbohydr. Res.* Nov. 24, 2008, 343:2853-2862; available online on Jun. 18, 2008.

Chen et al., "Microbial subversion of heparan sulfate proteoglycans," *Mol. Cells* Nov. 30, 2008, 26:415-426; available online on Sep. 18, 2008.

Chen and Yu, "Efficient synthesis of Idraparinux, the anticoagulant pentasaccharide," *Bioorg. Med. Chem. Lett.* Jul. 15, 2009, 19:3875-9; available online Apr. 5, 2009.

Codee et al., "The synthesis of well-defined heparin and heparan sulfate fragments," *Drug Discovery Today: Technologies* Dec. 2004, 1:317-326.

Crich et al., "Does neighboring group participation by non-vicinal esters play a role in glycosylation reactions? Effective probes for the detection of bridging intermediates," *J. Org. Chem.* Nov. 21, 2008, 73:8942-8953; available online on Oct. 22, 2008.

Davis and Flitsch, "Selective oxidation of monosaccharide derivatives to uronic acids," *Tetrahedron Lett.* Feb. 12, 1993, 34:1181-1184.

de Kort et al., "Synthetic heparin derivatives as new anticoagulant drugs," *Drug Discov. Today* Jun. 1, 2005, 10:769-779.

Demchenko et al., "Stereoselective 1,2-cis-galactosylation assisted by remote neighboring group participation and solvent effects," *Tetrahedron Lett.* Sep. 3, 1999, 40:6523-6526.

Demchenko, "Stereoselective Chemical 1,2-cis O-Glycosylation: From 'Sugar Ray' to Modern Techniques of the 21st Century," *Syn. Lett.* 2003 9:1225-1240.

Demchenko, "Chapter 1: General Aspects of the Glycosidic Bond Formation," in *Handbook of Chemical Glycosylation: Advances in Stereoselectivity and Therapeutic Relevance* (Demchenko, Ed). WILY-VCH Verlag GmbH & Co. KGaA: Weinheim, Germany; copyright 2008. Title page, publisher's page, and pp. 1-27. Published on Feb. 20, 2008.

de Mico et al., "A Versatile and Highly Selective Hypervalent Iodine (III)/2,2,6,6-Tetramethyl-1-piperidinyloxyl-Mediated Oxidation of Alcohols to Carbonyl Compounds," *J. Org. Chem.* 1997, 62, 6974-7; available online Oct. 3, 1997.

de Paz et al., "The activation of fibroblast growth factors by heparin: synthesis, structure, and biological activity of heparin-like oligosaccharides," *Chembiochem* Sep. 3, 2001, 2:673-685.

de Paz and Martin-Lomas, "Synthesis and Biological Evaluation of a Heparin-Like Hexasaccharide with the Structural Motifs for Binding to FGF and FGFR," *Eur. J. Org. Chem.* May 2005:1849-1858; available online on Apr. 25, 2005.

Dhanawat et al., "Solid-phase synthesis of oligosaccharide drugs: a review," *Mini-Rev. Med. Chem.* Feb. 2009, 9(2):169-185.

Dilhaus et al. "Mixture Synthesis and "Charge Tagging" Based Demixing: An Efficient Strategy for the Preparation of Heparan Sulfate Libraries," 2008 *Journal of Combinatorial Chemistry* 10(2):166-169. Available online on Feb. 16, 2008.

Esko et al., "Order out of chaos: assembly of ligand binding sites in heparan sulfate," *Ann. Rev. Biochem.* 2002, 71:435-471; available online on Nov. 9, 2001.

Fan et al., "Orthogonal sulfation strategy for synthetic heparan sulfate ligands," Oct. 27, 2005 *Org. Lett.* 7:5095-5098.

Gallagher and Turnbull, "Heparan sulphate in the binding and activation of basic fibroblast growth factor," *Glycobiology* Dec. 1992, 2:523-528.

Galonic et al., "Chemical glycosylation in the synthesis of glycoconjugate antitumour vaccines," *Nature* Apr. 26, 2007, 446(7139):1000-1007.

Gama et al., "Sulfation patterns of glycosaminoglycans encode molecular recognition and activity," *Nat. Chem. Biol.* Sep. 2006, 2:467-473; available online on Jul. 30, 2006.

Gandhi et al., "The structure of glycosaminoglycans and their interactions with proteins," *Chem. Biol. Drug Des.* Dec . 2008, 72:455-482; available online on Nov. 19, 2008.

Gavard et al., "Efficient Preparation of Three Building Blocks for the Synthesis of Heparan Sulfate Fragments: Towards the Combinatorial Synthesis of Oligosaccharides from Hypervariable Regions," *Eur. J. Org. Chem.* 2003:3603-3620; available online on Sep. 5, 2003.

Golde, "Alzheimer disease therapy: can the amyloid cascade be halted?" *J. Clin. Invest.* Jan. 1, 2003, 111:11-18.

Greene et al., Protective Groups in Organic Synthesis, 2$_{nd}$ Edn., John Wiley, 1991, pp. 42-45, 53-55, 88, 90, 97, 102, and 156-157.

(56) References Cited

OTHER PUBLICATIONS

Grootenhuis et al., "Rational design of synthetic heparin analogues with tailor-made coagulation factor inhibitory activity," *Nat. Struct. Biol.* Sep. 1995, 2:736-739.

Guimond and Turnbull, "Fibroblast growth factor receptor signalling is dictated by specific heparan sulphate saccharides," *Curr. Biol.* Nov. 18, 1999, 9:1343-1346.

Haag et al. "Carbohydrate-Based VEGF Inhibitors," 2007 *European Journal of Organic Chemistry* 2007(36):6016-6033. Available online on Oct. 29, 2007.

Häcker et al., "Heparan sulphate proteoglycans: the sweet side of development," *Nat. Rev. Mol.* Cell Biol. Jul. 2005, 6:530-541.

Haller and Boons, "Towards a modular approach for heparin synthesis," *J. Chem. Soc., Perkin Trans.* 1 2001, 8:814-822; available online on Mar. 20, 2001.

Haller and Boons, "Selectively Protected Disaccharide Building Blocks for Modular Synthesis of Heparin Fragments," *Eur. J. Org. Chem.* 2002: 2033-2038.

Hamza et al. "First Synthesis of Heparan Sulfate Tetrasaccharides Containing both N-Acetylated and N-Unsubstituted Glucosamine—Search for Putative 10E4 Epitopes," 2006 *ChemBioChem* 7(12):1856-1858. Available online on Oct. 19, 2006.

Harris and Turvey, "Sulphates of monosaccharides and derivatives: Part VII. Synthesis of some disulphates and a new synthesis of d-galactose 4-sulphate,"*Carbohydr. Res.* Apr. 1969, 9:397-405.

Horibe and Oshita, "A Novel Regioselective Desulfation Method Specific to Silyl Ester of Primary Sulfate Using Silylating Agents. Selective Preparation of Secondary Alkyl Sulfates Having a Primary Hydroxy Group," *Bull. Chem. Soc. Jpn.* 2001 74:181-182.

Ingale et al., "Synthesis of glyco(lipo)peptides by liposome-mediated native chemical ligation," *Org. Lett.* Dec. 7, 2006, 8(25):5785-5788; available online on Nov. 16, 2006.

Jacquinet et. al., "Synthesis of heparin fragments. A chemical synthesis of the trisaccharide O-(2-deoxy-2-sulfamido-3,6-di-O-sulfo-α-d-glucopyranosyl)-(1→4)-O-(2-O-sulfo-α-1-idopyranosyluronic acid)-(1→4)-2-deoxy-2-sulfamido-6-O-sulfo-d-glucopyranose heptasodium salt," *Carbohydr. Res.* Jul. 15, 1984, 130:221-241.

Jacquinet et al., "Multigram syntheses of the disaccharide repeating units of chondroitin 4- and 6-sulfates," *Carbohydr. Res.* Dec. 31, 1998, 314:283-288.

Jacquinet, "An expeditious preparation of various sulfoforms of the disaccharide β-d-Galp-(1 → 3)-d-Galp, a partial structure of the linkage region of proteoglycans, as their 4-methoxyphenyl β-d-glycosides," *Carbohydr. Res.* Jan. 22, 2004 339:349-359.

Jacquinet et al., "From polymer to size-defined oligomers: a highly divergent and stereocontrolled construction of chondroitin sulfate A, C, D, E, K, L, and M oligomers from a single precursor: part 2," *Chem. Eur. J.* Sep. 21, 2009 15:9579-9595; available online on Jul. 20, 2009.

Jarowicki and Kocienski, "Protecting groups," *J. Chem. Soc., Perkin Trans.* 1998, 1:4005-4037.

Johnson et al., "Interaction of chemokines and glycosaminoglycans: a new twist in the regulation of chemokine function with opportunities for therapeutic intervention," *Cytokine Growth Factor Rev.* Dec. 2005, 16:625-636; available online on Jun. 28, 2005.

Kariya et al., "Preparation of completely 6-O-desulfated heparin and its ability to enhance activity of basic fibroblast growth factor," *J. Biol. Chem.* Aug. 25, 2000, 275:25949-25958; available online on Jun. 2, 2000.

Karst et al., "Chemical synthesis of β-D-GlcpA(2SO$_4$)-(1→3)-D-GalpNAc(6SO$_4$), the disaccharide repeating unit of shark cartilage chondroitin sulfate D, and of its methyl β-D-glycoside derivative," *J. Chem. Soc., Perkin Trans.1,* 2000:2709-2717.

Karst and Linhardt, "Recent chemical and enzymatic approaches to the synthesis of glycosaminoglycan oligosaccharides," *Curr. Med. Chem.* Oct. 2003, 10:1993-2031.

Karst et al. "Trifluoroethylsulfonate protected monosaccharides in glycosylation reactions" *Tetrahedron Letters,* 2004; 45(34):6433-7. Available online Jul. 19, 2004.

Kawatkar, Arati, "Heparan Sulfate Synthesis: Challenges and Prospects," Thesis paper for Master of Science in Chemistry; University of Georgia. Degree Date Dec. 2004. 118 pages.

Kocienski, *Protecting Groups, Third Edition,* Georg Thieme: New York, NY: 2004. Cover page, publisher's page, and table of contents.

Kreuger et al., "Interactions between heparan sulfate and proteins: the concept of specificity," *J. Cell Biol.* Jul. 31, 2006, 174:323-327.

Kuberan et al., "Chemoenzymatic Synthesis of Classical and Nonclassical Anticoagulant Heparan Sulfate Polysaccharides," *J. Biol. Chem.* Dec. 26, 2003, 278:52613-52621; available online on Sep. 29, 2003.

Leach et al., "Negative electron transfer dissociation Fourier transform mass spectrometry of glycosaminoglycan carbohydrates," 2011 *Eur. J. Mass. Spec.* 17:167-176.

Lee et al., "Synthesis of Heparin Oligosaccharides," *J. Am. Chem. Soc.* 2004, 126:476-477; available online on Dec. 19, 2003.

Lindahl et al., "Evidence for a 3-O-sulfated D-glucosamine residue in the antithrombin-binding sequence of heparin," *Proc. Natl. Acad. Sci. USA* Nov. 1980, 77:6551-6555.

Lindahl et al., "Generation of 'neoheparin' from *E. coli* K5 capsular polysaccharide," *J. Med. Chem.* Jan. 27, 2005, 48:349-352; available online on Dec. 31, 2004.

Linhardt et al., "Enzymatic synthesis of glycosaminoglycan heparin," *Semin. Thromb. Hemost.* Jul. 2007, 33:453-465.

Liu et al., "Chemoenzymatic Design of Heparan Sulfate Oligosaccharides," *J. Biol. Chem.* Oct. 29, 2010, 285:34240-34249; available online on Aug. 21, 2010.

Lohman et al. "A Sterochemical Surprise at the Late Stage of the Synthesis of Fully N-Differentiated Heparin Oligosaccharides Containing Amino, Acetamido, and NSulfonate Groups," 2004 *Journal of Organic Chemistry* 69:4081-4093.

Lopin et al., "From polymer to size-defined oligomers: an expeditious route for the preparation of chondroitin oligosaccharides," *Angew. Chem. Int. Ed.* Apr. 10, 2006, 45:2574-2578.

Lu et al., "Synthesis of 48 disaccharide building blocks for the assembly of a heparin and heparan sulfate oligosaccharide library," *Org. Lett.* Dec. 21, 2006, 8:5995-5998; available online on Nov. 18, 2006.

Lubineau et al., "Synthesis of Tailor-Made Glycoconjugate Mimetics of Heparan Sulfate That Bind IFN-γ in the Nanomolar Range," *Chem. Eur. J.* Sep. 6, 2004, 10:4265-4282; available online on Jul. 12, 2004.

Lucas et al., "Syntheses of heparin-like pentamers containing 'opened' uronic acid moieties," *Tetrahedron* 1990, 46:8207-8228.

Lucas et al. "Synthesis of Glycosaminoglycan Oligosaccharides—An Unexpected Inhibitory Effect of a Remote N-Acetyl Group upon Trichloroacetimidate-Mediated Couplings," 2004 *European Journal of Organic Chemistry* 2004(10):2107-2117.

Markad and Schmidt, "Temporary Carbohydrate Diol Protection with Ester Groups—Orthogonality under Solid-Phase Oligosaccharide Synthesis Conditions," *Eur J. Org. Chem.* 2009:5002-5011; available online on Sep. 2, 2009.

Matsuo et al., "A novel regioselective desulfation of polysaccharide sulfates: Specific 6-O-desulfation with N,O-bis(trimethylsilyl)acetamide," *Carbohydr. Res.* Mar. 17, 1993, 241:209-215.

Merrifield, "Some recent developments in solid phase peptide synthesis," *Proceedings of the 5$^{th}$ America Peptide Symposium.* University of California, San Diego; 1977. Cover page, publisher's pages, and pp. 488-502.

Nagasawa et al., "Chemical sulfation of preparations of chondroitin 4- and 6-sulfate, and dermatan sulfate. Preparation of chondroitin sulfate E-like materials from chondroitin 4-sulfate," *Carbohydrate Res.* Dec. 15, 1986 158:183-190.

Nguyen et al., "A synthetic heparan sulfate oligosaccharide library reveals the novel enzymatic action of D-glucosaminyl 3-O-sulfotransferase-3a," Feb. 2012 *Mol. Biosyst.* 8:609-614. Available online on Nov. 24, 2011.

Noti and Seeberger, "Chemical approaches to define the structure-activity relationship of heparin-like glycosaminoglycans," *Chem. Biol.* Jul. 2005, 12:731-756.

(56) References Cited

OTHER PUBLICATIONS

Noti et al., "Preparation and use of microarrays containing synthetic heparin oligosaccharides for the rapid analysis of heparin-protein interactions," *Chem. Eur. J.* Nov. 24, 2006, 12:8664-8686; available online on Oct. 25, 2006.
Ogamo et al., "Reactivity toward chemical sulfation of hydroxyl groups of heparin," *Carbohydrate Res.* Oct. 31, 1989, 193:165-172.
Oh et al., "Multivariate analysis of electron detachment dissociation and infrared multiphoton dissociation mass spectra of heparan sulfate tetrasaccharides differing only in hexuronic acid stereochemistry," Mar. 2011 *J. Am. Soc. Mass. Spec.* 22:582-590. Available online on Jan. 28, 2011.
Orgueira et al., "Modular synthesis of heparin oligosaccharides," *Chem. Eur. J.* Jan. 3, 2003, 9:140-169; available online on Dec. 30, 2002.
Ori et al., "The heparanome and regulation of cell function: structures, functions and challenges," *Front. Biosci.* May 1, 2008, 13:4309-4338.
Oscarson Ch. 3 "Protective Group Strategies" in *The Organic Chemistry of Sugars* (Levy et al., Ed.), CRC Press, Taylor & Francis Group, Boca Raton, FL (2006) pp. 53-33.
Parish, "The role of heparan sulphate in inflammation," *Nat. Rev. Immunol.* Sep. 2006, 6:633-64; available online on Aug. 18, 2006.
Patey et al., "Heparin derivatives as inhibitors of BACE-1, the Alzheimer's beta-secretase, with reduced activity against factor Xa and other proteases," *J. Med. Chem.* Oct. 5, 2006, 49:6129-6132; available online on Sep. 7, 2006.
Patey et al., "Engineered heparins: novel beta-secretase inhibitors as potential Alzheimer's disease therapeutics," *Neurodegener. Dis.* 2008, 5:197-199; available online on Mar. 6, 2008.
Petitou et al., "Experimental proof for the structure of a thrombin-inhibiting heparin molecule," *Chem. Eur. J.* 2001, 7:858-873; available online on Feb. 16, 2001.
Petitou and van Boeckel, "A synthetic antithrombin III binding pentasaccharide is now a drug! What comes next?" *Angew. Chem. Int. Ed. Engl.* Jun. 14, 2004, 43:3118-3133; available online on Jun. 9, 2004.
Polat and Wong, "Anomeric reactivity-based one-pot synthesis of heparin-like oligosaccharides," *J. Am. Chem. Soc.* Oct. 24, 2007, 129:12795-12800; available online on Oct. 3, 2007.
Poletti and Lay, "Chemical Contributions to Understanding Heparin Activity: Synthesis of Related Sulfated Oligosaccharides," *Eur. J. Org. Chem.* 2003:2999-3024.
Prabhu et al., "New Set of Orthogonal Protecting Groups for the Modular Synthesis of Heparan Sulfate Fragments," *Org. Lett.* 2003, 5:4975-4978; available online on Nov. 27, 2003.
Remko and Hricovini, "Theoretical study of structure and properties of hexuronic acid and D-glucosamine structural units of glycosaminoglycans," *Struct. Chem.* 2007 18:537-547; available online on Jun. 5, 2007.
Rochepeau-Jobron and Jacquinet, "Multigram syntheses of the disaccharide repeating units of chondroitin 4- and 6-sulfates," *Carbohydrate Res.* Dec. 31, 1998, 305:181-191.
Rostand and Esko, "Microbial adherence to and invasion through proteoglycans," *Infect. Immun* Jan. 1997, 65:1-8.
Roy et al., "Bioactivity screening of partially desulfated low-molecular-weight heparins: a structure/activity relationship study," *Glycobiology* Sep. 21, 2011 21:1194-1205; available online on Apr. 22, 2011.
Sasisekharan et al., "Roles of heparan-sulphate glycosaminoglycans in cancer," *Nat. Rev. Cancer* Jul. 2002, 2:521-528.
Schelhaas and Waldmann, "Protecting Group Strategies in Organic Synthesis," *Angew. Chem. Int. Ed. Engl.* 1996, 35:2056-2083.
Schmidt and Kinzy, "Anomeric-oxygen activation for glycoside synthesis: the trichloroacetimidate method," in *Adv. Carbohydr. Chem. Biochem.*, Horton (Ed.). Academic Press, Inc., San Diego, CA: 1994. Cover page, publisher's page and pp. 21-123.

Scholefield et al., "Heparan sulfate regulates amyloid precursor protein processing by BACE1, the Alzheimer's beta-secretase," *J. Cell Biol.* Oct. 13, 2003, 163:97-107; available online on Oct. 6, 2003.
Seeberger and Werz, "Automated synthesis of oligosaccharides as a basis for drug discovery," *Nature Rev. Drug Disc.* Sep. 2005, 4:751-763.
Shukla et al., "A novel role for 3-O-sulfated heparan sulfate in herpes simplex virus 1 entry," *Cell* Oct. 1, 1999, 99:13-22.
Spillmann et al., "Glycosaminoglycan-protein interactions: a question of specificity," *Curr. Opin. Struct. Biol.* Oct. 1994, 4:677-682.
Sun et al., "Heparan sulfate: Structure, Function, modification and Synthesis," *Prog. Chem.* Aug. 24, 2008, 20:1136-1142. English language abstract included.
Tabeur et al., "L-iduronic acid derivatives as glycosyl donors," *Carbohydr. Res.* Feb. 23, 1996, 281:253-276.
Takano et al., "A Novel Regioselective Desulfation Method Specific to Carbohydrate 6-Sulfate Using Silylating Reagents," *Biosci. Biotech. Biochem.* 1992 56:1577-1580.
Takano et al., "Desulfation of Sulfated Carbohydrates Mediated by Silylating Reagents," *J. Carb. Chem.* 1995 14:885-888.
Tanaka et al., "One-Pot Synthesis of Sialo-Containing Glycosyl Amino Acids by Use of an N-Trichloroethoxycarbonyl-b-thiophenyl Sialoside," *Chem. Eur. J.* 2005, 11(3):849-862; available online on Dec. 6, 2004.
Tatai et al., "An efficient synthesis of L-idose and L-iduronic acid thioglycosides and their use for the synthesis of heparin oligosaccharides," *Carbohydrate Res.* Mar. 17, 2008, 343:596-606; available online on Dec. 25, 2007.
Taylor and Gallo, "Glycosaminoglycans and their proteoglycans: host-associated molecular patterns for initiation and modulation of inflammation," *FASEB J.* Jan. 2006, 20:9-22.
Teo et al., "Glycopeptide-specific monoclonal antibodies suggest new roles for O-GlcNAc," May 2010 *Nat. Chem. Biol.* 6:338-343. Available online on Mar. 21, 2010.
Usov et al., "Solvolytic desulphation of sulphated carbohydrates," *Carbohydr. Res.* Jun. 1971 18:336-338.
van Boeckel et al., "Synthesis of a Pentasaccharide Corresponding to the Antithrombin III Binding Fragment of Heparin," *J. Carbohydr. Chem.* 1985, 4:293-321.
van den Bos et al., "Thioglycuronides: synthesis and application in the assembly of acidic oligosaccharides," *Org. Lett.* Jun. 24, 2004, 6:2165-2168; available online on May 22, 2004.
van den Bos et al., "Uronic Acids in Oligosaccharide Synthesis," *Eur. J. Org. Chem.* 2007:3963-3976; available online on Jul. 3, 2007.
van Vactor et al., "Heparan sulfate proteoglycans and the emergence of neuronal connectivity," *Curr. Opin. Neurobiol.* Feb. 2006, 16:40-51; available online on Jan. 18, 2006.
Vasella et al., "Convenient Synthesis of 2-Azido-2-deoxy-aldoses by Diazo Transfer," *Helv. Chim. Acta* Dec. 11, 1991, 74:2073-2077.
Veeneman et al., "Iodonium ion promoted reactions at the anomeric centre. II An efficient thioglycoside mediated approach toward the formation of 1,2-trans linked glycosides and glycosidic esters," *Tetrahedron Lett.* 1990, 31:1331-1334.
Venot et al., "Disaccharide Mimetics of the Aminoglycoside Antibiotic Neamine," *Chembiochem* Sep. 6, 2004, 5:1228-1236; available online on Sep. 2, 2004.
Wells, Lance, "Role of O-GLCNAC in Metabolic Signaling," Grant Abstract, Grant No. DK075069 [online]. National Institute of Diabetes and Digestive and Kidney Diseases, National Institutes of Health, project dates Jan. 1, 2007 to Dec. 31, 2012 [retrieved on Feb. 18, 2013]. Retrieved from the Internet: <http://projectreporter.nih.gov/pr_Prj_info_desc_dtls.cfm?aid=8010657&icde=15329199&ddparam=&ddvalue=&ddsub=&cr=1&csb=default&cs=ASC&print=yes>; 2 pgs.
Whitelock and Iozzo, "Heparan sulfate: a complex polymer charged with biological activity," *Chem. Rev.* Jul. 2005, 105:2745-2764; available online on Jun. 25, 2005.
Wong et al., "Assembly of Oligosaccharide Libraries with a Designed Building Block and an Efficient Orthogonal Protection-Deprotection Strategy," *J. Am Chem. Soc.* 1998, 120:7137-7138; available online on Jul. 3, 1998.

(56) References Cited

OTHER PUBLICATIONS

Yates et al., "Highly diverse heparan sulfate analogue libraries: providing access to expanded areas of sequence space for bioactivity screening," *J. Med. Chem.* Jan. 1, 2004, 47:277-280; available online on Dec. 2, 2003.

Zacharski and Lee, "Heparin as an anticancer therapeutic," *Expert Opin. Investig. Drugs* Jul. 2008, 17:1029-1037.

Zhang et al., "Innate Immune Responses of Synthetic Lipid A Derivatives of *Neisseria meningitidis*," *Chem. Eur. J.* 2008, 14:558-569; available online on Oct. 17, 2007.

Zhang et al., "Synthetic tetra-acylated derivatives of lipid A from *Porphyromonas gingivalis* are antagonists of human TLR4," *Org. Biomol. Chem.* 2008, 6:3371-3381; available online on Jul. 25, 2008.

Zhang, "Fluorous linker-facilitated chemical synthesis" *Chem. Rev.* 2009; 109(2):749-95.

Zhou et al., "Toward synthesis of the regular sequence of heparin: synthesis of two tetrasaccharide precursors," *Carbohydrate Res.* Jul. 24, 2006, 341:1619-1629; available online on Mar. 10, 2006.

Zhu and Boons, "A new set of orthogonal-protecting groups for oligosaccharide synthesis on a polymeric support," *Tetrahedron: Assymetry* 2000, 11:199-205.

Zhu and Schmidt, "New principles for glycoside-bond formation," *Angew. Chem. Int. Ed.* 2009, 48:1900-1934; available online on Jan. 28, 2009.

International Search Report Form PCT/ISA/210 dated Jan. 13, 2011, in International Patent Application No. PCT/US2010/029235, filed Mar. 30, 2010.

Written Opinion Form PCT/ISA/237 dated Jan. 13, 2011, in International Patent Application No. PCT/US2010/029235, filed Mar. 30, 2010.

International Preliminary Report on Patentability Form PCT/IB/373 dated Oct. 4, 2011, in International Patent Application No. PCT/US2010/029235, filed Mar. 30, 2010.

European Patent Application No. EP 10762186.4, filed Mar. 30, 2010; Extended European Search Report, dated May 22, 2014; 13 pages.

* cited by examiner

β-D-GlcA(1-4)-α-D-GlcNAc(6S)(1-4)-β-D-GlcA(1-4)-α-D-GlcNAc(6S)(1)-(CH$_2$)$_5$NH$_2$ (76)

β-D-GlcA(1-4)-α-D-GlcNS(6S)(1-4)-β-D-GlcA(1-4)-α-D-GlcNS(6S)(1)-(CH$_2$)$_5$NH$_2$ (77)

β-D-GlcA(1-4)-α-D-GlcNAc(6S)(1-4)-α-L-IdoA(1-4)-α-D-GlcNAc(6S)(1)-(CH$_2$)$_5$NH$_2$ (78)

β-D-GlcA(1-4)-α-D-GlcNS(6S)(1-4)-α-L-IdoA(1-4)-α-D-GlcNS(6S)(1)-(CH$_2$)$_5$NH$_2$ (79)

α-L-IdoA(1-4)-α-D-GlcNAc(6S)(1-4)-β-D-GlcA(1-4)-α-D-GlcNAc(6S)(1)-(CH$_2$)$_5$NH$_2$ (80)

α-L-IdoA(1-4)-α-D-GlcNS(6S)(1-4)-β-D-GlcA(1-4)-α-D-GlcNS(6S)(1)-(CH$_2$)$_5$NH$_2$ (81)

α-L-IdoA(1-4)-α-D-GlcNAc(6S)(1-4)-α-L-IdoA(1-4)-α-D-GlcNAc(6S)(1)-(CH$_2$)$_5$NH$_2$ (82)

α-L-IdoA(1-4)-α-D-GlcNS(6S)(1-4)-α-L-IdoA(1-4)-α-D-GlcNS(6S)(1)-(CH$_2$)$_5$NH$_2$ (83)

α-L-IdoA(1-4)-α-D-GlcNAc(6S)(1-4)-α-L-IdoA(2S)(1-4)-α-D-GlcNAc(6S)(1)-(CH$_2$)$_5$NH$_2$ (84)

β-D-GlcA(1-4)-α-D-GlcNAc(6S)(1-4)-α-L-IdoA(2S)(1-4)-α-D-GlcNAc(6S)(1)-(CH$_2$)$_5$NH$_2$ (85)

β-D-GlcA(1-4)-α-D-GlcNS(6S)(1-4)-α-L-IdoA(2S)(1-4)-α-D-GlcNS(6S)(1)-(CH$_2$)$_5$NH$_2$ (86)

Figure 3

Levels of Sulfation

FIGURE 6A

Unsulfated disaccharide    Triply sulfated disaccharide

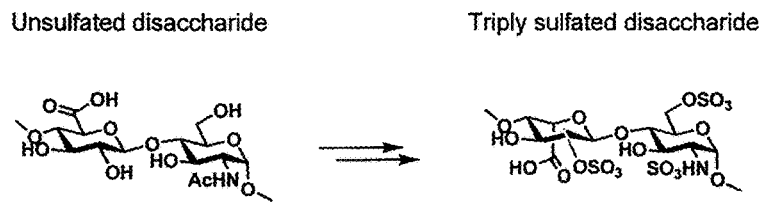

FIGURE 6B

| Hexuronic acid moiety | Glucosamine moiety | | Hexuronic acid moiety | Glucosamine moiety |
|---|---|---|---|---|
| GluA | → GlucNAc | | IdoA | → GlucNAc |
| GluA | → GlucNAc-(-6-SO$_3^-$) | | IdoA | → GlucNAc-(-6-SO$_3^-$) |
| GluA | → GlucNSO$_3^-$ | | IdoA | → GlucNSO$_3^-$ |
| GluA | → GlucNSO$_3^-$ (6-SO$_3^-$) | | IdoA | → GlucNSO$_3^-$ (6-SO$_3^-$) |
| GluA | → GlucNSO$_3^-$ (3-SO$_3^-$) | | IdoA | → GlucNSO$_3^-$ (3-SO$_3^-$) |
| GluA | → GlucNSO$_3^-$ (3,6-SO$_3^-$) | | IdoA | → GlucNSO$_3^-$ (3,6-SO$_3^-$) |
| GluA-(2-SO$_3^-$) | → GlucNAc | | Ido-(2-SO$_3^-$) | → GlucNAc |
| GluA-(2-SO$_3^-$) | → GlucNAc-(-6-SO$_3^-$) | | Ido-(2-SO$_3^-$) | → GlucNAc-(-6-SO$_3^-$) |
| GluA-(2-SO$_3^-$) | → GlucNSO$_3^-$ | | Ido-(2-SO$_3^-$) | → GlucNSO$_3^-$ |
| GluA-(2-SO$_3^-$) | → GlucNSO$_3^-$ (6-SO$_3^-$) | | Ido-(2-SO$_3^-$) | → GlucNSO$_3^-$ (6-SO$_3^-$) |
| GluA-(2-SO$_3^-$) | → GlucNSO$_3^-$ (3-SO$_3^-$) | | Ido-(2-SO$_3^-$) | → GlucNSO$_3^-$ (3-SO$_3^-$) |
| GluA-(2-SO$_3^-$) | → GlucNSO$_3^-$ (3,6-SO$_3^-$) | | Ido-(2-SO$_3^-$) | → GlucNSO$_3^-$ (3,6-SO$_3^-$) |

HEPARAN SULFATE SYNTHESIS

This application is a continuation application of U.S. Ser. No. 13/250,651, filed Sep. 30, 2011, which is a continuation-in-part application of international application PCT/US2010/029235, filed Mar. 30, 2010, which claims the benefit of U.S. Provisional Applications Ser. Nos. 61/211,479, filed Mar. 30, 2009, and 61/276,627, filed Sep. 14, 2009, each of which is incorporated herein by reference in its entirety.

STATEMENT OF GOVERNMENT RIGHTS

This invention was made with Government support under Grant Nos. R01CA088986, P41RR005351-20, and R01DK075069 awarded by the National Institutes of Health. The Government has certain rights in this invention.

BACKGROUND OF THE INVENTION

Glycoaminoglycans (GAGs) such as heparin and heparan sulfate (HS) are naturally occurring polydisperse linear polysaccharides that are heavily O- and N-sulfated (Esko et al., Annu Rev. Biochem. 2002, 71, 435-471; Gandhi et al., Chem. Biol. Drug Des. 2008, 72, 455-482). The interaction between GAGs and proteins can have profound physiological effects on hemostasis, lipid transport and adsorption, cell growth and migration and development (Capila et al., Nat. Rev. Mol. Cell Biol. 2005, 6, 530-541; Whitelock Iozzo, R. V. Chem. Rev. 2005, 105, 2745-2764; Van Vactor et al., Curr. Opin. Neurobiol. 2006, 16, 40-51; Bishop et al., Nature 2007, 446, 1030-1037; On et al., Front. Biosci. 2008, 13, 4309-4338; see also Gallagher et al., Glycobiology 1992, 2, 523-528; Spillmann et al., Curr. Opin. Struct. Biol. 1994, 4, 677-682; Rostand et al., Infect. Immun. 1997, 65, 1-8; and Sasisekharan et al., Nat. Rev. Cancer 2002, 2, 521-528. Binding of GAGs can result in the immobilization of proteins at their sites of production, regulation of enzyme activity, binding of ligands to their receptors and protection of proteins against degradation. Alteration in GAG expression has been associated with disease. For example, significant structural changes have been reported in proteoglycans surrounding the stroma of tumors and it has been suggested that these alterations may support tumor growth and invasion (Johnson et al., Cytokine Growth Factor Rev. 2005, 16, 625-636; Parish, Nat. Rev. Immunol. 2006, 6, 633-643; Taylor and Gallo, FASEB J. 2006, 20, 9-22; Chen et al., Mol. Cells 2008, 26, 415-426; Zacharski and Lee, Expert Opin. Investig. Drugs 2008, 17, 1029-1037).

Currently, more than a hundred heparan sulfate-binding proteins have been identified (Ori et al., Front. Biosci. 2008, 13, 4309-4338) and it is to be expected that in the near future many more will be discovered. For a small number of HS binding proteins, it has been established that a specific sulfation pattern is required for mediating biological activity. The best-studied case represents the interaction of antithrombin with heparin (Lindahl et al., Proc. Natl. Acad. Sci. USA 1980, 77, 6551-6555; Petitou and van Boeckel, Angew. Chem. Int. Ed. Engl. 2004, 43, 3118-3133; de Kort et al., Drug Discov. Today 2005, 10, 769-779). Each of the sulfates of the pentasaccharide GlcNAc6S-GlcA-GlcN3S-IdoA-GlcNS is essential for high affinity binding to antithrombin and anticoagulant activity. Interestingly, the pentasaccharide contains a rare glucosamine moiety that has a sulfate ester at C-3. The latter moiety is also required for binding of Herpes simplex gD protein to HS, which in turn is important for viral infection (Shukla et al., Cell 1999, 99, 13-22). On the other hand, it has been proposed that for some HS binding proteins, the spatial organization of clusters of negative charge in HS is an important determinant of binding and biological activity. It appears that in these cases, the HS binding proteins have a relaxed selectivity for short HS oligosaccharides. An example is thrombin, which requires a highly sulfated structure for binding (Grootenhuis et al., Nat. Struct. Biol. 1995, 2, 736-739). This diversity of interactions emphasizes the need for more detailed structure-activity studies on a wider range of HS binding proteins (Gama et al., Nat. Chem. Biol. 2006, 2, 467-73).

For most HS binding there is very little or no information about ligand requirements for binding and mediating biological activity (Kreuger et al, J. Cell Biol. 2006, 174, 323-327) although there is great interest in evaluating heparan sulfate variants for research and drug screening. Progress has been hampered by the difficulties of identifying HS-binding motifs for specific proteins. This difficulty is due to a lack of technology for establishing structure-activity-relations (SAR), which in turn is due to the structural complexity of natural HS and difficulties of preparing well-defined compounds (Karst and Linhardt, Curr. Med. Chem. 2003, 10, 1993-2031; Poletti and Lay, Eur. J. Org. Chem. 2003, 2999-3024; Noti and Seeberger, Chem. Biol. 2005, 12, 731-756; Linhardt et al., Semin. Thromb. Hemost. 2007, 33, 453-465; van den Bos et al., Eur. J. Org. Chem. 2007, 3963-3976; Sun et al., Prog. Chem. 2008, 20, 1136-1142). Initial approaches to establish structure-activity-relations (SAR) employed modified derivatives of heparin in which acetamido, sulfonamido, or sulfate esters were chemically modified to produce polysaccharides that have simpler compositions than the parent compound have proved useful (Yates et al., J. Med. Chem. 2004, 47, 277-280). In addition, HS has been sulfated at specific positions using biosynthetic enzymes (Lindahl et al., J. Med. Chem. 2005, 48, 349-352; Chen et al., Chem. Biol. 2007, 14, 986-993). Although these approaches make it possible to draw some conclusions about the requirement of particular functionalities for binding or biological activity, they do not allow determination of the structure of binding epitopes. Natural libraries of HS oligosaccharides have been generated and screened (Guimond and Turnbull, Curr. Biol. 1999, 9, 1343-1346) but sequencing of identified hits is still a technical challenge.

The biosynthesis of HS involves the initial formation of a simple polysaccharide composed of alternating β-D-glucuronic acid (GlcA) and α-N-acetyl-D-glucosamine (GlcNAc) units joined by 1-4 anomeric linkages. This structure is then modified by a series of enzymatic transformations involving N-deacetylation followed by N-sulfation, C-5 epimerization of GlcA to L-iduronic acid (IdoA), and finally O-sulfation. Ultimately, these modifications result in the formation of an IdoA(2-OSO$_3$)-GlcNSO$_3$(6-OSO$_3$) sequence. Structural studies have, however, shown that HS contains nineteen other disaccharide sub-units arising from incomplete or additional enzymatic modifications. Combining these different disaccharides into larger structures results potentially in enormous structural diversity (Esko et al., *Annu. Rev. Biochem.* 2002, 71, 435-471). While it would be useful to screen a relatively large panel of well-defined HS fragments for binding to a target protein, chemical synthesis of the HS fragments has proven difficult and pain-staking. Only about 100 heparan sulfate oligosaccharides had been reported in the literature as of October, 2009, and synthesizing even a single one can take several months.

In principle, synthetic and chemoenzymatic approaches have the potential to provide a sufficiently large range of well-defined HS oligosaccharides for SAR or array development. Elegant synthetic approaches for heparin synthesis have been described (Karst and Linhardt, Curr. Med. Chem. 2003, 10, 1993-2031; Poletti and Lay, Eur. J. Org. Chem. 2003, 2999-3024; Noti and Seeberger, Chem. Biol. 2005, 12, 731-756; Linhardt et al., Semin. Thromb. Hemost. 2007, 33, 453-465; de Paz et al., Chembiochem 2001, 2, 673-685; Petitou et al., Chem. Eur. J. 2001, 7, 858-873; Codee et al., Drug Discovery Today: Technologies 2004, 1, 317-326; Lubineau et al., Chem. Eur. J. 2004, 10, 4265-4282; de Paz and Martin-Lomas, Eur. J. Org. Chem. 2005, 1849-1858; Zhou et al., Carbohydr. Res. 2006, 341, 1619-1629; Chen et al., Carbohydr. Res. 2008, 343, 2853-2862; Chen and Yu, Bioorg. Med. Chem. Lett. 2009, 19, 3875-3879; Lee et al., J. Am. Chem. Soc. 2004, 126, 476-477; Noti et al., Chem. Eur. J. 2006, 12, 8664-8686); however, no efficient strategy for the synthesis of a wide range of HS structures has been reported. Haller et al. proposed a modular approach for the chemical synthesis of a wide range of HS oligosaccharides whereby a set of properly protected disaccharide building blocks that resemble the different disaccharide motifs found in HS are assembled by a parallel combinatorial manner into larger structures (Haller and Boons, J. Chem. Soc., Perkin Trans. 1 2001, 814-822; Haller and Boons, Eur. J. Org. Chem. 2002, 2002, 2033-2038; Prabhu et al., Org. Lett. 2003, 5, 4975-4978). These efforts suffered, however, from difficulties in preparing key mono- and disaccharide intermediates, difficulties in removing temporary protecting groups, unreliability in glycosylations and difficulties in the final deprotection. Others have attempted to develop modular approaches for HS synthesis (Lee et al., J. Am. Chem. Soc. 2004, 126, 476-47; Gavard et al., Eur. J. Org. Chem. 2003, 3603-3620; Orgueira et al., Chem. Eur. J. 2003, 9, 140-169; Lu et al., Org. Lett. 2006, 8, 5995-5998; Polat and Wong, J. Am. Chem. Soc. 2007, 129, 12795-12800); however, these methods provided unnatural sulfation patterns, were unable to make structures larger than disaccharides or did not demonstrate the convenient preparation of a wide range of structural motifs. A robust strategy for the organic synthesis of a wide range of well-defined HS oligosaccharides has not been reported.

SUMMARY OF THE INVENTION

The invention provides an efficient modular synthesis for oligosaccharides. A parallel combinatorial method is used to produce oligosaccharides that were heretofore very difficult to synthesize. Modular disaccharide building blocks are combined in numerous ways to produce a range of oligosaccharides, preferably sulfated oligosaccharides, such as but not limited to heparan sulfate fragments. The invention allows diverse oligosaccharides to be produced reliably and economically in quantities sufficient to evaluate their properties and their potential as drugs.

In one aspect, the invention provides an orthogonally protected disaccharide, exemplified as formula (I), as the basic building block for tetra-, hexa- and higher order oligosaccharides. This basic disaccharide building block is formed from a hexuronic acid unit, preferably a glucuronic acid or an iduronic acid, at the non-reducing end, linked in an α- or β-(1,4) glycosidic linkage to a glucosamine unit at the reducing end. In the case of L-iduronic acid (L-IdoA), the linkage is preferably an α-(1,4) linkage; in the case of D-glucuronic acid (D-GlcA), the linkage is preferably a β-(1,4) linkage.

A preferred orthogonally protected disaccharide building block contains at least two orthogonal temporary protecting groups, and has the formula (I)

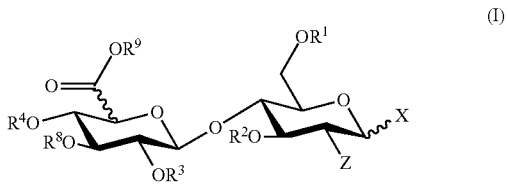

wherein each of $R^1$, $R^2$ and $R^3$ is independently a temporary protecting group or a permanent protecting group; wherein the temporary protecting group is preferably selected from levulinoyl (Lev), 9-fluorenylmethoxycarbonyl (Fmoc), pivaloyl levulinoyl (PivLev), pivaloyl benzoyl (PivBz), [2,2,2-trichloroethoxycarbonyl] (Troc) or allyloxycarbonyl (Alloc); the permanent protecting group for $R^1$ and $R^2$ is preferably selected from acetyl (Ac), benzyl (Bn), benzoyl (Bz), difluorobenzoyl (dfBz), pivaloyl benzoyl (PivBz), pivaloyl, anisoyl, 2-naphthylmethyl (NAP) or 1-naphthylmethyl (1-NAP); and the permanent protecting group for $R^3$ is preferably selected from Ac, benzoyl (Bz), difluorobenzoyl (dfBz), pivaloyl benzoyl (PivBz), pivaolyl or anisoyl;

Z is $—N_3$ or $—NHR^7$;

$R^4$ is H or a protecting group; wherein the protecting group is preferably selected from 9-fluorenylmethoxycarbonyl (Fmoc), allyloxycarbonyl (Alloc), [2,2,2-trichloroethoxycarbonyl] (Troc), levulinoyl (Lev), benzoyl (Bz), difluorobenzoyl, (dfBz), pivaloyl levulinoyl (PivLev), or pivaloyl benzoyl (PivBz) or a NAP ether; wherein $R^4$ is preferably a temporary protecting group; and wherein preferably, $R^4$ is different from $R^1$, $R^2$ and $R^3$;

X is $—OR^5$ or $—SR^6$;

$R^5$ is H, alkyl, cycloalkyl, substituted alkyl or cycloalkyl, alkenyl, substituted alkenyl, alkynyl, substituted alkynyl, aryl or substituted aryl, silyl or substituted silyl, benzyl; a temporary protecting group such as a silyl or substituted silyl, preferably thexyldimethylsilyl (TDS), t-butyldimethylsilyl (TBS), t-butyldiphenyl silyl (TBDPS), triisopropylsilyl (TIPS), trimethylsilyl (TMS), or triethylsilyl (TES); a permanent protecting group such as methyl (Me), acetyl (Ac), benzyl (Bn), 2-naphthylmethyl (NAP) or 1-naphthylmethyl (1-NAP); an anomeric spacer or linker; a fluorous tag; or a leaving group such as trichloroacetimidate $C(NH)—CCl_3$, phenyltrifluoroacetimidate $C(NPh)—CF_3$, trifluoroacetimidate $C(NH)—CF_3$; thioformimidate, S-glycosyl or N-phenyltrifluoroacetimidate;

$R^6$ is H, alkyl, cycloalkyl, substituted alkyl or cycloalkyl, alkenyl, substituted alkenyl, alkynyl, substituted alkynyl, aryl, or substituted aryl, preferably methyl, ethyl, phenyl, tosyl, or tolyl;

$R^7$ is H or a temporary protecting group, wherein the temporary protecting group is preferably selected from 9-fluorenylmethoxycarbonyl (Fmoc), allyloxycarbonyl (Alloc), [2,2,2-Trichloroethoxycarbonyl] (Troc), trichloroacetyl (TCA), acetyl (Ac), phthalimido (Phthal), carbobenzyloxy (Cbz) or tert-butoxycarbonyl (Boc);

$R^8$ is a permanent protecting group, preferably selected from benzyl (Bn), a substituted benzyl such as p-Methoxybenzyl (pMB), 2-naphthylmethyl (NAP) or 1-naphthylmethyl (1-NAP);

$R^9$ is a permanent protecting group, wherein the permanent protecting group is preferably selected from methyl (Me), acetyl (Ac), benzyl (Bn), a substituted benzyl such as p-Methoxybenzyl (pMB), Tert-butyl ($^t$Bu), 2-naphthylmethyl (NAP) or 1-naphthylmethyl (1-NAP);

wherein at least two protecting groups are orthogonal; preferably, wherein at least two of $R^1$, $R^2$, $R^3$, $R^4$, $R^5$ and $R^7$ are temporary protecting groups that are orthogonal; more preferably, wherein at least two of $R^1$, $R^2$ and $R^3$ are temporary protecting groups that are orthogonal; in yet another preferred embodiment, at least one of the orthogonal temporary protecting groups is at $R^4$.

Notwithstanding the above, in some embodiments of the orthogonally protected disaccharide building block of the invention, $R^4$ is a permanent protecting group such as acetyl (Ac). For example, when the protecting group does not need to be selectively removed at the end of a synthetic sequence, $R^4$ can be a permanent protecting group.

As noted, $R^5$ can be a leaving group, more particularly an anomeric leaving group. Any anomeric leaving group can be used; the invention is not limited by the choice of leaving group. See Zhu et al., Angew. Chem. Int. Ed. 2009, 48, 1900-1934, for a review of exemplary leaving groups that can be incorporated into the dissaccharide building block of the invention. Such leaving groups include, without limitation, those known to the art, those described elsewhere herein and in references cited herein, and include for example and without limitation trichloroacetimidates, silyl ethers, thioglycosylates (X-SR), halides, phosphates, phosphites, and the like.

Silyl or substituted silyl groups that are O-linked at the anomeric carbon to form silyl ethers are preferably cleavable with HF/pyridine and tetrahydrofuran (THF) or tetrabutylammonium fluoride (TBAF)/acetic acid/THF. Silyl or substituted silyl groups function as temporary protecting groups when O-linked at the anomeric carbon of the disaccharide and higher order saccharides of the invention.

Alkyl, alkenyl and alkynyl may include one, two, three, four, five, six, seven, eight, nine, ten, eleven, twelve or more carbon atoms. Aryl includes any aromatic hydrocarbon including phenyl, benzyl, tosyl and the like.

Conditions effective to cause cleavage of each of the different orthogonal protecting groups do not cause cleavage of other protecting groups present on the disaccharide building block.

Optionally, if $R^4$ is H, thereby providing a hydroxyl group at position C-4' and allowing the disaccharide to function as a glycosyl acceptor, the disaccharide is protected at the anomeric carbon such that it does not simultaneously function as a glycosyl donor. Likewise, if the disaccharide is activated at position C-1 to function as a glycosyl donor, it is optionally protected at C-4' so that it does not simultaneously function as a glycosyl acceptor.

The disaccharide building block is optionally equipped with a spacer or linker at the C-1 position to facilitate conjugation chemistry. The invention is not limited to a particular anomeric spacer, which can be selected based upon the intended purpose for including the spacer. The spacer can function as a chain terminating linker. Inclusion of a spacer is useful, for example, for the fabrication of heparan sulfate arrays and for the preparation of immunogens. Exemplary spacers include —$(CH_2)_n$NRCbz and —$[(CH_2)_2$—O—$(CH_2)_2]_n$NRCbz where n=3-6 and R=Bn, Ph, or H, fluorous linkers, and linkers or spacers that are attached to or are activated for attachment to a solid support.

The disaccharide building block of the invention is particularly well suited for employment in the combinatorial synthesis of a heparan sulfate oligosaccharide.

The invention includes tetrasaccharides, hexasaccharides and higher order oligosaccharides, particularly higher order heparan sulfate oligosaccharides, which oligosaccharides include one or more of the disaccharide building blocks described herein.

In another aspect, the invention includes a method for making an orthogonally protected oligosaccharide. An orthogonally protected tetrasaccharide (or higher order oligosaccharide) is formed via chain extension by reacting a first orthogonally protected disaccharide (or higher order oligosaccharide) that has been activated at the reducing end (i.e., a glycosyl donor) with a second orthogonally protected disaccharide (or higher order oligosaccharide) having a free hydroxyl, preferably at the C-4 position on the non-reducing end (i.e., glycosyl acceptor). It should be understood that while the oligosaccharide chain is ordinarily extended by two units at time, chain extension can also be effected by three, four, five, six or more units at a time by utilizing an orthogonally protected tri-, tetra-, penta-, hexa- or higher order glycosyl donor, or by one unit at a time if a monomeric glycosyl donor is utilized. Extending an orthogonally protected disaccharide acceptor using a monosaccharide glycosyl donor produces an orthogonally protected trisaccharide, which is also included in the invention.

The resulting orthogonally protected oligosaccharide is selectively deprotected in a series of reactions that removes one protecting group at a time. Cleavage conditions for each of the different orthogonal protecting groups do not cause cleavage of other protecting groups. Deprotection reactions removing orthogonal protecting groups can therefore be carried out in any order. As each orthogonal protecting group is cleaved, the deprotected site(s), which are typically hydroxyl or amine, are optionally sulfated to yield —O—$SO_3$ or —N—$SO_3$ groups, respectively. Permanent protecting groups are usually removed in later reaction steps, yielding a deprotected, sulfated oligosaccharide. A large number of oligosaccharides can be produced using the modular synthetic method of the invention, which oligosaccharides can be collected to form a chemical library. The oligosaccharides produced using the invention, as well as chemical libraries containing these oligosaccharides, are also included in the invention.

In an exemplary embodiment shown in Example I, the synthesis of the orthogonally protected disaccharide building block is based on the use of six strategically chosen monosaccharide building blocks that can conveniently be assembled into eight disaccharides (representing the orthogonally protected disaccharide building block). These disaccharides can be converted into eight glycosyl donors and eight glycosyl acceptors. These compounds can be combined in parallel combinatorially to give sixty-four different tetrasaccharides. The resulting tetrasaccharides can again be converted into glycosyl donors and acceptors and coupled, for example, with the set of disaccharide donors or acceptors to give a wide range of hexasaccharides, in principle up to 512 in number. The compounds are appropriately protected in such a way that N- and O-sulfate moieties can be selectively installed as in natural heparan sulfate. We have also developed glycosylation conditions that select for the desired alpha-(α-) or beta-(β-) anomer. Example I shows the synthesis of an exemplary collection of HS sulfate oligosaccharides designed to probe inhibition of the protease BACE-1, which has been implicated in Alzheimer's disease. Surprisingly, it was found that a tetrasaccharide is large enough to bind to the protease.

BRIEF DESCRIPTION OF THE DRAWINGS

FIG. 3 shows putative synthetic heparan sulfate (HS) ligands for BACE-1.

FIG. 6A shows a range of sulfation levels for a heparin sulfate disaccharide.

FIG. 6B shows disaccharides commonly found in HS.

DETAILED DESCRIPTION OF ILLUSTRATIVE EMBODIMENTS

Unless otherwise specified, "a," "an," "the," and "at least one" are used interchangeably and mean one or more than one.

The invention provides an efficient modular synthesis for oligosaccharides. An oligosaccharide is a saccharide that contains two or more monosaccharide units. A parallel combinatorial method is used to produce oligosaccharides that were heretofore very difficult to synthesize. Modular disaccharide building blocks, themselves the product of a novel combinatorial synthesis, are combined in numerous ways to produce a range of oligosaccharides. The synthetic method is particularly useful to produce heparan sulfate oligosaccharides (also referred to herein as heparan sulfate fragments), because it can be used to effect sulfation at specified hydroxyl groups and, optionally, amino groups.

The chemical syntheses used in the invention make use of orthogonal protection strategies. Orthogonal protecting groups are temporary protecting groups that are complementary to each other, such that each protecting group is independently removable. Orthogonal protecting groups can be cleaved under different reaction conditions without affecting the other functions present (Merrifield, Pept., Proc. Am. Pept. Symp., $5^{th}$, 1977, 488). Orthogonal protecting group strategies and conditions are reviewed in the textbooks, Greene and Wicks, Protecting Groups in Organic Synthesis, Third Edition, Wiley, New York, 1999, and Kocienski, Protecting Groups, Third Edition, Thieme, New York, 2004. A compound of the invention, such as a disaccharide building block or tetra-, hexa- or higher order oligosaccharide, that is "orthogonally protected" contains at least two different protecting groups that are orthogonal to each other, i.e., that can be removed independently without affecting the other orthogonal protecting group or any permanent protecting groups that are present on the compound. Orthogonal protecting groups used in the present invention are preferably hydroxyl protecting groups and/or amine protecting groups. The use of orthogonal protecting groups allows for controlled sulfation at selected sites, because selected sites can be deprotected and sulfated without disturbing the protecting groups at other sites which are removed at a later point in the oligosaccharide synthesis. Orthogonal cleavage in the context of the present invention is selective cleavage of a temporary hydroxy or amino protecting group from a saccharide, in which the cleavage conditions do not compromise the stability of the other protecting or functional groups on the molecule. Cleavages of protecting groups that are orthogonal to each other can be effected in any order of priority.

Figure 2:
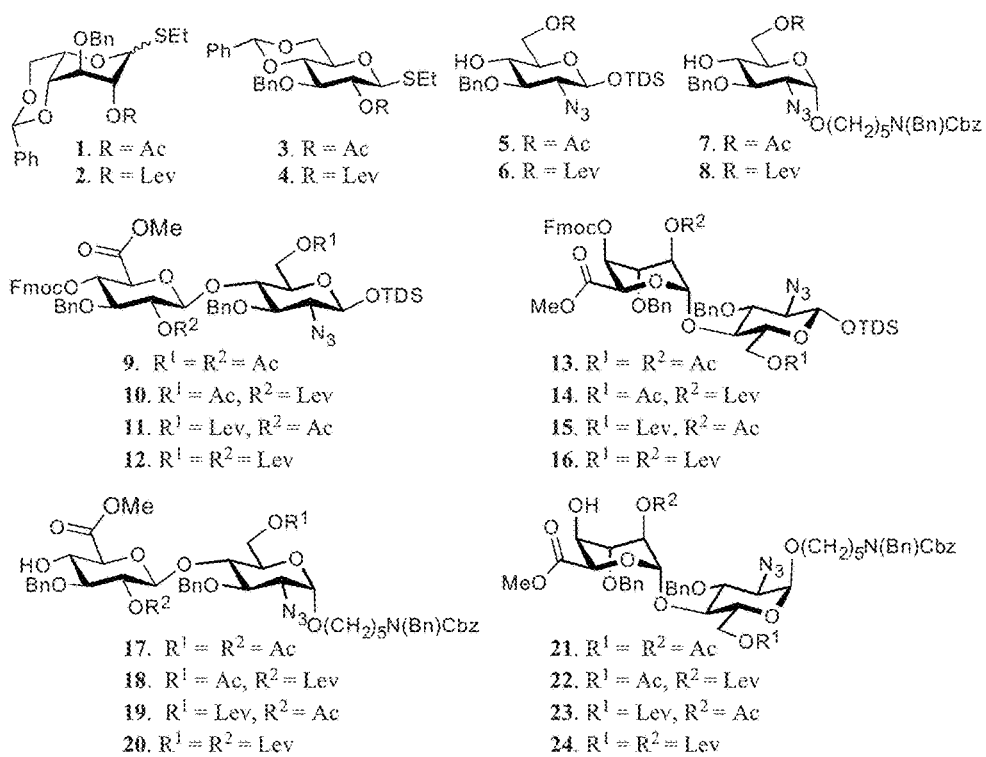
FIG. 2 shows exemplary modular mono- and disaccharide building blocks.

Orthogonally protected disaccharide building blocks are formed by combining monomeric protected glycosyl donors, as exemplified by compound 1-4 in FIG. 2, and monomeric protected glycosyl acceptors, as exemplified by compounds 5-8 in FIG. 2. The resulting orthogonally protected disaccharides, exemplified by compounds 9-24 in FIG. 2 and compounds 37-60 in Scheme 3 in Example I, are combined to produce orthogonally protected tetrasaccharides, hexasaccharides or higher order oligosaccharides. Oligosaccharide extension involves a disaccharide (or higher order) glycosyl donor and a disaccharide (or higher order) glycosyl acceptor. Typically, chain extension is effected one disaccharide at a time, from the nonreducing end of the oligosaccharide acceptor, but it can occur from the reducing end of an oligosaccharide donor as well, particularly where reducing end contains a good leaving group such as -SR where R is alkyl or aryl. To make a disaccharide (or higher order) acceptor, an orthogonally protected oligosaccharide which is protected at position C-4 on the nonreducing end (exemplified by compounds 37-40 and 49-52 in Scheme 3, Example I; compound 61 in Scheme 4, Example I; and compounds 70-75 in Scheme 5, Example I), is deprotected at that position to form an oligosaccharide acceptor having a hydroxyl at the C-4 position on the terminal monosaccharide unit. The oligosaccharide acceptor is thereby activated at the terminal C-4 position such that it can participate in a (1,4) glycosidic linkage, preferably an α-(1,4) linkage, with an oligosaccharide donor. Exemplary steps that can be employed during the synthesis of a disaccharide (or higher order) acceptor may include removal of benzylidene, oxidation of a primary hydroxyl (6-OH), esterification, and selective deprotection at C-4 of the benzylidene. Examples of orthogonally protected disaccharide acceptors include compounds 41-44 and 53-56 in Scheme 3 (Example I). To make a disaccharide (or higher order) donor, an oligosaccharide which is protected at the anomeric carbon, preferably with TDS (exemplified by compounds 37-44 and 49-56 in Scheme 3, Example I), is deprotected, then activated, preferably by installation of a leaving group such as an anomeric imidate such as trichloacetimidate at C-1. This enables the anomeric carbon to participate in a glycosidic linkage with the oligosaccharide acceptor, thereby extending the oligosaccharide by two residues. Exemplary steps that can be employed during the synthesis of a disaccharide (or higher) donor may include protection of a hydroxyl at 4-OH, removal of TDS, and activation at the C-1 hydroxyl. Examples of orthogonally protected disaccharide donors include compounds 45-48 and 57-60 in Scheme 3 (Example I).

When chain extension is complete (i.e., when the desired orthogonally protected tetrasaccharide, hexasaccharide or higher order saccharide is formed), the resulting oligosaccharide can be deprotected in a controlled fashion that permits sulfation at only selected positions. See Scheme 4 (Example I) and Scheme 8 (Example III) and Scheme 10 (Example V) for examples of deprotection and sulfation steps that can be employed sequentially to yield an exemplary heparan sulfate oligosaccharide. Example VI shows how various deprotection and derivatization sequences, including selective N-sulfation, selective sulfation of the primary hydroxyl groups (also referred to herein as selective 6-O-sulfation), and selective O-desulfation of the primary O-sulfate groups (also referred to herein as selective 6-O-desulfation) can be used to further diversify the library of oligosaccharides that can be formed from the disaccharide building blocks of the invention. It should be noted that, consistent with the principles of orthogonal protection, the various deprotection and sulfation steps can be carried out in different orders, with the proviso that removal of the permanent protecting groups (e.g., benzyl, acetyl, alkyl) is typically a later or the last deprotection step in the reaction scheme. Preferably, acetyl groups are removed prior to benzyl groups, and benzyl groups are removed in the last deprotection step.

Protecting Group Strategy

As noted above, the invention utilizes an orthogonal protection strategy, which is a strategy that permits the removal of multiple independent temporary protective groups one at the time, each with a dedicated set of reaction conditions without affecting the other. As the last step(s) in an orthogonal synthesis scheme, permanent protecting groups, if present, are removed. Examples of protecting groups for oligosaccharide synthesis are found in U.S. Pat. No. 6,953,850 (Dekany et al.) and U.S. Pat. No. 7,541,445 (Seifert et al.). Protecting groups, together with conditions for their introduction and removal, are also exemplified in *The Organic Chemistry of Sugars* (Levy et al., Ed.), Ch. 3 "Protective Group Strategies" pp. 53-33 (Stefan Oscarson), CRC Press, Taylor & Francis Group, Boca Raton, Fla. (2006); Zhu et al., Tetrahedron 11, 199-205 (2000); Jarowicki et al., J. Chem. Soc., Perkin Trans. 1, 4005-4037 (1998); Schelhaas et al., Angew. Chem. Int. Ed. Engl., 35, 2056-2083 (1996); Aly et al., Eur. J. Org. Chem, 4382-4392 (2005); Markad et al., Eur J. Org. Chem., 5002-5011 (2009); Wong et al., J. Am Chem. Soc, 120, 7137-7138 (1998); Zhang et al., Org. Biomol. Chem., 6, 3371-3381 (2008); Zhu et al., Angew. Chem., Int. Ed., 48, 1900-1934 (2009); Boltje et al., Nature Chem 1, 611-622 (Nov. 1, 2009); and Zhang et al., Chem. Eur. J. 14, 558-569 (2008).

The orthogonally protected disaccharide building block exemplified by formula (I) includes one or more preferred protecting groups utilized in the methods and compounds of the invention, but many other temporary and permanent protecting groups can be used. Some of the protecting groups useful in the methods and compounds of the invention are exemplified in the following lists.

Temporary hydroxyl protecting groups include but are not limited to the following:

Esters: Acetyl (Ac), Benzoyl (Bz), Chloroacetyl (ClAc), Pivaloyl (Piv), Levulinoyl (Lev), Pivaloyl levulinoyl (PivLev), Pivaloyl acetyl (PivAc), Pivaloyl benzoyl (PivBz), Difluorobenzoyl (dfBz), Bromoacetyl (BrAc).

Alkoxyalkyl ethers: Methoxymethyl (MOM), (2-Methoxyethoxy) methyl (MEM) Benzyloxymethyl (BOM), p-Methyl benzyloxymethyl (pMBOM), Trimethylsilylethoxymethyl (SEM).

Carbonates: 9-Fluorenylmethyl carbonyl (Fmoc), [2,2,2-Trichloroethoxycarbonyl] (Troc), Allyloxycarbonyl (Alloc).

Ethers: Naphthylmethyl (Nap) (which includes both 2-naphthylmethyl, 2-methyl naphthyl, NAP, and 1-naphthylmethyl, 1-NAP, and Nap ethers; Nap can be used as either a temporary or permanent protecting group), p-Methoxybenzyl (pMB), Trityl (Tr), Tetrahydro-2-pyranyl (THP), Methoxytrityl (MTr), Dimethoxytrityl (DMTr), Allyl (All).

Tosylates: p-toluene sulfonyl (Tos), methanesulfonyl (Ms).

Any of these temporary hydroxyl protecting groups can be used independently at the C-3 (corresponding to $R^2$ in formula I), C-6 (corresponding to $R^1$ in formula I) and/or C-4' (corresponding to $R^4$ in formula I) positions of the disaccharide building block. When used at the C-4' position of the hexuronic acid unit, any of these groups can be removed to permit extension of the saccharide chain from the non-reducing end. At the C-2' position (corresponding to $R^3$ in formula I) on the hexuronic acid unit, the ester and carbonate hydroxyl protecting groups are preferably used because they are able to participate in the formation of 1,2-trans linkage for formation of disaccharides. Generally, ethers cannot be used at position C-2' as they are not participating groups in glycosylations.

Temporary protecting groups for the anomeric position (corresponding to X in formula I) include but are not limited to the following:

Silyl ethers: t-butyldimethylsilyl (TBS), thexyldimethylsilyl (TDS), t-butyldiphenyl silyl (TBDPS), triisopropylsilyl (TIPS), trimethylsilyl (TMS), triethylsilyl (TES), triphenylsilyl (TPS), di-tert-butylmethylsilyl (DTBMS), diethylisopropylsilyl (DEIPS), dimethylisopropylsilyl (DMIPS), di-tert-butylsilylene (DTBS), tetra-tert-butoxydisiloxan-1,3-diyl (TBDS), and 1,1,3,3,-tetra-isopropyldisiloxane (TIPDS); these can be used as $R^5$ in formula (I) when $X=OR^5$.

Thioethers: Thiophenyl (SPh), Thioethyl (SEt), s-Tolyl (STol), Thiomethyl (SMe); these can be used as $X=SR^6$ in formula (I) wherein $R^6$ is phenyl, ethyl, tolyl, and methyl, respectively.

Temporary amine protecting groups that can be used at position C-2 in the disaccharide building block include but are not limited to the following:

Azide ($N_3$)
Phthalimido (Phthal)
Tetrachlorophthaloyl (TCP)
N-dithiasuccinyl (Dts) (this protecting group could be cleaved orthogonally in presence of an azide using propane-1,3-dithiol (PDT) and DIPEA)
N—$R_2$, R=Acetyl or other permanent or temporary protecting group
[2,2,2-Trichloroethoxycarbonyl] (Troc)
Acetyl (Ac)
Levulinoyl (Lev)
Pivaloyl acetyl chloride (PivAc)
Pivaloyl levulinoyl chloride (PivLev)
Tosyl (Tos)
Nosyl (Nos)
Allyloxycarbonyl (Alloc)
Trichloroacetyl (TCA)
Trifluoroacetyl (TFA)
Trityl (Tr)
Benzylideneamine
Tert-butyloxycarbonyl (Boc)
Benzyloxy carbonyl (Cbz)
Oxazolidine
Dimethylmaleoyl (DMM)
Thiodiglycolyl (TDG)
Diphenylmaleoyl (DPM)
Diglycolyl (DG)
Dimethylglutamyl (DMG)

Amine protecting groups as used in the invention are orthogonal with the azido moiety and stable under conditions for the removal of the temporary protecting groups. Once glycosylation has taken place (i.e., the anomeric center becomes -OR) the azido group that was masking the amine at C-2 can be converted to another group, thereby providing chemical flexibility that allows differentiation between amine groups.

Permanent protecting groups include but are not limited to:

Alkoxyalkyl ethers: Methoxymethyl (MOM), (2-Methoxyethoxy) methyl (MEM) Benzyloxymethyl (BOM), p-Methyl benzyloxymethyl (pMBOM), Trimethylsilylethoxymethyl (SEM).

Ethers: Naphthylmethyl (Nap) (both and 1- and 2-Nap), p-Methoxybenzyl (pMB), Trityl (Tr), Tetrahydro-2-pyranyl (THP), Methoxytrityl (MTr), Dimethoxytrityl (DMTr), Allyl (All).

Alkyl ethers: Methyl (Me), Ethyl (Et), Pentenyl, Benzyl (Bn), allyl (OAR), isopropyl (i-Pr).

Fluorous tags (Zhang, Chem. Rev., 2009, 109(2), 749-795).

Resin-Functionalized Linkers

Other illustrative examples of permanent protecting groups include benzoyl and benzoyl derivatives, such as diflurobenzoyl and pivaloylbenzoyl; pivaloyl and anisoyl.

Permanent protecting groups are stable to glycosylation conditions as well as conditions used to add and remove temporary protecting groups. Permanent protecting groups are used to protect hydroxyls that are not to be sulfated as well as other groups, such as the acid functionality on the hexuronic acid unit, which do not participate in the orthogonal protection scheme. Some protecting groups on this list, such as certain ethers and alkoxyethers, can serve as either temporary or permanent protecting groups, depending on the protection/deprotection scheme employed in the multi-step chemical synthesis. Any of these permanent protecting groups can be used independently to protect the disaccharide building block at the C-3 position (corresponding to $R^2$ in formula I), the C-6 position (corresponding to $R^1$ in formula I) and/or the C-3' position (corresponding to $R^8$ in formula I) of the hexuronic acid unit. At position C-2' on the hexuronic acid unit (corresponding to $R^3$ in formula I), acetyl (Ac) is preferred over Bn for use as a protecting group. As noted above, the acetyl protecting group is preferred because it can perform neighboring group participation, but is stable under the conditions used for the removal of other temporary protecting groups, such as Lev esters. Thus acetyl (Ac), while it may function as a temporary protecting group, can also be used as semi-permanent protecting group. Because it is somewhat less stable than benzyl, it can be removed separate from, and typically in the reaction just preceding, removal of any Bn group, thus allowing for selective deprotection and optional derivatization of Ac-protected hydroxyls.

Protecting groups that can be used to protect the acid moiety of the hexuronic acid unit (corresponding to $R^9$ in formula I) include but are not limited to: Methyl (Me), Benzyl (Bn), Tert-butyl ($^t$Bu), and Naphthyl methyl (Nap).

At the anomeric position, any of the alkyl ethers can be used. Any of the fluorous tags or the linkers for solid support can be used to protect the anomeric position.

Linkers or spacers that are preferred for use at the anomeric position include but are not limited to the following:

(CH$_2$—CH$_2$—O)$_n$—NH$_2$—R, R=NH$_2$ or OH
(CH$_2$—CH$_2$—O)$_n$—NH$_2$—NH$_2$
(CH$_2$—CH$_2$—O)$_n$—NH-Lev
CH$_2$—O—NH$_2$—R, R=NH$_2$ or OH
CH$_2$—O—NH$_2$—NH$_2$
CH$_2$—NH-Lev
(CH$_2$)$_n$NHCbz
(CH$_2$)$_n$—CH=CH$_2$
(CH$_2$)$_n$N(Bn)Cbz
[(CH$_2$)$_2$—O—(CH$_2$)$_2$]$_n$-NBnCbz
[(CH$_2$)$_2$—O—(CH$_2$)$_2$]$_n$-NHCbz
wherein n=1, 2, 3, 4, 5, 6, 7, 8, 9 or 10.

Linkers or spacers can also be installed as permanent protecting groups at other sites on the disaccharide module. For example, ester-based linkers can be used at the carboxylic acid position (corresponding to $R^9$ in formula I) or the C-4' position (corresponding to the $R^4$ position in formula I).

Resin-functionalized linkers for solid phase oligosaccharide synthesis are described in Seeberger et al., Nature Rev. Drug Discovery, 4(9), 751-763; Smoot et al., Chem Rev., 109(2), 749-795; Dhanawat et al., Mini-reviews in medicinal chemistry, 9 (2), 169-185; Galonic et al., Nature, 446 (7139), 1000-1007 (2007); and Tanaka et al., Chem. Eur. J., 11(3), 849-6 (2005).

Additionally, the C-4' and C-6' positions can together be protected by an acetal such as:

Isopropylidene (exemplified using formula I)

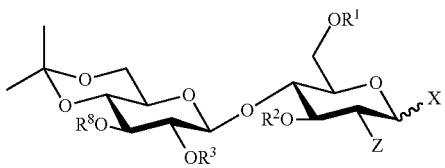

benzylidene acetal (exemplified using formula I)

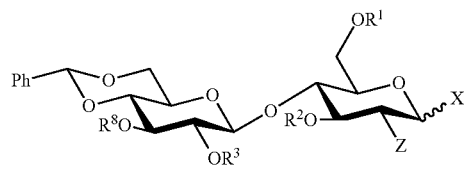

naphthylidene acetal (exemplified using formula I)

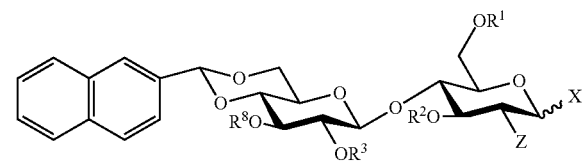

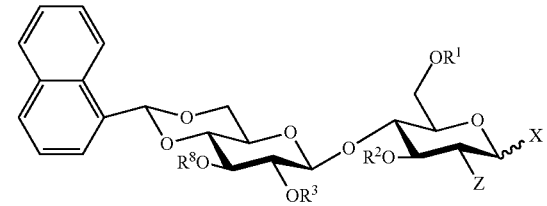

or p-methoxybenzylide acetal.

Figure 1:
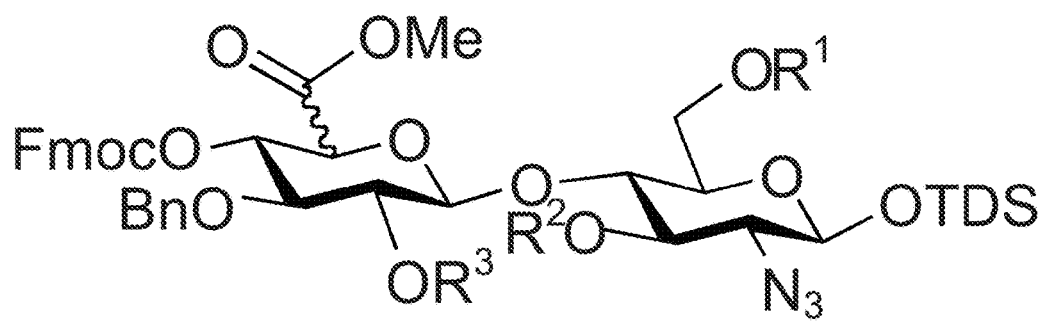
FIG. 1 shows an exemplary orthogonal protection strategy for a disaccharide building block.

An example of an orthogonally protected disaccharide building block is shown in FIG. 1. The structure shown in FIG. 1 encompasses eight different compounds. It would encompass 16 different compounds if another orthogonal dimension were added at the amine functionality (e.g., by choosing either azido or Fmoc as the protecting group). Other protecting groups can be used as well. For example, $R^1$ and $R^2$ could each independently be Ac instead of Bn. It should be noted the protecting groups can be, and often are, introduced into the monomeric constituents (i.e., the hexuronic acid moiety and the glucosamine moiety) prior to synthesis of the disaccharide.

O-sulfation in heparan sulfate (HS) principally occurs at C-2 of the hexuronic acid moiety, C-6 of the glucosamine moiety, and somewhat less commonly, C-3 of glucosamine moiety. Preferred monosaccharides and disaccharides of the invention thus contain orthogonal protecting groups at positions C-3 of the glucosamine moiety, C-6 the glucosamine moiety, and/or C-2 of the hexuronic acid moiety (which is also notated as the C-2' position in the disaccharide). The presence of orthogonal protecting groups permits controlled, selective introduction of sulfate groups at any one position, any two positions, or all three positions during subsequent synthesis of a higher order oligosaccharide.

The identity of the protecting group utilized is determined by the sulfation pattern of the targeted disaccharide module. To protect hydroxyl groups at any or all of positions C-3, C-6 or C-2' of the disaccharide (or at analogous positions in the constituent monosaccharide) which are to be later sulfated, a preferred temporary protecting group is a levulinoyl ester (Lev) (Zhu et al., Tetrahedron: Asymmetry 2000, 11, 199-205).

If the hydroxyl group at position C-3 or C-6 or both of the disaccharide (or at the analogous position in the constituent monosaccharide) is not to be later sulfated, a permanent protecting group is used instead of a temporary protecting group. Permanent protecting groups that are preferred for use at those positions are benzyl (Bn) or acetyl (Ac).

If the C-2' position in a disaccharide building block is to be later sulfated, it is preferably protected using Lev as the temporary protecting group. Advantageously, when a Lev ester is present at the C-2' position in a disaccharide, it can direct the formation of a 1,2-trans-glycoside by neighboring group participation (Boons, Contemp. Org. Synth. 1996, 3, 173-200; Demchenko, Syn Lett 2003, 1225-1240). If the hydroxyl group at the C-2' position of a disaccharide module does not need sulfation, an acetyl group (Ac) is preferably employed as a permanent protecting group, although other permanent protecting groups as described elsewhere herein can be used. The acetyl ester is preferred because it can perform neighboring group participation, but is stable under the conditions used for the removal of Lev esters and other temporary protecting groups.

An azido group is preferably used at C-2 of the glucosamine moiety as an amino-masking functionality (Bongat et al., Carbohydr. Res. 2007, 342, 374-406). This derivative does not perform neighboring group participation and therefore allows the introduction of α-glucosides. An azido group can easily be reduced to an amine, which can either be acetylated or sulfated.

It is possible to produce oligosaccharides containing both acetylated amines and sulfated amines by employing an orthogonal protection scheme. After an initial glycosylation reaction, the azido group at C-2 of the glucosamine is reduced, for example using trimethylphosphine, to an amine, then protected with a temporary protecting groups such as Fmoc or Alloc. Subsequent glycosylation with a glucosamine moiety that contains an azido group at C-2 yields an oligosaccharide wherein the amines are protected by orthogonal protecting groups (for example, azide and Fmoc). This enables selective sulfation or acetylation at the different amines to yield an oligosaccharide containing both N-sulfate and acetamido groups.

It is also possible to produce oligosaccharides containing acetylated amines, sulfated amines and free amines by employing an orthogonal protection scheme. Example V shows how an orthogonally protected oligosaccharide having azide and Fmoc protecting groups can be further protected by first reducing the azido group and protecting the amine with a different temporary protecting group, such as carbobenzyloxy (Cbz), followed by glycosylation with yet another glucosamine moiety that contains an azido group at C-2 to yield an oligosaccharide wherein at least three amines are protected by orthogonal protecting groups (for example, azide, Cbz and Fmoc). This enables selective deprotection and optional sulfation or acetylation at the different amines to yield an oligosaccharide containing N-sulfate groups, N-acetyl groups (acetamido) and free amino moieties.

The C-4' hydroxyl (on the hexuronic acid moiety) is required for extension of the oligosaccharide. It is preferably protected as 9-fluorenylmethyl carbonate (Fmoc). The Fmoc group can be removed with triethylamine ($Et_3N$) in dichloromethane (DCM) or dimethylformamide (DMF), or with piperidene in DMF, or with 1,8-Diazabicylco[5.4.0]undec-7-ene (DBU) in dichloromethane (DCM), without affecting the Lev ester, whereas the Lev group can be cleaved with hydrazine buffered with acetic acid and these conditions do not affect the Fmoc carbonate (Zhu et al., Tetrahedron: Asymmetry 2000, 11, 199-205). Removal of the Fmoc group activates the molecule as a glycosyl acceptor.

It should be noted that the temporary protecting group used to protect hydroxyls to be sulfated (e.g., Lev) and the temporary protecting group used to protect the C-4' hydroxyl (e.g., Fmoc) are interchangeable. For example, Fmoc can be used for the hydroxyls to be sulfated (particularly when the hydroxyl at the C-2' position is not to be sulfated), and Lev can be used for the C-4' hydroxy.

The anomeric center of the disaccharide can be protected as a silyl ether, for example as a thexyldimethyl silyl (TDS) glycoside. This functionality can easily be removed by treatment with hydrogen fluoride pyridine complex in tetrahydrofuran without affecting the other protecting groups. The resulting lactol can then be converted into a trichloroacetimidate by employing potassium carbonate ($K_2CO_3$) or cesium carbonate ($Cs_2CO_3$) or NaH and trichloroacetonitrile in DCM (Prabhu et al., Org. Lett. 2003, 5, 4975-4978), thereby activating the molecule as a glycosyl donor. Alternatively, the anomeric center can be protected via a covalent linkage to a spacer, preferably a (C1-C8) amino benzyloxycarbonyl protected spacer, such as an α-anomeric N-(benzyl)benzyloxycarbonyl protected aminopentenyl spacer.

Accordingly, in a preferred embodiment, the invention provides a method for making an oligosaccharide that includes providing one or more orthogonally protected disaccharide building blocks, for example having formula (I); forming one or more glycosyl donors from one or more of the disaccharide building blocks; forming one or more glycosyl acceptors from one of more of the disaccharide building blocks; and reacting the one or more glycosyl donors and the one or more glycosyl acceptors to form an orthogonally protected oligosaccharide The glycosyl acceptor is formed by deprotecting an orthogonally protected disaccharide building block at the hydroxyl that will participate in the glycosidic linkage, preferably at position C-4' of the disaccharide, to form a free hydroxyl group. In one embodiment, the glycosyl acceptor is temporarily protected at the anomeric carbon, C-1. In another embodiment, the glycosyl acceptor is permanently protected at the anomeric carbon, for example by linkage at position C-1 to an anomeric spacer or another saccharide. The glycosyl donor is formed by deprotecting an orthogonally protected disaccharide building block at position C-1 of the disaccharide and installing a leaving group at the C-1 position. The glycosyl donor is preferably protected at position C-4', preferably using a temporary protecting group such as Fmoc. The leaving group at C-1 of the glycosyl donor is preferably selected from trichloroacetimidate -C(NH)—CCl₃, phenyltrifluoroacetimidate -C(NPh)-CF₃, trifluoroacetimidate -C(NH)—CF₃, thioformimidate, or S-glycosyl N-phenyltrifluoroacetimidate.

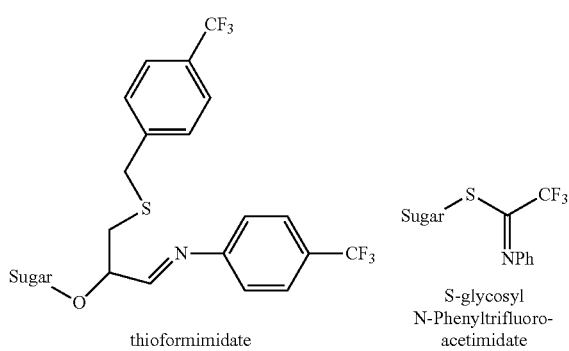

thioformimidate

S-glycosyl N-Phenyltrifluoroacetimidate

The orthogonally protected oligosaccharide formed by reacting the glycosyl donor with the glycosyl acceptor can be a tetrasaccharide comprising four monosaccharide units, a hexasaccharide comprising six monosaccharide units, or any other order of oligosaccharide.

An orthogonally protected oligosaccharide can be activated for chain extension by removing a temporary protecting group from position C-4 of the terminal monosaccharide unit at the non-reducing end of the orthogonally protected oligosaccharide, or removing a temporary protecting group from position C-1 of the terminal monosaccharide unit at the reducing end of the orthogonally protected oligosaccharide.

Different protecting groups can be removed sequentially from the orthogonally protected oligosaccharide. Optionally, the method includes removing a temporary hydroxyl protecting group, such as Lev, from one or more positions on the oligosaccharide to form a free hydroxyl, and sulfating the free hydroxyl. Additionally or alternatively, the method includes removing a temporary amine protecting group, such as azido, Fmoc, Alloc, Ac, TCA and Phthal from the C-2 position of a glucosamine unit of the oligosaccharide to form a free amine, and sulfating the free amine. The method also optionally includes removing permanent protecting groups from the oligosaccharide to form an unprotected, sulfated oligosaccharide. The sulfated oligosaccharide can be sulfated at one or more hydroxyls at a C-3 position on a glucosamine unit, a C-6 position on a glucosamine unit, and a C-2 position on a hexuronic acid unit. In some sulfated oligosaccharides made according to the method of the invention, all amines on the sulfated oligosaccharide are N-sulfated. In other sulfated oligosaccharides made according to the method of the invention, the sulfated oligosaccharide includes both N-sulfated amines and N-acetylated amines. In a particular preferred embodiment, the sulfated oligosaccharide is a heparan sulfate oligosaccharide or fragment.

The invention also provides a glycolipopeptide that includes, as its carbohydrate moiety, an oligosaccharide described herein or made according to a method described herein. In that regard reference is made to US Patent Publication 2009-0041836-A1, entitled "Glycopeptide and Uses Thereof," published Feb. 12, 2009, which describes the structure of a glycolipopeptide and methods for making the same.

The invention further provides an antibody, both polyclonal and monoclonal, that binds to an oligosaccharide described herein or made according to a method described herein.

The invention further provides method for detecting a biological molecule comprising a heparan sulfate, heparan sulfate fragment, or heparan sulfate precursor, which method includes contacting a biological material with the antibody that binds to an oligosaccharide described herein, and detecting binding of the antibody to the biological molecule.

The invention further provides a method for inhibiting an enzyme, wherein the enzyme is contacted with an oligosaccharide of the invention under conditions to inhibit the enzyme.

The present invention, as exemplified in the inventor's publication, Arungundram et al. (Nov. 11, 2009, *J. Am. Chem. Soc.* 131:17394-17405), dramatically advances the art of oligosaccharide synthesis. In this excerpt from *Chemical & Engineering News*, 87(47), Nov. 23, 2009, commenting on the Arungundram et al. publication, Stuart Borman quotes heparin specialist Robert J. Linhardt of Rensselaer Polytechnic Institute as stating that heparan sulfates are "incredibly difficult to generate" and that "[n]o one's ever delivered a collection like this. This approach could be very important for supplying diverse libraries to biologists and medicinal chemists for evaluating structure-activity relationships and novel pharmacological agents." Borman quotes Linhardt further in noting that "the sugars Boons's team put together via the new method 'are all pretty complicated and have high structural diversity'" and ""[t]hat suggests this method is workable at least for tetrasaccharides and hexasaccharides, which are the critical size for protein binding in most cases. I think this holds a lot of promise for the field.'"

The present invention is illustrated by the following examples. It is to be understood that the particular examples, materials, amounts, and procedures are to be interpreted broadly in accordance with the scope and spirit of the invention as set forth herein.

EXAMPLES

Example I

Modular Synthesis of Heparan Sulfate Oligosaccharides for Structure-Activity Relationship Studies Although hundreds of heparan sulfate binding proteins have been identified, and implicated in a myriad of physiological and pathological processes, very little information is known about ligand requirements for binding and mediating biological activities by these proteins. This difficulty results from a lack of technology for establishing structure-activity-relationships, which in turn is due to the structural complexity of natural heparan sulfate (HS) and difficulties of preparing well-defined HS-oligosaccharides. To address this deficiency, we have developed a modular approach for the parallel combinatorial synthesis of HS oligosaccharides that utilizes a relatively small number of selectively protected disaccharide building blocks, which can easily be converted into glycosyl donors and acceptors. The utility of the modular building blocks has been demonstrated by the preparation of a library of twelve oligosaccharides, which has been employed to probe structural features of HS for inhibiting the protease, BACE-1. The complex variations in activity with structural changes support the view that important functional information is embedded in HS sequences. Furthermore, the most active derivative provides an attractive lead compound for the preparation of more potent compounds, which may find use as a therapeutic agent for Alzheimer's disease.

We report here a robust modular synthetic approach for the preparation of a wide range of well-defined HS oligosaccharides for SAR studies (Arungundram et al., Nov. 11, 2009, J. Am. Chem. Soc. 131:17394-17405). The synthetic methodology is based on the use of a relatively small number properly protected disaccharide donors and acceptors that in a parallel combinatorial manner, using a standard set of reaction conditions, can be assembled into a large number of HS-oligosaccharides. The compounds are equipped with an anomeric aminopentyl spacer, which provides an opportunity for conjugation to a solid surface, which for example is required for microarray technology development (Noti et al., Chem. Eur. J. 2006, 12, 8664-8686). To illustrate the convenience of the modular building blocks, a library of twelve oligosaccharides has been prepared to probe the requirement for inhibition of the protease, β-secretase (or BACE-1). The cleavage of amyloid precursor protein (APP) by the protease BACE-1 is a key step in generating amyloid plaques, which are a characteristic of Alzheimer disease; synthetic compounds that inhibit this enzyme have potential as novel agents to treat this diseases (Patey et al., J. Med. Chem. 2006, 49, 6129-6132; Patey et al., Neurodegener. Dis. 2008, 5, 197-199).

Results and Discussion

Synthetic strategy for modular HS oligosaccharide synthesis. Heparan sulfate consists of 1,4-linked disaccharide units of α-L-iduronic or β-D-glucuronic acid and either N-acetyl or N-sulfo-α-D-glucosamine. The principal positions of O-sulfation are C-2 of iduronate and C-6 of glucosamine, as well as, more rarely, C-3 of glucosamine. Variable substitution during biosynthesis results in the formation of at least twenty different disaccharide motifs. Combining these different disaccharides into larger structures potentially results in enormous structural diversity (Esko et al., Annu Rev. Biochem. 2002, 71, 435-471).

A modular approach that employs a set of properly protected disaccharide building blocks that resemble the different disaccharide motives found in HS, and can easily and repeatedly be used for the preparation of multiple targets, has the potential to provide a library of HS oligosaccharides for structure activity relationship studies. A key issue of such a modular approach is the selection of a set of protecting groups that meet the following requirements: i) the C-2 hydroxyl-protecting groups of the glucuronic or iduronic acid moieties should allow the stereoselective introduction of 1,2-trans-glycosidic linkages, whereas the C-2 amino group of the glucosamine derivatives need to be derivatized in such a way that 1,2-cis-glycosidic linkages can be formed; ii) temporary protecting groups for the anomeric center and C-4 need to be selected for the preparation of glycosyl donors and acceptors; iii) a protecting group is required that can selectively be removed to reveal those hydroxyls that need sulfation; iv) the removal of the permanent protecting groups should be compatible with the presence of base and acid labile sulfate esters; v) the protecting group scheme should be applicable to synthesize each of disaccharide modules found in natural HS; and finally vi) a unified set of chemical conditions is required for the preparation of the various disaccharide modules, oligosaccharide assembly, sulfation and deprotection.

The protecting group strategy that we have developed for the disaccharide modules is summarized in FIG. 1. Thus, levulinoyl esters (Lev; Zhu and Boons, Tetrahedron: Asymmetry 2000, 11, 199-205) will be employed for those hydroxyls that need sulfation. In HS, the C-3 and C-6 of glucosamine and C-2 hydroxyls of hexuronic acid moiety can be sulfated and therefore depending on the sulfation pattern of a targeted disaccharide module, one or more of these positions will be protected as Lev esters. An important feature of the Lev ester is that when present at the C-2' position, it will be able to direct the formation of 1,2-trans-glycosides by neighboring group participation (Boons, Contemp. Org. Synth. 1996, 3, 173-200; Demchenko, Syn Lett 2003, 1225-1240) In case that the C-2' position of a disaccharide module does not need sulfation, an acetyl group is employed as a permanent protecting group. This ester can also perform neighboring group participation but is stable under the conditions used for the removal of Lev esters. An azido group will be used as an amino-masking functionality (Bongat and Demchenko, Carbohydr. Res. 2007, 342, 374-406). This derivative does not perform neighboring group participation and therefore allows the introduction of α-glucosides. An azido-group can easily be reduced to an amine, which can either be acetylated or sulfated. The C-4' hydroxyl, which is required for extension, will be protected as 9-fluorenylmethyl carbonate (Fmoc). The Fmoc group can be removed with Et$_3$N in dichloromethane or DMF without affecting the Lev ester whereas the Lev group can be cleaved with hydrazine buffered with acetic acid and these conditions do not affect the Fmoc carbonate (Zhu and Boons, Tetrahedron: Asymmetry 2000, 11, 199-205). The anomeric center of the disaccharides will be protected as thexyldimethyl silyl (TDS) glycosides and this functionality can easily be removed by treatment with HF in pyridine without affecting the other protecting groups. The resulting lactol can then be converted into a trichloroacetimidate by employing K$_2$CO$_3$ and trichloroacetonitrile in DCM (Prabhu et al., Org. Lett. 2003, 5, 4975-4978). Finally, benzyl ethers are used as permanent protecting groups for the other hydroxyls.

Preparation of modular building blocks. Based on these considerations, the six strategically chosen monosaccharide building blocks 1-6 were prepared, which were employed for the preparation of the eight disaccharide modules 9-16 (FIG. 2). It was observed that installment of an aminopentyl linker at the disaccharide stage led to mixtures of anomers, which were difficult to separate by traditional silica column chromatography and therefore the spacer containing glycosyl acceptors 7 and 8 were employed for the preparation of disaccharide modules 17-24.

Glycosyl acceptors 5-8 could be prepared form readily available lactol 25 (Vasella et al., Helv. Chim. Acta 1991, 74, 2073-2077; Alper et al., Tetrahedron Lett. 1996, 37, 6029-6032) (Scheme 1). Thus, for the preparation of 5 and 6, the anomeric center of 25 was protected as a TDS ether by reaction with TDSC1 in the presence of imidazole in DCM to give 26 in an excellent yield of 90%. The chemical synthesis of compounds 7 and 8 required the installation of an α-anomeric N-(benzyl)benzyloxycarbonyl protected aminopentenyl spacer, which was achieved by conversion of lactol 25 into a trichloroacetimidate 27, which was coupled with N-(benzyl)benzyloxycarbonyl aminopentanol in the presence of TMSOTf in a mixture of dichloromethane and diethyl ether to give 28 as a mixture of anomers (α/β=3/1), which could be separated by silica gel column chromatography to afford the individual anomers. A number of other anomeric spacers were examined and for example, lower yields in subsequent glycosylations was obtained when benzyloxycarbonyl amino propanol was employed. Furthermore, the use of N-(benzyl)benzyloxycarbonyl propanol gave compounds having complex $^1$H-NMR due to E/Z isomerism of the amino-protecting groups (Noti et al., Chem. Eur. J. 2006, 12, 8664-8686). Fortunately, the latter problem could be partially alleviated by employing N-(benzyl)benzyloxycarbonyl protected aminopentanol.

Scheme 1: Synthesis of 2-azido-2-deoxy-α-D-glucopyranoside acceptors

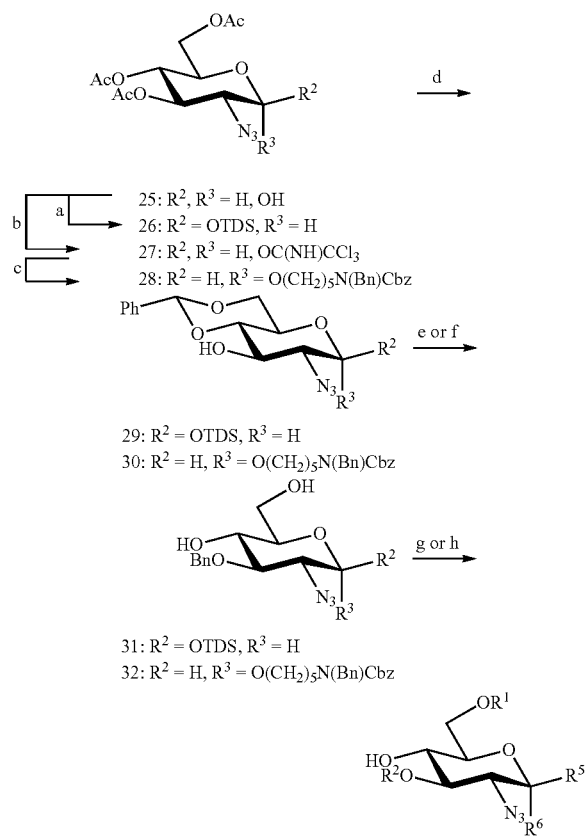

(a) TDSCl, imidazole, DCM (90%); (b) CCl$_3$CN, DBU, DCM (90%); (c) HO(CH$_2$)$_5$N(Bn)Cbz, DCM:Et$_2$O, TMSOTf, molecular sieves, −20° C. (α-anomer, 62%) (d) i) NaOMe, MeOH; ii) PhCH(OMe)$_2$, CSA, DMF (29: 92% and 30: 76%, 2 steps); (e) i) BnBr, Ag$_2$O, molecular sieves, DCM; ii) DCM:TFA:H$_2$O (31: 95%, 2 steps); (f) NaH, BnBr, DMF; ii) DCM:TFA:H$_2$O (32: 93%, 2 steps); (g) AcOH, 2-chloro-1-methyl-1-pyridinium iodide, DABCO, DCM (5: 65%, 7: 68%), (h) LevOH, 2-chloro-1-methyl-1-pyridinium iodide, DABCO, DCM (6: 86%, 8: 82%)

The acetyl esters of 26 and 28 were cleaved by treatment with sodium methoxide in methanol and the 4,6-diol of the resulting compound was protected as a benzylidene acetal by treatment with PhCH(OMe)$_2$ in the presence of a catalytic amount of camphorsulfonic acid in DMF to give 29 and 30, respectively. The C-3 hydroxyl of 29 was benzylated with benzyl bromide in the presence of Ag$_2$O and the benzylidene acetal of the resulting compound was hydrolyzed by treatment with TFA in DCM and water to afford diol 31. The more robust compound 30 was benzylated with benzyl bromide and NaH in DMF and the benzylidene acetal of the resulting compound was removed by TFA in DCM and water to give 32. The C-6 hydroxyl of 31 and 32 were regioselectively protected as an acetyl ester by reaction with acetic acid and the activator 2-chloro-1-methyl-1-pyridinium iodide in the presence of DABCO in DCM to give the target compounds 5 and 7, respectively. Compounds 6 and 8, which have a Lev ester at C-6, were prepared by a similar procedure using levulinic acid instead of acetic acid.

Idosyl donors 1 and 2 were easily prepared by starting from readily available 1,6-anhydro-idose 33 (Scheme 2) (Lee et al., J. Am. Chem. Soc. 2004, 126, 476-477; van Boeckel et al., J. Carbohydr. Chem. 1985, 4, 293-321; Tabeur et al., Carbohydr. Res. 1996, 281, 253-276; Tatai et al., Carbohydr. Res. 2008, 343, 596-606) Thus, the treatment of 33 with acetic anhydride, trifluoroacetic acid and acetic acid followed by treatment with (Lee et al., J. Am. Chem. Soc. 2004, 126, 476-477) with ethanethiol and BF$_3$ Et$_2$O in DCM (Basten et al., Bioorg. Med. Chem. Lett. 1998, 8, 1201-1206) gave thio-idoside 34, which was deacetylated to give a triol, which was protected as 4,6-O-benzyldine acetal to give 35. The C-2 hydroxyl of 35 was protected as an acetyl or Lev ester by reaction with acetic anhydride in pyridine or levulinic acid in the presence of the activator DCC to provide the required idosyl donors 1 and 2. Alternatively, the thioidoside 34 could be obtained by peracetylation of 3-O-benzyl-L-idose (Barroca et al., Carbohydr. Res. 2000, 329, 667-679) followed by treatment with ethanethiol and BF$_3$ Et$_2$O in DCM. Glucosyl donors 3 and 4 were readily obtained by saponification of the acetyl ester of ethyl 2,3,4-tri-O-acetyl thioglucoside using standard conditions followed by selective protection of the 4,6-diol of the resulting compound as a benzylidene acetal by treatment with PhCH(OMe)$_2$ and camphorsulfonic acid in DMF and then regioselective benzylation of the C-3 hydroxyl by first preparing a stannylidene acetal by treatment with dibutyl tin oxide followed by reaction with benzyl bromide in the presence of CsF in DMF to give 36. The intermediate 36 can also be synthesized by a multistep procedure starting with 3-O-benzylation of commercially available 1,2:5,6-Di-O-isopropylidene-α-D-glucofuranose(Orgueira et al., Chem. Eur. J. 2003, 9, 140-169 and Jacquinet et. al., Carbohydr. Res. 1984, 130, 221-241). The latter compound was a convenient starting material for the preparation of glucosyl donors 3 and 4 by protecting of the C-2 hydroxyl as an acetyl- or Lev esters, respectively, using standard conditions.

Scheme 2: Synthesis of thioethyl gluco- and idosyl donor.

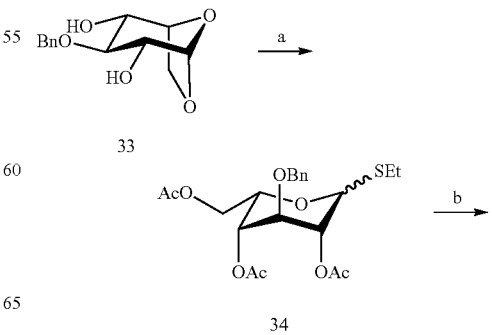

-continued

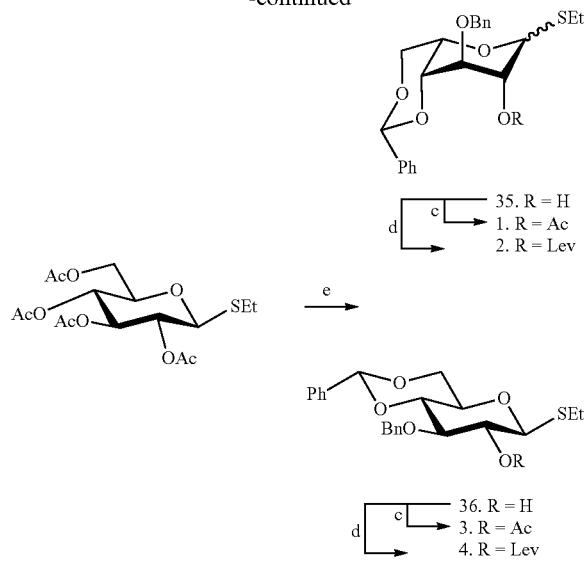

(a) i) AcOH, Ac₂O, TFA, r.t; ii) EtSH, BF₃Et₂O, DCM, 0° C. to room temperature; (b) i) NaOMe, MeOH; ii) PhCH(OMe)₂, CSA, DMF, 70%; (c) Ac₂O, Py, r.t. 85%; (d) LevOH, DCC, DMAP, DCM, 72%; (e) (i) NaOMe, MeOH; ii) PhCH(OMe)₂, p-TsOH, DMF, 61% (2 steps); iii) (Bu₂Sn)O, MeOH, 75-80° C., BnBr, CsF, DMF, 16 hr, r.t, 61%; (c) Ac₂O, Py, 60%: 1: 93%, 3: 85%; (d) LevOH, DCC, DMAP, DCM, r.t.; 2: 89% 4: 70%

Having glycosyl donors 1-4 and acceptors 5-8 in hand, attention was focused on the parallel combinatorial synthesis of a range of disaccharide modules (Scheme 3). Thus, a NIS/TMSOTf mediated coupling (Veeneman et al., Tetrahedron Lett. 1990, 31, 1331-1334) of each of the thioglycosyl donors 1-4 with each the glycosyl acceptors 5 and 6 gave eight different disaccharides (37-40 and 49-52) having either a glucoside or idoside at the non reducing end and a Lev ester at C-6 or C-2' or at both hydroxyls. In each glycosylation, only a 1,2-trans-glycoside was formed due to neighboring group participation by the C-2 acetyl or Lev ester of the glycosyl donors giving the disaccharides in excellent yields ranging from 70%-95%. Next, the disaccharides 37-40 and 49-52 were converted into glycosyl acceptors 41-44 and 53-56 and glycosyl donors 45-48 and 57-60 by a unified set of reaction conditions. Thus, the benzylidene acetals of 37-40 and 49-52 was removed by treatment with p-toluenesulfonic acid in the presence of ethanethiol or by a mixture of TFA, DCM and water to give the corresponding diols, which were oxidized with 2,2,6,6-tetramethyl-1-piperidinyloxy (TEMPO) in the presence of iodobenzene diacetate (BAIB) as the cooxidant (Davis and Flitsch, Tetrahedron Lett. 1993, 34, 1181; DeMico et al., Org. Chem. 1997, 62, 6974-6977; van den Bos et al., Org. Lett. 2004, 6, 2165-2168). The resulting carboxylic acids were protected as methyl esters by treatment with diazomethane to give compounds 41-44 and 53-56 in an overall yield ranging from 65-90%. Interestingly, the use of sodium hypochloride as the co-oxidant in the TEMPO oxidation (Davis and Flitsch, Tetrahedron Lett. 1993, 34, 1181) led to a lower yield of product due to partial oxidation of the secondary hydroxyl. The disaccharides were also the starting material for the preparation of glycosyl donors 45-48 and 57-60 by protection of the C-4' alcohols as an Fmoc carbonate by treatment with FmocCl in pyridine in the presence of DMAP followed by removal of the anomeric TDS with HF in pyridine and installation of the anomeric trichloroacetimidate using trichloroacetonitrile and K₂CO₃ in DCM. The latter reaction conditions did not affect the base labile Fmoc protecting group. Each reaction was high yielding regardless of the chemical composition of the disaccharide. The spacer containing disaccharide acceptors 17-24 (FIG. 2) were prepared by a similar strategy by coupling glycosyl donors 1-4 with glycosyl acceptors 7 and 8 followed by benzylidene acetal removal, selective oxidation of the C-6' hydroxyl of the resulting compound and protection of the resulting carboxylic acid as a methyl ester (for details see Example II).

In principle, parallel combinatorial coupling of the eight glycosyl donors 45-48 and 57-60 with the eight glycosyl acceptors 41-44 and 53-56 (or the corresponding spacer containing acceptors 17-24) will give sixty four different tetrasaccharides. These compounds can easily be converted into glycosyl acceptors by removal of the Fmoc carbonate and each of the resulting compounds can then again be coupled with the eight glycosyl donors to provide five hundred and twelve different hexasaccharides. After the assembly of the oligosaccharides, the azido moieties can be converted into acetamido or N-sulfate derivatives further increasing the structural diversity of synthetic compounds. It may also be possible to obtain additional compounds by converting the azido moiety of the disaccharides into NHAlloc and then employ it in a glycosylation with an azido-containing disaccharide. The Alloc and azido offer a convenient set of orthogonal amino-protecting groups that allow selective modification of each function (Zhang et al., Chem. Eur. J. 2008, 14, 558-569).

Scheme 3. Synthesis of glucuronyl and idouronyl disacchardies.

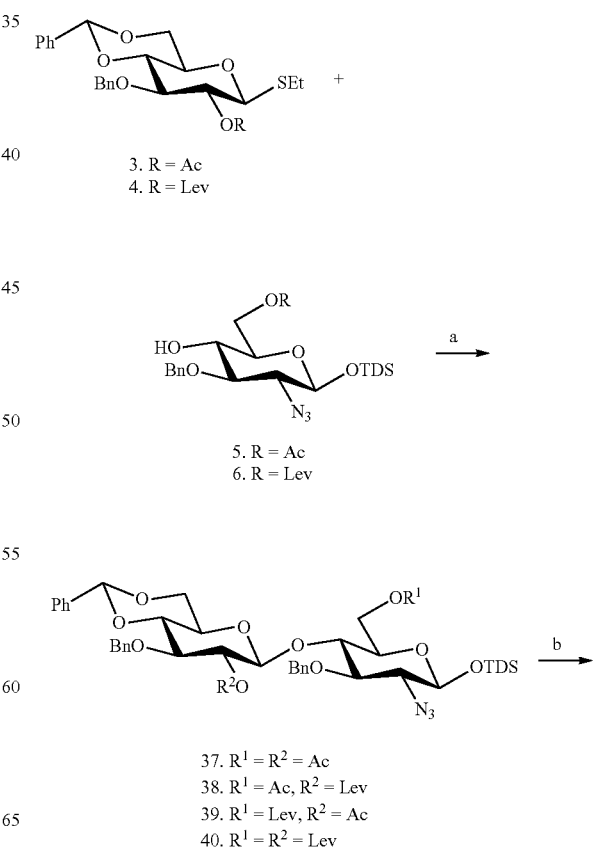

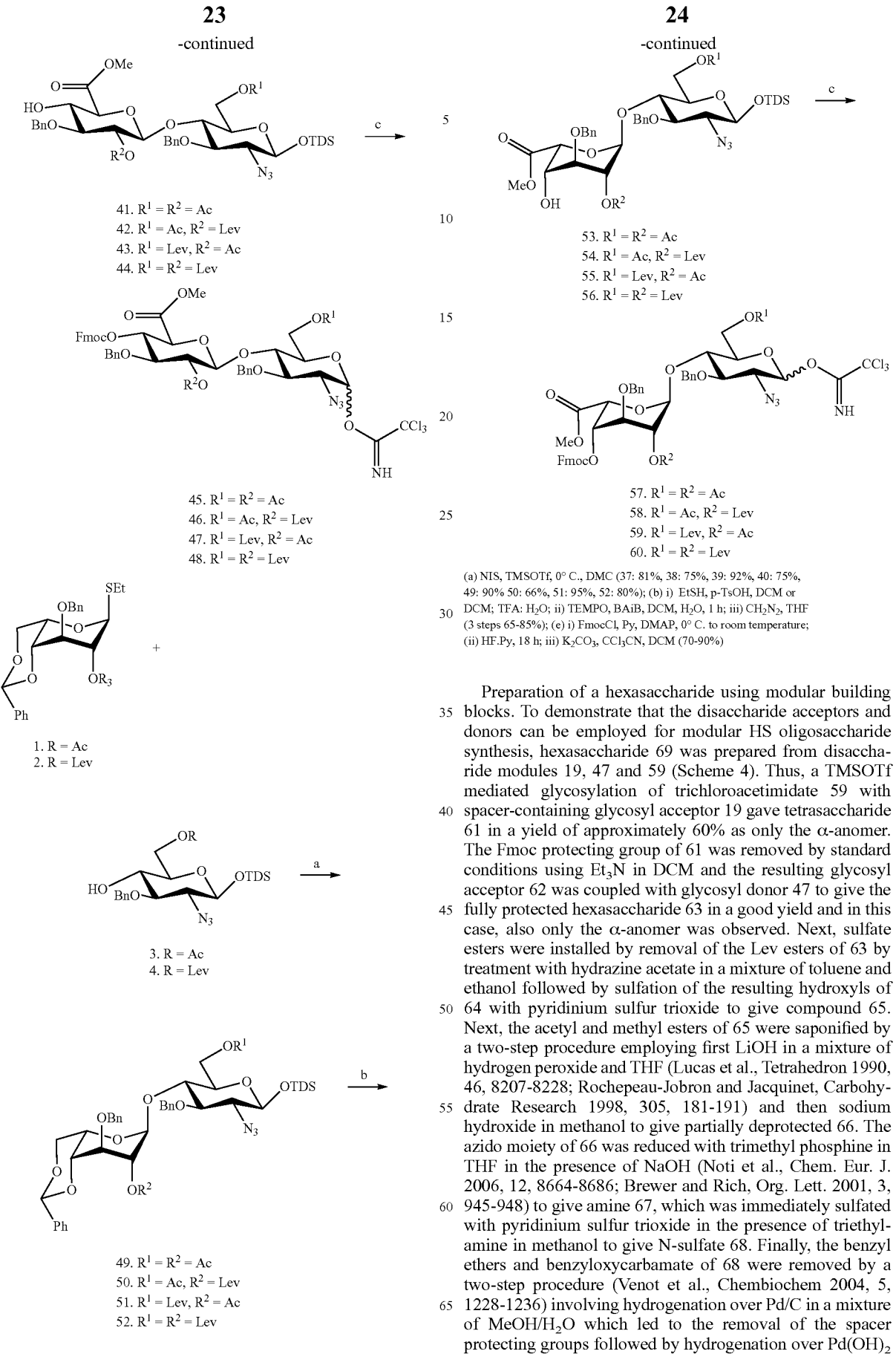

(a) NIS, TMSOTf, 0° C., DMC (37: 81%, 38: 75%, 39: 92%, 40: 75%, 49: 90% 50: 66%, 51: 95%, 52: 80%); (b) i) EtSH, p-TsOH, DCM or DCM; TFA: H₂O; ii) TEMPO, BAiB, DCM, H₂O, 1 h; iii) CH₂N₂, THF (3 steps 65-85%); (e) i) FmocCl, Py, DMAP, 0° C. to room temperature; (ii) HF.Py, 18 h; iii) K₂CO₃, CCl₃CN, DCM (70-90%)

Preparation of a hexasaccharide using modular building blocks. To demonstrate that the disaccharide acceptors and donors can be employed for modular HS oligosaccharide synthesis, hexasaccharide 69 was prepared from disaccharide modules 19, 47 and 59 (Scheme 4). Thus, a TMSOTf mediated glycosylation of trichloroacetimidate 59 with spacer-containing glycosyl acceptor 19 gave tetrasaccharide 61 in a yield of approximately 60% as only the α-anomer. The Fmoc protecting group of 61 was removed by standard conditions using Et₃N in DCM and the resulting glycosyl acceptor 62 was coupled with glycosyl donor 47 to give the fully protected hexasaccharide 63 in a good yield and in this case, also only the α-anomer was observed. Next, sulfate esters were installed by removal of the Lev esters of 63 by treatment with hydrazine acetate in a mixture of toluene and ethanol followed by sulfation of the resulting hydroxyls of 64 with pyridinium sulfur trioxide to give compound 65. Next, the acetyl and methyl esters of 65 were saponified by a two-step procedure employing first LiOH in a mixture of hydrogen peroxide and THF (Lucas et al., Tetrahedron 1990, 46, 8207-8228; Rochepeau-Jobron and Jacquinet, Carbohydrate Research 1998, 305, 181-191) and then sodium hydroxide in methanol to give partially deprotected 66. The azido moiety of 66 was reduced with trimethyl phosphine in THF in the presence of NaOH (Noti et al., Chem. Eur. J. 2006, 12, 8664-8686; Brewer and Rich, Org. Lett. 2001, 3, 945-948) to give amine 67, which was immediately sulfated with pyridinium sulfur trioxide in the presence of triethylamine in methanol to give N-sulfate 68. Finally, the benzyl ethers and benzyloxycarbamate of 68 were removed by a two-step procedure (Venot et al., Chembiochem 2004, 5, 1228-1236) involving hydrogenation over Pd/C in a mixture of MeOH/H₂O which led to the removal of the spacer protecting groups followed by hydrogenation over Pd(OH)₂ which led to the removal of the benzyl ethers to give HS oligosaccharides 69. Interestingly, a one step hydrogenation procedure proceeded very sluggishly and did not provide the target compound.

The $^1$H NMR spectra of the oligosaccharides were fully assigned by 1D and 2D NMR spectroscopy. The α-anomeric configuration of 2-azido-glucosides was confirmed by $J_{1,2}$ coupling constants and by $^{13}$C chemical shifts of C-1 (~97 ppm). Furthermore, a downfield shifts of 0.5 ppm of H-6 was observed for 0-sulfation of C-6 hydroxyls and 0.4 ppm of H-2 for N-sulfation.

Synthesis of a library of HS-oligosaccharides to probe inhibition of BACE-1.

Alzheimer's disease is a progressive neurodegenerative disorder of the central nervous system that is characterized by the formation of β-amyloid peptides, which accumulate as perivascular or parenchymal deposits in brains. Cleavage of amyloid precursor protein (APP) by the aspartyl protease beta-site APP-cleaving enzyme 1 (BACE-1) generates a membrane-bound protein, which is further processed by the γ-secretase enzyme complex to generate the neurotoxic amyloid β-peptide. Selective inhibition of β-amyloid peptide formation could potentially slow or even reverse the devastating consequences of the disease (Golde, J. Clin. Invest. 2003, 111, 11-18). Indeed, experimental data from transgenic mouse models of Alzheimer's disease, BACE-1 knockout mice and pharmacological studies corroborate the potential usefulness of drugs that interfere with BACE-1 expression and/or enzymatic activity for the treatment of Alzheimer's disease (Chang et al., J. Neurochem. 2004, 89, 1409-1416; Asai et al., J. Neurochem. 2006, 96, 533-540).

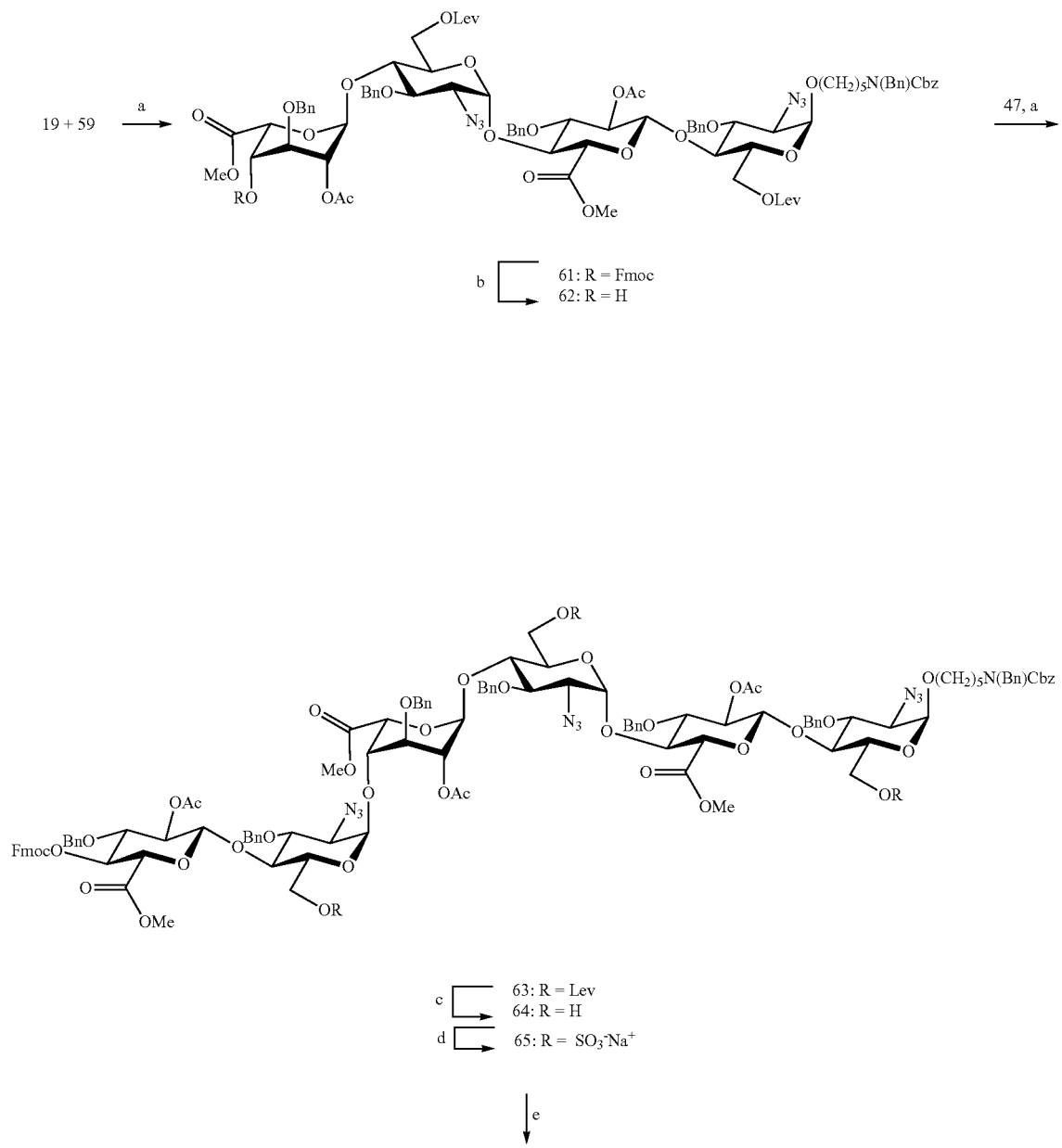

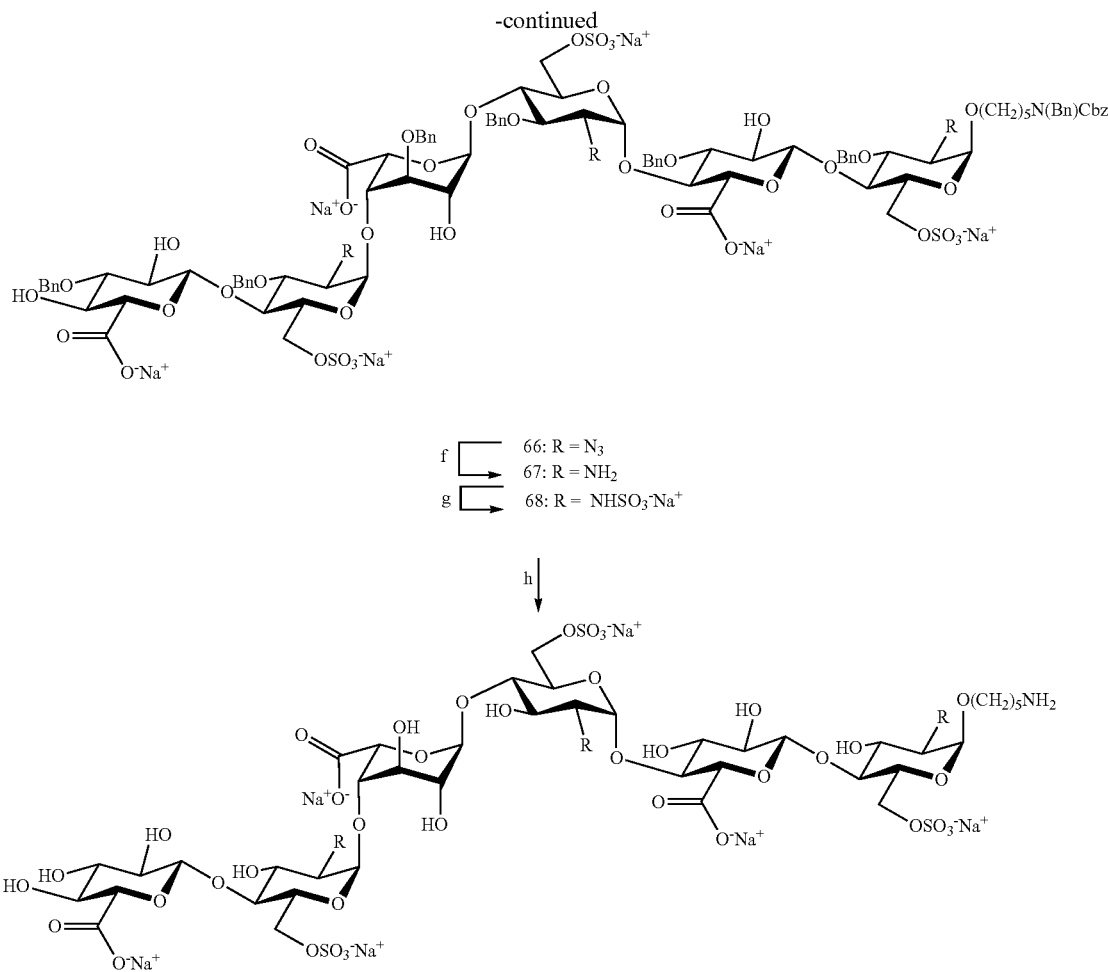

69: R = NHSO₃⁻Na⁺

(a) Synthesis of hexasaccharide 69: (a) TMSOTf, -20° C. to +5° C., 4° A sieves, 61: 64%; 63: 65%:
(b) Et₃N, DCM, 82%; (c) NH₂NH₂.HOAc, toluene/EtOH, 90%; (d) Py.SO₃, DMF, 80%; (e) i) Et₃N, DMF; ii) LiOH, H₂O₂, THF; ii) 4M NaOH, MeOH (58%, 3 steps), 80%; (f) PMe₃, THF, NaOH, 65%; (g) N-sulfation: Py.SO₃, MeOH, Et₃N, 0.1 M NaOH, 50%; (i) i) Pd/C, H₂, MeOH:H₂O; ii) Pd(OH)₂/C, H₂, H₂O, 67%

Heparan sulfate, which is a constituent of amyloid plaques, can interact with amyloid proteins, peptides, and fibrils, promote aggregation, and enhance the stability of fibrils. Soluble heparin and heparin analogues have been shown to inhibit these processes both in vitro and in vivo. Recently, however, it was shown that HS can inhibit the proteolytic activity of BACE-1; the putative mechanism is by blocking access to the enzyme active site, without interfering with APP processing by α- or γ-secretases (Scholefield et al., J. Cell Biol. 2003, 163, 97-107). Systematic modification of porcine intestinal mucosal heparin was used to demonstrate a critical importance of 6-O-sulfates for inhibition of BACE-1 (Patey et al., J. Med. Chem. 2006, 49, 6129-6132). Furthermore, replacement of N-sulfate groups by acetamido moieties slightly impairs activity (Patey et al., J. Med. Chem. 2006, 49, 6129-6132; Patey et al., Neurodegener. Dis. 2008, 5, 197-199) and derivatives containing N-acetyl and 2-O— and 6-O-sulfates had the highest anti-BACE-1 to anti-Xa activity ratio (Patey et al., J. Med. Chem. 2006, 49, 6129-6132), demonstrating opportunities for optimizing therapeutic activities.

To probe the requirement of HS oligosaccharides for inhibition of BACE-1, a library of twelve tetrasaccharides (76-85, FIG. 3) was prepared employing the disaccharide modules. Thus, tetrasaccharides 76-83, which contain C-6 sulfate esters but differ in the modification of the C-2 amino groups and the presence of glucuronic acid or idouronic acid moieties, were prepared. These compounds should reveal the importance of nature of the uronic acid moiety and the presence of an acetamido or N-sulfate group, for inhibitory activity. Furthermore, compounds 84 and 85 are derived from 80 and 78, respectively but have an additional sulfate ester at C-2 of an iduronic acid moiety.

The target HS fragments could easily be prepared by employing the disaccharide modules 19, 23, 24, 47 and 59 combined with the sulfation and deprotection protocols described for the preparation of hexasaccharide 69. Thus, standard TMSOTf mediated glycosylation of glycosyl donors 19, 23 and 24 with glycosyl acceptor 47 and 59 in DCM gave the tetrasaccharides 70-75 in yields of approximately 60%, and fortunately in each case only the α-anomer was obtained (Scheme 5). Our preliminary studies had indicated that 2-deoxy-2-azido-glucopyranosyl trichloroacetimidates give excellent α-anomeric selectivities when modified with an acyl-protecting group at C-6 and employed in glycosylations with glycosyl acceptors of relatively low reactivity. This observation may be due to remote neighboring group participation of the C-6 ester (Demchenko et al., Tetrahedron Lett. 1999, 40, 6523-6526; Crich et al., Org. Chem. 2008, 73, 8942-8953). O-sulfation, deprotection and N-acetylation or N-sulfation was performed by standard procedures to give the target tetrasaccharides 76-86.
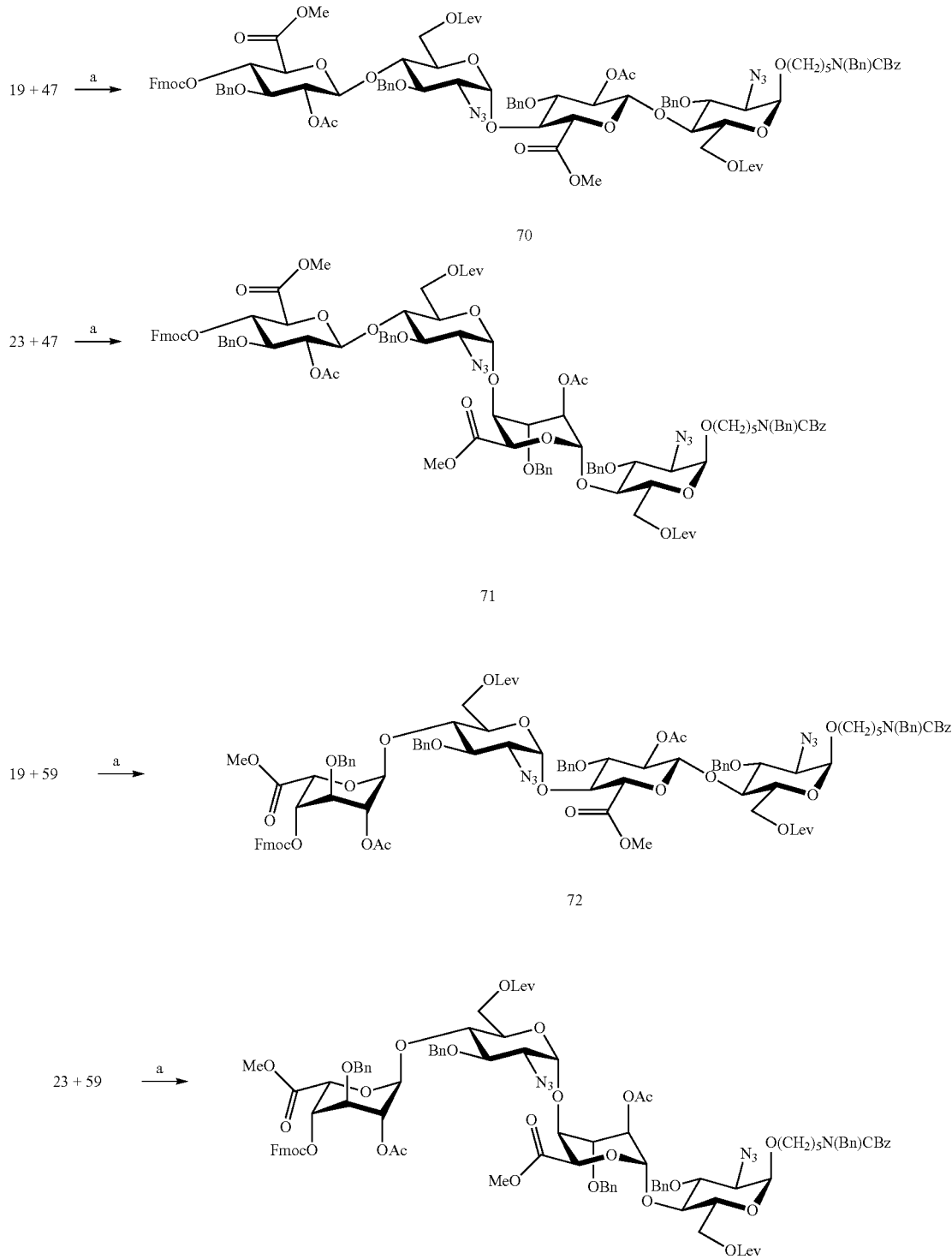

-continued

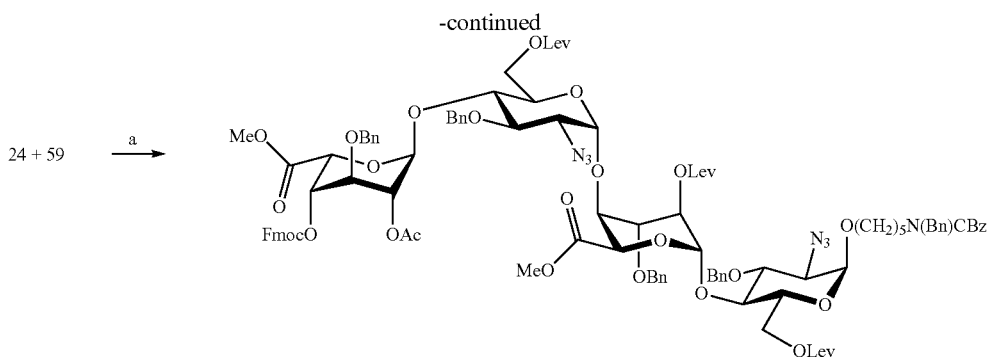

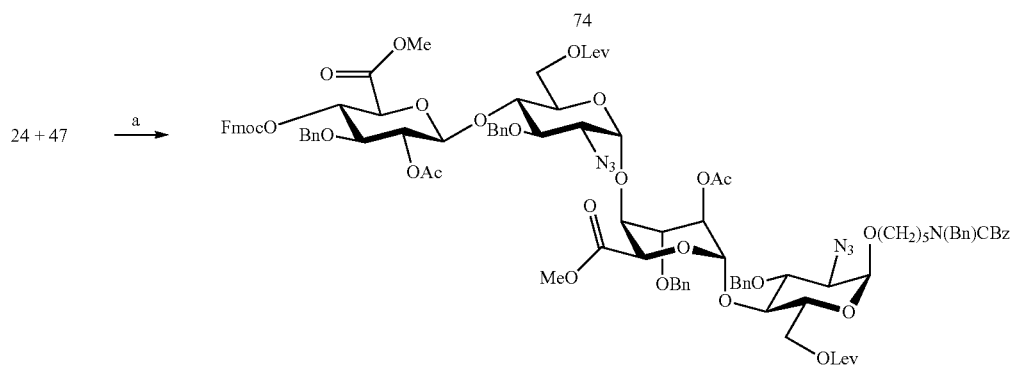

(a) Synthesis of library of tetrasaccharides. (a) TMSOTf, DCM, -20° C. to 5° C., molecular sieves (70: 61%, 71: 62%, 72: 64%, 73: 62%, 74: 51%, 75: 59%)

The ability of the HS oligosaccharides to inhibit BACE-1 cleavage of APP was assessed using a fluorescent resonance energy transfer (FRET) peptide cleavage assay employing the Swedish amino acid variant FRET peptide 5-FAM-Glu-Val-Asn-Leu-Asp-Ala-Phe-Lys(QXL520)-OH. When intact, the amino terminal fluorophore is quenched, but upon enzymatic cleavage, it is released from quencher and fluoresces at 520 nm.

TABLE 1

Inhibitory activities of synthetic compounds and heparin for cleavage of FRET peptide by BACE-1

| HS | $IC_{50}$ (µg/ml) | $IC_{50}$ (µmol) |
|---|---|---|
| heparin | 0.02 | — |
| 76 | 39 | 35 |
| 77 | 97 | 78 |
| 78 | >300 | — |
| 79 | 240 | 195 |
| 80 | 104 | 94 |
| 81 | 290 | 236 |
| 82 | 35 | 32 |
| 83 | 4.6 | 3.7 |
| 84 | >300 | — |
| 85 | 167 | 138 |
| 86 | >300 | — |
| 69 | 64 | 36 |

Figure 4:
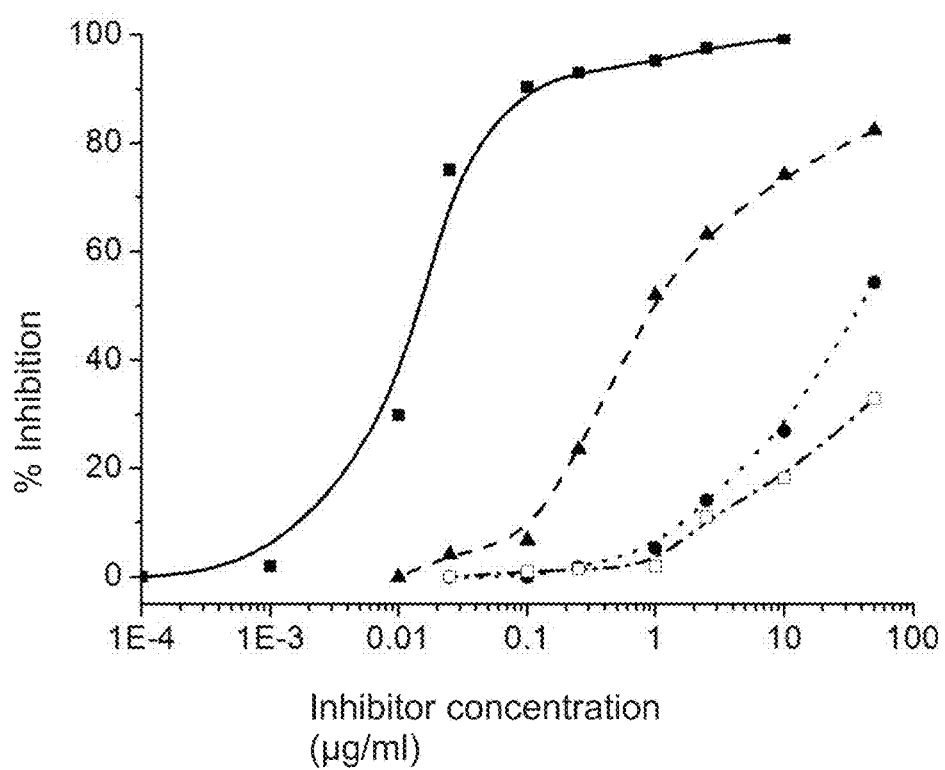
FIG. 4 shows dose response inhibition curves for selected compounds compared to porcine mucosal heparin in the FRET peptide cleavage assay (solid squares, heparin; triangles, compound 83; circles, compound 77 and open squares, compound 81).

As can be seen in Table 1 and FIG. 4, HS-oligosaccharide 83 was able to inhibit the cleavage of the peptide by BACE-1 with relatively high potency. Several derivatives such as 76, 77 and 82 displayed modest activity whereas compounds 78, 79, 81, 84, and 86 had low- or no inhibitory activity. Compound 83 is a tetrasaccharide composed of two iduronic acid moieties that are sulfated at the C-6 hydroxyls and two glucosamine moieties modified by N-sulfates. Interestingly, compound 82, which has acetamido moieties instead of N-sulfates, has 10-fold reduced potency highlighting the importance of the N-sulfates of 83 for optimal inhibitory activity. Replacement of one of the iduronic acid moieties by a glucuronic acid derivative, as in compounds 79 and 81, led to a large reduction in inhibitory activity. Surprisingly compounds 76 and 77, which contain two glucuronic acid moieties, displayed reasonable activity and in this case, HS oligosaccharide 76 having acetamido moieties was somewhat more active than compound 77 modified by N-sulfates. Previous studies have indicated that the binding cleft of BACE-1 can accommodate relatively large HS oligosaccharides (Patey et al., J. Med. Chem. 2006, 49, 6129-6132), and thus it is conceivable that derivatives 76/77 and 82/83 bind in different regions of the cleft explaining the difference in structure-activity-relationship. Finally, a sulfate ester at C-2 of an uronic acid moiety, as in compound 84-86, had low- or no inhibitory activity.

The synthetic HS-oligosaccharides are less active than full-length HS polysaccharide, which was expected because previous observations with natural oligosaccharides suggest that the binding site of BACE-1 can accommodate relatively large HS-oligosaccharides (Patey et al., J. Med. Chem. 2006, 49, 6129-6132). However, the fact that a tetrasaccharide displayed considerable inhibitory activity indicates that a library of such compounds is appropriate for identifying lead compounds, which provide an attractive starting point for the synthesis of a focused library of larger oligosaccharides. The attraction of such an approach is that the preparation of a representative library of tetrasaccharides is an achievable task whereas preparation of a library of larger HS-oligosaccharides remains a considerable challenge.

Conclusions

The modular synthetic approach reported here utilizes a relatively small number of selectively protected disaccharide building blocks that can easily be converted into glycosyl donors and acceptors, which in turn can be employed for the convenient preparation of libraries of well-defined HS oligosaccharides. Such a collection of compounds can be employed for structure activity relationship studies for HS binding proteins. Key features of the approach include the use of Lev esters for those hydroxyls that need sulfation, an Fmoc carbonate as a temporary protecting group for the C-4' hydroxyl for the preparation of glycosyl acceptors, an anomeric TDS group for glycosyl donor synthesis and acetyl esters and benzyl ethers as permanent protecting groups. Trichloroacetimidate methodology (Schmidt and Kinzy, Adv. Carbohydr. Chem. Biochem. 1994, 50, 21-123) was employed for reliable oligosaccharide assembly and in each glycosylation only the required α-anomer was obtained. Furthermore, it was found that installation of the uronic acid moieties could best be performed at the disaccharide stage by selective TEMPO/BIAB mediated oxidation of the C-6 hydroxyl of a glucoside or idoside to the corresponding carboxylic acid. The utility of the modular building blocks has been illustrated by the preparation of a library of twelve oligosaccharides and importantly, a standard set of reaction conditions could be employed for the preparation of all target compounds. The HS oligosaccharides were employed to probe structural features of HS for inhibition of the protease, BACE-1. The significant and complex variations in activity with structural changes observed in this study support the view that important functional information is embedded in HS sequences (Kreuger et al, J. Cell Biol. 2006, 174, 323-327; Guimond and Turnbull, Curr. Biol. 1999, 9, 1343-1346). Furthermore, the most active derivative identified in this study provides an attractive lead compound for the preparation more potent compounds for BACE-1, which may find use as a therapeutic agent for Alzheimer's disease. The synthetic compounds are also equipped with an artificial aminopentyl spacer, which offers an opportunity for HS-oligosaccharide array development. Such an array is expected to provide a unique tool for rapid ligand identification for HS-binding proteins.

Experimental Section

General Glycosylation Procedure for Synthesis of Disaccharides (37-40, 49-52):

Glycosyl thioethyl donor (1.2 equiv based on acceptor) and 2-azido-2-deoxy-α-D-glucopyranoside acceptor (1.0 equiv) were combined in a flask, co-evaporated with toluene (3×3 mL) and dissolved in DCM to maintain a concentration of 0.02 M (based on donor). Powdered freshly activated 4 Å molecular sieves (weight of sieves equal to the combined weight of donor and acceptor) were added and the mixture was stirred for 30 min at ambient temperature and then cooled to 0° C. NIS (1.2 equiv) and TMSOTf (0.1 equiv) were added to the mixture and stirring was continued until TLC indicated disappearance of glycosyl donor (~15 min). The reaction mixture was allowed to warm to +5° C. and then quenched by the addition of DTBMP. The mixture was filtered, the filtrate was concentrated in vacuo and the residue was purified by silica gel column chromatography using a stepwise gradient of toluene and EtOAc (90/10→65/35, v/v).

General procedure for benzylidene acetal cleavage of disaccharides: Method A. To a solution of disaccharide (37, 49) in DCM was added ethanethiol (6 equiv) and p-TsOH (0.2 equiv) and the resulting solution was stirred at ambient temperature for 1 h. The reaction mixture was quenched by the addition of $Et_3N$ and concentrated in vacuo and the residue was purified by silica gel column chromatography to give pure product. Method B. A solution of a disaccharide (38-40, 50-52) in a mixture of DCM:TFA:$H_2O$ (0.06 M, 10/1/0.1, v/v/v) was stirred at ambient temperature for 30 min. The reaction mixture was concentrated in vacuo and the residue co-evaporated with toluene. The residue was purified by silica gel column chromatography using a mixture of toluene and EtOAc to give pure product.

General procedure for TEMPO/BAIB mediated oxidation and esterification by diazomethane (41-44, 53-56): To a vigorously stirred solution of the diol (0.3 M solution) in a mixture of DCM: $H_2O$ (2/1, v/v) was added TEMPO (0.2 equiv) and BAIB (2.5 equiv). Stirring was continued until TLC indicated complete conversion of the starting material to a spot of lower $R_f$ (~45 min). The reaction mixture was quenched by the addition of aqueous $Na_2S_2O_3$ (10%, 10 mL). The mixture was extracted with EtOAc (2×10 mL) and the combined aqueous layers were back-extracted with EtOAc (10 mL). The combined organic layers were dried ($MgSO_4$), filtered and the filtrate was concentrated in vacuo. The oily residue was dissolved in THF (0.1 M) and treated with an excess of freshly prepared ethereal solution of diazomethane until the reaction mixture stayed yellow. The excess diazomethane was quenched by the addition of AcOH until the reaction mixture became colorless. The mixture was concentrated in vacuo, co-evaporated with toluene and the residue was purified by silica gel column chromatography to yield a methyl ester.

General procedure for synthesis of Fmoc protected disaccharides: To a 0.03 M solution of disaccharide in DCM at 0° C. was added FmocCl (10 equiv) and DMAP (0.01 equiv). The reaction mixture was brought to room temperature and stirring was continued until TLC indicated complete consumption of the starting material (~2 h). After quenching the reaction with MeOH (50 μL), the mixture was diluted with DCM (50 mL), washed with saturated aqueous sodium bicarbonate (2×50 mL), brine (50 mL). The organic phase was dried ($MgSO_4$) filtered and the filtrate concentrated in vacuo. The residue was chromatographed over silica gel using a gradient of hexanes and EtOAc to give Fmoc carbonate protected disaccharide.

General procedure for silyl ether cleavage: A disaccharide was dissolved in THF (0.05 M) followed by the addition of HF.pyridine (100 equiv). After stirring for 18 h, the reaction mixture was diluted with DCM (50 mL), and washed with water (50 mL), saturated aqueous sodium bicarbonate (50 mL), and brine (50 mL). The organic phase was dried ($MgSO_4$), filtered and the filtrate concentrated in vacuo. The residue was chromatographed over silica gel using a gradient of hexanes and EtOAc to give pure lactol.

General procedure for preparation of trichloroacetimidates (45-48, 57-60): To a solution of the lactol in DCM (2 mL for 0.08 mmol) was added finely powdered anhydrous $K_2CO_3$ (2 equiv). After stirring at room temperature for 1.5 h, the reaction mixture was filtered and the filtrate concentrated in vacuo. The residue was chromatographed over silica gel using a mixture of hexanes and EtOAc containing 0.01% pyridine to yield a trichloroacetimidate donor.

General procedure for preparation of tetrasaccharides (70-75): Disaccharide trichloroacetimidate donor (1.2 eq based on acceptor) and disaccharide acceptor (1.0 eq) were combined in a flask, co-evaporated with toluene (3×3 mL) and dissolved in DCM to maintain a concentration of (0.04-0.05 M). Powdered freshly activated 4 Å molecular sieves (weight of sieves equal to the combined weight of donor and acceptor) were added and the mixture was stirred for 30 min at ambient temperature and then cooled to −20° C. TMSOTf (0.1 equiv) was added and stirring was continued until TLC indicated the disappearance of donor (~15 min). The reaction was allowed to warm to +5° C. and then quenched by the addition of pyridine (5 µL) after 1 hour. The mixture was filtered, the filtrate was concentrated in vacuo and the residue was purified by silica gel column chromatography using a gradient of toluene and EtOAc to give pure tetrasaccharide.

General procedure for Fmoc cleavage of tetrasaccharide: A tetrasaccharide was dissolved in a mixture of DCM (2.4 mL for 0.12 mmol) and triethylamine (0.6 mL). After stirring for 2 h, the reaction mixture was concentrated in vacuo and the residue was purified by silica gel column chromatography using a gradient of hexanes and EtOAc to afford a tetrasaccaharide acceptor.

General procedure for cleavage of Lev esters: Anhydrous hydrazine acetate (5 equiv per Lev group) was added to a solution of the starting material in a mixture of ethanol and toluene (2/1, v/v, 5 mL for 150 mg). Stirring was continued until TLC analysis (toluene/EtOAc 1/1, v/v or hexanes/EtOAc 1/1, v/v) indicated disappearance of starting material (~2 h). The reaction mixture was diluted with DCM (30 mL), washed with water (3×25 mL), brine (25 mL), dried ($MgSO_4$) and filtered. The filtrate was concentrated and the residue was purified by silica gel column chromatography using a gradient of hexanes or toluene and EtOAc to afford product.

General procedure for O-sulfation: Sulfur trioxide pyridine complex (10 equiv per OH) was added to a solution of the starting material in DMF (1.0 mL for 0.02 mmol). The mixture was stirred at ambient temperature for 2-4 h until TLC ($CHCl_3$, $CH_3OH$ 90/10, v/v) indicated completion of the reaction. After the addition of pyridine (0.2 mL) and $CH_3OH$ (0.5 mL) stirring was continued for 30 min. The mixture was concentrated in vacuo (bath temperature 20° C.) and the residue was applied to a column of Iatrobeads (1.5 g), which was eluted with a gradient of $CH_3OH$ in $CHCl_3$ (96/4→88/12 v/v, containing 0.2% pyridine). The fractions containing product were concentrated in vacuo (bath temperature 20° C.) and the residue was immediately passed through a column of Biorad 50×8 $Na^+$resin (0.6×5 cm) using $CH_3OH$ as eluent providing the product as sodium salt.

General Procedure for Fmoc Cleavage:

$Et_3N$ (0.1 mL) was added to a solution of the starting material in DMF (1.0 mL for 0.02 mmol). The reaction mixture was stirred for ~1.5 hrs until TLC ($CHCl_3/CH_3OH$, 85/15, v/v) indicated disappearance of starting material. The reaction mixture was concentrated in vacuo (bath temperature 20° C.), and the residue was passed through a column of Biorad 50×8 $Na^+$resin (0.6×5 cm) using $CH_3OH$ as eluent. Fractions containing product were concentrated in vacuo and the residue chromatographed over Iatrobeads (1.2 g) using a gradient of $CH_3OH$ in $CHCl_3$ (94/5→88/12, v/v) as eluent. Appropriate fractions were concentrated in vacuo providing product, which was directly used in the next step.

General procedure for saponification of methyl esters and de-O-acetylation: A premixed solution of 30% solution of $H_2O_2$ in water (100 equiv per $CO_2Me$) and 1M LiOH (50 equiv per $CO_2Me$) were added to a solution of the starting material in THF (0.02 M). The reaction mixture was stirred at room temperature for 8 h. A 4N solution of NaOH (1.0 mL) was added until pH 14. The reaction mixture was left stirring for 18 h at room temperature. In the case that the reaction had not gone to completion, stirring was continued at 35° C. for an additional 12 h. The mixture was then brought to pH 8-8.5 by addition of AcOH and the mixture was concentrated in vacuo (bath temperature 20° C.). The residue was vortexed with water and applied to a RP-18 column (10 times the weight of starting material), which was eluted with a stepwise gradient of $H_2O$ and $CH_3OH$ (from 90/10→70/30, v/v). The appropriate fractions were concentrated in vacuo (bath temperature 20° C.) and the residue was passed through a column of Biorad 50×8 $Na^+$resin (0.6×5 cm) using $CH_3OH$ as eluent providing product.

General procedure for reduction of azide group: A 1M solution of $PMe_3$ in THF (8 equiv per azide group)) was added to the solution of the starting material in THF (1.0 mL for 0.013 mmol). 0.1 M NaOH (10 equiv per azido group) was added and the mixture was stirred at room temperature for 5 h. The progress of the reaction was monitored by TLC ($CHCl_3/CH_3OH/H_2O$ 70/30/5, v/v/v and RP-18 plates with $H_2O/CH_3OH$ 40/60, v/v). The presence of amino groups was confirmed using ninhydrin as visualizing agent (In some cases, an additional amount of $PMe_3$ solution was added to achieve completion of the reaction). The pH was then adjusted to 8.5 by careful addition of AcOH and the mixture concentrated in vacuo (bath temperature 20° C.). The residue was vortexed with water and applied to a small RP-18 silica gel column (10 times the weight of starting material), which was eluted with a stepwise gradient of $H_2O$ and $CH_3OH$ (from 90/10→40/60, v/v). The appropriate fractions were concentrated in vacuo and the residue was passed through a column Biorad 50×8 $Na^+$resin (0.6×5 cm) using $CH_3OH$ as eluent providing product.

General procedure for selective N-acetylation: Acetic anhydride (10 equiv per $NH_2$) was added to a solution of the starting material in a mixture of anhydrous $CH_3OH$ (500 µL for 0.011 mmol) and $Et_3N$ (20 equiv per $NH_2$) at 0° C. The progress of the reaction was monitored by TLC (silica gel: $CHCl_3/CH_3OH/H_2O$, 60/30/3, v/v/v, and RP18 silica gel: $H_2O/CH_3OH$, 40/60, v/v). After 5 h, another portion of $Et_3N$ and $Ac_2O$ was added at 0° C. After stirring for 1 h at room temperature, the mixture was co-evaporated with toluene in vacuo (bath temperature 20° C.), and the residue passed through a short column of Biorad 50×8 $Na^+$resin (0.6×5 cm) using a mixture of $CH_3OH$ and $H_2O$ (90/10, v/v) as eluent and appropriate fractions were concentrated in vacuo. The residue was vortexed with water and applied to small RP-18 column (20 times the weight of starting material), which was eluted with a stepwise gradient of $H_2O$ and $CH_3OH$ (from 90/10→40/60, v/v). The appropriate fractions were concentrated in vacuo to obtain N-acetylated product.

General procedure for selective N-sulfation: $SO_3 \cdot Py$ (5 equiv per $NH_2$) was added to the starting material in $CH_3OH$ (lmL for 0.006 mmol) in a mixture of triethylamine (0.3 mL) and 0.1M NaOH (2 equiv per $NH_2$) at 0° C. The progress of the reaction was monitored by TLC (silica gel TLC: EtOAc/pyridine/water/$CH_3CO_2H$, 8/5/3/1, v/v/v/v and RP-18 TLC: $H_2O/CH_3OH$, 60/40, v/v). Two additional portions of $SO_3 \cdot Py$ were added at 0° C. after 1 h and 2 h. After stirring for an additional 8 h, the reaction mixture was co-evaporated with water (bath temperature 20° C.) and the residue passed through a short column of Biorad 50×8 $Na^+$resin (0.6×5 cm) using $CH_3OH$ and $H_2O$ (90/10, v/v) as eluent. Appropriate fractions were concentrated in vacuo and the residue was vortexed with water and applied to small RP-18 silica gel column (20 times the weight of starting material), which was then eluted with a stepwise gradient of H₂O and CH₃OH (90/10→40/60, v/v). The appropriate fractions were concentrated in vacuo to provide N-sulfated product.

General procedure for global debenzylation: Pd/C (10%, 1.5 time the weight of starting material) was added to a solution of the starting material in CH₃OH and H₂O (1/1, v/v, 1 mL for 5 mg). The mixture was placed under an atmosphere of hydrogen and the progress of the reaction monitored by TLC (silica gel, CHCl₃/CH₃OH/H₂O 60/40/10, v/v/v and EtOAc/pyridine/water/CH₃CO₂H, 3/5/3/1, v/v/v). The hydrogenation was stopped when TLC indicated the disappearance of the starting material and the presence of a ninhydrin positive-main spot (2 h). The mixture was filtered through a PTFE syringe filter (0.2 mm, 13 mm) and washed with mixture of CH₃OH and H₂O (1/1, v/v, 2 mL) and the solvents were concentrated in vacuo. The residue was dissolved in distilled water (1.5 mL) and palladium hydroxide on carbon (Degussa type, 20%, 1.5 times the weight of starting material) added. The resulting mixture was placed under an atmosphere of hydrogen and after 12 h, TLC (EtOAc/pyridine/water/CH₃CO₂H 4/5/3/1, v/v/v/v) indicated the completion of the reaction. The mixture was filtered through a PTFE syringe filter and the residue was washed with H₂O (2 mL). The filtrate was freeze-dried and the residue was passed through a short column of Biorad 50×8 Na⁺resin (0.6×2.5 cm) using H₂O as the eluent and the appropriate fractions were freeze dried to provide the final product.

5-aminopentyl [(β-D-glucopyranosyluronate)-(1→4)-(2-deoxy-2-sulfoamino-6-O-sulfonato-α-D-glucopyranoside)-(1→4)-O-(α-L-idopyranosyluronate)-(1→4)-O-(2-deoxy-2-sulfoamino-6-O-sulfanate-α-D-glucopyranoside)-(1→4)-(β-D-glucopyranosyluronate)]-(1→4)-O-2-deoxy-N-sulfoamino-6-O-sulfonate-α-D-glucopyranoside nonasodium salt (69)

Hexasaccharide 63 (73.5 mg, 0.028 mmol) was subjected to the sequence of deprotection steps including delevulinoylation, O-sulfation, Fmoc cleavage, saponification, deacetylation, azide reduction, N-sulfation and global debenzylation according to the general procedures to provide hexasaccharide 69 (4.8 mg).

[α]$_D^{25}$: +126.4 (c=0.33, H₂O): ¹H NMR (800 MHz, D₂O): d 5.58 (d, 1H, J=3.7 Hz, H1$^C$), 5.33 (d, 1H, J=3.6 Hz, H1$^E$), 5.13 (d, 1H, J=3.6 Hz, H1$^A$), 4.99 (bs, 1H, H1$^E$), 4.80 (d, 1H, J=2.17 Hz, H5$^D$), 4.59 (s, 1H, J=8.0 Hz, H1$^F$), 4.58 (s, 1H, J=8.0 Hz, H1$^B$), 4.46 (bd, 1H, J=9.7 Hz, H6a$^E$), 4.41 (bd, 1H, J=9.6 Hz, H6a$^A$), 4.31 (bd, 1H, J=10.4 Hz, H6a$^C$), 4.25 (dd, 1H, J=6.0 Hz, J=11.1 Hz, H6b$^A$), 4.17 (m, 2H, H6b$^E$, H6b$^C$), 4.10 (t, 1H, J=3.6 Hz, H3$^D$), 4.04-4.01 (m, 3H, H4$^D$, H5$^A$, H5$^E$), 3.97 (bd, 1H, J=10.04 Hz, H5$^C$), 3.84 (t, 1H, J=9.1 Hz, H3$^B$), 3.80-3.65 (m, 10H, H5$^B$, H5$^F$, H4$^E$, H2$^D$, H4$^B$, H3$^A$, OCHH Linker, H4$^C$, H3$^E$, H4$^A$), 3.62 (t, 1H, J=9.7 Hz, H3$^C$), 3.56-3.56-3.47 (m, 3H, OCHHLinker, H3$^F$, H4$^F$), 3.36 (t, 1H, J=8.6 Hz, H2$^B$), 3.32 (t, 1H, J=8.5 Hz, H2$^F$), 3.27 (dd, 1H, J=3.6 Hz, J=10.2 Hz, H2$^A$), 3.26 (dd, 1H, J=3.6 Hz, J=10.0 Hz, H2$^C$), 3.24 (dd, 1H, J=3.6 Hz, J=10.5 Hz, H2$^E$) 3.0 (m, 2H, CH₂N Linker), 1.72-1.62 (m, 4H, 2×CH₂ Linker), 1.52-1.45 (m, 2H, CH₂ Linker). ESI-MS: m/z: calcd. for C₄₁H₆₈N₄O₄₉S₆: 796.0644, found: 796.0634 [M−2H]²⁻; calcd. for C₄₁H₆₇N₄O₄₉S₆: 530.3738, found: 530.3721 [M−3H]³⁻.

5-aminopentyl [(β-D-glucopyranosyluronate)-(1→4)-(2-acetamido-2-deoxy-6-O-sulfanate-α-D-glucopyranoside)-(1→4)-O-(β-D-glucopyranosyluronate-(1→4)-O-2-acetamido-2-deoxy-6-O-sulfanate-α-D-glucopyranoside tetrasodium salt (76)

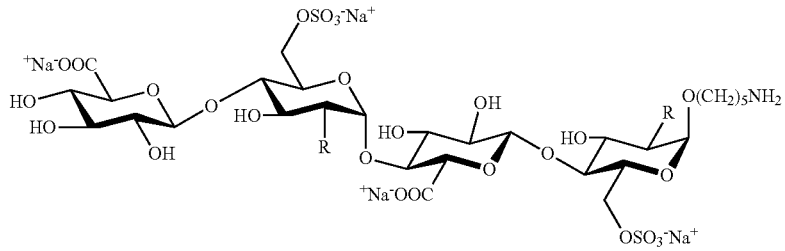

76: R = NHAc

Tetrasaccharide 70 (101 mg, 0.052 mmol) was subjected to the sequence of deprotection steps including delevulinoylation, O-sulfation, Fmoc cleavage, saponification, deacetylation, azide reduction to give a diamino tetrasaccharide. Part of this material was subjected to N-acetylation and global debenzylation according to the general procedures to give the tetrasaccharide 76 (3.0 mg). [α]$_D^{25}$: +70 (c=1, H₂O); ¹H NMR (800 MHz, D₂O): d 5.40 (d, 1H, J=3.8 Hz, H1$^C$), 4.85 (d, 1H, J=3.2 Hz, H1$^A$), 4.55-4.54 (m, 2H, H1$^B$, H1$^D$), 4.42 (bd, 2H, H6a$^C$, H6a$^A$), 4.23 (dd, 1H, J=6.2 Hz, J=11.4 Hz, H6b$^A$), 4.16 (dd, 1H, J=1.9 Hz, J=11.1 Hz, H6b$^C$), 4.04-4.00 (m, 2H, H5$^C$, H5$^A$), 3.96 (m, 3H, H2$^C$, H2$^A$, H3$^A$), 3.82-3.78 (m, 2H, H3$^C$, H5$^B$), 3.74-3.67 (m, 6H, H4$^B$, H4$^C$, H5$^D$, OCHH Linker, H3$^B$, H4$^A$), 3.51 (t, 1H, J=9.3 Hz, H3$^D$), 3.50-3.46 (m, 2H, OCHHLinker, H4$^D$), 3.32 (dd, 2H, J=7.9 Hz, J=9.3 Hz, H2$^B$, H2$^D$), 2.98 (t, 2H, J=7.7 Hz, CH₂N Linker), 2.02, 2.00 (2s, 3H each, 2×CH₃, NAc), 1.69-1.59 (m, 4H, 2×CH₂Linker), 1.46-1.43 (m, 2H, CH₂ Linker). ESI-MS: m/z: calcd. for C₃₃H₅₄N₃O₂₉S₂: 1020.2290, found: 1020.2312 [M-H]¹⁻, calcd. for C₃₃H₅₃N₃O₂₉S₂: 509.6109, found: 509.6118 [M−2H]²⁻.

5-aminopentyl [((3-D-glucopyranosyluronate)-(1→4)-(2-deoxy-2-N-sulfoamino-6-O-sulfonate-α-D-glucopyranoside)-(1→4)-O-(β-D-glucopyranosyluronate-(1→4)-O-2-deoxy-2-N-sulfoamino-2-deoxy-6-O-sulfonate-α-D-glucopyranoside hexasodium salt (77)

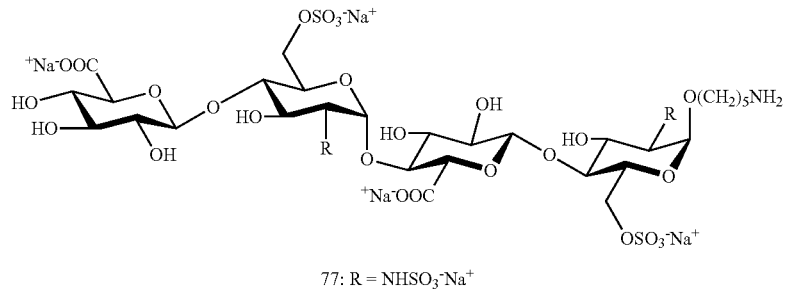

77: R = NHSO₃⁻Na⁺

A diamino tetrasaccharide obtained by partial deprotection of 70 was subjected to N-sulfation and global debenzylation according to the general procedures to give tetrasaccharide 77 (6.8 mg). [α]$_D^{25}$: +33 (c=1, H₂O); ¹H NMR (800 MHz, D₂O): d 5.62 (d, 1H, J=3.7 Hz, H1$^C$), 5.12 (d, 1H, J=3.7 Hz, H1$^A$), 4.58 (d, 1H, J=7.9 Hz, H1$^B$), 4.56 (d, 1H, J=7.9 Hz, H1$^D$), 4.43 (dd, 1H, J=1.9 Hz, J=11.0 Hz, H6a$^C$), 4.41 (dd, 1H, J=2.0 Hz, J=11.2 Hz, H6a$^A$), 4.23 (dd, 1H, J=6.0 Hz, J=11.2 Hz, H6b$^A$), 4.15 (dd, 1H, J=1.9 Hz, J=11.0 Hz, H6b$^C$), 4.01 (ddd, 1H, J=2.0 Hz, J=6.0 Hz, J=10.0 Hz, H5$^A$), 3.99 (bd, 1H, J=10.0 Hz, H5$^C$), 3.84 (t, 1H, J=8.8 Hz, H3$^B$), 3.80-3.71 (m, 6H, H5$^B$, H4$^B$, H4$^C$, H5$^D$, OCHH Linker, H3$^A$), 3.66-3.64 (m, 2H, H3$^C$, H4$^A$), 3.56-3.54 (m, 1H, OCHH Linker), 3.53-3.46 (m, 2H, H3$^D$, H4$^D$), 3.35 (dd, 1H, J=7.9 Hz, J=9.4 Hz, H2$^B$), 3.32 (dd, 1H, J=8.0 Hz, J=9.2 Hz, H2$^D$), 3.26 (dd, 1H, J=3.7 Hz, J=8.2 Hz, H2$^A$), 3.23 (dd, 1H, J=3.7 Hz, J=10.8 Hz, H2$^C$), 2.99 (t, 2H, J=7.4 Hz, CH₂N Linker), 1.70-1.61 (m, 4H, 2×CH₂ Linker), 1.50-1.44 (m, 2H, CH₂ Linker). ESI-MS: m/z: calcd. for C₂₉H₅₀N₃O₃₃S₄: 1096.1215, found: 1096.1237 [M–H]¹⁻; calcd. for C₂₉H₄₉N₃O₃₃S₄: 547.5571, found: 547.5580 [M–2H]²⁻

5-Aminopentyl[β-D-glucopyranosyluronate-(1→4)-(2-acetamido-2-deoxy-6-O-sulfonate-α-D-glucopyranoside)-(1→4)-α-L-idopyranosyluronate)]-(1→4)-2-acetamido-2-deoxy-6-O-sulfonate-α-D-glucopyranoside tetrasodium salt (78)

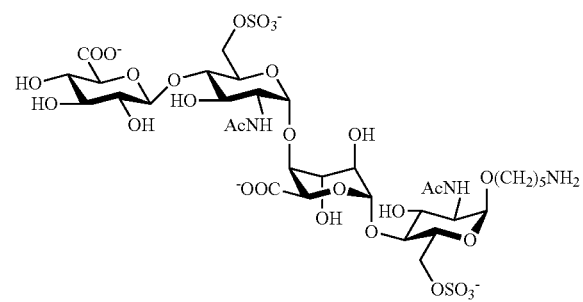

Tetrasaccharide 71 (53 mg, 0.027 mmol) was subjected to the sequence of deprotection steps including delevulinoylation, O-sulfation, Fmoc cleavage, saponification, deacetylation, azide reduction to obtain a diamino tetrasaccharide. Part of this material was subjected to N-acetylation and global debenzylation according to the general procedure to give tetrasaccharide 78 (2.5 mg). [α]$_D^{25}$: +22 (c=0.5, H₂O); ¹H NMR (800 MHz, D₂O): d 5.16 (d, 1H, J=3.8 Hz, H1$^C$), 4.96 (d, 1H, J=3.3 Hz, H1$^B$), 4.86 (d, 1H, J=3.6 Hz, H1$^A$), 4.70 (d, 1H, J=2.9 Hz, H5$^B$), 4.56 (d, 1H, J=7.9 Hz, H1$^D$), 4.43 (dd, 1H, J=2.6 Hz, J=11.2 Hz, H6a$^C$), 4.33 (dd, 1H, J=2.0 Hz, J=11.2 Hz, H6$_a^A$), 4.25 (dd, 1H, J=5.7 Hz, H6b$^A$), 4.01 (dd, 1H, J=1.9 Hz, H6b$^C$), 4.08 (m, 1H, H5$^C$), 4.06 (t, 1H, J=3.4 Hz, H4$^B$), 4.03 (m, 1H, H5$^A$), 3.96 (dd, 1H, J=10.4 Hz, H2$^C$), 3.94 (dd, 1H, J=3.6 Hz, J=10.7 Hz, H2$^A$), 3.88 (dd, J=3.4 Hz, J=5.9 Hz, H3$^B$), 3.82 (dd, J=8.7 Hz, H3$^A$, J=10.7 Hz), 3.78-3.73 (m, 3H, H3$^C$, H4$^C$, H5$^D$), 3.72-3.65 (m, 3H, H2$^B$, H4$^A$, OCHH Linker), 3.53-3.47 (m, 3H, H3$^D$, H4$^D$, OCHH Linker), 3.33 (dd, 1H, J=7.9 Hz, J=9.4 Hz, H2$^D$), 2.98 (t, 2H, J=7.6 Hz, CH₂NH₂ Linker), 2.01, 1.98 (2s, 3H each, 2×CH₃, NHAc), 1.70-1.58 (m, 4H, 2×CH₂ Linker) and 1.48-1.40 (m, 2H, CH₂ Linker). ESI-MS: m/z: calcd. for C₃₃H₅₄N₃O₂₉S₂: 1020.2290, found: 1020.2273 [M–J]¹⁻; calcd. for C₃₃H₅₃N₃O₂₉S₂: 509.6109, found: 509.6119 [M–2H]²⁻; calcd. for C₃₃H₅₂N₃O₂₉S₂: 339.4048, found: 339.4051 [M–3H]³⁻.

5-Aminopentyl [β-D-glucopyranosyluronate-(1→4)-(2-deoxy-2-sulfoamino-6-O-sulfonate-α-D-glucopyranoside)-(1→4)-α-L-idopyranosyluronate)]-(1→4)-2-deoxy-2-sulfoamino-6-O-sulfonate-α-D-glucopyranoside hexasodium salt (79)

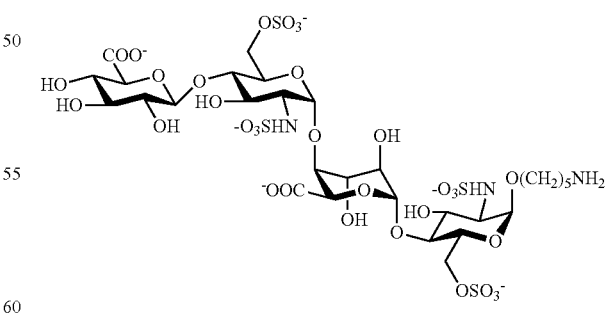

The second portion of the diamino tetrasaccharide obtained above was subjected to N-sulfation and global debenzylation according to the general procedure described above to obtain the tetrasaccharide 79 (4.1 mg). [α]$_D^{25}$: +40 (c=0.5, H₂O); ¹H NMR (800 MHz, D₂O): d 5.36 (d, 1H, J=3.6 Hz, H1$^C$), 5.13 (d, 1H, J=3.7 Hz, H1$^A$), 4.99 (d, 1H, J=2.4 Hz, H1$^B$), 4.72 (d, 1H, J=2.3 Hz, H5$^B$), 4.57 (d, 1H, J=8.0 Hz, H1$^D$), 4.46 (dd, 1H, J=2.0 Hz, J=11.0 Hz, H6a$^C$), 4.32 (dd, 1H, J=1.7 Hz, J=11.0 Hz, H6a$^A$), 4.23 (dd, 1H, J=5.5 Hz, J=11.0 Hz, H6b$^A$), 4.18 (dd, 1H, J=1.7 Hz, J=11.0 Hz, H6b$^C$), 4.10 (dd, 1H, J=3.5 Hz, J=4.4 Hz, H3$^B$), 4.05 (bt, 1H, J=4.0 Hz, H$_4^B$), 4.04-4.00 (m, 2H, H5$^A$, H5$^C$), 3.77-3.64 (m, 7H, H2$^B$, H3$^A$, H3$^C$, H4$^A$, H4$^C$, H5$^D$, OCHH Linker), 3.57-3.51 (m, 2H, H3$^D$, OCHH Linker), 3.48 (t, 1H, J=9.3 Hz, H4$^D$), 3.33 (dd, 1H, J=8.0 Hz, J=9.1 Hz, H2$^D$), 3.27 (dd, 1H, J=3.7 Hz, J=9.9 Hz, H2$^A$), 3.24 (dd, 1H, J=10.5 Hz, H2$^C$), 3.02 (t, 2H, J=7.4 Hz, CH$_2$NH$_2$), 1.70-1.60 (m, 4H, 2×CH$_2$ Linker), 1.52-1.42 (m, 2H, CH$_2$ Linker). ESI-MS: m/z: calcd. for C$_{29}$H$_{50}$N$_3$O$_{33}$S$_4$: 1096.1215, found: 1096.1247 [M-H]$^{1-}$; calcd. for C$_{29}$H$_{49}$N$_3$O$_{33}$S$_4$: 547.5571, found: 547.5591 [M-2H]$^{2-}$; C$_{29}$H$_{48}$N$_3$O$_{33}$S$_4$: 364.7023, found: 364.7034 [M-3H]$^{3-}$.

5-aminopentyl [(α-L-idopyranosyluronate)-(1→4)-O-(2-acetamido-2-deoxy-6-O-sulfonate-α-D-glucopyranoside)-(1→4)-O-(β-D-glucopyranosyluronate)]-(1→4)-(2-acetamido-2-deoxy-6-O-sulfonate-α-D-glucopyranoside tetrasodium salt (80)

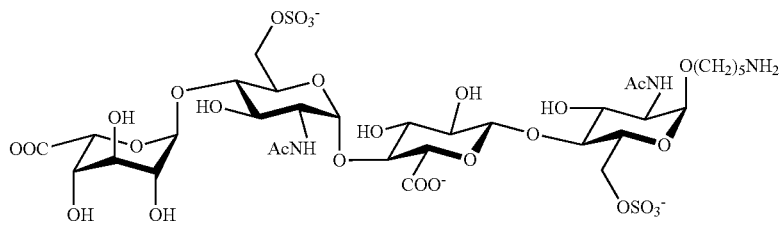

Tetrasaccharide 72 (89 mg, 0.045 mmol) was subjected to the sequence of deprotection steps including delevulinoylation, O-sulfation, Fmoc cleavage, saponification, deacetylation, azide reduction to obtain the diamino tetrasaccharide. One portion of the diamino tetrasaccharide was subjected to N-acetylation and global debenzylation according to the general procedure described above to give tetrasaccharide 80 (5.8 mg). [α]$_D^{25}$: +140 (c=0.5, H$_2$O); $^1$H NMR (800 MHz, D$_2$O): d 5.38 (d, 1H, J=3.8 Hz, H1$^C$), 4.87-4.85 (m, 2H, H1$^A$, H1$^D$), 4.57 (d, 1H, J=3.8 Hz, H5$^D$), 4.55 (d, 1H, J=7.9 Hz, H1$^B$), 4.42 (dd, 1H, J=1.9 Hz, J=11.2 Hz, H6a$^A$), 4.35 (dd, 1H, J=2.0 Hz, J=11.0 Hz, H6a$^C$), 4.25 (dd, 1H, J=6.0 Hz, J=11.2 Hz, H6b$^A$), 4.17 (dd, 1H, J=1.8 Hz, J=11.0 Hz, H6b$^C$), 4.05-4.02 (m, 1H, H5$^A$), 4.01-3.98 (m, 1H, H5$^C$), 3.94-3.88 (m, 3H, H2$^A$, H2$^C$, H3$^A$), 3.87 (dd, 1H, J=4.2 Hz, J=5.6 Hz (H4$^D$), 3.79 (d, 1H, J=9.5 Hz, H5$^B$), 3.77-3.66 (m, 6H, H3$^B$, H3$^C$, H3$^D$, H4$^B$, H4$^C$, OCHH Linker), 3.64 (dd, 1H, J=8.0 Hz, J=10.0 Hz, H4$^A$), 3.56 (dd, 1H, J=2.6 Hz, J=7.1 Hz, H2$^D$), 3.50 (m, 1H, OCHH Linker), 3.33 (dd, 1H, J=9.6 Hz, J=9.6 Hz, H2$^B$), 2.98 (t, 2H, J=7.7 Hz, CH$_2$NH$_2$), 2.05 and 2.03 (2s, 3H each, 2×CH$_3$, NHAc), 1.74-1.60 (m, 4H, 2×CH$_2$ Linker), 1.50-1.42 (m, 2H, CH$_2$ Linker). C$_{33}$H$_{54}$N$_3$O$_{29}$S$_2$: 1020.2290, found: 1020.2319 [M-H]$^{1-}$; calcd. for C$_{33}$H$_{53}$N$_3$O$_{29}$S$_2$: 509.6109, found: 509.6129 [M-2H]$^{2-}$; calcd. for C$_{33}$H$_{52}$N$_3$O$_{29}$S$_2$: 339.4048, found: 339.4056 [M-3H]$^{3-}$.

5-aminopentyl [(α-L-idopyranosyluronate)-(1→4)-O-(2-deoxy-2-sulfoamino-6-O-sulfonate-α-D-glucopyranoside)-(1→4)-O-(β-D-glucopyranosyluronate)]-(1→4)-2-deoxy-2-sulfoamino-6-O-sulfonate-α-D-glucopyranoside hexasodium salt (81)

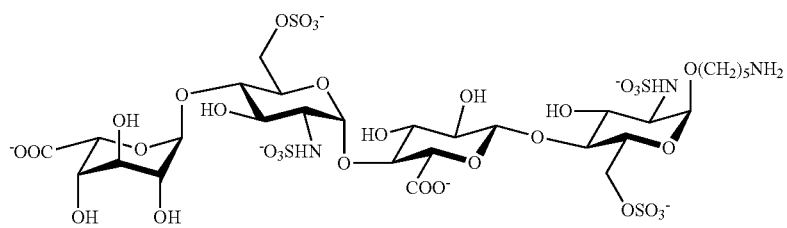

The second portion of the diamino tetrasaccharide obtained above was subjected to N-sulfation and global debenzylation according to the general procedure described above to give tetrasaccharide 81 (5.7 mg). $[\alpha]_D^{25}$: −5.4 (c=0.5, H$_2$O); $^1$H NMR (800 MHz, D$_2$O): d 5.61 (d, 1H, J=3.8 Hz, H1$^C$), 5.13 (d, 1H, J=3.6 Hz, H1$^A$), 4.86 (d, 1H, J=4.7 Hz, H1$^D$), 4.58-4.54 (m, 2H, H1$^B$, H5$^D$), 4.43 (dd, 1H, J=1.8 Hz, J=11.1 Hz, H6a$^A$), 4.35 (dd, 1H, J=2.0 Hz, J=11.1 Hz, H6a$^C$), 4.24 (dd, 1H, J=6.1 Hz, J=11.1 Hz, H6b$^A$), 4.17 (dd, 1H, J=2.0 Hz, J=11.1 Hz, H6b$^C$), 4.04-4.01 (m, 1H, H5$^A$), 3.97-3.92 (m, 1H, H5$^C$), 3.88 (dd, 1H, J=4.0 Hz, J=6.0 Hz, H4$^D$), 3.84 (dd, 1H, J=8.7 Hz, J=9.3 Hz, H3$^B$), 3.80 (d, 1H, J=9.6 Hz, H5$^B$), 3.76 (dd, 1H, J=8.6 Hz, J=9.3 Hz, H4$^B$), 3.75-3.70 (m, 4H, H3$^A$, H3$^D$, H4$^C$, OCHH Linker), 3.65 (dd, 1H, J=9.0 Hz, J=10.0 Hz, H4$^A$), 3.62 (dd, 1H, J=9.2 Hz, J=10.3 Hz, H3$^C$), 3.57-3.53 (m, 2H, H2$^D$, OCHH Linker), 3.36 (dd, 1H, J=8.0 Hz, H2$^B$), 3.29-3.26 (m, 2H, H2$^A$, H2$^C$), 3.00 (t, J=7.6 Hz, CH$_2$NH$_2$), 1.72-1.60 (m, 4H, 2×CH$_2$ Linker), 1.52-1.42 (m, 2H, CH$_2$ Linker). ESI-MS: m/z: calcd. for C$_{29}$H$_{50}$N$_3$O$_{33}$S$_4$: 1096.1215, found: 1096.1251 [M−H]$^1$; calcd. for C$_{29}$H$_{49}$N$_3$O$_{33}$S$_4$: 547.5571, found: 547.5590 [M−2H]$^{2−}$; C$_{29}$H$_{48}$N$_3$O$_{33}$S$_4$: 364.7023, found: 364.7030 [M−3H]$^{3−}$.

5-aminopentyl [(α-L-idopyranosyluronate)-(1→4)-(2-acetamido-2-deoxy-6-O-sulfonate-α-D-glucopyranoside)-(1→4)-O-(α-L-idopyranosyluronate-(1→4)-O-2-acetamido-2-deoxy-6-O-sulfonate-α-D-glucopyranoside tetrasodium salt (82)

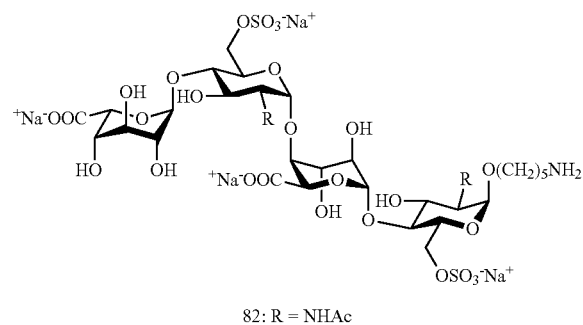

82: R = NHAc

Tetrasaccharide 73 (148 mg, 0.076 mmol) was subjected to the sequence of deprotection steps including delevulinoylation, O-sulfation, Fmoc cleavage, saponification, deacetylation, azide reduction to obtain the diamino tetrasaccharide. One portion of the diamino tetrasaccharide was subjected to N-acetylation and global debenzylation according to the general procedure described above to give tetrasaccharide 82 (4.32 mg). $[\alpha]_D^{23}$: +70 (c=0.35, H$_2$O); $^1$H NMR (800 MHz, D$_2$O): d 5.14 (d, 1H, J=3.7 Hz, H1$^C$), 4.94 (d, 1H, J=3.2 Hz, H1$^B$), 4.85 (d, 1H, J=3.7 Hz, H1$^A$), 4.83 (d, 1H, J=4.6 Hz, H1$^D$), 4.68 (d, 1H, J=2.7 Hz, H5$^B$), 4.55 (d, 1H, J=3.9 Hz, H5$^D$), 4.34-4.31 (m, 2H, H6a$^C$, H6a$^A$), 4.23 (dd, 1H, J=6.6 Hz, J=11.2 Hz, H6b$^A$), 4.2 (dd, 1H, J=1.7 Hz, J=11 Hz, H6b$^C$), 4.05 (t, 1H, J=3.2 Hz, H4$^B$), 4.04-4.01 (m, 2H, H5$^C$, H5$^A$), 3.96 (dd, 1H, J=3.7 Hz, J=10.2 Hz, H2$^C$), 3.91 (dd, 1H, J=3.7 Hz, J=10.7 Hz, H2$^A$), 3.87 (dd, 1H, J=3.7 Hz, J=5.9 Hz, H3$^B$), 3.85 (dd, 1H, J=4.1 Hz, J=6.1 Hz, H4$^D$), 3.80 (t, 1H, J=9.8 Hz, H3$^A$), 3.74-3.64 (m, 7H, H4$^C$, H3$^C$, H3$^D$, H2$^B$, H4$^A$, H2$^B$, OCHH Linker), 3.53 (dd, 1H, J=4.6 Hz, J=7.3 Hz), 3.50-3.47 (m, 1H, OCHH Linker), 2.97 (t, 2H, J=7.6 Hz, CH$_2$N Linker), 2.00, 1.98 (2s, 3H each, 2×CH$_3$, NHAc), 1.69-1.56 (m, 4H, 2×CH$_2$ Linker), 1.45-1.41 (m, 2H, CH$_2$ Linker). C$_{33}$H$_{54}$N$_3$O$_{29}$S$_2$: 1020.2290, found: 1020.2279 [M−H]$^1$; calcd. for C$_{33}$H$_{53}$N$_3$O$_{29}$S$_2$: 509.6109, found: 509.6113 [M−2H]$^{2−}$; calcd. for C$_{33}$H$_{52}$N$_3$O$_{29}$S$_2$: 339.4048, found: 339.4046 [M−3H]$^{3−}$.

5-aminopentyl [(α-L-idopyranosyluronate)-(1→4)-(2-deoxy-2-N-sulfoamino-6-O-sulfonate-α-D-glucopyranoside)-(1→4)-O-(α-L-idopyranosyluronate-(1→4)-O-2-deoxy-2-N-sulfoamino-6-O-sulfonate-α-D-glucopyranoside hexasodium salt (83)

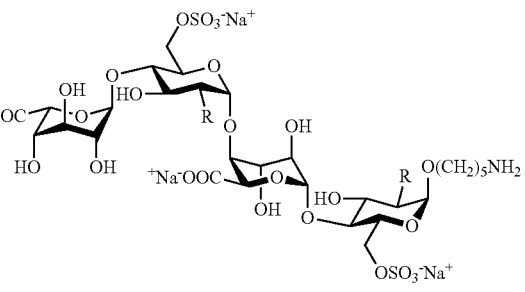

83: R = NHSO$_3$$^-$Na$^+$

The second portion of the diamino tetrasaccharide obtained above was subjected to N-sulfation and global debenzylation according to the general procedure described above to give tetrasaccharide 83 (6.5 mg). $[\alpha]_D^{23}$: +24.4 (c=0.3, H$_2$O); $^1$H NMR (800 MHz, D$_2$O): d 5.33 (d, 1H, J=3.7 Hz, H1$^C$), 5.11 (d, 1H, J=3.7 Hz, H1$^A$), 4.97 (d, 1H, J=2.0 Hz, H1$^B$), 4.85 (d, 1H, J=4.9 Hz, H1$^D$), 4.71 (d, 1H, J=2.2 Hz, H5$^B$), 4.57 (d, 1H, J=3.9 Hz, H5$^D$), 4.35 (dd, 1H, J=2.2 Hz, J=11.2 Hz, H6a$^C$), 4.29 (dd, 1H, J=1.7 Hz and 11 Hz, H6a$^A$), 4.23 (dd, 1H, J=5.4 Hz, J=11.2 Hz, H6b$^A$), 4.17 (dd, 1H, J=1.7 Hz, J=11 Hz, H6b$^C$), 4.08 (t, 1H, J=4.0 Hz, H3$^B$), 4.04 (t, 1H, J=2.6 Hz, H4$^B$), 4.00-3.98 (bm, 2H, H5$^A$, H5$^C$), 3.85 (dd, 1H, J=3.9 Hz, J=5.9 Hz, H4$^D$), 3.74-3.61 (m, 7H, OCHH Linker, H2$^B$, H4$^C$, H3$^D$, H4$^A$, H3$^A$, H3$^C$), 3.55-3.52 (m, 2H, OCHH Linker, H2$^D$), 3.25 (dd, 1H, J=3.9 Hz, J=10.3 Hz, H2$^A$), 3.23 (dd, 1H, J=3.7 Hz, J=10.8 Hz, H2$^C$), 2.98 (t, 2H, J=7.5 Hz, CH$_2$N Linker), 1.69-1.62 (m, 4H, 2×CH$_2$Linker), 1.49-1.44 (m, 2H, CH$_2$ Linker). ESI-MS: m/z: calcd. for C$_{29}$H$_{50}$N$_3$O$_{33}$S$_4$: 1096.1215, found: 1096.1251 [M−H]$^1$; calcd. for C$_{29}$H$_{49}$N$_3$O$_{33}$S$_4$: 547.5571, found: 547.5563 [M−2H]$^{2−}$; C$_{29}$H$_{48}$N$_3$O$_{33}$S$_4$: 364.7023, found: 364.7012 [M−3H]$^{3−}$.

5-Aminopentyl [(α-L-idopyranosyluronate)-(1→4)-O-(2-acetamido-2-deoxy-6-O-sulfonate-α-D-glucopyranoside)-(1→4)-O-(2-O-sulfonato-α-L-idopyranosyl-uronate)]-(1→4)-2-deoxy-2-acetamido-6-O-sulfonate-α-D-glucopyranoside penta sodium salt (84)

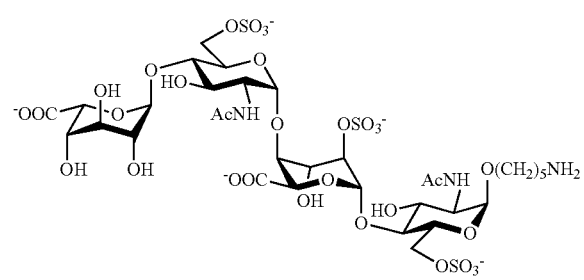

Tetrasaccharide 74 (17 mg, 0.0085 mmol) was subjected to the sequence of deprotection steps including delevulinoylation, O-sulfation, Fmoc cleavage, saponification, deacetylation, azide, N-acetylation and global debenzylation according to the general procedure described above to give tetrasaccharide 84 (1.6 mg). $[\alpha]_D^{25}$: 26 (c=0.5, H$_2$O); $^1$H NMR (500 MHz, D$_2$O): d 5.22 (bs, 1H, H1$^B$), 5.14 (d, 1H, J=3.6 Hz, H1$^C$), 4.87 (d, 1H, J=3.6 Hz, H1$^A$), 4.85 (d, 1H, J=5.2 Hz, H1$^D$), 4.80 (d, 1H, J=2.3 Hz, H5$^B$), 4.57 (d, 1H, J=4.1 Hz, H5$^D$), 4.40 (dd, 1H, J=1.5 Hz, J=11.5 Hz, H6a$^{A\ or\ C}$), 4.36 (dd, 1H, J=3.0 Hz, J=11.0 Hz, H6a$^{A\ or\ C}$), 4.29 (bs, 1H, H2$^B$), 4.28-4.20 (m, 3H, H6b$^A$, H6b$^C$, H3$^B$), 4.09-4.01 (m, 4H, H2$^C$, H4$^B$, H5$^A$, H5$^C$), 3.94 (dd, 1H, J=3.6 Hz, J=10.5 Hz, H2$^A$), 3.89-3.83 (m, 2H, H3$^A$, H4$^D$), 4.78-4.67 (m, 5H, H3$^C$, H3$^D$, H4$^A$, H4$^C$, OCHH Linker), 3.55 (dd, 1H, J=7.3 Hz, H2$^D$), 3.53-3.48 (m, 1H, OCHH Linker), 3.10 (t, 2H, J=7.4 Hz, CH$_2$NH$_2$) 2.05 and 2.02 (2s, 3H each, 2×CH$_3$, NHAc) 1.74-1.5 (m, 2H, 2×CH$_2$ Linker), 1.59-1.48 (m, 2H, CH$_2$ Linker). ESI-MS: m/z: calcd. for C$_{33}$H$_{53}$N$_3$O$_{32}$S$_3$: 549.5893, found: 549.5890 [M-H]$^{2-}$; calcd. for C$_{33}$H$_{52}$N$_3$O$_{32}$S$_3$: 366.0571, found: 366.0582 [M-3H]$^{3-}$.

5-Aminopentyl [((3-D-glucopyranosyluronate)-(1→4)-O-(2-acetamido-2-deoxy-6-O-sulfonato-α-D-glucopyranoside)-(1→4)-O-(2-O-sulfonato-α-L-idopyranosyluronate)]-(1→4)-2-deoxy-2-acetamido-6-O-sulfonate-α-D-glucopyranoside penta sodium salt (85)

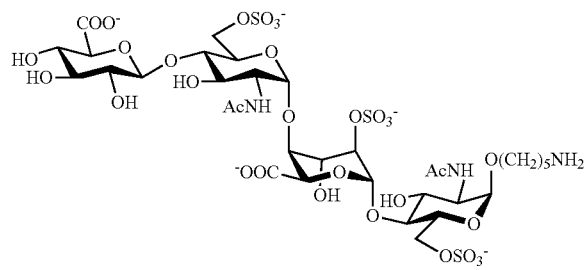

Tetrasaccharide 75 (159 mg, 0.079 mmol) was subjected to the sequence of deprotection steps including delevulinoylation, O-sulfation, Fmoc cleavage, saponification, deacetylation, azide reduction to obtain the diamino tetrasaccharide. One portion of the diamino tetrasaccharide was subjected to N-acetylation and global debenzylation according to the general procedure described above to give tetrasaccharide 85 (9.3 mg). $[\alpha]_D^{25}$: +26 (c=0.5, H$_2$O); $^1$H NMR (800 MHz, D$_2$O): d 5.14 (bs, 1H, H1$^B$), 5.10 (d, 1H, J=3.7 Hz, H1$^C$), 4.83 (d, 1H, J=3.7 Hz, H1$^A$), 4.78 (d, 1H, J=2.3 Hz, H5$^B$), 4.54 (d, 1H, J=7.9 Hz, H1$^D$), 4.41 (dd, 1H, J=2.7 Hz, J=11.0 Hz, H6a$^C$), 4.36 (d, 1H, J=1.8 Hz, J=11.2 Hz, H6a$^A$), 4.26 (bd, J=3.2 Hz, H2$^B$), 4.25-4.21 (m, 2H, H6b$^A$, H6b$^C$), 4.18 (bt, 1H, H3$^B$), 4.09-4.05 (m, 1H, H5$^C$), 4.05-4.01 (m, 2H, H4$^B$, H5$^A$), 3.99 (dd, 1H, J=3.7 Hz, J=10.2 Hz, H2$^C$), 3.92 (dd, 1H, J=3.7 Hz, J=10.6 Hz, H2$^A$), 3.82 (dd, 1H, J=8.8 Hz, J=10.4 Hz, H3$^A$), 3.76-3.72 (m, 3H, H3$^C$, H4$^C$, H5$^D$), 3.71-3.68 (m, 2H, H4$^A$, OCHH Linker), 3.53-3.46 (m, 3H, H3$^D$, H4$^D$, OCHH Linker), 3.32 (dd, 1H, J=9.2 Hz, H2$^D$), 2.98 (t, 2H, J=7.6 Hz, CH$_2$NH$_2$), 2.03 and 2.00 (2s, 3H each, 2×CH$_3$, NHAc), 1.70-1.58 (m, 4H, 2×CH$_2$ Linker), 1.48-1.42 (m, 2H, CH$_2$ Linker). ESI-MS: m/z: calcd. for C$_{33}$H$_{53}$N$_3$O$_{32}$S$_3$: 549.5893, found: 549.5879 [M-H]$^{2-}$; calcd. for C$_{33}$H$_{52}$N$_3$O$_{32}$S$_3$: 366.0571, found: 366.0559 [M-3H]$^{3-}$.

5-Aminopentyl [(β-D-glucopyranosyluronate)-(1→4)-O-(2-deoxy-2-sulfamino-6-O-sulfonate-α-D-glucopyranoside)-(1→4)-O-(2-O-sulfonate-α-L-idopyranosyluronate)-(1→4)-2-deoxy-2-sulfoamino-6-O-sulfonate-α-D-glucopyranoside heptasodium salt (86)

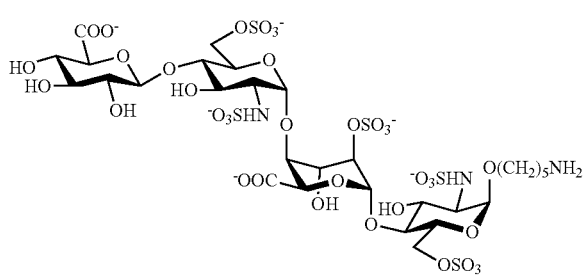

A second portion of the diamino tetrasaccharide obtained above was subjected to N-sulfation and global debenzylation according to the general procedure described above to give tetrasaccharide 86 (5.0 mg). $[\alpha]_D^{25}$: +79 (c=1.3, H$_2$O); $^1$H-NMR (800 MHz, D$_2$O): d 5.40 (d, 1H, J=3.3 Hz, H1$^C$), 5.23 (d, 1H, J=2.7 Hz, H1$^B$), 5.10 (d, 1H, J=3.3 Hz, H1$^A$), 4.70 (d, 1H, J=2.7 Hz, H1$^B$), 4.57 (d, 1H, J=7.9 Hz, H1$^D$), 4.45 (bd, 1H, J=11.0 Hz, H6a$^C$), 4.35 (bd, 1H, J=11.0 Hz, H6a$^A$), 4.30-4.25 (m, 2H, H2$^B$, H6b$^A$), 4.20 (m, 1H, H6b$^C$), 4.16 (dd, 1H, J=4.0 Hz, J=5.7 Hz, H3$^B$), 4.09-4.06 (m, 2H, H4$^B$ and H5$^C$), 4.00 (m, 1H, H5$^A$), 3.77-3.68 (m, 5H, H3$^A$, H4$^A$, H4$^C$, H5$^D$, OCHH Linker), 3.66 (dd, 1H, J=9.1 Hz, J=9.5 Hz, H3$^C$), 3.56-3.53 (m, 1H, OCHH Linker), 3.51 (t, 1H, J=9.2 Hz, H3$^D$), 3.47 (t, 1H, J=9.2 Hz, H4$^D$), 3.32 (dd, 1H, J=8.4 Hz, J=9.2 Hz, H2$^D$), 3.27-3.23 (m, 2H, H2$^A$, H2$^C$), 3.00 (t, 2H, J=7.4 Hz, CH$_2$NH$_2$), 1.72-1.55 (m, 4H, 2×CH$_2$ Linker), 1.50-1.40 (m, 2H, CH$_2$ Linker). ESI-MS: m/z: calcd. for C$_{29}$H$_{49}$N$_3$O$_{36}$S$_5$: 587.5355, found: 587.5347 [M-H]$^{2-}$; calcd. for C$_{29}$H$_{48}$N$_3$O$_{36}$S$_5$: 391.3546, found: 391.3535 [M−3H]$^{3-}$.

BACE inhibition assays: The ability of the compounds to inhibit BACE-1 cleavage of APP was assessed using a fluorescent resonance energy transfer (FRET) peptide cleavage assay employing the FRET peptide HiLyteFluor™488-Glu-Val-Asn-Leu-Asp-Ala-Glu-Phe-Lys(QXL520)-OH (Anaspec Inc, San Jose, Calif.), containing the Swedish amino acid variant. Assays were performed in triplicate in 96-well black plates (Greiner Bio-One Ltd) in a total volume of 100 µl of 20 mM sodium acetate, 0.1% Triton-X-100, pH 4.5 using 114 pmoles FRET peptide/well and 0.1 µg of recombinant human BACE-1 (R & D Systems; specific activity >3.5 pmol/min/µg). Inhibitors were added at 0.01 to 50 µg/mL and mixed with enzyme prior to addition of substrate. Appropriate controls for enzyme activity and background fluorescence were employed and plates were incubated (2 h, 25° C.) with reaction stopped by addition of 100 µl 2.5 M sodium acetate. Fluorescence 480ex/520em was measured on a Polarstar plate reader (BMG LabTechnologies, U.K.) and data were analyzed by plotting log concentration of inhibitor against percent inhibition and using a logistic sigmoidal curve fitting function using OriginPro 8 software (OriginLab Corporation, MA).

This data is also available in Arungundram et al., 2009, *J. Amer. Chem. Soc.* 131:17394-17405. Supporting information for Arungundram et al., 2009, *J. Amer. Chem. Soc.*

Example II

Experimental Procedure for Synthesis and Characterization of Heparan Sulfate Oligosaccharides General Procedures All moisture sensitive reactions were performed under an argon atmosphere by using vacuum dried glassware. All commercial materials were used without purification, unless otherwise noted. $CH_2Cl_2$ was freshly distilled from calcium hydride under nitrogen prior to use. Toluene, DMF, diethylether, methanol and THF were purchased anhydrous and used without further purification. Molecular sieves (4 Å) were flame activated in vacuo prior to use. All reactions were performed at room temperature unless specified otherwise. TLC-analysis was conducted on Silica gel 60 $F_{254}$ (EMD Chemicals Inc.) with detection by UV-absorption (254 nm) were applicable, and by spraying with 20% sulfuric acid in ethanol followed by charring at ~150° C. or by spraying with a solution of $(NH_4)_6Mo_7O_{24}H_2O$ (25 g/L) in 10% sulfuric acid in ethanol followed by charring at ~150° C. Column chromatography was performed on silica gel G60 (Silicycle, 60-200 μm, 60 Å) or on Bondapak C-18 (Waters). $^1H$ and $^{13}C$ NMR spectra were recorded on a Varian inova-300 (300/75 MHz), a Varian inova-500 (500/125 MHz) and a Varian inova-600 (600/150 MHz) spectrometer equipped with sun workstations. Chemical shifts are reported in parts per million (ppm) relative to tetramethylsilane (TMS) as the internal standard. NMR data is presented as follows: Chemical shift, multiplicity (s=singlet, d=doublet, t=triplet, dd=doublet of doublet, m=multiplet and/or multiple resonances), coupling constant in Hertz (Hz), integration. All NMR signals were assigned on the basis of $^1HNMR$, $^{13}C$ NMR, COSY and HSQC experiments. Optical rotations were measured using a Jasco P-1020 polarimeter. Mass spectra were recorded on an Applied Biosystems 4700 MALDI-TOF proteomics analyzer. The matrix used was 2,5-dihydroxy-benzoicacid (DHB) and ultamark 1621 as the internal standard. The ESI-MS spectra were recorded on 9.4 T Bruker Apex Ultra QeFTMS (Billerica, Mass.) mass spectrometer.

Scheme A

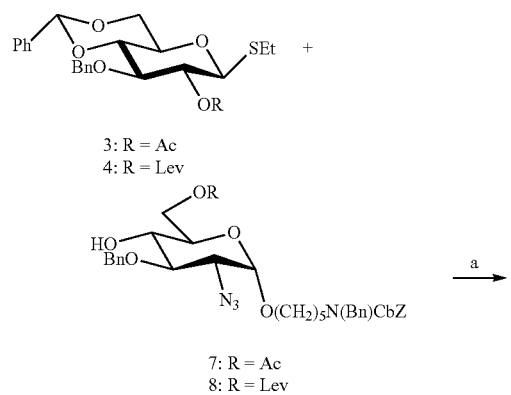

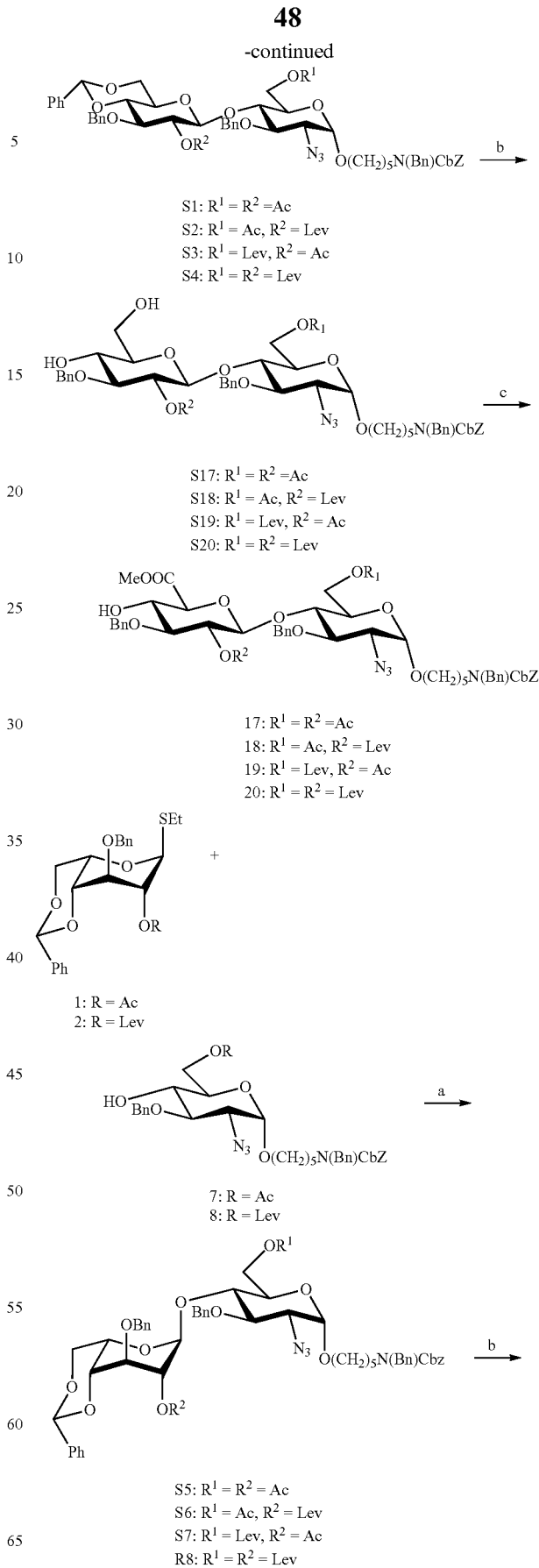

49
-continued

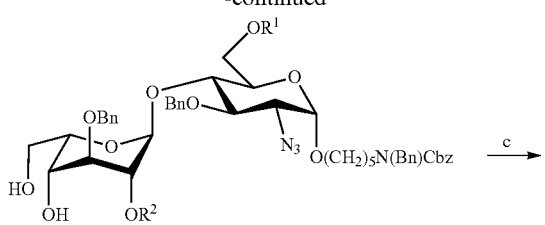

S21: R¹ = R² = Ac
S22: R¹ = Ac, R² = Lev
S23: R¹ = Lev, R² = Ac
S24: R¹ = R² = Lev

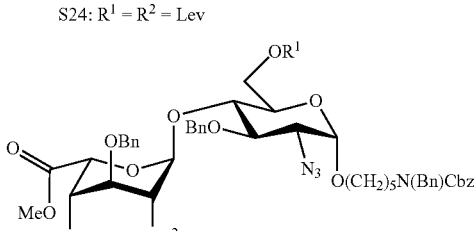

21: R¹ = R² = Ac
22: R¹ = Ac, R² = Lev
23: R¹ = Lev, R² = Ac
24: R¹ = R² = Lev (a) NIS, TMSOTf, 0° C., DCM; (b) (i) EtSH, p-TsOH, DCM, 1 h, room temperature or DCM: TFA: H₂O, 30 min, room temperature; ii) TEMPO, BAIB, DCM, H₂O, 1 h, room temperature; iii) CH₂N₂, THF, 0° C.; (c) (i) FmocCl, Py, DMAP, 0° C. to room temperature; (ii) HF Py, THF, room temperature, 18 h; (iii) CCl₃CN, K₂CO₃, 0° C., DCM.

Monosaccharides 1-32

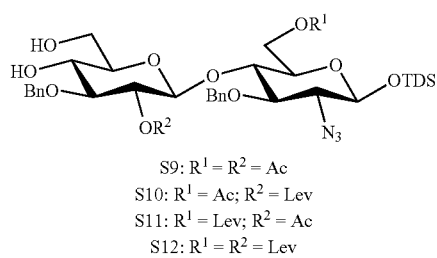

S9: R¹ = R² = Ac
S10: R¹ = Ac; R² = Lev
S11: R¹ = Lev; R² = Ac
S12: R¹ = R² = Lev

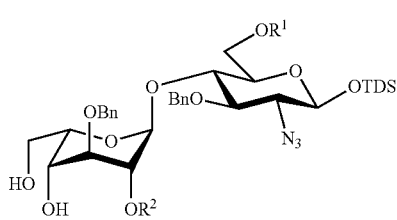

S13: R¹ = R² = Ac
S14: R¹ = Ac; R² = Lev
S15: R¹ = Lev; R² = Ac
S16: R¹ = R² = Lev

50

Ethyl 2-O-acetyl-3-O-benzyl-4,6-O-benzylidene-1-thio-α/β-L-idopyranoside (1)

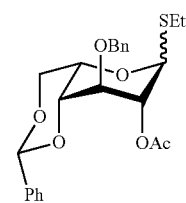

A solution of compound 35 (1.0 g, 2.48 mmol) in pyridine: acetic anhydride (4/1, v/v, 0.2 M) was stirred for 6 hr at ambient temperature. The mixture was concentrated in vacuo. The residue was purified by silica gel column chromatography using a gradient of hexanes/EtOAc (85/15, v/v) to obtain 1 (1.04 g, 93%). $[\alpha]_D^{25}$ −30.4 (c=1, CHCl₃); ¹HNMR (300 MHz, CDCl₃): δ 7.51-7.31 (m, 10H, CH Aromatic), 5.50 (s, 1H, CH benzylidene α), 5.44 (m, 2H, H2α, CH benzylidene β), 5.08 (s, 1H, H1α), 5.05 (s, 1H, H1β), 4.96 (bs, 1H, H2(3)), 4.83 (d, 1H, J=7.2 Hz, CHHBn), 4.74 (d, 1H, J=7.2 Hz, CHHBn), 4.66 (d, 1H, J=7.2 Hz, CHHBn), 4.60 (d, 1H, J=7.2 Hz, CHHBn), 4.35 (d, 1H, J=7.5 Hz, H6αβ), 4.30 (s, 1H, H5α), 4.27 (d, 1H, J=7.5 Hz, H6aα), 4.12 (dd, 1H, J=0.9 Hz, J=6.6 Hz, H6bα), 4.04 (dd, 1H, J=0.9 Hz, J=6.6 Hz, H6bβ), 3.97 (s, 1H, H4α), 3.91 (s, 1H, H4β), 3.87 (bs, 1H, H3β), 3.74 (s, 1H, H3α), 3.69 (s, 1H, H5β), 2.80-2.75 (m, 2H,CH₂SEt α), 2.71-2.61 (m, 2H,CH₂SEt β), 2.06 (s, 3H, CH₃ Ac), 2.05 (s, 3H, CH₃ Ac), 1.33-1.30 (m, 6H, CH₃SEt α/β). ¹³CNMR (75.5 MHz, CDCl₃): δ 170.5, 170.0, 137.9, 137.9, 137.2, 129.0, 128.9, 128.6, 128.4, 128.2, 128.1, 127.9, 127.8, 127.7, 127.6, 127.5, 126.5, 126.4, 126.3, 126.1, 125.9, 101.3, 100.9, 100.8, 95.6, 82.3, 82.2, 79.9, 77.4, 77.0, 76.5, 75.1, 73.5, 73.2, 77.2, 72.9, 72.7, 72.3, 72.2, 72.1, 71.9, 71.9, 71.7, 69.6, 69.5, 69.4, 69.4, 69.0, 68.7, 68.7, 68.6, 68.2, 68.2, 67.8, 67.4, 66.9, 65.4, 64.9, 63.6, 61.1, 59.7, 26.6, 26.1, 25.3, 21.0, 20.9, 20.7, 14.9, 14.8, 14.7. HRMS-MALDI: (M+Na⁺) calcd. 467.1504, found: 467.1576

Ethyl 2-O-levulinoyl-3-O-benzyl-4,6-O-benzylidene-1-thio-α/β-L-idopyranoside (2)

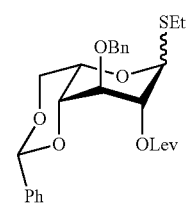

A solution of DCC (0.51 g, 2.48 mmol) and DMAP (0.03 g, 0.25 mmol) in DCM (2 mL) was added to a solution of compound 35 (0.5 g, 1.24 mmol) and levulinic acid (0.21 g, 1.86 mmol) in DCM (0.2 M) at 0° C.

After stirring for 4 hr at ambient temperature, the mixture was filtered and the filtrate was concentrated in vacuo. The residue was purified by silica gel column chromatography using a gradient of hexanes/EtOAc (75/25, v/v) to obtain 2 (0.45 g, 89%). $[\alpha]_D^{25}$ −90.9 (c=2, CHCl₃); ¹H NMR (300

MHz, CDCl$_3$): δ 7.51-7.31 (m, 10H, CH Aromatic), 5.51 (s, 1H, CH benzylidene α), 5.46 (s, 1H, CH benzylidene (3), 5.41 (s, 1H, H2a), 5.09 (s, 1H, H1a), 5.03-5.04 (m, 1H, H1β), 4.97-4.98 (bs, 1H, H2β), 4.83 (d, 1H, J=7.2 Hz, CHHBn), 4.78 (d, 1H, J=11.7 Hz, CHHBn), 4.66 (d, 1H, J=11.7 Hz, CHHBn), 4.57 (d, 1H, J=11.7 Hz, CHHBn), 4.35 (d, 1H, J=12.6 Hz, H6aβ), 4.29-4.25 (m, 2H, H6aα, H5α), 4.10 (dd, 1H, J=1.8 Hz, J=10.5 Hz, H6bα), 4.04 (dd, 1H, J=2.7 Hz, J=10.8 Hz, H6$_b$β), 3.97 (s, 1H, H4α), 3.91 (bs, 1H, H4β), 3.85 (bs, 1H, J=2.4 Hz, H3β), 3.71-3.68 (m, 2H, H3α, H5β), 2.80-2.53 (m, 12H, CH$_2$ SEt α/β, 4×CH$_2$ Lev α/β), 1.99 (s, 3H, CH$_3$ Lev), 1.98 (s, 3H, CH$_3$ Lev), 1.33-1.27 (m, 6H, CH$_3$ SEtα/β). $^{13}$CNMR (75.5 MHz, CDCl$_3$): δ 206.4, 171.7, 138.0, 137.3, 128.9, 128.5128.4, 128.3, 128.0, 128.0, 127.8, 127.8, 127.7, 127.6, 126.3, 126.2, 126.1, 100.9, 82.4, 77.4, 77.9, 76.6, 73.8, 73.1, 72.9, 72.1, 72.0, 69.8, 68.3, 67.9, 67.3, 63.2, 59.8, 37.9, 37.8, 37.6, 29.6, 29.5, 28.3, 28.2, 28.0, 26.7, 14.9. HRMS-MALDI: (M+Na$^+$) calcd. 523.1766 found 523.1796

Ethyl 2-O-acetyl-3-O-benzyl-4,6-O-benzylidene-1-thio-O-D-glucopyranoside (3)

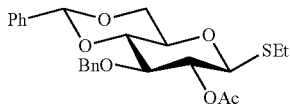

3

A solution of compound 36 (13.9 g, 34.5 mmol) in pyridine: acetic anhydride (4/1, v/v, 0.2 M) was stirred for 6 hr at ambient temperature. TLC (hexanes/EtOAc, 70/30, v/v) indicated the consumption of the starting material, after which the mixture was concentrated in vacuo. The residue was purified by silica gel column chromatography using a gradient of hexanes/EtOAc (80/20, v/v) to obtain 1 (13.0 g, 85%). [α]$_D^{25}$ −5.7 (c=1, CHCl$_3$); $^1$H NMR (300 MHz, CDCl$_3$): δ 7.51-7.25 (10H, CH Aromatic), 5.58 (s, 1H, CH benzylidene), 5.09-5.02 (m, 1H,H2), 4.89 (d, 1H, J=12.0 Hz, CHHBn), 4.68 (d, 1H, J=12.0 Hz, CHHBn), 4.48 (d, 1H, J=10.2 Hz, H1), 4.38 (dd, 1H, J=4.8 Hz, J=5.7 Hz,H6a), 3.82-3.71 (m, 3H, H3, H4, H6b), 3.503-3.46 (m, 1H, H5), 2.74-2.67 (m, 2H, CH$_2$SEt), 2.01 (s, 1H, CH$_3$ Ac), 1.25 (t, 3H, J=7.5 Hz, CH$_3$SEt). $^{13}$C NMR (75.5 MHz, CDCl$_3$): δ 169.3, 138.1, 138.1, 137.1, 128.9, 128.2, 128.2, 127.7, 127.6, 125.9, 101.1, 84.1, 81.4, 79.6, 77.4, 77.0, 76.6, 74.2, 71.1, 70.5, 68.5, 23.8, 20.8, 14.7. HRMS-MALDI: (M+Na$^+$) calcd. 467.1504, found: 467.1585

Ethyl 2-O-levulinoyl-3-O-benzyl-4,6-O-benzylidene-1-thio-β-D-glucopyranoside (4)

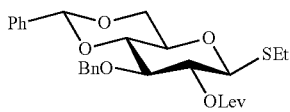

4

A solution of DCC (0.5 g, 1.24 mmol) and DMAP (0.03 g, 0.25 mmol) in DCM (2 mL) was added to a solution of compound 36 (0.5 g, 1.24 mmol) and levulinoylic acid (0.21 g, 1.86 mmol) in DCM (0.2 M) at 0° C. After stirring for 4 hr at ambient temperature TLC (hexanes/EtOAc, 70/30, v/v) indicated the consumption of the starting material, the mixture was filtered and the filtrate was concentrated in vacuo. The residue was purified by silica gel column chromatography using a gradient of hexanes/EtOAc to obtain 2 (0.42 g, 70%). [α]$_D^{25}$ −22.9 (c=1, CHCl$_3$); $^1$HNMR (300 MHz, CDCl$_3$): δ 7.47-7.25 (10H, CH Aromatic), 5.58 (s, 1H, CH benzylidene), 5.08-5.02 (m, 1H, H2), 4.89 (d, 1H, J=12.0 Hz, CHHBn), 4.68 (d, 1H, J=12.0 Hz, CHHBn), 4.48 (d, 1H, J=9.9 Hz, H1), 4.38 (dd, 1H, J=4.8 Hz, J=5.7 Hz, H6a), 3.81-3.71 (m, 3H, H3, H4, H6b), 3.50-3.47 (m, 1H, H5), 2.75-2.64 (m, 4H, CH$_2$ SEt, CH$_2$ Lev), 2.54 (t, 2H, J=6.6 Hz, CH$_2$ Lev), 2.17 (s, 3H, CH$_3$ Lev), 1.25 (t, 3H, J=7.5 Hz, CH$_3$ SEt). $^{13}$C NMR (75.5 MHz, CDCl$_3$): δ 206.1, 171.4, 138.1, 137.1, 129.0, 128.2, 127.9, 127.6, 125.9, 101.2, 84.1, 81.4, 79.5, 77.4, 77.0, 76.6, 74.3, 71.6, 70.6, 68.5, 37.8, 29.8, 27.9, 24.0, 14.8. HRMS-MALDI: (M+Na$^+$) calcd. 523.1766, found 523.1773.

Dimethylthexylsilyl 6-O-acetyl-2-azido-3-O-benzy2-deoxy-β-D-glucopyranoside (5)

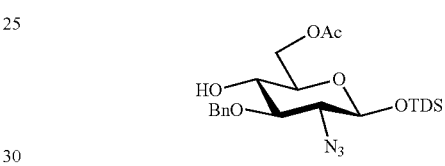

5

To a solution of compound 31 (1.62 g, 3.70 mmol) in DCM (62 mL) was added acetic acid (0.44 g, 7.4 mmol) and 2-chloromethyl pyridinium iodide (CMPI) (2.36 g, 9.25 mmol). The mixture was stirred for 15 minutes at room temperature followed by the addition of 1,4-diazabicyclo[2,2,2]octane (DABCO) (0.980 g, 8.75 mmol). Stirring was continued until TLC indicated consumption of starting material (~1.5 hr). The reaction mixture was filtered through Celite, diluted with EtOAc (40 mL), and washed with brine (2×20 mL). The combined organic layers were dried (MgSO$_4$), filtered and the filtrate concentrated in vacuo. Silica gel column chromatography of the residue (hexanes/EtOAc, 75/25, v/v) afforded 5 (1.20 g, 67%). $^1$H NMR (300 MHz, CDCl$_3$): δ 7.37-7.24 (m, 5H, CH aromatic), 4.93 (d, 1H, J=11.4 Hz, CHHBn), 4.71 (d, 1H, J=11.4 Hz, CHHBn), 4.50 (d, 1H, J=7.2 Hz, H1), 4.28 (m, 2H, H6a, H6b), 3.46-3.36 (m, 2H, H4, H5), 3.28 (dd, J=7.2 Hz, J=9.7 Hz, 1H, H2), 3.10 (dd, J=8.0 Hz, J=9.7 Hz, 1H, H3), 2.05 (s, 3H, CH$_3$ Lev), 1.65-1.56 [m, 1H, CH(CH$_3$)$_2$], 0.89-0.87 [4s, 12H, C(CH$_3$)$_2$ and CH(CH$_3$)$_2$], 0.18-0.17 [2s, 6H, Si(CH$_3$)$_2$]. HRMS-MALDI: (M+Na$^+$) calcd. 502.2349, found 502.2367.

Dimethylthexylsilyl 6-O-levulinoyl-2-azido-3-O-benzyl-2-deoxy-β-D-glucopyranoside (6)

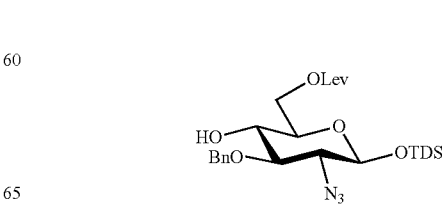

6

To a solution of 31 (1.82 g, 4.16 mmol) in DCM (70 mL) was added levulinic acid (0.96 g, 8.32 mmol) and 2-chloromethyl pyridinium iodide (CMPI) (2.66 g, 10.4 mmol). The mixture was stirred for 15 minutes at room temperature followed by the addition of 1,4-diazabicyclo[2,2,2]octane (DABCO) (1.77 g, 15.8 mmol). Stirring was continued until TLC indicated consumption of the starting material (2 hr). The reaction mixture was filtered through Celite, diluted with EtOAc (50 mL), and washed with brine (2×25 mL). The combined organic layers were dried (MgSO$_4$), filtered, the filtrate was concentrated in vacuo. Silica gel column chromatography (Hexanes/EtOAc, 75/25, v/v) afforded 6 (2.0 g, 89%). [α]$_D^{25}$ +24.2 (c=1, CHCl$_3$); $^1$H NMR (300 MHz, CDCl$_3$): δ 7.49-7.07 (m, 5H, CH Aromatic), 4.94 (d, 1H, J=11.3 Hz, CHHBn), 4.74 (d, 1H, J=11.3 Hz, CHHBn), 4.50 (d, 1H, J=7.6 Hz, H1), 4.36 (dd, 1H, J=5.0 Hz, J=11.7 Hz, H6a), 4.30 (bd, J=11.7, 1H, H6b), 3.48-3.39 (m, 2H, H4, H5), 3.30 (dd, 1H, J=7.6 Hz, J=10.0 Hz, H2), 3.21 (dd, 1H, J=8.5 Hz, J=10.0 Hz, H3), 2.76-2.72 (m, 2H, CH$_2$ Lev), 2.59 (m, 3H, CH$_2$ Lev, 4-OH), 2.17 (s, 3H, CH$_3$ Lev), 1.70-1.62 [m, 1H, CH(CH$_3$)$_2$], 0.89-0.87 [4s, 12H, C(CH$_3$)$_2$ and CH(CH$_3$)$_2$], 0.18-0.17 [2s, 6H, Si(CH$_3$)$_2$]. $^{13}$C NMR (75.5 MHz, CDCl$_3$): δ 206.8, 173.2, 138.1, 128.7, 128.1, 97.1, 82.1, 75.0, 73.6, 70.2, 68.3, 63.5, 37.9, 33.9, 29.8, 27.9, 24.8, 19.9, 19.8, 18.5, 18.4, −2.1, −3.3. HRMS-MALDI: (M+Na$^+$) calcd. 558.2611, found 558.2637.

N-(Benzyl)-benzyloxycarbonyl-5-aminopentyl O-6-O-acetyl-2-azido-3-O-benzyl-2-deoxy-α-D-glycopyranoside (7)

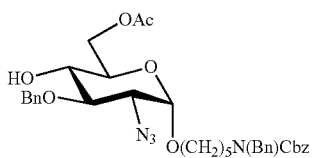

7

To a solution of compound 32 (1.5 g, 2.50 mmol) in DCM (45 mL) was added acetic acid (0.165 g, 2.50 mmol) and 2-chloromethyl pyridinium iodide (CMPI) (1.59 g, 6.25 mmol). The mixture was stirred for 15 minutes at room temperature and then cooled to −20° C. followed by the addition of 1,4-diazabicyclo[2,2,2]octane (0.98 g, 8.75 mmol). The reaction was slowly warmed to room temperature in about 1.5 hr and the progress of the reaction was monitored by TLC (hexanes/EtOAc, 1/1, v/v). The reaction mixture was filtered through Celite, diluted with EtOAc (100 mL) and washed with 5% solution of NaCl (2×25 mL). The organic layers were dried (MgSO$_4$), filtered and the filtrate was concentrated in vacuo. Silica gel column chromatography of the residue (hexanes/EtOAc, 75/25, v/v) provided 7 (1.10 g, 68%). [α]$_D^{25}$ +50 (c=1.00, CHCl$_3$); $^1$HNMR (500 MHz, 95:5 CD$_3$COCD$_3$/CD$_3$OD): δ 7.40-7.10 (m, 15H, CH Aromatic), 5.22-5.12 (m, 2H, CH$_2$ Cbz), 5.00 (d, 1H, J=11.2 Hz, CHHBn), 4.92-4.84 (m, 1H, H1), 4.78 (d, 1H, J=11.2 Hz, CHHBn), 4.54 (bs, 1H, NCH$_2$Bn), 4.14 (bd, 1H, J=11.8 Hz, H6a), 4.20 (dd, 1H, J=6.2 Hz, J=11.8 Hz, H6b), 3.86-3.77 (m, 2H, H3, H5), 3.77-3.64 (m, 1H, OCHH Linker), 3.60 (dd, 1H, J=9.1 Hz, J=9.5 Hz, H4), 3.48-3.36 (m, 1H, OCHH Linker), 3.32-3.22 (m, 3H incl. H2: dd, J=3.4 Hz, J=10.2 Hz, CH$_2$N Linker), 2.00 (s, 3H, CH$_3$ Ac), 1.67-1.53 (m, 4H, 2×CH$_2$ Linker), 1.45-1.34 (m, 2H, CH$_2$ Linker). $^{13}$C NMR (75.5 MHz, CDCl$_3$): δ 171.6, 156.7, 156.2, 137.9, 137.8, 136.8, 136.5, 128.6, 128.5, 128.4, 128.1, 128.0, 127.9, 127.8, 127.3, 87.9, 79.4, 75.1, 70.9, 70.6, 70.0, 68.1, 67.2, 62.9, 62.8, 50.4, 47.3, 46.0, 28.8, 27.3, 23.5, 23.3, 20.7. HRMS-MALDI: (M+Na$^+$) calcd. 669.2895, found 669.2901.

N-(Benzyl)-benzyloxycarbonyl-5-aminopentyl O-2-azido-6-O-levulinoyl-3-O-benzyl-2-deoxy-α-D-glycopyranoside (8)

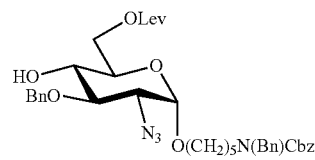

8

To a solution of 32 (2.0 g, 3.30 mmol) in DCM (45 mL) was added levulinic acid (0.42 g, 3.63 mmol) and 2-chloromethyl pyridinium iodide (CMPI) (2.10 g, 8.25 mmol). The mixture was stirred for 15 minutes at room temperature and then cooled to −20° C. followed by the addition of 1,4-diazabicyclo[2,2,2]octane (1.29 g, 11.55 mmol). The reaction mixture was allowed to warm up slowly to room temperature. Stirring was continued until TLC (hexanes/EtOAc, 1/1, v/v) indicated consumption of starting material (1.5 hr). The reaction mixture was filtered through Celite, diluted with EtOAc (100 mL) and washed with a 5% solution of NaCl (2×25 mL). The organic layers were dried (MgSO$_4$), filtered and the filtrate was concentrated in vacuo. Silica gel column chromatography of the residue (hexanes/EtOAc, 26/74, v/v) afforded 6 (3.80 g, 82%). [α]$_D^{25}$ +63 (c=1.00, CHCl$_3$); $^1$H NMR (500 MHz, 95:5 CD$_3$COCD$_3$/CD$_3$OD): δ 7.40-7.10 (m, 15H, CH Aromatic), 5.22-5.12 (m, 2H, CH$_2$ Cbz), 5.0 (d, 1H, J=11.2 Hz, CHHBn), 4.92-4.83 (m, 1H, H1), 4.78 (d, 1H, J=11.2 Hz, CHHBn), 4.54 (bs, 2H, NCH$_2$Bn), 4.17 (bd, 1H, J=11.8 Hz, H6a), 4.20 (dd, 1H, J=6.2 Hz, J=11.8 Hz, H6b), 3.86-3.77 (m, 2H, H3, H5), 3.77-3.64 (m, 1H, OCHH Linker), 3.60 (dd, 1H, J=9.1 Hz, J=9.5 Hz, H4), 3.48-3.36 (m, 1H, OCHH Linker), 3.32-3.22 (m, 3H incl. H2: dd, J=3.4 Hz, J=10.2 Hz, CH$_2$N Linker), 2.76-2.71 (t, 2H, J=6.5 Hz, CH$_2$ Lev), 2.52 (t, 2H, J=6.5 Hz, CH$_2$ Lev), 2.11 (s, 3H, CH$_3$ Ac), 1.67-1.53 (m, 4H, 2×CH$_2$ Linker), 1.45-1.34 (m, 2H, CH$_2$ Linker). $^{13}$C NMR (75.5 MHz, CDCl$_3$): δ 206.5, 173.3, 138.0, 137.8, 128.5, 128.4, 128.0, 127.9, 127.8, 127.2, 97.8, 79.3, 75.0, 70.8, 70.6, 70.0, 68.1, 67.1, 63.1, 62.7, 50.3, 47.3 46.0, 37.8, 29.7, 28.8, 27.7, 27.3, 23.5. HRMS-MALDI: (M+Na$^+$) calcd. 725.3157, found 725.3145.

Dimethylthexylsilyl O-(methyl-2-O-acetyl-3-O-benzyl-4-O-(9-fluorenylmethoxycarbonyl)-β-D-glucopyranosyluronate)-(1→4)-O-2-azido-3-O-benzyl-2-deoxy-6-O-acetyl-β-D-glucopyranoside (9)

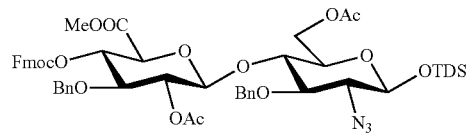

9

Disaccharide 41 (63 mg, 0.078 mmol) was subjected to to the general procedure for synthesis of Fmoc protected disaccharides. Silica gel chromatography (toluene/EtOAc, 95/5 to 90/10, v/v) afforded 9 (50 mg, 62%). $[\alpha]_D^{25}$ +34.3 (c=1, CHCl$_3$); $^1$H NMR (500 MHz, CDCl$_3$): δ 7.36-7.25 (m, 20H, CH Aromatic), 5.06-5.00 (m, 2H, H4$^B$, H2$^B$), 4.95 (d, 1H, J=12.0, CHHBn), 4.82 (d, 1H, J=12.0 Hz, CHHBn), 4.66 (d, 1H, J=11.5 Hz, CHHBn), 4.62 (d, 1H, J=8.0 Hz, H1$^B$), 4.53 (d, 1H, J=12.0 Hz, CHHBn), 4.46 (d, 1H, J=7.5 Hz, H1$^A$), 4.42 (dd, 1H, J=7.0 Hz, J=10.5 Hz, CHH Fmoc), 4.37-4.31 (m, 2H, CHHFmoc, H6b$^A$), 4.20 (t, 1H, J=7.5 Hz, CH Fmoc), 4.08 (dd, 1H, J=6.5 Hz, J=11.5 Hz, H6a$^A$), 3.82 (d, 1H, H5$^B$), 3.71 (t, 1H, J=9.0 Hz, H3$^B$), 3.64 (t, 1H, J=9.5 Hz, H4$^A$), 3.46 (s, 1H, CO$_2$CH$_3$), 3.47-3.44 (m, 1H, H5$^A$), 3.39 (t, 1H, J=9.5 Hz, H3$^A$), 3.30-3.26 (m, 1H, H2$^A$), 2.05 (s, 3H, CH$_3$ Ac), 1.92 (s, 3H, CH$_3$ Ac), 1.66-1.61 [m, 1H, CH(CH$_3$)$_2$], 0.88-0.86 [4s, 12H, C(CH$_3$)$_2$, CH(CH$_3$)$_2$], 0.16-0.15 [2s, 6H, Si(CH$_3$)$_2$]. HRMS-MALDI: (M+Na$^+$) calcd. 1046.4082, found 1046.4091.

Dimethylthexylsilyl O-(methyl-2-O-levulinoyl-3-O-benzyl-4-O-(9-O-fluorenylmethoxycarbonyl)-β-D-glucopyranosyluronate)-(1→4)-O-2-azido-3-O-benzyl-2-deoxy-6-O-acetyl-β-D-glucopyranoside (10)

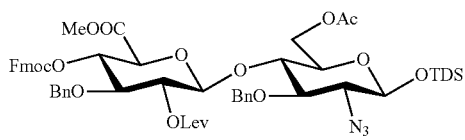

Disaccharide 42 (20 mg, 0.023 mmol) was subjected to the general procedure for synthesis of Fmoc protected disaccharides. Silica gel chromatography (toluene/EtOAc 95/5 to 90/10, v/v) afforded 10 (17 mg, 68%). $[\alpha]_D^{25}$ −9.6 (c=1, CHCl$_3$); $^1$H NMR (500 MHz, CDCl$_3$): δ 7.60-7.02 (m, 20H, CH Aromatic), 4.93-4.87 (m, 2H, H4$^B$, H2$^B$), 4.81 (d, 1H, J=11.5 Hz, CHHBn), 4.63 (d, 1H, J=11.5 Hz, CHHBn), 4.47-4.46 (m, 2H, CHHBn, H1$^B$), 4.42 (d, 1H, J=12.0 Hz, CHHBn), 4.33 (d, 1H, J=8.0 Hz, H1$^A$), 4.27-4.22 (m, 2H, CHH Fmoc, H6a$^A$), 4.17-4.13 (m, 1H, CHHFmoc), 4.04 (t, 1H, J=7.0 Hz, CH Fmoc), 3.96 (dd, 1H, J=6.5 Hz, J=12.0 Hz, H6b$^A$), 3.68 (d, 1H, J=10.0 Hz, H5$^B$), 3.57 (t, 1H, J=9.5 Hz, H3$^B$), 3.52 (t, 1H, J=8.5 Hz, H4$^A$), 3.42-3.39 (m, 1H, H5$^A$), 3.31 (s, 3H, CO$_2$CH$_3$), 3.21 (t, 1H, J=8.5 Hz, H3$^A$), 3.13 (t, 1H, J=8.0 Hz, H2$^A$), 2.61-2.55 (m, 1H, CHH Lev), 2.50-2.36 (m, 2H, CH$_2$ Lev), 2.23-2.17 (m, 1H, CHH Lev), 1.99 (s, 3H, CH$_3$ Lev), 1.19 (s, 3H, CH$_3$ Ac), 1.51-1.45[m, 1H, CH(CH$_3$)$_2$], 0.72-0.70 [4s, 12H, C(CH$_3$)$_2$ and CH(CH$_3$)$_2$], 0.014-0.00 [2s, 6H, Si(CH$_3$)$_2$]. $^{13}$C NMR (75.5 MHz, CDCl$_3$): δ 206.0, 171.2, 170.6, 168.6, 167.0, 153.9, 143.2, 142.9, 141.3, 138.6, 137.5, 128.3, 128.2, 127.9, 127.7, 127.7, 127.3, 127.2, 125.1, 125.0, 120.1, 101.0, 96.7, 81.0, 79.4, 78.7, 77.4, 77.06, 76.6, 75.0, 74.8, 74.4, 72.5, 72.4, 68.7, 62.7, 61.0, 58.3, 52.6, 46.6, 37.5, 33.9, 29.8, 29.7, 27.6, 24.8, 20.7, 19.9, 19.8, 18.4, 18.3, −2.2, −3.2. HRMS-MALDI: (M+Na$^+$) calcd. 1102.4344, found 1102.4363.

Dimethylthexylsilyl O-(methyl-2-O-acetyl-3-O-benzyl-4-O-(9-fluorenylmethoxycarbonyl)-β-D-glucopyranosyluronate)-(1→4)-O-2-azido-3-O-benzyl-2-deoxy-6-O-levulinoyl-β-D-glucopyranoside) (11)

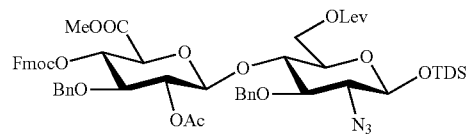

Disaccharide 43 (30 mg, 0.033 mmol) was subjected to the general procedure for synthesis of Fmoc protected disaccharides. Silica gel chromatography of the residue (toluene/EtOAc, 95/5 to 90/10, v/v) afforded 11 (30 mg, 81%). $[\alpha]_D^{25}$ +14.2 (c=1, CHCl$_3$); $^1$H NMR (500 MHz, CDCl$_3$): δ 7.60-7.02. (m, 20H, CH Aromatic), 4.93-4.87 (m, 3H, H4$^B$, H2$^B$, CHHBn), 4.60 (d, 1H, J=12.0 Hz, CHHBn), 4.55 (d, 1H, J=8.0 Hz, H1$^B$), 4.51 (d, 1H, J=11.5 Hz, CHHBn), 4.40 (d, 1H, J=12.0 Hz, CHHBn), 4.30 (d, 1H, J=7.5 Hz, H1$^A$), 4.25 (dd, 1H, J=7.0 Hz, J=10.5 Hz, CHH Fmoc), 4.16-4.13 (m, 2H, CHH Fmoc, H6a$^A$), 4.06-4.00 (m, 2H, H6b$^A$, CH Fmoc), 3.95-3.86 (m, 1H, H5$^B$), 3.73 (t, 1H, J=9.5 Hz, H3$^B$), 3.60 (t, 1H, J=9.5 Hz, H4$^A$), 3.30 (s, 3H, CO$_2$CH$_3$), 3.26-3.24 (m, 1H, H5$^A$), 321 (t, 1H, J=9.0 Hz, H3$^A$), 3.12 (t, 1H, J=8.0 Hz, H2$^A$), 2.72-2.66 (m, 1H, CHH Lev), 2.58-2.52 (m, 1H, CHHLev), 2.49-2.42 (m, 1H, CHH Lev), 2.39-2.33 (m, 1H, CHHLev), 2.19 (s, 3H, CH$_3$ Lev), 2.04 (s, 3H, CH$_3$ Ac), 1.67-1.61 [m, 1H, CH(CH$_3$)$_2$], 0.88-0.86 [4s, 12H, C(CH$_3$)$_2$ and CH(CH$_3$)$_2$], 0.16-0.15 [2s, 6H, Si(CH$_3$)$_2$]. $^{13}$C NMR (75.5 MHz, CDCl$_3$): δ 206.5, 172.4, 169.2, 167.2, 154.0, 143.3, 143.0, 141.2, 138.6, 137.6, 128.3, 128.2, 127.9, 127.7, 127.6, 127.5, 127.3, 127.1, 125.1, 125.0, 120.0, 100.9, 96.8, 80.8, 79.4, 78.3, 77.4, 77.0, 76.6, 75.2, 75.0, 74.3, 72.5, 72.4, 72.3, 70.3, 68.6, 62.4, 52.6, 46.6, 37.9, 33.9, 29.8, 29.7, 27.8, 24.8, 20.7, 19.9, 19.8, 18.4, 18.3, −2.1, −3.2. HRMS-MALDI: (M+Na$^+$) calcd. 1102.4344, found 1102.4363.

Dimethylthexylsilyl O-(methyl-2-O-levulinoyl-3-O-benzyl-4-O-(9-fluorenylmethoxycarbonyl)-β-D-glucopyranosyluronate)-(1→4)-O-2-azido-3-O-benzyl-2-deoxy-6-O-levulinoyl-θ-D-glucopyranoside) (12)

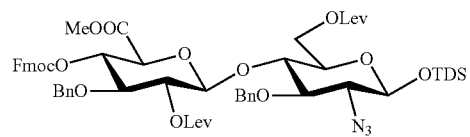

Disaccharide 44 (40 mg, 0.043 mmol) was subjected to the general procedure for synthesis of Fmoc protected disaccharides. Silica gel chromatography of the residue (toluene/EtOAc, 95/5 to 90/10, v/v) afforded 12 (40 mg, 82%). $[\alpha]_D^{25}$ +15.5 (c=1, CHCl$_3$); $^1$H NMR (500 MHz, CDCl$_3$): δ 7.75-7.20 (m, 25H, CH Aromatic), 5.10-5.04 (m, 3H, H4$^B$, H2$^B$, CHHBn), 4.74-4.71 (m, 2H, CHHBn, H1$^B$), 4.66 (d, J=11.5 Hz, 1H, CHHBn), 4.60 (d, J=11.5 Hz, CHHBn), 4.47 (d, J=7.5 Hz, 1H, H1$^A$), 4.40 (dd, J=7.0 Hz, J=10.5 Hz, 1H, H6a$^A$), 4.34 (dd, J=1.5 Hz, J=11.5 Hz, 1H, H6b$^A$), 4.30-4.26 (m, 2H, CHH Fmoc, CHHFmoc), 4.20 (t, 1H, J=7.5 Hz, CH Fmoc), 3.14 (d, 1H, J=10.0 Hz, H5$^B$), 3.89 (t, 1H, J=9.5 Hz, H3$^B$), 3.76 (t, 1H, J=8.5 Hz, H4$^A$), 3.42-3.40 (m, 1H, H5$^A$), 3.46 (s, 3H, CO$_2$CH$_3$), 3.37 (t, 1H, J=9.5 Hz, H3$^A$), 3.27 (t, 1H, J=8.0 Hz, H2$^A$), 2.88-2.49 (m, 8H, 4×CH$_2$ Lev) 2.21 (s, 3H, CH$_3$ Lev), 1.15 (s, 3H, CH$_3$ Lev), 1.66-1.61 [m, 1H, CH(CH$_3$)$_2$], 0.88-0.86 [4s, 12H, C(CH$_3$)$_2$ and CH(CH$_3$)$_2$], 0.16-0.15 [2s, 6H, Si(CH$_3$)$_2$]. $^{13}$C NMR (75.5 MHz, CDCl$_3$): δ 206.6, 206.0, 172.5, 171.2, 167.3, 154.0, 143.3, 143.0, 141.2, 138.7, 137.8, 128.5, 128.2, 128.1, 127.9, 127.6, 127.5, 127.3, 127.1, 126.2, 126.1, 125.8, 125.1, 125.0, 120.0, 100.8, 96.8, 80.9, 79.5, 78.2, 77.9, 77.4, 77.0, 76.6, 75.1, 74.4, 72.7, 72.3, 72.2, 70.3, 68.6, 67.3, 62.7, 62.6, 52.5, 46.5, 37.5, 33.9, 29.7, 27.9, 27.6, 24.8, 19.9, 19.8, 18.4, 18.3, −2.1, −3.2. HRMS-MALDI: (M+Na$^+$) calcd. 1135.4709, found 1135.4715.

Dimethylthexylsilyl O-(methyl-2-O-acetyl-3-O-benzyl-4-O-(9-fluorenylmethoxycarbonyl)-α-L-idopyranosyluronate)-(1→4)-O-2-azido-3-O-benzyl-2-deoxy-6-O-acetyl-α-D-glucopyranoside (13)

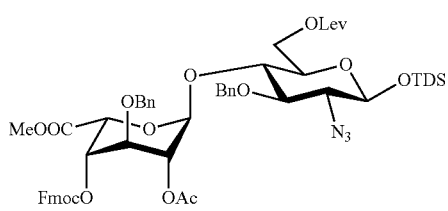

Disaccharide 53 (19.3 mg, 0.023 mmol) was subjected to the general procedure for synthesis of Fmoc protected disaccharides. Silica gel chromatography (Toluene/EtOAc, 95/5 to 90/10) afforded 13 (18 mg, 76%). [α]$_D$$^{25}$ −32.4 (c=0.7, CHCl$_3$); $^1$H NMR (500 MHz, CDCl$_3$): δ 7.74-7.73 (m, 2H, CH Aromatic), 7.55-7.54 (m, 2H,CH Aromatic), 7.39-7.21 (m, 25H, CH Aromatic), 5.13 (bs, 1H, H1$^B$), 4.99-4.98 (m, 2H, H5$^B$, H4$^B$), 4.85 (bs, 1H, H2$^B$), 4.73-4.69 (m, CHHBn, CHHBn, CHHBn), 4.61 (d, 1H, J=11.0 Hz, CHHBn), 4.53-4.48 (m, 2H, H1$^A$, H6a$^A$), 4.42 (dd, 1H, J=7.3 Hz, J=10.4 Hz, CHH Fmoc), 4.33 (dd, 1H, J=7.3 Hz J=10.4 Hz, CHHFmoc), 4.19 (t, 1H, J=7.3 Hz, CH Fmoc), 4.12 (dd, 1H, J=5.3 Hz, J=12.0 Hz, H6$_b$$^A$), 3.86-3.83 (m, 2H, H3$^B$, H4$^A$), 3.45-3.44 (m, 4H incl. s at 3.44: CO$_2$CH$_3$,H5$^A$), 3.33 (t, 1H, J=7.8 Hz, J=9.8 Hz, H2$^A$), 3.23 (t, 1H, J=9.3 Hz, J=9.6 Hz, H3$^A$), 2.06-1.96 (s, 6H, CH$_3$ Ac), 1.65-1.53 [m, 1H, CH(CH$_3$)$_2$], 0.88-0.75 [4s, 12H, C(CH$_3$)$_2$ and CH(CH$_3$)$_2$], 0.17-0.16 [2s, 6H, Si(CH$_3$)$_2$]. $^{13}$C NMR (75.5 MHz, CDCl$_3$): δ 170.5, 169.9, 168.3, 154.2, 143.2, 143.0, 141.3, 141.3, 137.9, 137.2, 128.5, 128.2, 128.1, 128.0, 127.9, 127.7, 127.5, 127.4, 127.2, 127.1, 125.1, 125.0, 120.1, 97.5, 97.0, 80.9, 80.6, 77.4, 77.2, 77.0, 76.6, 74.7, 73.3, 72.8, 72.8, 72.6, 71.2, 70.2, 68.9, 67.3, 66.6, 62.2, 52.2, 46.6, 33.9, 29.7, 24.8, 2 20.8, 20.8, 19.9, 19.8, 18.5, 18.3,−2.2, −3.3. HRMS-MALDI: (M+Na$^+$) calcd. 1046.4082, found 1046.4091.

Dimethylthexylsilyl O-(methyl-3-O-benzyl-4-O-(9-fluorenylmethoxycarbonyl)-2-O-levulinoyl-α-L-idopyranosyluronate)-(1→4)-O-2-azido-3-O-benzyl-2-deoxy-6-O-acetyl-β-D-glucopyranoside (14)

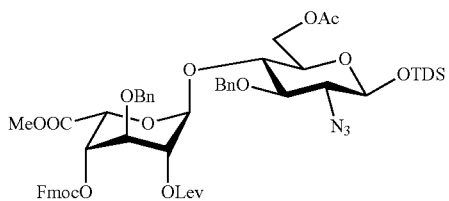

Disaccharide 54 (15 mg, 0.017 mmol) was subjected to the general procedure for synthesis of Fmoc protected disaccharides. Silica gel chromatography of the residue (toluene/EtOAc, 95/5 to 90/10, v/v) afforded 14 (16.9 mg, 90%). [α]$_D$$^{25}$ −16.1 (c=1.7, CHCl$_3$); $^1$H NMR (500 MHz, CDCl$_3$): δ 7.74-7.72 (m, 2H, CH Aromatic), 7.55-7.54 (m, 2H,CH Aromatic), 7.39-7.20 (m, 24H, CH Aromatic), 5.10 (bs, 1H, H1$^B$), 4.99 (d, 1H, J=3.0 Hz, J=4.0 Hz, H4$^B$), 4.97 (t, 1H, J=3.0 Hz, H5$^B$), 4.86 (t, 1H, J=2.3 Hz, H2$^B$), 4.72 (d, 1H, J=11.3 Hz, CHHBn), 4.70-4.67 (m, 2H, CHHBn, CHHBn), 4.60 (d, 1H, J=11.0 Hz, CHHBn), 4.50-4.46 (m, 2H, H1$^A$, H6a$^A$), 4.45 (dd, 1H, J=7.3 Hz, J=10.5 Hz, CHH Fmoc), 4.35 (dd, 1H, J=7.3 Hz, J=10.5 Hz, CHHFmoc), 4.19 (t, 1H, J=7.3 Hz, CH Fmoc), 4.12 (dd, 1H, J=5.0 Hz, J=12.1 Hz, H6b$^A$), 3.88-3.84 (m, 2H, H3$^B$, H4$^A$), 3.46 (ddd, 1H, J=2.2 Hz, J=4.8 Hz, J=11.9 Hz, H5$^A$), 3.42 (s, 3H, CO$_2$CH$_3$), 3.32 (dd, 1H, J=7.6 Hz, J=9.9 Hz, H2$^A$), 3.22 (t, 1H, J=9.3 Hz, H3$^A$), 2.81-2.54 (m, 2H, CH$_2$ Lev), 2.55-2.40 (m, 3H, CH$_2$ Lev), 2.07 (s, 3H, CH$_3$ Lev), 2.04 (s, 3H, CH$_3$ Ac), 1.64-1.42 [m, 1H, CH(CH$_3$)$_2$], 0.88-0.85 [4s, 12H,C(CH$_3$)$_2$ and CH(CH$_3$)$_2$], 0.12-0.11 (2s, 6H, Si(CH$_3$)$_2$]. $^{13}$C NMR (75.5 MHz, CDCl$_3$): δ 206.1, 171.7, 170.6, 168.3, 154.3, 143.2, 143.1, 141.3, 141.3, 137.9, 137.3, 128.4, 128.2, 128.0, 127.9, 127.5, 127.4, 127.12, 125.1, 125.0, 124.3, 120.1, 97.5, 97.0, 80.9, 77.4, 77.0, 76.6, 74.8, 74.7, 73.2, 72.9, 72.7, 71.2, 70.1, 68.9, 67.3, 66.8, 62.3, 52.2, 46.6, 37.6, 33.9, 29.5, 27.9, 24.8, 20.8, 20.9, 19.9, 19.8, 18.4, 18.5, 18.3, −2.2, −3.3. HRMS-MALDI: (M+Na$^+$) calcd. 1102.4344, found 1102.4363.

Dimethylthexylsilyl O-(methyl 2-O-acetyl-3-O-benzyl4-O-(9-fluorenylmethoxycarbonyl)-α-L-idopyranosyluronate)-(1→4)-O-2-azido-3-O-benzyl-2-deoxy-6-O-levylinyl-β-D-glucopyranoside (15)

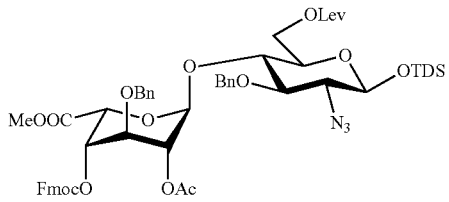

Disaccharide 55 (56.5 mg, 0.065 mmol) was subjected to the general procedure for synthesis of Fmoc protected disaccharides. Silica gel chromatography of the residue (toluene/EtOAc, 95/5 to 90/10, v/v) afforded 15 (51.4 mg, 73%). [α]$_D^{25}$ +13 (c=1.5, CHCl$_3$); $^1$H NMR (500 MHz, CDCl$_3$): δ 7.74-7.73 (m, 2H, CHAromatic), 7.54-7.53 (m, 2H,CHAromatic), 7.28-7.08 (m, 25H, CH Aromatic), 5.07 (bs, 1H, H1$^B$), 4.99 (d, 1H, J=2.6 Hz, H5$^B$), 4.97 (t, 1H, J=3.2 Hz, H4$^B$), 4.84 (bs, 1H, H2$^B$), 4.72 (d, 1H, J=11.3 Hz, CHHBn), 4.69 (d, 1H, J=11.3 Hz,CHHBn), 4.66 (d, 1H, J=11.0 Hz, CHHBn), 4.60 (d, 1H, J=11.0 Hz, CHHBn), 4.55 (dd, 1H, J=2.0 Hz, J=12.0 Hz, H6a$^A$), 4.49 (d, 1H, J=7.3 Hz, H1$^A$), 4.41 (dd, 1H, 7.3 Hz, 10.4 Hz, CHH Fmoc), 4.32 (dd, 1H, J=7.3 Hz, J=10.4 Hz, CHHFmoc), 4.18 (t, 1H, J=7.3 Hz, CHFmoc), 4.08 (dd, 1H, J=4.9 Hz, J=12.0 Hz, H6b$^A$), 3.87-3.84 (m, 2H, H3$^B$, H4$^A$), 3.46-3.43 (m, 4H incl. s at 3.43: CO$_2$CH$_3$, H5$^A$), 3.43 (dd, 1H, J=7.8 Hz, J=9.9 Hz, H2$^A$), 3.11 (t, 1H, J=9.3 Hz, H3$^A$), 2.81-2.42 (m, 1H, CH$_2$ Lev), 2.72-2. (m, 1H, CH$_2$ Lev), 2.54- (m, 2H,CH$_2$ Lev), 2.13 (s, 3H, CH$_3$ Lev), 1.94 (s, 3H, CH$_3$ Ac), 1.60-1.52 [m, 1H, CH(CH$_3$)$_2$], 0.84-0.81 [4s, 12H, C(CH$_3$)$_2$ and CH(CH$_3$)$_2$], 0.12-0.11 [2s, 6H, Si(CH$_3$)$_2$]. $^{13}$C NMR (75.5 MHz, CDCl$_3$): δ 206.6, 172.1, 169.9, 168.3, 154.2, 143.2, 143.0, 141.3, 141.3, 137.9, 137.1, 128.5, 128.2, 128.1, 128.0, 127.9, 127.5, 127.4, 127.1, 127.0, 125.0, 124.9, 120.1, 97.3, 97.0, 80.9, 77.4, 77.0, 76.6, 74.8, 74.1, 73.2, 72.8, 72.7, 71.2, 70.1, 68.9, 67.1, 66.6, 62.4, 52.1, 46.6, 37.9, 33.9, 29.7, 29.6, 28.0, 24.8, 20.8, 20.8, 19.9, 19.8, 18.4, 18.3, −2.2, −3.3. HRMS-MALDI: (M+Na$^+$) calcd. 1102.4344, found 1102.4363.

Dimethylthexylsilyl O-(methyl-2-O-levulinoyl-3-O-benzyl-4-O-(9-fluorenylmethoxycarbonyl)-α-L-idopyranosyluronate)-(1→4)-O-2-azido-3-O-benzyl-2-deoxy-6-O-levulinoyl-β-D-glucopyranoside (16)

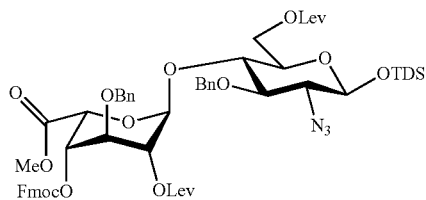

Compound 56 (20 mg, 0.0218 mmol) was subjected to the general procedure for synthesis of Fmoc protected disaccharides. Silica gel chromatography of the residue (toluene/EtOAc, 95/5 to 90/10, v/v) afforded 16 (17 mg, 68%). [α]$_D^{25}$ +17 (c=1, CHCl$_3$); $^1$H NMR (500 MHz, CDCl$_3$): δ 7.75-7.19 (m, 25H, CH Aromatic), 5.04 (bs, 1H, H5$^B$), 4.98 (bs, 2H, H2$^B$, H1$^B$), 4.86 (bs, 2H, H4$^B$), 4.73 (d, 1H, J=11.0 Hz, CHHBn), 4.69 (d, 1H, J=11.5 Hz, CHHBn), 4.66 (d, 1H, J=11.0, CHHBn), 4.58 (d, 1H, J=10.5 Hz, CHHBn), 4.54 (dd, 1H, J=2.0 Hz, J=12.0 Hz, H6a$^A$), 4.50 (d, 1H, J=8.0 Hz, H1$^A$), 4.45 (dd, 1H, J=7.5 Hz, J=10.5 Hz, CHH Fmoc), 4.37 (dd, 1H, J=7.5 Hz, J=10.5 Hz, CHHFmoc), 4.20 (t, 1H, J=7.0 Hz, CH Fmoc), 4.11 (dd, 1H, J=4.5 Hz, J=12.0 Hz, H6b$^A$), 3.911-3.87 (m, 2H, H3$^B$, H4$^A$), 3.48-3.45 (m, 1H, H5$^A$), 3.43 (s, 3H, CO$_2$CH$_3$) 3.33 (dd, 1H, J=7.5 Hz, J=10.0 Hz, H2$^A$), 3.22 (t, 1H, J=9.5 Hz, H3$^A$), 2.86-2.70 (m, 3H, CH$_2$ Lev, CHH Lev), 2.61-2.48 (m, 5H, 2×CH$_2$ Lev, CHHLev), 2.18 (s, 3H, CH$_3$ Lev), 2.06 (s, 3H, CH$_3$ Lev), 1.68-1.60 [m, 1H, CH(CH$_3$)$_2$], 0.90-0.88 [4s, 12H, C(CH$_3$)$_2$ and CH(CH$_3$)$_2$], 0.19-0.17 [2s, 6H, Si(CH$_3$)$_2$]. $^{13}$C NMR (75.5 MHz, CDCl$_3$): δ 206.7, 206.3, 172.1, 171.7, 168.3, 154.2, 143.2, 141.3, 137.9, 137.2, 128.4, 128.3, 128.2, 128.0, 127.9, 127.5, 127.4, 127.1, 125.1, 125.0, 120.0, 97.1, 97.0, 80.9, 77.4, 77.0, 76.6, 74.8, 74.0, 73.1, 72.9, 72.7, 71.2, 70.1, 68.9, 67.1, 66.5, 62.5, 52.1, 46.6, 37.9, 37.6, 33.9, 33.7, 31.9, 30.1, 29.7, 29.5, 29.3, 28.1, 27.9, 24.8, 22.7, 19.9, 19.8, 18.4, 18.3, 14.1, 14.1, −2.1, 3.2. HRMS-MALDI: (M+Na$^+$) calcd. 1135.4709, found 1135.4715.

N-(Benzyl)-benzyloxycarbonyl-5-aminopentyl O-(methyl-2-O-acetyl-3-O-benzyl-β-D-glucopyranosyluronate)-(1→4)-O-2-azido-3-O-benzyl-2-deoxy-6-O-acetyl-α-D-glucopyranoside (17)

Compound S17 (85 mg, 0.090 mmol) was subjected to TEMPO/BAIB mediated oxidation and esterification using diazomethane according to the general procedure. Silica gel chromatography of the residue (toluene/EtOAc, 50/50, v/v) afforded 17 (57.4 mg, 66%, two steps). [α]$_D^{25}$ +25.5 (c=1, CHCl$_3$); $^1$H NMR (500 MHz, CDCl$_3$): δ 7.31-7.13 (m, 20H, CH Aromatic), 5.14-5.11 (m, 2H, CH$_2$ Cbz), 5.01 (d, 1H, J=11.2 Hz, CHHBn), 4.94 (t, 1H, J=8.7 Hz, H2$^B$), 4.78 (d, 1H, J=11.8 Hz, CHHBn), 4.75 (bd, 1H, J=12.0 Hz, H1$^A$), 4.69 (d, 1H, J=11.2 Hz, CHHBn), 4.64 (d, 1H, J=11.8 Hz, CHHBn), 4.53 (d, 1H, J=7.9 Hz, H1$^B$), 4.45 (bd, 2H,J=5.8HzNCH$_2$Bn), 4.33 (bd, 1H, J=11.7 Hz, H6a$^A$), 4.10 (bm, 1H, H6$_b^A$), 3.90-3.86 (m, 2H, H4$^B$, H3$^A$) 3.72-3.71 (m, 2H, H4$^A$, H5$^A$), 3.61-3.59 (bm, 2H,H5$^B$, OCHH Linker), 3.48 (s, 3H, CO$_2$CH$_3$), 3.45 (t, 1H, J=9.3 Hz, H3$^B$), 3.36-3.17 (bm, 4H, OCHH Linker, CH$_2$N Linker), 3.02 (d, 1H, J=2.4 Hz, 4-OH), 2.03-1.98 (2s, 6H, 2×CH$_3$ Ac), 1.55-1.19 (m, 6H, 3×CH$_2$ Linker). $^{13}$C NMR (75.4 MHz, CDCl$_3$): δ 170.7, 169.6, 169.5, 138.8, 138.1, 128.8-127.5, 101.5, 97.9, 81.6, 78.7, 78.2, 77.7, 77.5, 77.3, 76.9, 75.0, 74.9, 74.5, 72.8, 72.3, 68.8, 68.7, 67.4, 63.1, 62.5, 60.6, 52.9, 50.8, 50.5, 47.3, 46.4, 29.2, 28.1, 23.5, 21.3, 21.1, 21.0. HRMS-MALDI: (M+Na$^+$) calcd. 991.3952, found 991.3975.

N-(Benzyl)-benzyloxycarbonyl-5-aminopentyl 0-(methyl-2-O-levulinoyl-3-O-benzyl-β-D-glucopyranosyluronate)-(1→4)-O-2-azido-3-O-benzyl-2-deoxy-6-O-acetyl-α-D-glucopyranoside (18)

Compound S18 (35 mg, 0.035 mmol) was subjected to TEMPO/BAIB mediated oxidation and esterification using diazomethane according to the general procedure. Silica gel chromatography of the residue (toluene/EtOAc, 50/50, v/v) afforded 18 (28 mg, 77%, two steps). [α]$_D^{25}$ 20.3 (c=1, CHCl$_3$); $^1$H NMR (500 MHz, CDCl$_3$): δ 7.36-7.24 (m, 20H, CH Aromatic), 5.16-5.11 (m, 2H, CH$_2$Cbz), 5.08 (d, 1H, J=11.5 Hz, CHHBn), 5.01 (m, 1H, H2$^B$), 4.82 (bd, J=12.0 Hz, 1H,H1$^A$, CHHBn), 4.71-4.65 (m, 2H,CHHBn, CHHBn), 4.57 (d, 1H, J=8.0 Hz, H1$^B$), 4.49 (bs, 2H, NCH$_2$Bn), 4.48 (dd, 1H, J=2.0 Hz, J=12.5 Hz, H6a$^A$), 4.28 (dd, 1H, J=4.5 Hz, J=12.5 Hz, H6b$^A$), 3.96-3.81 (m, 3H, H3$^A$, H5$^A$, H4$^B$), 3.72 (t, 1H, J=9.5 Hz, H5$^B$), 3.68-3.64 (m, 2H, H4$^A$ OCHH Linker), 3.55-3.51 (m, 1H, H3$^B$), 3.51 (s, 3H, CO$_2$CH$_3$), 3.41-3.36 (m, 1H, OCHH Linker), 3.27-3.20 (m, 3H, H2$^A$, CH$_2$N Linker), 2.94 (s, 1H, 4-OH), 2.79-2.74 (m, 0.5H, CHH Lev), 2.71-2.61 (m, 1.5H, CH$_2$ Lev), 2.56-2.36 (m, 0.5H, CHH Lev), 2.18 (bs, 6H, CH$_3$ Ac, CH$_3$ Lev), 1.61-1.26 (m, 6H, 3×CH$_2$ Linker). $^{13}$C NMR (75.5 MHz, CDCl$_3$): δ 205.8, 171.3, 170.6, 169.2, 138.6, 138.1, 137.9, 128.4, 128.2, 127.8, 127.7, 127.7, 127.3, 101.2, 97.5, 81.4, 78.4, 78.0, 77.4, 76.9, 76.5, 74.8, 74.6, 74.1, 72.8, 72.0, 68.3, 68.1, 67.1, 62.8, 62.4, 52.6, 37.5, 37.3, 33.6, 33.3, 32.3, 31.9, 30.6, 30.1, 30.0, 29.6, 29.3, 28.9, 27.8, 27.7, 26.6, 26.3, 23.2, 23.1, 22.6, 22.6, 20.9, 14.1, 14.1. HRMS-MALDI: (M+Na$^+$) calcd. 1047.4215, found 1047.4223.

N-(Benzyl)-benzyloxycarbonyl-5-aminopentyl O-(methyl-O-2-O-acetyl-3-O-benzyl-β-D-glucopyranosyluronate)-(1→4)-O-2-azido-3-O-benzyl-2-deoxy-6-O-levulinoyl-α-D-glucopyranoside (19)

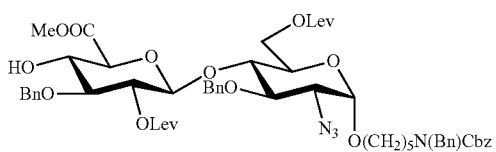

Compound S19 (1.79 g, 1.84 mmol) was subjected to TEMPO/BAIB mediated oxidation and esterification using diazomethane according to the general procedure. Silica gel chromatography of the residue (toluene/EtOAc, 50/50, v/v) afforded 19 (1.5 g, 79%, two steps). [α]$_D^{25}$ +47.3 (c=1, CHCl$_3$); $^1$H NMR (500 MHz, CDCl$_3$): δ 7.37-7.18 (m, 20H, CH Aromatic), 5.19-5.13 (m, 2H, CH$_2$Cbz, CHHBn), 5.02 (t, 1H, J=8.5 Hz, H2$^B$), 4.86-4.80 (m, 1H, H1$^A$, CHHBn), 4.71-4.65 (m, 3H, CHHBn, CHHBn, H1$^B$), 4.48 (bd, 2H, J=6.5 Hz, NCH$_2$Bn), 4.36 (bd, 1H, J=11.5 Hz, H6a$^A$), 4.23 (d, 1H, J=12.0 Hz, H6b$^A$), 4.02 (d, 1H, J=9.5 Hz, H5$^B$), 3.97-3.86 (m, 3H, H3$^A$, H4$^A$, H4$^B$), 3.76 (bs, 1H, H5$^A$), 3.69 (t, 1H, J=9.0 Hz, H3$^B$), 3.64-3.56 (m, 1H, OCHH), 3.50 (s, 3H, CO$_2$CH$_3$), 3.42-3.19 (m, 4H, H2$^A$, CH$_2$N Linker, OCHH Linker), 2.92-2.86 (m, 1H, CHH Lev), 2.70-2.61 (m, 2H, CH$_2$ Lev), 2.51-2.46 (m, 2H, CHH Lev), 2.18 (s, 3H, CH$_3$ Lev), 2.01 (s, 3H, CH$_3$ Ac), 1.61-1.56 (m, 2H, CH$_2$ Linker), 1.34-1.26 (m, 2H, CH$_2$ Linker). $^{13}$C NMR (75.5 MHz, CDCl$_3$): δ 206.7, 172.4, 169.6, 169.4, 138.6, 138.3, 137.9, 128.5, 128.4, 128.2, 127.9, 127.8, 127.7, 127.6, 127.5, 127.3, 101.0, 97.7, 81.3, 78.2, 77.8, 77.4, 77.0, 76.6, 75.0, 74.5, 74.0, 72.5, 72.3, 68.6, 68.3, 67.1, 62.8, 62.2, 52.5, 50.5, 50.2, 47.0, 46.1, 37.8, 29.8, 28.9, 27.8, 23.2, 20.8. HRMS-MALDI: (M+Na$^+$) calcd. 1047.4215, found 1047.4223.

N-(Benzyl)-benzyloxycarbonyl-5-aminopentyl O-(methyl-O-2-O-levulinoyl-3-O-benzyl-β-D-glucopyranosyluronate)-(1→4)-O-2-azido-3-O-benzyl-2-deoxy-6-O-levulinoyl-α-D-glucopyranoside (20)

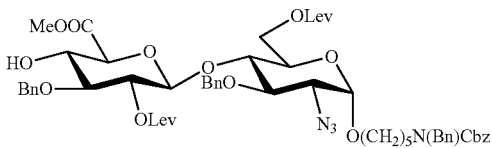

Compound S20 (100 mg, 0.097 mmol) was subjected to TEMPO/BAIB mediated oxidation and esterification using diazomethane according to the general procedure. Silica gel chromatography of the residue (toluene/EtOAc, 50/50, v/v) afforded 20 (70 mg, 67%, two steps). [α]$_D^{25}$ −18.4 (c=1, CHCl$_3$); $^1$H NMR (500 MHz, CDCl$_3$): δ 7.39-7.26 (m, 20H, CH Aromatic), 5.19-5.15 (m, 2H, CHHBn, CH$_2$Cbz), 5.02 (t, 1H, J=8.0 Hz, H2$^B$), 4.83 (bd, 1H, J=12.0 Hz, H1$^A$, CHHBn), 4.71-4.65 (m, 3H, CHHBn, CHHBn, H1$^B$), 4.48 (dd, 1H, J=2.0 Hz, J=12.5 Hz, H6a$^A$), 4.48 (bd, 2H, J=8.0 Hz, NCH$_2$Bn), 4.28 (d, 1H, J=11.0 Hz, H6b$^A$), 4.10 (d, 1H, J=10.0 Hz, H5$^B$), 4.01 (bd, 1H, J=8.5 Hz, H5$^A$), 3.96-3.89 (m, 3H, H3$^A$, H4$^A$, H4$^B$), 3.72 (t, 1H, J=9.0 Hz, H3$^B$), 3.68-3.64 (m, 1H, OCHH Linker), 3.47 (s, 3H, CO$_2$CH$_3$), 3.39-3.19 (m, 4H, H2$^A$, CH$_2$N Linker, OCHH Linker), 2.92-2.79 (m, 2H, CH$_2$ Lev), 2.71-2.61 (m, 4H, 2×CH$_2$ Lev), 2.56-2.36 (m, CH$_2$ Lev), 2.18 (s, 3H, CH$_3$ Lev), 2.11 (bd, 3H, J=10.1 Hz, CH$_3$ Lev), 1.61-1.56 (m, 6H, 3×CH$_2$ Linker. $^{13}$C NMR (75.5 MHz, CDCl$_3$): δ 206.8, 205.8, 172.5, 169.7, 138.8, 138.4, 137.9, 136.8, 128.5, 128.4, 128.3, 128.1, 127.8, 127.8, 127.5, 127.2, 101.0, 97.7, 81.4, 78.3, 77.9, 77.4, 77.0, 76.6, 75.2, 74.5, 74.0, 72.8, 72.3, 68.3, 68.1, 67.1, 62.8, 62.6, 52.4, 50.5, 50.2, 46.1, 37.9, 37.5, 29.8, 29.7, 29.6, 28.9, 27.8, 27.7, 23.2. HRMS-MALDI: (M+Na$^+$) calcd. 1103.4477. found 1103.4456.

N-(Benzyl)-benzyloxycarbonyl-5-aminopentyl O-(methyl-3-O-benzyl-2-O-acetyl)-α-L-idopyranosyluronate)-(1→4)-O-2-azido-3-O-benzyl-2-deoxy-6-O-acetyl-α-D-glucopyranoside (21)

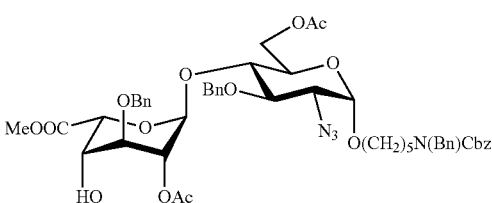

Compound S21 (80 mg, 0.087 mmol) was subjected to TEMPO/BAIB mediated oxidation and esterification using diazomethane according to the general procedure. Silica gel chromatography (toluene/EtOAc, 50/50, v/v) afforded 21 (70 mg, 83%, two steps). [α]$_D^{25}$ +98.3 (c=1, CHCl$_3$); $^1$H NMR (500 MHz, CDCl$_3$): δ 7.36-7.26 (m, 20H, CH Aromatic), 5.17 (bd, 2H, J=14.0 Hz, CH$_2$ Cbz), 5.07 (s, 1H, H1$^B$), 4.98-4.90 (m, 1H, H2$^B$, H5$^B$), 4.84 (bd, 2H, J=14.5 Hz, H1$^A$), 4.74 (bd, 2H, J=11.0 Hz, CHHBn, CHHBn), 4.66-4.62 (m, 2H, CHHBn, CHHBn), 4.49-4.47 (m, 2H, NCH$_2$Bn, H6a$^A$), 4.22 (bd, 1H, J=12.0 Hz, H6b$^A$), 3.95 (bs, 1H, H4$^B$), 3.86-3.82 (m, 3H, H4$^A$, H3$^A$), 3.71 (bs, 1H, H3$^B$), 3.65-3.52 (m, 2H, OCHH Linker, H5$^A$), 3.47 (s, 3H, CO$_2$CH$_3$), 3.40-3.18 (m, 4H incl.: d, J=9.0 Hz at 3.27, H2$^A$, OCHH Linker, CH$_2$N Linker), 2.06 (s, 3H, CH$_3$ Ac), 2.07 (s, 3H, CH$_3$ Ac), 1.61-1.19 (m, 6H, 3×CH$_2$ Linker). HRMS-MALDI: (M+Na+) calcd. 991.3952, found 991.3975.

N-(Benzyl)-benzyloxycarbonyl-5-aminopentyl O-(methyl-3-O-benzyl-2-O-levulinoyl)-α-L-idopyranosyluronate)-(1→4)-O-2-azido-3-O-benzyl-2-deoxy-6-O-acetyl-α-D-glucopyranoside (22)

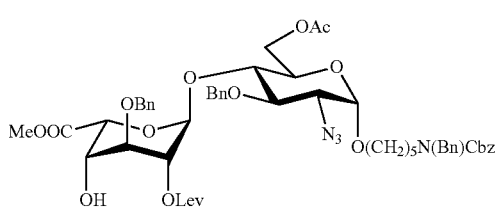

22

Compound S22 (84.7 mg, 0.087 mmol) was subjected to TEMPO/BAIB mediated oxidation and esterification using diazomethane according to the general procedure. Silica gel chromatography (toluene/EtOAc, 9/1 to 1/1, v/v) afforded 22 (65.6 mg, 73%, two steps). [α]$_D^{25}$ 21.1 (c=1, CHCl$_3$); $^1$H NMR (500 MHz, CDCl$_3$): δ 7.32-7.13 (m, 20H, CH Aromatic), 5.13 (bd, 2H, J=13.2 Hz, CH$_2$ Cbz), 5.03 (s, 1H, H1$^B$), 4.90 (bs, 1H, H2$^B$), 4.83-4.79 (m, 2H, H5$^B$, H1$^A$), 4.72-4.70 (m, 2H, CHHBn, CHHBn), 4.61-4.57 (m, 2H, CHHBn, CHHBn), 4.46 (bd, 2H, J=7.0 Hz, NCH$_2$Bn), 4.35 (bd, 1H, J=12.5 Hz, H6a$^A$), 4.19 (bd, 1H, J=12.5 Hz, H6b$^A$), 3.93 (bd, 1H, J=9.2 Hz, H4$^B$), 3.86-3.78 (m, 3H, H4$^A$, H3$^A$, H5$^A$), 3.69 (bs, 1H, H3$^B$), 3.63-3.53 (m, 1H, OCHH Linker), 3.43 (s, 3H, CO$_2$CH$_3$), 3.40-3.18 (m, 4H incl.: dd, J=3.5 Hz, J=10.3 Hz at 3.27, H2$^A$, OCHH Linker, CH$_2$N Linker), 2.69-2.63 (m, 4H, 2×CH$_2$Lev), 2.51-2.49 (m, 2H, 2×CH$_2$ Lev), 2.05 (s, 3H, CH$_3$ Ac), 2.11 (s, 3H, CH$_3$ Lev), 1.61-1.19 (m, 6H, 3×CH$_2$Linker). $^{13}$CNMR(75.5 MHz, CDCl$_3$): δ 206.1, 172.3, 171.1, 170.6, 169.5, 156.1, 137.8, 137.8, 137.3, 136.8, 128.5, 128.4, 128.1, 128.1, 128.0, 127.8, 127.3, 127.3, 97.9, 97.6, 78.3, 77.5, 77.2, 77.0, 76.6, 75.0, 74.6, 74.3 72.3, 69.0, 68.7, 68.2, 67.5, 67.1, 63.3, 62.2, 60.3, 51.9, 50.5, 50.2, 47.0, 46.1, 37.7, 29.6, 29.0, 27.9, 27.4, 23.2, 21.0, 20.8, 14.1. HRMS-MALDI: (M+Na$^+$) calcd. 1047.4215, found 1047.4223.

N-(Benzyl)-benzyloxycarbonyl-5-aminopentyl O-(methyl-2-O-acetyl-3-O-benzyl-α-L-idopyranosyluronate)-(1>4)-O-2-azido-3-O-benzyl-6-O-levulinoyl-α-D-glucopyranoside (23)

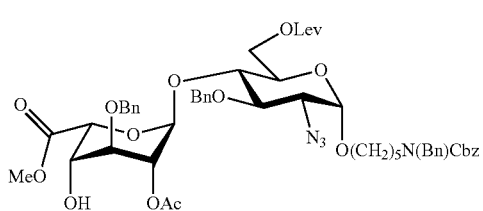

23

Compound S23 (263 mg, 0.211 mmol) was subjected to TEMPO/BAIB mediated oxidation and esterification using diazomethane according to the general procedure. Silica gel chromatography of the residue (toluene/EtOAc 1/1 tot/2, v/v) afforded 23 (210 mg, 97%). [α]$_D^{25}$ +23.4 (c=1, CHCl$_3$); $^1$H NMR (500 MHz, CDCl$_3$): δ 7.42-7.19 (m, 20H, Aromatic), 5.23-5.15 (m, 2H, CH$_2$ Cbz), 5.04 (bs, 1H, H1$^B$), 4.96 (bs, 1H, H2$^B$), 4.92 (bs, 1H, H5$^B$), 4.89-4.83 (m, 1H, H1$^A$), 4.80-4.73 (m, 2H, CHHBn, CHHBn), 4.69-4.62 (m, 2H, CHHBn, CHHBn), 4.55-4.48 (bs, 2H, NCH$_2$Bn), 4.44 (dd, 1H, J=1.5 Hz, J=12.2 Hz, H6a$^A$), 4.24 (bd, 1H, H6b$^A$), 3.93 (bs, 1H, H4$^B$), 3.94-3.78 (m, 3H, H3$^A$, H4$^A$, H5$^A$), 3.74 (t, 1H, J=2.5 Hz, H3$^B$), 3.70-3.59 (m, 1H, OCHH Linker), 3.52-3.18 (7H incl. CO$_2$CH$_3$: s, 3.48, H2$^A$: dd, 3.33, J=3.3 Hz, J=10.0 Hz, OCHH Linker, CH$_2$N Linker), 2.82-2.75 (m, 2H, CH$_2$ Lev), 2.72-2.55 (m, 2H CH$_2$ Lev), 2.20 (s, 3H, CH$_3$ Lev), 2.10 (s, 3H, CH$_3$Ac), 1.72-1.40 (m, 4H, CH$_2$ Linker), 1.40-1.20 (m, 2H, CH$_2$ Linker). $^{13}$C NMR (75.5 MHz, CDCl$_3$): δ 201.4172.3, 168.4 168.3, 156.6, 156.4, 136.9, 136.8 136.2, 127.5, 127.4, 127.2, 127.1, 126.9, 126.8, 126.4, 126.3, 96.8, 96.6, 77.3, 73.7, 73.4, 71.2, 68.0, 67.4, 67.2, 66.7, 66.1, 66.0, 62.4, 61.4, 51.0, 49.9, 46.8, 46.0, 36.8, 28.8, 28.0, 26.9, 22.3, 29.9. HRMS-MALDI: (M+Na$^+$) calcd. 1047.4215, found 1047.4223.

N-(Benzyl)-benzyloxycarbonyl-5-aminopentyl O-(methyl 2-O-levulinoyl-3-O-benzyl-α-L-idopyranosyluronate)-(1→4)-O-2-azido-3-O-benzyl-6-O-levulinoyl-α-D-glycopyranoside (24)

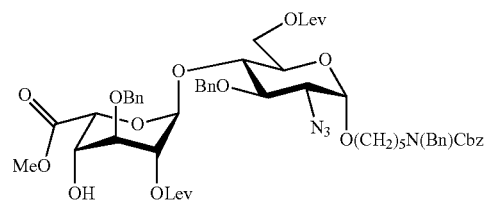

24

Compound S24 (400 mg, 0.380 mmol) was subjected to TEMPO/BAIB mediated oxidation and esterification using diazomethane according to the general procedure. Silica gel chromatography (toluene/EtOAc 1/1, v/v) provided 24 (299 mg, 73%). [α]$_D^{25}$ +28 (c=1, CHCl$_3$); $^1$H NMR (500 MHz, CDCl$_3$): δ 7.40-7.15 (m, 20H, CH Aromatic), 5.18-5.12 (m, 2H, CH$_2$ Cbz), 4.99 (bs, 1H, H1$^B$), 4.92 (bs, 1H, H2$^B$), 4.86, 4.78 (m, 2H, H1$^A$, H5$^B$), 4.75-4.70 (m, 2H, CHHBn, CHHBn), 4.62-4.58 (m, 2H, CHHBn, CHHBn), 4.51-4.45 (m, 2H, NCH$_2$Bn), 4.39 (dd, 1H, J=1.5 Hz, J=12.3 Hz, H6a$^A$), 4.20 (bd, 1H, J=12.3 Hz, H6b$^A$), 3.94 (bd, 1H, J=10.5 Hz, H4$^B$), 3.88 (t, 1H, J=9.1 Hz, H4$^A$), 3.85-3.74 (m, 2H, H3$^A$, H5$^A$), 3.71 (t, 1H, J=2.7 Hz, H3$^B$), 3.68-3.54 (m, 1H, OCHH Linker), 3.45 (s, 3H, CO$_2$CH$_3$), 3.44-3.17 (m, 3H, incl. H2$^A$: dd, 3.36, J=3.5 Hz, J=10.1 Hz, OCHH Linker), 2.80-2.50 (m, 8H, 4×CH$_2$Lev), 2.16 (s, 3H, CH$_3$Lev), 2.14 (s, 3H, CH$_3$ Lev), 1.64-1.48 (m, 4H, CH$_2$ Linker), 1.38-1.24 (m, 2H, CH$_2$ Linker). $^{13}$C NMR (CDCl$_3$): δ 206.6, 206.3, 172.2, 171.4, 169.4, 156.6, 156.1, 137.9, 137.8, 137.2, 136.8, 128.5, 128.4, 128.1, 127.9, 127.8, 127.4, 127.3, 97.7, 97.5, 78.3, 74.5, 74.4, 72.3, 68.9, 68.5, 68.1, 67.6, 67.4, 67.1, 63.3, 62.4, 51.9, 50.5, 50.2, 47.0, 46.1, 37.8, 37.7, 29.8, 29.7, 28.0, 27.9, 23.2. HRMS-MALDI: (M+Na$^+$) calcd. 1103.4477, found 1103.4456.

N-(Benzyl)-benzyloxycarbonyl-5-aminopentyl O-2-azido-3,4,6-tri-O-acetyl-2-deoxy-α-D-glycopyranoside (28)

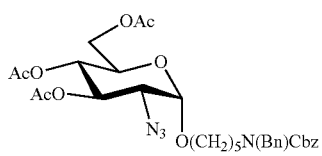

Trichloroacetimidate 27 (25.4 g, 53.0 mmol) and N-(benzyl)-N-benzyloxycarbonyl-5-aminopentan-1-ol (20.9 g, 64.0 mmol) were co-evaporated with toluene (3×50 mL) and dissolved in a mixture of DCM (120 mL) and diethyl ether (400 mL) and stirred in the presence of powdered molecular sieves (3 Å, 40 g) for 1 hr at room temperature. TMSOTf (2.65 mmol, 0.480 ml) was slowly added to the mixture at −20° C. After stirring at −20° C. for 1 h, the reaction mixture was allowed to reach room temperature and then quenched with pyridine (0.5 mL). After filtration, the reaction mixture was extracted with saturated sodium bicarbonate (500 mL), brine (2×200 mL) and dried (MgSO$_4$). The organic layers were filtered and the filtrate concentrated in vacuo. NMR of the crude residue indicated α/β ratio of 3:1. Silica gel column chromatography (hexanes/EtOAc, 80/20, v/v) provided the pure α-glycoside 28 (23.2 g, 68%). [α]$_D^{25}$ +10.8 (c=1.00, CHCl$_3$); $^1$H NMR (300 MHz, CDCl$_3$): δ 7.45-7.10 (m, 10H, CH Aromatic), 5.44 (dd, 1H, J=9.2 Hz, J=10.3 Hz, H3), 5.24-5.14 (m, 2H, CH$_2$ Cbz), 5.04 (dd, 1H, J=9.9 Hz, H4), 4.51 (bs, 2H, NCH$_2$Bn), 4.24 (dd, 1H, J=3.4 Hz, J=12.4 Hz, H6a), 4.10-3.94 (m, 2H, H6b, H5), 3.76-3.58 (m, 1H, OCHH Linker), 3.54-3.36 (m, 1H, OCHH Linker), 3.34-3.15 (m, 3H, H2, CH$_2$N Linker), 2.09-2.03 (3s, 9H, 3×CH$_3$ Ac), 1.70-1.40 (m, 6H, 3×CH$_2$ Linker). $^{13}$CNMR (75.5 MHz, CDCl$_3$): δ 170.5, 169.9, 169.6, 137.8, 136.9, 128.9, 128.5, 128.4, 128.2 127.9, 127.8, 127.2, 97.8, 70.3, 68.6, 68.5, 67.5, 67.1, 61.8, 60.7, 50.4, 50.1, 46.9, 46.1, 28.9, 27.8, 27.3, 23.3, 20.6 20.5. HRMS-MALDI: (M+Na$^+$) calcd. 663.2637, found 663.2656.

N-(Benzyl)-benzyloxycarbonyl-5-aminopentyl O-2-azido-4,6-O-benzylidene-2-deoxy-α-D-glycopyranoside (30)

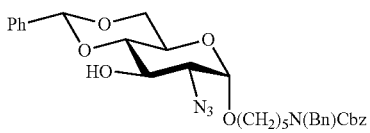

CH$_3$ONa in MeOH (0.5 M) was added to 28 (13.7 g, 22.0 mmol) dissolved in MeOH (80 mL) until the reaction mixture reached pH 12. The mixture was stirred overnight until TLC (chloroform/MeOH, 9/1, v/v) indicated the completion of the reaction. After neutralization with Dowex 50-H$^+$resin, the mixture was filtered through Celite and concentrated in vacuo. Silica gel column chromatography of the residue (chloroform/MeOH (95/5→93/7, v/v) provided (11.0 g, 97%) of the deacetylated compound which was directly used in the next step. p-toluene sulfonic acid (100 mg, 0.52 mmol) was added to the solution of the starting material (11.0 g, 21.4 mmol) and benzaldehyde dimethyl acetal (5.06 g, 33.0 mmol) in CH$_3$CN (110 mL). After 16 hr, the reaction mixture was neutralized with triethylamine and concentrated in vacuo. Silica gel chromatography of the residue (hexanes/EtOAc, 80/20→70/30, v/v) provided 30 (10.0 g, 76%). [α]$_D^{25}$ +45 (c=1.00, CHCl$_3$); $^1$H NMR (300 MHz, CDCl$_3$): δ 7.55-7.10 (m, 15H, Aromatic), 5.46 (s, 1H, benzylidene), 5.24-5.16 (m, 2H, CH$_2$Cbz), 4.86 (bs, 1H, H1), 4.50 (bs, 2H, NCH$_2$Bn), 4.30-4.18 (m, 2H, H6a, H3), 3.88-3.62 (m, 3H, H5, H6b, OCHH Linker), 3.50 (t, 1H, J=9.1 Hz, H4), 3.47-3.33 (m, 1H, CHH Linker), 3.32-3.16 (m, 3H, incl. H2: dd, J=3.7 Hz, J=10.2 Hz, CH$_2$N Linker), 2.75 (d, 1H, J=3.0 Hz, 3-OH), 1.67-1.53 (m, 4H, 2×CH$_2$Linker), 1.45-1.34 (m, 2H, CH$_2$ Linker). $^{13}$C NMR (75.5 MHz, CDCl$_3$): δ 137.8, 136.8, 129.3, 128.5, 128.4, 128.3, 127.9, 127.8, 127.2, 102.0, 98.5, 81.9, 68.8, 68.6, 68.4, 67.1, 63.0, 62.4, 29.0, 27.8, 27.4, 23.2. HRMS-MALDI: (M+Na$^+$) calcd. 625.2640, found 625.2721.

N-(Benzyl)-benzyloxycarbonyl-5-aminopentyl O-2-azido-3-O-benzyl-2-deoxy-α-D-glycopyranoside (32)

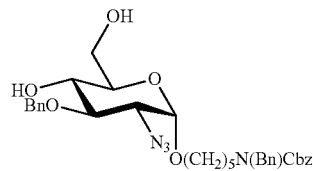

NaH (1.0 g, 26.0 mmol) was added to a solution 30 (10.0 g, 16.6 mmol) in DMF (85 mL). The mixture was stirred for 30 minutes at room temperature prior to addition of benzyl bromide (3.69 g, 21.5 mmol). The reaction was followed by TLC (hexanes/EtOAc, 2/1, v/v). After stirring overnight at room temperature, the reaction was quenched with acetic acid (0.5 mL) and concentrated in vacuo. The residue was dissolved in EtOAc (500 mL), washed with water and brine (2×100 mL) and dried (MgSO$_4$), filtered and concentrated in vacuo. Silica gel chromatography of the residue (hexanes/EtOAc, 95/15→70/30, v/v) provided N-(Benzyl)-benzyloxycarbonyl-5-aminopentyl O-2-azido-3-O-benzyl-4,6-O-benzylidene-2-deoxy-α-D-glycopyranoside (10.8 g, 93%). [α]$_D^{25}$ +58 (c=1.00, CHCl$_3$); $^1$H NMR (300 MHz, CDCl$_3$): δ 7.45-7.10 (m, 15H, Aromatic), 5.60 (s, 1H, CH benzylidene), 5.24-5.16 (m, 2H, CH$_2$Cbz), 4.96 (d, 1H, J=11.0 Hz, CHHBn), 4.90-4.78 (m, 2H, CHHBn, H1), 4.50 (bs, 2H, NCH$_2$Bn), 4.28 (dd, 1H, J=4.4 Hz, J=9.9 Hz, H6a), 4.08 (dd, 1H, J=9.1 Hz, J=10.2 Hz, H3), 3.91-3.60 (m, 4H, incl. H4, H5, H6b, OCHH Linker), 3.42-3.17 (m, 4H, OCHH Linker, CH$_2$N Linker, H2), 1.70-1.40 (m, 6H, 3×CH$_2$ Linker). $^{13}$C NMR (75.5 MHz, CDCl$_3$): δ 156.8, 156.3, 137.8, 136.8, 128.5, 128.4, 128.3, 128.2 127.9, 127.8, 127.3, 101.4, 98.5 (C1), 82.8, 76.0, 75.0, 66.9, 67.1 62.9, 62.7, 50.53, 50.25, 47.0, 46.1, 29.0, 27.8, 27.4 23.2. HRMS-MALDI: (M+NO calcd. 692.321, found 692.3321.

A solution of N-(Benzyl)-benzyloxycarbonyl-5-aminopentyl O-2-azido-3-O-benzyl-4,6-O-benzylidene-2-deoxy-α-D-glycopyranoside (4.6 g, 6.6 mmol) in acetic acid (60 mL) and H$_2$O (6 mL) was heated at 90° C. After 1 hr, TLC (hexanes/EtOAc, 2/1, v/v) indicated the consumption of the starting material. The reactions mixture was co-evaporated with an excess of toluene and the residue was purified using silica gel chromatography (hexanes/EtOAc, 60/40, v/v) affording 32 (6.9 g, 92%). $[\alpha]_D^{25}$ +54 (c=1.00, CHCl$_3$). $^1$H NMR (300 MHz, CDCl$_3$): δ 7.45-7.10 (m, 15H, CH Aromatic), 5.24-5.12 (m, 2H, CH$_2$ Cbz), 4.96-4.78 (m, 3H, CHHBn, CHHBn, H1), 4.51 (bs, 2H, NCH$_2$Bn), 3.85-3.55 (m, 6H, H3, H4, H5, H6a, H6b, OCHH Linker), 3.50-3.18 (m, 4H, H2, OCHH Linker, CH$_2$N Linker), 1.70-1.20 [m, 6H, (CH$_2$)$_3$]. $^{13}$CNMR (75.5 MHz, CDCl$_3$): δ 156.8, 156.4, 138.1, 137.7, 136.4, 128.5, 128.4 128.0, 127.9, 127.8, 127.3, 127.2, 97.8 C1, 79.8, 74.9, 72.0, 71.2, 68.0, 67.7, 67.3, 62.8, 62.7, 62.2, 50.4, 47.3, 46.0, 28.7, 27.8, 27.1, 23.4. HRMS-MALDI: (M+Na$^+$) calcd. 622.2797, found 622.2810. Disaccharides 37-56 and S1-S24

Dimethylthexylsilyl O-(2-O-acetyl-3-O-benzyl-4,6-O-benzylidene-β-D-glucopyranosyl)-(1→4)-O-2-azido-3-O-benzyl-6-O-acetyl-2-deoxy-β-D-glucopyranoside (37)

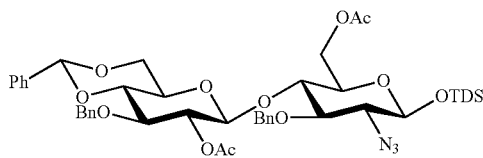

37

Glycosyl donor 3 (25 m g, 0.056 mmol) was coupled with acceptor 5 (22.5 mg, 0.047 mmol) according to the general glycosylation procedure for synthesis of disaccharides to give disaccharide 37 (33 mg, 81%). $[\alpha]_D^{25}$ +4.8 (c=1.00, CHCl$_3$); $^1$H NMR (500 MHz, CDCl$_3$): δ 7.44-7.25 (m, 15H, CH Aromatic), 5.48 (s, 1H, CH benzylidene), 5.00 (t, 1H, J=8.5 Hz, H2$^B$), 4.87 (d, 1H, J=10.5 Hz, CHHBn), 4.86 (d, 1H, J=12.0 Hz, CHHBn), 4.78 (d, 1H, J=10.5 Hz, CHHBn), 4.63 (d, 1H, J=12.0 Hz, CHHBn), 4.52 (d, 1H, J=8.0 Hz, H1$^B$), 4.46 (d, 1H, J=7.5 Hz, H1$^A$), 4.41 (dd, 1H, J=1.5 Hz, J=11.5 Hz, H6a$^A$), 4.09-4.05 (m, 2H, H6a$^B$, H6b$^A$), 3.72-3.65 (m, 3H, H3$^B$, H4$^A$, H4$^B$), 3.45-3.41 (m, 2H, H5$^A$, H6b$^B$), 3.36-3.27 (m, 3H, H2$^A$, H3$^A$, H5$^B$), 2.06 (s, 3H, CH$_3$Ac), 2.00 (s, 3H, CH$_3$ Ac), 1.62-1.56 [m, 1H, CH(CH$_3$)$_2$], 0.88-0.86 [4s, 12H, C(CH$_3$)$_2$ and CH(CH$_3$)$_2$], 0.17-0.15 [2s, 6H, Si(CH$_3$)$_2$]. $^{13}$C NMR (75.5 MHz, CDCl$_3$): δ 170.4, 169.3, 138.4, 138.0, 137.0, 129.0, 128.3, 128.2, 128.2, 127.7, 127.7, 127.6, 127.3, 125.9, 101.6, 101.1, 96.7, 81.4, 80.8, 78.6, 78.3, 77.4, 77.0, 76.5, 75.1, 74.2, 73.2, 72.8, 68.4, 68.3, 66.3, 62.4, 33.9, 24.8, 20.7, 19.9, 19.8, 18.4, 18.3, -2.2, -3.3. HRMS-MALDI: (M+Na$^+$) calcd. 884.3765, found 884.3772.

Dimethylthexylsilyl O-(2-O-levulinoyl-3-O-benzyl-4,6-O-benzylidene-β-D-glucopyranosyl)-(1→4)-O-2-azido-3-O-benzyl-6-O-acetyl-2-deoxy-β-D-glucopyranoside (38)

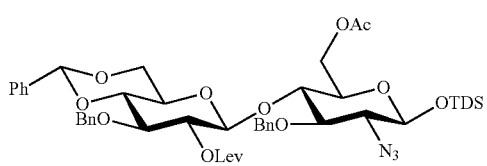

38

Glycosyl donor 4 (25 mg, 0.056 mmol) was coupled with acceptor 5 (22.5 mg, 0.047 mmol) according to the general glycosylation procedure for synthesis of disaccharides to give disaccharide 38 (30 mg, 75%). $[\alpha]_D^{25}$ −86.3 (c=0.22, CHCl$_3$); $^1$H NMR (500 MHz, CDCl$_3$): δ 7.45-7.25 (m, 15H, CH Aromatic), 5.48 (s, 1H, CH benzylidene), 5.00 (t, 1H, J=9.0 Hz, H2$^B$), 4.88-4.84 (m, 2H, CHHBn, CHHBn), 4.76 (d, 1H, J=12.0 Hz, CHHBn), 4.64 (d, 1H, J=11.0 Hz, CHHBn), 4.53 (d, 1H, J=8.0 Hz, H1$^B$), 4.47 (d, 1H, J=7.5 Hz, H1$^A$), 4.41 (dd, 1H, J=4.0 Hz, J=10.0 Hz, H6a$^A$), 4.14-4.09 (m, 2H, H6b$^A$, H6a$^B$), 3.73-3.68 (m, 2H, H3$^B$, H4$^A$), 3.57-3.55 (m, 1H, H5$^A$), 3.43 (t, 1H, J=10.0 Hz, H5$^B$), 3.34 (t, 1H, J=9.5 Hz, H4$^B$), 3.31-3.27 (m, 2H, H2$^A$, H3$^A$), 2.81-2.74 (m, 1H, CHH Lev), 2.65-2.55 (m, 2H, CH$_2$ Lev), 2.40-2.34 (m, 1H, CHH Lev), 2.16 (s, 3H, CH$_3$ Lev), 2.06 (s, 3H, CH$_3$Ac), 1.66-1.54 [m, 1H, CH(CH$_3$)$_2$], 0.88-0.86 [4s, 12H, C(CH$_3$)$_2$ and CH(CH$_3$)$_2$], 0.17-0.16 [2s, 6H, Si(CH$_3$)$_2$]. $^{13}$C NMR (75.5 MHz, CDCl$_3$): δ 205.9, 171.2, 170.4, 138.4, 138.0, 136.9, 128.9, 128.2, 128.1, 127.7, 127.5, 127.5, 127.4, 125.9, 101.4, 101.1, 96.6, 81.3, 80.7, 78.6, 78.0, 77.4, 77.0, 76.6, 75.1, 74.2, 73.4, 72.6, 68.4, 68.3, 66.2, 62.4, 37.5, 33.8, 29.7, 27.6, 24.7, 20.7, 19.9, 19.8, 18.4, 18.3, -2.2, -3.3. HRMS-MALDI: (M+Na$^+$) calcd. 940.4022, found 940.5577.

Dimethylthexylsilyl O-(2-O-acetyl-3-O-benzyl-4,6-O-benzylidene-β-D-glucopyranosyl)-(1→4)-O-2-azido-3-O-benzyl-6-O-levulinoyl-2-deoxy-O-D-glucopyranoside (39)

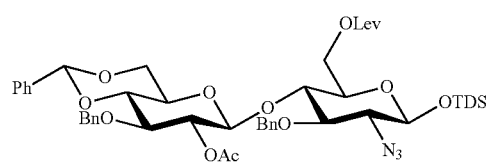

39

Glycosyl donor 3 (2.2 g, 5.15 mmol) was coupled with acceptor 6 (2.3 g, 4.29 mmol) according to the general glycosylation procedure for synthesis of disaccharides to give disaccharide 39 (3.65 g 3.97 mmol, 92%). $[\alpha]_D^{25}$ +4.8 (c=1.00, CHCl$_3$); $^1$H NMR (500 MHz, CDCl$_3$): δ 7.45-7.25 (m, 15H, CH Aromatic), 5.48 (s, 1H, CH benzylidene), 5.00 (t, 1H, J=8.0 Hz, H2$^B$), 4.89 (d, 1H, J=11.0 Hz, CHHBn), 4.85 (d, 1H, J=12.0 Hz, CHHBn), 4.76 (d, 1H, J=10.5 Hz, CHHBn), 4.63 (d, 1H, J=11.0 Hz, CHHBn), 4.60 (d, 1H, J=8.0 Hz, H1$^B$), 4.46 (d, 1H, J=7.0 Hz, H1$^A$), 4.37 (dd, 1H, J=1.5 Hz, J=11.5 Hz, H6a$^A$), 4.14-4.08 (m, 2H, H6a$^B$, H6b$^A$), 3.78 (t, 1H, J=9.5 Hz, H3$^B$), 3.74-3.66 (m, 3H, H4$^A$, H5$^B$, H4$^B$), 3.42-3.40 (m, 2H, H6b$^B$, H5$^A$), 3.35-3.26 (m, 2H, H2$^A$, H3$^A$), 2.82-2.67 (m, 2H, CH$_2$ Lev), 2.62-2.51 (m, 2H, CH$_2$ Lev), 2.17 (s, 3H, CH$_3$ Lev), 2.00 (s, 3H, CH$_3$ Ac), 1.67-1.61 [m, 1H, CH(CH$_3$)$_2$], 0.88-0.86 [4s, 12H, C(CH$_3$)$_2$ and CH(CH$_3$)$_2$], 0.17-0.16 [2s, 6H, Si(CH$_3$)$_2$]. $^{13}$C NMR (75.5 MHz, CDCl$_3$): δ 206.1, 172.3, 169.4, 138.4, 138.2, 137.1, 129.0, 128.3, 128.2, 127.6, 127.6, 127.5, 126.0, 101.5, 101.1, 96.7, 81.5, 80.8, 78.7, 77.9, 77.4, 77.0, 76.6, 75.2, 74.3, 73.3, 72.8, 66.1, 62.4, 37.8, 33.9, 29.8, 29.7, 27.8, 24.8, 20.8, 19.9, 19.8, 18.4, 18.3, -2.1, -3.2. HRMS-MALDI: (M+Na$^+$) calcd. 940.4029, found 940.5577.

Dimethylthexylsilyl O-(2-O-levulinoyl-3-O-benzyl-4,6-O-benzylidene-β-D-glucopyranosyl)-(1→4)-O-2-azido-3-O-benzyl-6-O-levulinoyl-2-deoxy-β-D-glucopyranoside (40)

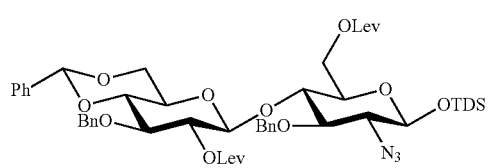

40

Glycosyl donor 4 (101.1 mg, 0.202 mmol) was coupled with acceptor 6 (90.0 mg, 0.168 mmol) according to the general glycosylation procedure for synthesis of disaccharides to give disaccharide 40 (100 mg, 75%). $[\alpha]_D^{25}$ −6.0 (c=1.00, CHCl$_3$); $^1$H NMR (500 MHz, CDCl$_3$): δ 7.45-7.25 (m, 15H, CH Aromatic), 5.48 (s, 1H, CH benzylidene), 5.01 (t, 1H, J=8.5 Hz, H2$^B$), 4.90 (d, 1H, J=11.0 Hz, CHHBn), 4.85 (d, 1H, J=12.0 Hz, CHHBn), 4.74 (d, 1H, J=10.5 Hz, CHHBn), 4.63 (d, 1H, J=13.0 Hz, CHHBn), 4.62 (d, 1H, J=8.5 Hz, H1$^B$), 4.49 (d, 1H, J=7.5 Hz, H1$^A$), 4.41 (dd, 1H, J=1.5 Hz, J=12.0 Hz, H6a$^A$), 4.22 (dd, 1H, J=5.5 Hz, J=11.5 Hz, H6b$^A$), 4.14-4.12 (m, 1H, H6a$^B$), 3.82 (t, 1H, J=9.0 Hz, H3$^B$), 3.76 (t, 1H, J=9.0 Hz, H4$^A$), 3.69-3.66 (m, 2H, H4$^B$, H6b$^B$) 3.59-3.56 (m, 1H, H5$^A$), 3.48-3.40 (m, 1H, H5$^B$), 3.35 (t, 1H, J=10.0 Hz, H2$^A$), 3.30-3.27 (m, 1H, H3$^A$), 2.84-2.50 (m, 5H, 2×CH$_2$ Lev and CHH Lev) 2.40-2.32 (m, 1H, CHH Lev), 2.17 (s, 3H, CH$_3$ Lev), 2.16 (s, 3H, CH$_3$ Lev), 1.69-1.62-1.55 [m, 1H, CH(CH$_3$)$_2$], 0.89-0.86 [4s, 12H, C(CH$_3$)$_2$ and CH(CH$_3$)$_2$], 0.17-0.16 [2s, 6H, Si(CH$_3$)$_2$]. $^{13}$C NMR (75.5 MHz, CDCl$_3$): δ 172.6, 171.6, 138.7, 138.5, 137.4, 129.2, 128.4, 128.4, 127.9, 127.8, 127.7, 126.2, 101.6, 101.4, 96.9, 81.8, 81.0, 79.0, 78.1, 77.6, 77.2, 76.8, 75.5, 74.5, 73.8, 72.9, 66.2, 62.9, 38.0, 37.8, 34.1, 30.0, 30.0, 28.1, 27.9, 20.13, 20.1, 18.7, 18.6. HRMS-MALDI: (M+NO calcd. 996.4290, found 996.5958.

Dimethylthexylsilyl O-(methyl-2-O-acetyl-3-O-benzyl-β-D-glucopyranosyluronate)-(1→4)-O-2-azido-3-O-benzyl-2-deoxy-6-O-acetyl-β-D-glucopyranoside (41)

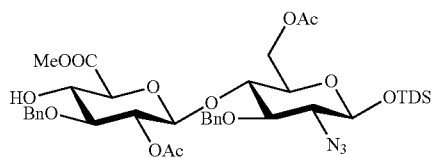

41

Compound 37 (0.29 g, 0.37 mmol) was subjected to TEMPO/BAIB mediated oxidation and esterification using diazomethane according to the general procedure to give 41 (230 mg, 76%, two steps). $[\alpha]_D^{25}$ +20.5 (c=1, CHCl$_3$); $^1$H NMR (500 MHz, CDCl$_3$): δ 7.36-7.25 (m, 10H, CH Aromatic), 4.97 (m, 2H, H2$^B$, CHHBn), 4.83-4.78 (m, 2H, CHHBn, CHHBn), 4.68 (d, 1H, J=12.0 Hz, CHHBn), 4.58 (d, 1H, J=8.0 Hz, H1$^B$), 4.46 (d, 1H, J=8.0 Hz, H1$^A$), 4.37 (dd, 1H, J=2.5 Hz, J=12.0 Hz, H6a$^A$), 4.12-4.06 (m, 2H, H6b$^A$, H5$^B$), 3.91 (m, 1H, H4$^B$), 3.67 (m, 1H, H4$^A$), 3.63 (m, 1H, H3$^B$), 3.57 (s, 3H, CO$_2$CH$_3$), 3.49 (t, 1H, J=9.0 Hz, H5$^A$), 3.37 (t, 1H, J=10.0 Hz, H3$^A$), 3.30 (t, 1H, J=8.0 Hz, H2$^A$), 2.06 (s, 3H, CH$_3$Ac), 1.99 (s, 3H, CH$_3$Ac), 1.67-1.61 [m, 1H, CH(CH$_3$)$_2$], 0.88-0.86 [4s, 12H, C(CH$_3$)$_2$ and CH(CH$_3$)$_2$], 0.17-0.15 [2s, 6H, Si(CH$_3$)$_2$]. HRMS-MALDI: (M+Na$^+$) calcd. 824.3401, found 824.3415.

Dimethylthexylsilyl O-(methyl-2-O-levulinoyl-3-O-benzyl-β-D-glucopyranosyluronate)-(1→4)-O-2-azido-3-O-benzyl-2-deoxy-6-O-acetyl-β-D-glucopyranoside (42)

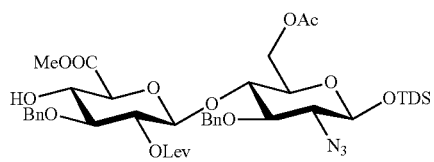

42

Compound 38 (0.20 g, 0.24 mmol) was subjected to TEMPO/BAIB mediated oxidation and esterification using diazomethane according to the general procedure to give 42 (150 mg, 72%, two steps). $[\alpha]_D^{25}$ +4.7 (c=1, CHCl$_3$); $^1$H NMR (500 MHz, CDCl$_3$): δ 7.36-7.25 (m, 10H, CH Aromatic), 4.98-4.94 (m, 2H, H2$^B$, CHHBn), 4.80 (d, 1H, J=12.0 Hz, CHHBn), 4.77 (d, 1H, J=11.0 Hz, CHHBn), 4.72 (d, 1H, J=12.0 Hz, CHHBn), 4.58 (d, 1H, J=8.5 Hz, H1$^B$), 4.48 (d, 1H, J=8.0 Hz, H1$^A$), 4.32 (dd, 1H, J=2.5 Hz, J=11.5 Hz, H6a$^A$), 4.18 (dd, 1H, J=6.5 Hz, J=11.5 Hz, H6b$^A$), 3.91 (t, 1H, J=9.5 Hz, H4$^B$), 3.71 (t, 1H, J=8.5 Hz, H4$^A$), 3.64 (d, 1H, J=10.0 Hz, H5$^B$), 3.58-3.52 (m, 1H, H5$^A$), 3.56 (s, 3H, CO$_2$CH$_3$), 3.50 (t, 1H, J=9.0 Hz, H3$^B$), 3.38 (t, 1H, J=8.5 Hz, H3$^A$), 3.32-3.29 (m, 1H, H2$^A$), 2.92 (bs, 1H, 4-OH), 2.78-2.74 (m, 1H, CHH Lev) 2.72-2.53 (m, 2H, CH$_2$ Lev), 2.43-2.37 (m, 1H, CHH Lev), 2.18 (s, 3H, CH$_3$ Lev), 2.00 (s, 3H, CH$_3$Ac), 1.67-1.61 [m, 1H, CH(CH$_3$)$_2$], 0.88-0.86 [4s, 12H, C(CH$_3$)$_2$ and CH(CH$_3$)$_2$], 0.16-0.15 [2s, 6H, Si(CH$_3$)$_2$]. $^{13}$C NMR (75.5 MHz, CDCl$_3$): δ 206.1, 171.3, 170.6, 169.2, 138.7, 138.1, 128.4, 128.2, 127.8, 127.3, 127.2, 101.1, 96.7, 81.3, 81.0, 78.3, 77.4, 77.0, 76.6, 74.8, 74.6, 74.1, 72.8, 72.5, 72.0, 68.6, 62.7, 52.6, 37.6, 33.9, 29.8, 29.7, 27.7, 24.8, 20.8, 19.9, 19.8, 18.4, 18.3, −2.2, −3.2. HRMS-MALDI: (M+NO calcd. 880.3664, found 880.3683.

Dimethylthexylsilyl O-(methyl-2-O-acetyl-3-O-benzyl-β-D-glucopyranosyluronate)-(1→4)-O-2-azido-3-O-benzyl-2-deoxy-6-O-levulinoyl-β-D-glucopyranoside (43)

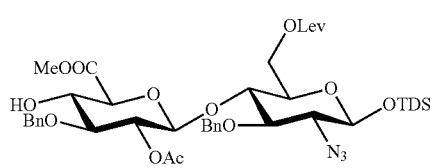

43

Compound 39 (3.65 g, 4.40 mmol) was subjected to TEMPO/BAIB mediated oxidation and esterification using diazomethane according to the general procedure to give 43 (3.3 g, 88%, two steps). $[\alpha]_D^{24}$ +17.1 (c=1, CHCl$_3$); $^1$H NMR (300 MHz, CDCl$_3$): δ 7.36-7.25 (m, 10H, CH Aromatic), 4.97 (m, 2H, H2$^B$, CHHBn), 4.82 (d, 1H, J=12.0 Hz, CHHBn), 4.73 (d, 1H, J=11.0 Hz, CHHBn), 4.68 (d, 1H, J=12.0 Hz, CHHBn), 4.640 (d, 1H, J=8.0 Hz, H1$^B$), 4.46 (d, 1H, J=7.5 Hz, H1$^A$), 4.32 (dd, 1H, J=1.0 Hz, J=10.5 Hz, H6a$^A$), 4.18 (dd, 1H, J=5.0 Hz, J=11.5 Hz, H6b$^A$), 3.93 (t, 1H, J=9.5 Hz, H4$^B$), 3.85 (d, 1H, J=9.5 Hz, H5$^B$), 3.78 (t, 1H, J=9.0 Hz, H4$^A$), 3.63 (t, 1H, J=9.0 Hz, H3$^B$), 3.54 (s, 3H, CO$_2$CH$_3$), 3.42-3.40 (m, 1H, H5$^A$), 3.35 (t, 1H, J=10.0 Hz, H3$^A$), 3.30 (t, 1H, J=7.5 Hz, H2$^A$), 3.02 (bs, 1H, 4-OH), 2.87-2.81 (m, 1H, CHH Lev) 2.72-2.49 (m, 3H, CH$_2$ Lev, CHH Lev), 2.18 (s, 3H, CH$_3$ Lev), 2.00 (s, 3H, CH$_3$ Ac), 1.67-1.61 [m, 1H, CH(CH$_3$)$_2$], 0.88-0.86 [4s, 12H, C(CH$_3$)$_2$,CH(CH$_3$)$_2$], 0.16-0.15 [2s, 6H, Si(CH$_3$)$_2$]. $^{13}$C NMR (75.5 MHz, CDCl$_3$): δ 206.5, 172.3, 169.4, 169.4, 138.6, 138.2, 128.4, 128.1, 127.7, 127.6, 127.4, 127.3, 101.0, 96.7, 81.3, 80.9, 77.9, 77.4, 77.0, 76.6, 74.9, 74.5, 74.0, 72.6, 72.5, 72.1, 68.4, 62.5, 52.5, 37.8, 33.9, 29.8, 27.7, 24.7, 20.8, 19.9, 19.8, 18.4, 18.3, −2.1, −3.2. HRMS-MALDI: (M+Na$^+$) calcd. 880.3664, found 880.3683.

Dimethylthexylsilyl O-(methyl-2-O-levulinoyl-3-O-benzyl-β-D-glucopyranosyluronate)-(1→4)-O-2-azido-3-O-benzyl-2-deoxy-6-O-levulinoyl-β-D-glucopyranoside (44)

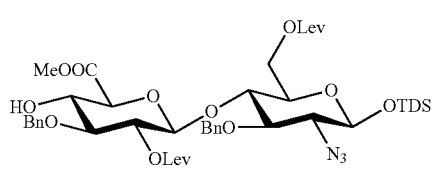

44

Compound 40 (0.297 g, 0.33 mmol) was subjected to TEMPO/BAIB mediated oxidation and esterification using diazomethane according to the general procedure to give 44 (217.2 mg, 71%, 2 steps). [α]$_D^{25}$ −7.2 (c=1, CHCl$_3$); $^1$H NMR (500 MHz, CDCl$_3$): δ 7.36-7.25 (m, 10H, CH Aromatic), 4.95-4.89 (m, 2H, H2$^B$, CHHBn), 4.74 (d, J=12.0 Hz, 1H, CHHBn), 4.63 (d, J=12.0 Hz, 1H, CHHBn), 4.62 (d, J=11.0 Hz, 1H, CHHBn), 4.640 (d, J=8.0 Hz, 1H, H1$^B$), 4.41 (d, J=7.5 Hz, 1H, H1$^A$), 4.28 (dd, J=2.0 Hz, J=12.0 Hz, 1H, H6a$^A$), 4.21 (dd, J=4.5 Hz, J=12.0 Hz, 1H, H6b$^A$), 3.85 (bd, 1H, J=3.5 Hz, H4$^B$, H5$^B$), 3.75 (t, 1H, J=8.5 Hz, H4$^A$), 3.63-3.57 (m, 1H, H3$^B$), 3.52-3.48 (m, 1H, H5$^A$), 3.46 (s, 3H, CO$_2$CH$_3$), 3.29 (t, 1H, J=8.0 Hz, H3$^A$), 3.25-3.21 (m, 1H, H2$^A$), 2.87 (bs, 1H, 4-OH), 2.81-2.41 (m, 8H, 4 xCH$_2$ Lev) 2.11 (s, 3H, CH$_3$ Lev), 2.08 (s, 3H, CH$_3$ Lev), 1.67-1.61 [m, 1H, CH(CH$_3$)$_2$], 0.88-0.86 [4s, 12H, C(CH$_3$)$_2$ and C(CH$_3$)$_2$], 0.16-0.15 [2s, 6H, Si(CH$_3$)$_2$]. $^{13}$C NMR (75.5 MHz, CDCl$_3$): δ 206.6, 206.0, 172.4, 171.3, 169.5, 138.7, 138.3, 129.0, 128.3, 128.1, 127.6, 127.5, 127.2, 100.9, 96.7, 81.4, 80.9, 77.8, 77.4, 76.9, 76.5, 75.0, 74.5, 74.0, 72.8, 72.4, 72.1, 68.5, 62.7, 52.5, 37.8, 37.5, 33.9, 33.6, 31.9, 30.1, 29.8, 29.7, 29.6, 29.3, 27.8, 27.7, 26.6, 24.8, 23.1, 22.6, 19.9, 19.8, 18.4, 18.3, 14.0, −2.1, −3.2. HRMS-MALDI: (M+Na$^+$) calcd. 936.3926, found 936.3956.

Dimethylthexylsilyl O-(2-O-acetyl-3-O-benzyl-4,6-O-benzylidene-α-L-idopyranosyl)-(1→4)-O-2-azido-3-O-benzyl-6-O-acetyl-2-deoxy-β-D-glucopyranoside (49)

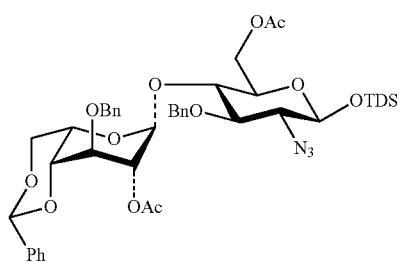

49

Glycosyl donor 1 (110.6 mg, 0.249 mmol) was coupled with the acceptor 5 (100 mg, 0.208 mmol) according to the general glycosylation procedure for synthesis of disaccharides to give disaccharide 49 (162 mg, 90%). [α]$_D^{25}$ −6.8 (c=1.00, CHCl$_3$); $^1$H NMR (500 MHz, CDCl$_3$): δ 7.44-7.25 (m, 15H, CH Aromatic), 5.30 (s, 1H, CH benzylidene), 4.98 (bs, 2H, H2$^B$, H1$^B$), 4.85 (d, 1H, J=11.0 Hz, CHHBn), 4.74 (d, 1H, J=11.5 Hz, CHHBn), 4.65 (d, 1H, J=12.0 Hz, CHHBn), 4.55 (d, 1H, J=12.0 Hz, CHHBn), 4.53 (m, 2H, H1$^A$, H6a$^A$), 4.05 (dd, 1H, J=5.5 Hz, J=12.0 Hz, H6b$^A$), 3.90 (bs, 1H, H5$^B$), 3.84-3.78 (m, 3H, H4$^A$, H4$^B$, H6a$^B$), 3.72-3.70 (m, 1H, H3$^B$), 3.49-3.45 (m, 1H, H5$^A$), 3.37-3.35 (m, 1H, H2$^A$), 3.24 (t, 1H, J=9.5 Hz, H3$^A$), 3.18 (dd, 1H, J=2.0 Hz, J=13.0 Hz, H6b$^B$), 2.06 (s, 3H, CH$_3$Ac), 2.05 (s 3H, CH$_3$Ac), 1.67-1.54 [m, 1H, CH(CH$_3$)$_2$], 0.90-0.88 [4s, 12H, C(CH$_3$)$_2$ and CH(CH$_3$)$_2$], 0.19-0.17 [2s, 6H, Si(CH$_3$)$_2$]. $^{13}$C NMR (75.5 MHz, CDCl$_3$): δ 170.4, 170.2, 138.1, 137.9, 137.6, 128.9, 128.4, 128.3, 128.0, 127.9, 127.9, 127.6, 127.4, 127.1, 126.1, 100.4, 98.0, 97.0, 81.2, 77.4, 77.0, 76.5, 75.0, 74.9, 73.8, 73.7, 73.5, 72.1, 69.0, 69.0, 67.1, 62.3, 60.3, 33.9, 24.8, 20.9, 20.8, 19.9, 19.8, 18.4, 18.3, −2.1, −3.3. HRMS-MALDI: (M+Na$^+$) calcd. 884.3765, found 884.5333.

Dimethylthexylsilyl O-(2-O-levulinoyl-3-O-benzyl-4,6-O-benzylidene-α-L-idopyranosyl)-(1→4)-O-2-azido-3-O-benzyl-6-O-acetyl-2-deoxy-β-D-glucopyranoside (50)

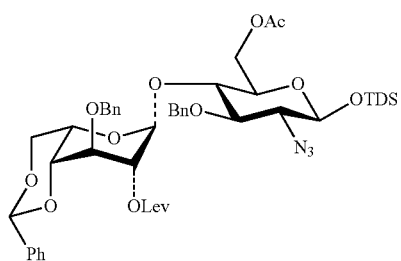

50

Glycosyl donor 2 (124.6 mg, 0.249 mmol) was coupled with acceptor 5 (100 mg, 0.208 mmol) according to the general glycosylation procedure for synthesis of disaccharides to give disaccharide 50 (170 mg, 66%) [α]$_D^{25}$ −12.0 (c=1.00, CHCl$_3$); $^1$H NMR (500 MHz, CDCl$_3$): δ 7.45-7.254

(m, 15H, CH Aromatic), 5.30 (s, 1H, CH benzylidene), 4.97 (bd, 2H, J=14.5 Hz, H2$^B$, H1$^B$), 4.83 (d, 1H, J=11.0 Hz, CHHBn), 4.74 (d, 1H, J=12.0 Hz, CHHBn), 4.63 (d, 1H, J=11.5 Hz, CHHBn), 4.55-4.49 (m, H, H1$^A$, H6a$^A$, CHHBn), 4.08 (dd, 1H, J=5.0 Hz, J=11.5 Hz, H6b$^A$), 3.89 (bs, 1H, H5$^B$), 33.84-3.79 (m, 3H, H4$^A$, H4$^B$, H6a$^B$), 3.68 (bs, 1H, H3$^B$), 3.49-3.45 (m, 1H, H5$^A$), 3.36 (t, 1H, J=10.0 Hz, H2$^A$), 3.24 (t, 1H, J=9.5 Hz, H3$^A$), 3.17 (d, 1H, J=13.0 Hz, H6b$^B$), 2.64-2.62 (m, 2H, CH$_2$ Lev), 2.56-2.52 (m, 2H, CH$_2$ Lev), 2.06 (s, 3H, CH$_3$ Lev), 2.02 (s, 3H, CH$_3$Ac), 1.67-1.54 [m, 1H, CH(CH$_3$)$_2$], 0.90-0.88 [4s, 12H, C(CH$_3$)$_2$ and CH(CH$_3$)$_2$], 0.19-0.17 [2s, 6H, Si(CH$_3$)$_2$]. $^{13}$C NMR (75.5 MHz, CDCl$_3$): δ 206.2, 171.8, 170.5, 138.1, 137.9, 137.6, 128.9, 128.4, 128.3, 128.1, 127.9, 127.6, 127.4, 126.1, 100.4, 97.9, 97.0, 81.2, 77.4, 77.0, 76.6, 75.0, 75.0, 73.9, 73.7, 73.5, 72.1, 69.1, 69.0, 67.1, 62.3, 60.3, 37.7, 33.9, 29.6, 28.1, 24.8, 20.8, 19.9, 19.8, 18.4, 18.3, −2.1, −3.2. HRMS-MALDI: (M+NO calcd. 940.4022, found 940.5577.

Dimethylthexylsilyl O-(2-O-acetyl-3-O-benzyl-4,6-O-benzylidene-α-L-idopyranosyl)-(1→4)-O-2-azido-3-O-benzyl-6-O-levulinoyl-2-deoxy-β-D-glucopyranoside (51)

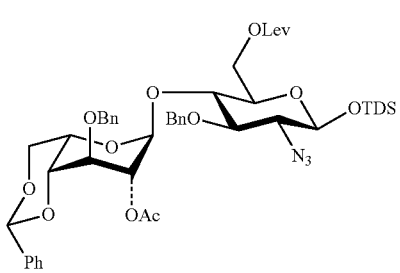

Glycosyl donor 1 (100 mg, 0.22 mmol) was coupled with the acceptor 6 (96.4 mg, 0.18 mmol) according to the general reacted procedure for synthesis of disaccharides to give disaccharide 51 (156.9 mg, 95%). [α]$_D^{25}$ +21.0 (c=1.00, CHCl$_3$); $^1$H NMR (500 MHz, CDCl$_3$): δ 7.26-7.06 (m, 15H, CH Aromatic), 5.12 (s, 1H, CH benzylidene), 4.80-4.79 (m, 1H, H2$^B$), 4.77 (s, 1H, H1$^B$), 4.65 (d, 1H, J=10.5 Hz, CHHBn), 4.57 (d, 1H, J=11.5 Hz, CHHBn), 4.47 (d, 1H, J=11.5 Hz, CHHBn), 4.37 (d, 2H, J=11.0 Hz, H6a$^A$, CHHBn), 4.34 (d, 1H, J=7.5 Hz, H1$^A$), 3.86 (dd, 1H, J=6.0 Hz, J=12.0 Hz, H6b$^A$), 3.73 (bs, 1H, H5$^B$), 3.65-3.3.60 (m, 3H, H4$^A$, H4$^B$, H6a$^B$), 3.68 (bt, 1H, J=3.0 Hz, H3$^B$), 3.30-3.28 (m, 1H, H5$^A$), 3.36 (t, 1H, J=7.5 Hz, H2$^A$), 3.02 (t, 1H, J=9.5 Hz, H3$^A$), 3.00 (d, J=13.0 Hz, 1H, H6b$^B$), 2.58-2.54 (m, 2H, CH$_2$ Lev), 2.42-2.39 (m, 2H, CH$_2$ Lev), 1.98 (s, 3H, CH$_3$ Lev), 1.88 (s, 3H, CH$_3$Ac), 1.49-1.45 [m, 1H, CH(CH$_3$)$_2$], 0.72-0.70 [4s, 12H, C(CH$_3$)$_2$ and CH(CH$_3$)$_2$], 0.018-0.00 [2s, 6H, Si(CH$_3$)$_2$]. $^{13}$C NMR (75.5 MHz, CDCl$_3$): δ 206.3, 172.1, 170.2, 138.1, 138.0, 137.6, 129.1, 128.9, 128.4, 128.4, 128.3, 128.0, 127.9, 127.6, 127.4, 126.1, 100.5, 97.9, 97.0, 81.2, 77.4, 77.0, 76.6, 75.0, 74.9, 73.8, 73.5, 73.5, 72.1, 69.1, 69.0, 67.0, 62.6, 60.2, 37.9, 33.9, 29.8, 29.7, 27.9, 24.8, 21.0, 19.9, 19.8, 18.5, 18.4, −2.1, −3.3. HRMS-MALDI: (M+NO calcd. 940.4029, found 940.5577.

Dimethylthexylsilyl O-(2-O-levulinoyl-3-O-benzyl-4,6-O-benzylidene-α-L-idopyranosyluronate)-(1→4)-O-2-azido-3-O-benzyl-6-O-levulinoyl-2-deoxy-β-D-glucopyranoside (52)

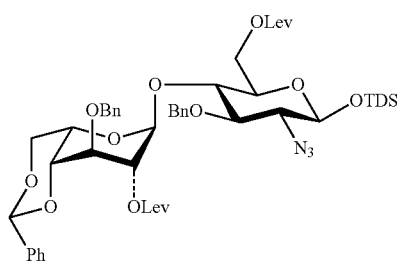

Glycosyl donor 2 (140 mg, 0.280 mmol) was coupled with acceptor 6 (140 mg, 0.260 mmol) according to the general glycosylation procedure for synthesis of disaccharides to give disaccharide 52 (200 mg, 80%). [α]$_D^{25}$ −11.2 (c=1.00, CHCl$_3$); $^1$H NMR (500 MHz, CDCl$_3$): δ 7.44-7.25 (m, 15H, CH Aromatic), 5.30 (s, 1H, CH benzylidene), 4.98-4.97 (m, 1H, H2$^B$), 4.92 (bs, 1H, H1$^B$), 4.82 (d, 1H, J=11.0 Hz, CHHBn), 4.74 (d, 1H, J=11.5 Hz, CHHBn), 4.63 (d, 1H, J=11.5 Hz, CHHBn), 4.55-4.51 (m, 3H, H1$^A$, H6a$^A$, CHHBn), 4.07 (dd, 1H, J=5.5 Hz, J=12.0 Hz, H6b$^A$), 3.89 (bs, 1H, H5$^B$), 3.84-3.79 (m, 3H, H4$^A$, H4$^B$, H6a$^B$), 3.68 (bt, 1H, J=3.0 Hz, H3$^B$), 3.49-3.45 (m, 1H, H5$^A$), 3.38-3.34 (m, 1H, H2$^A$), 3.23 (t, 1H, J=9.0 Hz, H3$^A$), 3.18 (dd, 1H, J=1.5 Hz, J=12.5 Hz, H6b$^B$), 2.78-2.68 (m, 2H, CH$_2$ Lev), 2.66-2.60 (m, 2H, CH$_2$ Lev), 2.58-2.51 (m, 4H, 2×CH$_2$ Lev), 2.17 (s, 3H, CH$_3$ Lev), 2.01 (s, 3H, CH$_3$ Lev), 1.67-1.54 [m, 1H, CH(CH$_3$)$_2$], 0.90-0.88 [4s, 12H, C(CH$_3$)$_2$ and CH(CH$_3$)$_2$], 0.19-0.17 [2s, 6H, Si(CH$_3$)$_2$]. $^{13}$C NMR (75.5 MHz, CDCl$_3$): δ 206.7, 206.3 172.1, 171.9, 138.1, 138.0, 137.6, 128.9, 128.3, 128.2, 128.0, 127.9, 127.9, 127.6, 127.4, 126.6, 100.4, 97.8, 96.9, 81.2, 77.4, 77.0, 76.5, 75.0, 74.9, 73.9, 73.4, 73.4, 72.1, 69.0, 69.0, 67.0, 62.5, 60.2, 37.9, 37.7, 33.9, 29.7, 29.6, 28.1, 27.9, 24.7, 19.9, 19.8, 18.4, 18.3, −2.1, −3.2. HRMS-MALDI: (M+Na$^+$) calcd. 996.4290, found 996.5962.

Dimethylthexylsilyl O-(methyl-2-O-acetyl-3-O-benzyl-α-L-idopyranosyluronate)-(1→4)-O-2-azido-3-O-benzyl-2-deoxy-6-O-acetyl-β-D-glucopyranoside (53)

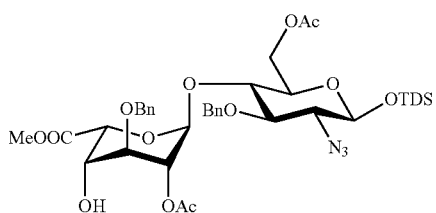

Compound 49 (116 mg, 0.149 mmol) was subjected to TEMPO/BAIB mediated oxidation and esterification using diazomethane according to the general procedure to give 53 (63.7 mg, 54%, two steps). [α]$_D^{25}$ +16.2 (c=1, CHCl$_3$); $^1$H NMR (500 MHz, CDCl$_3$): δ 7.24-7.13 (m, 10H, CH Aromatic), 4.93 (s, 1H, H1$^B$), 4.83 (bs, 1H, H5$^B$), 4.79 (bs, 1H, H2$^B$), 4.61 (d, 1H, J=11.5 Hz, CHHBn), 4.60 (d, 1H, J=11.0 Hz, CHHBn), 4.56 (d, 1H, J=11.0 Hz, CHHBn), 4.51 (d, 1H, J=11.5 Hz, CHHBn), 4.39-4.34 (m, 2H, H1$^A$, H6a$^A$), 4.99 (dd, 1H, J=5.5 Hz, J=12.0 Hz, H6b$^A$), 3.85 (bd, 1H, J=11.0 Hz, H4$^B$), 3.70 (t, 1H, J=9.5 Hz, H4$^A$), 3.60 (bs, 1H, H3$^B$), 3.36 (s, 3H, CO$_2$CH$_3$), 3.34-3.32 (m, 1H, H5$^A$), 3.22 (dd, 1H, J=8.0 Hz, J=10.0 Hz, H2$^A$), 3.14 (t, 1H, J=10.0 Hz, H3$^A$), 2.52 (d, 1H, J=11.5 Hz, 4-OH), 1.95 (s, 3H, CH$_3$ Ac), 1.92 (s, 3H, CH$_3$ Ac), 1.58-1.51 [m, 1H, CH(CH$_3$)$_2$], 0.77-0.75 [4s, 12H, C(CH$_3$)$_2$ and CH(CH$_3$)$_2$], 0.06-0.05 [2s, 6H, Si(CH$_3$)$_2$]. $^{13}$C NMR (75.5 MHz, CDCl$_3$): δ 173.8, 172.7, 172.5, 141.3, 140.6, 132.0, 131.8, 131.5, 131.4, 131.3, 131.1, 130.7, 130.6, 129.3, 101.2, 100.3, 84.3, 80.8, 80.6, 80.4, 79.9, 79.3, 78.2, 77.9, 77.7, 76.5, 75.6, 72.2, 71.7, 71.0, 70.4, 70.2, 65.7, 55.4, 37.2, 28.1, 24.3, 24.2, 24.1, 23.2, 23.1, 21.8, 21.7, −2.2, −3.2. HRMS-MALDI: (M+Na$^+$) calcd. 824.3401, found 824.3415.

Dimethylthexylsilyl O-(methyl-2-O-levulinoyl-3-O-benzyl-4-O-(9-fluorenylmethoxycarbonyl)-α-L-idopyranosyluronate)-(1→4)-O-2-azido-3-O-benzyl-2-deoxy-6-O-acetyl-β-D-glucopyranoside (54)

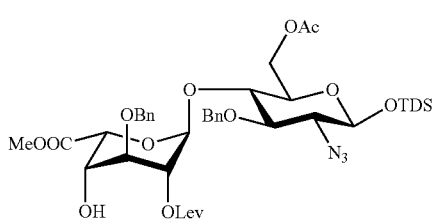

Compound 50 (71 mg, 0.086 mmol) was subjected to TEMPO/BAIB mediated oxidation and esterification using diazomethane according to the general procedure to give 54 (56.6 mg, 76%, two steps). [α]$_D^{25}$ +24.3 (c=1.3, CHCl$_3$); $^1$H NMR (500 MHz, CDCl$_3$: δ 7.25-7.11 (m, 10H, CH Aromatic), 4.93 (s, 1H, H1$^B$), 4.81 (d, 1H, J=1.7 Hz, H5$^B$), 4.79 (bs, 1H, H2$^B$), 4.62 (d, 1H, J=11.5 Hz, CHHBn), 4.59 (d, 1H, J=11.4 Hz, CHHBn), 4.55 (d, 1H, J=11.4 Hz, CHHBn), 4.51 (d, 1H, J=11.5 Hz, CHHBn), 4.39 (d, 1H, J=7.7 Hz, H1$^A$), 4.34 (dd, 1H, J=2.0 Hz, J=11.9 Hz, H6a$^A$), 4.00 (dd, 1H, J=4.8 Hz, J=11.7 Hz, H6b$^A$), 3.86 (bd, 1H, J=8.6, H4$^B$), 3.72 (t, 1H, J=9.3 Hz, H4$^A$), 3.61 (bs, 1H, H3$^B$), 3.36 (s, 1H, CO$_2$CH$_3$), 3.33 (ddd, 1H, J=3.3 Hz, J=5.7 Hz, J=10.1 Hz, H5$^A$), 3.22 (dd, 1H, J=7.7 Hz, J=9.9 Hz, H2$^A$), 3.12 (t, 1H, J=9.2 Hz, H3$^A$), 2.64 (dd, 2H, J=2.7 Hz, J=7.0 Hz, CH$_2$ Lev), 2.54 (d, 1H, J=10.4 Hz, 4-OH), 2.44 (t, 1H, J=7.0 Hz, CH$_2$ Lev), 2.05 (s, 3H, CH$_3$ Lev), 1.95 (s, 3H, CH$_3$ Ac), 1.54-1.42 [m, 1H, CH(CH$_3$)$_2$], 0.77-0.75 [4s, 12H, C(CH$_3$)$_2$ and CH(CH$_3$)$_2$], 0.06-0.05 [2s, 6H, Si(CH$_3$)$_2$]. $^{13}$C NMR (75.5 MHz, CDCl$_3$): δ 206.1, 171.3, 171.1, 170.5, 169.4, 138.0, 137.3, 128.4, 128.1, 128.0, 127.9, 127.4, 127.3, 97.9, 97.0, 77.4, 77.0, 76.6, 74.7, 74.6, 74.5, 73.2, 72.3, 68.9, 68.4, 67.6, 67.3, 63.2, 52.0, 37.8, 33.9, 29.6, 29.7, 27.9, 24.8, 22.7, 20.8, 19.9, 19.8, 18.4, 18.4, −2.2, −3.3. HRMS-MALDI: (M+Na$^+$) calcd. 880.3664, found 880.3683.

Dimethylthexylsilyl O-(methyl-2-O-acetyl-3-O-benzyl-(3-L-idopyranosyluronate)-(1→4)-O-2-azido-3-O-benzyl-2-deoxy-6-O-levulinoyl-β-D-glucopyranoside (55)

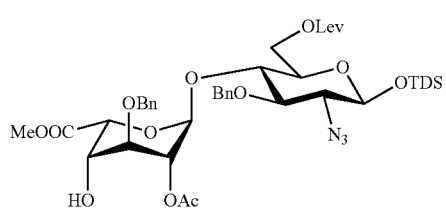

Compound 51 (90 mg, 0.108 mmol) was subjected to TEMPO/BAIB mediated oxidation and esterification using diazomethane according to the general procedure to give 55 (56.5 mg, 60%, two steps). [α]$_D^{25}$ +32.2 (c=1, CHCl$_3$); $^1$H NMR (500 MHz, CDCl$_3$): δ 7.24-7.14 (m, 10H, CH Aromatic), 4.89 (s, 1H, H1$^B$), 4.83 (bs, 1H, H5$^B$), 4.80 (bs, 1H, H2$^B$), 4.61 (d, 1H, J=11.5 Hz, CHHBn), 4.56 (m, 2H, CHHBn, CHHBn), 4.50 (d, 1H, J=11.5 Hz, CHHBn), 4.39-4.37 (m, 2H, H1$^A$, H6a$^A$), 4.00 (dd, 1H, J=4.0 Hz, J=11.0 Hz, H6b$^A$), 3.84 (bd, 1H, J=8.0 Hz, H4$^B$), 3.71 (t, 1H, J=9.5 Hz, H4$^A$), 3.60 (bs, 1H, H3$^B$), 3.36 (s, 1H, CO$_2$CH$_3$), 3.33-3.30 (m, 1H, H5$^A$), 3.21 (t, 1H, J=10.0 Hz, H2$^A$), 3.11 (t, 1H, J=10.0 Hz, H3$^A$), 2.66-2.63 (m, 2H, CH$_2$ Lev), 2.53-2.47 (m, 3H, CH$_2$ Lev, 4-OH), 2.07 (s, 3H, CH$_3$Lev), 1.97 (s, 3H, CH$_3$Ac), 1.54-1.52 [m, 1H, CH(CH$_3$)$_2$], 0.77-0.75 [4s, 12H, C(CH$_3$)$_2$ and CH(CH$_3$)$_2$], 0.06-0.05 [2s, 6H, Si(CH$_3$)$_2$]. $^{13}$C NMR (75.5 MHz, CDCl$_3$): δ 206.4, 172.2, 169.4, 169.3, 138.0, 137.3, 128.5, 128.2, 128.1, 128.0, 127.5, 127.3, 97.8, 97.0, 77.5, 77.0, 76.6, 74.6, 74.5, 74.3, 73.2, 72.2, 68.9, 68.3, 67.7, 67.0, 62.5, 52.0, 49.3, 37.8, 33.9, 29.8, 29.7, 29.3, 27.9, 24.8, 22.7, 21.0, 19.9, 19.8, 18.5, 18.4, −2.2, −3.3. HRMS-MALDI: (M+Na$^+$) calcd. 880.3664, found 880.3683.

Dimethylthexylsilyl O-(methyl-2-O-levulinoyl-3-O-benzyl-β-D-idopyranosyluronate)-(1→4)-O-2-azido-3-O-benzyl-2-deoxy-6-O-levulinoyl-β-D-glucopyranoside (56)

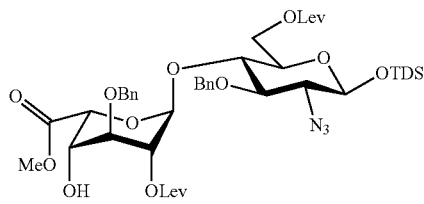

Compound 52 (50 mg, 0.056 mmol) was subjected to TEMPO/BAIB mediated oxidation and esterification using diazomethane according to the general procedure to give 56 (27 mg, 53%, two steps). [α]$_D^{25}$ −40.9 (c=1, CHCl$_3$); $^1$H NMR (500 MHz, CDCl$_3$): δ 7.44-7.25 (m, 10H, CH Aromatic), 4.99 (s, 1H, H2$^B$), 4.91 (bs, 2H, H1$^B$, H5$^B$), 4.73 (d, 1H, J=11.5 Hz, CHHBn), 4.66 (bs, 2H, CHHBn, CHHBn), 4.61 (d, 1H, J=11.5 Hz, CHHBn), 4.49 (d, 1H, J=7.5 Hz, H1$^A$), 4.46 (dd, 1H, J=2.0 Hz, J=12.5 Hz, H6a$^A$), 4.11 (dd, 1H, J=5.0 Hz, J=12.5 Hz, H6b$^A$), 3.97 (bd, 1H, J=9.0 Hz, H4$^B$), 3.85 (t, 1H, J=9.5 Hz, H4$^A$), 3.73 (t, 1H, J=2.5 Hz, H3$^B$), 3.47 (s, 3H, CO$_2$CH$_3$), 3.45-3.44 (m, 1H, H5$^A$), 3.34-3.30 (m, 1H, H2$^A$), 3.22 (t, 1H, J=9.0 Hz, H3$^A$), 2.80-2.73 [m, 4H, 2×CH$_2$ Lev], 2.61-2.58 [m, 4H, 2×CH$_2$ Lev], 2.19 (s, 3H, CH$_3$ Lev), 2.17 (s, 3H, CH$_3$ Lev), 1.67-1.63 [m, 1H, CH(CH$_3$)$_2$], 0.90-0.88 [4s, 12H, C(CH$_3$)$_2$, CH(CH$_3$)$_2$], 0.19-0.17 [2s, 6H, Si(CH$_3$)$_2$]. $^{13}$C NMR (75.5 MHz, CDCl$_3$): δ 206.5, 206.3, 172.1, 171.3, 169.4, 138.0, 137.3, 128.4, 128.3, 128.1, 128.1, 128.0, 127.9, 127.5, 127.3, 97.7, 97.0, 81.0, 77.4, 77.0, 76.6, 74.7, 74.5, 74.3, 72.3, 68.9, 68.4, 67.7, 67.3, 62.5, 51.9, 37.8, 37.8, 33.9, 33.7, 31.9, 30.1, 29.8, 29.7, 29.3, 27.9, 24.8, 19.9, 19.8, 18.4, 18.3, 14.1, −2.1, −3.2. HRMS-MALDI: (M+Na$^+$) calcd. 936.3926. found 936.3956.

N-(Benzyl)-benzyloxycarbonyl-5-aminopentyl O-(2-O-acetyl-3-O-benzyl-4,6-O-benzylidene-β-D-glucopyranosyl)-(1→4)-O-2-azido-3-O-benzyl-6-O-acetyl-2-deoxy-α-D-glucopyranoside (S1)

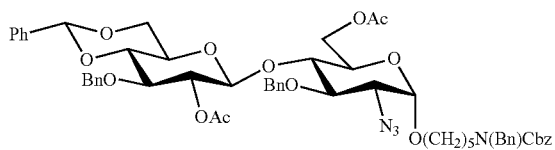

S1

Glycosyl donor 3 (82.1 mg, 0.185 mmol) was coupled with acceptor 7 (100 mg, 0.154 mmol) according to the general glycosylation procedure for synthesis of disaccharides to give disaccharide S1 (120 mg, 75%). [α]$_D^{25}$ +53.4 (c=1.00, CHCl$_3$); $^1$H NMR (500 MHz, CDCl$_3$): δ 7.44-7.24 (m, 20H, CH Aromatic), 5.47 (s, 1H, CH benzylidene), 5.17 (bd, 2H, J=17.5 Hz, CH$_2$ Cbz), 5.03 (t, 1H, J=8.5 Hz, H2$^B$), 4.96 (d, 1H, J=10.5 Hz, CHHBn), 4.86 (d, 1H, J=12.0 Hz, CHHBn), 4.81-4.75 (bd, 2H, H1$^A$, CHHBn), 4.63 (d, 1H, J=12.0 Hz, CHHBn), 4.51 (bd, 3H, J=8.0 Hz, H1$^B$ and NCH$_2$Bn), 4.39 (d, 1H, J=11.5 Hz, H6a$^A$), 4.13 (bd, 1H, J=11.5 Hz, H6b$^A$), 4.06 (dd, 1H, J=4.5 Hz, J=10.0 Hz, H6a$^B$), 3.89 (t, 1H, J=9.5 Hz, H4$^A$), 3.75-3.74 (m, 2H, H5$^A$, OCHH Linker), 3.68 (t, 2H, J=5.0 Hz, H3$^B$, H4$^B$), 3.65-3.34 (m, 1H, OCHHLinker), 3.44-3.22 (m, 6H, H2$^A$, H5$^B$, H3$^A$, H6b$^B$, CH$_2$N Linker), 2.07 (s, 3H, CH$_3$Ac), 2.00 (s, 3H, CH$_3$Ac), 1.66-1.24 (m, 6H, 3×CH$_2$ Linker). $^{13}$C NMR (75.5 MHz, CDCl$_3$):δ 170.4, 169.3, 138.4, 138.0, 137.9, 137.0, 129.1, 128.5, 128.4, 128.3, 128.3, 127.8, 127.7, 127.6, 127.4, 125.9, 101.6, 101.1, 97.5, 81.4, 78.7, 78.4, 77.8, 77.4, 77.0, 76.6, 75.0, 74.3, 73.2, 68.8, 68.3, 67.2, 66.3, 62.9, 62.1, 50.6, 50.2, 47.0, 46.1, 29.7, 28.9, 27.9, 23.3, 22.7, 20.8, 20.8. HRMS-MALDI: (M+Na$^+$) calcd. 1051.4316, found 1051.6359.

N-(Benzyl)-benzyloxycarbonyl-5-aminopentyl O-(2-O-levulinoyl-3-O-benzyl-4,6-O-benzylidene-β-D-glucopyranosyl)-(1→4)-O-2-azido-3-O-benzyl-6-O-acetyl-2-deoxy-α-D-glucopyranoside (S2)

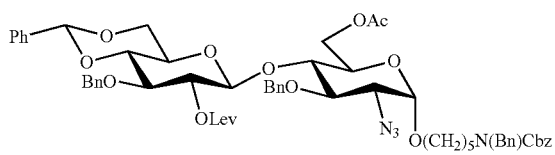

S2

Glycosyl donor 4 (92.61 mg, 0.185 mmol) was coupled with acceptor 7 (100 mg, 0.154 mmol) according to the general glycosylation procedure for synthesis of disaccharides to obtain disaccharide S2 (160 mg, 95%). [α]$_D^{25}$ +50.1 (c=1.00, CHCl$_3$); $^1$H NMR (500 MHz, CDCl$_3$): δ 7.44-7.24 (m, 25H, CH Aromatic), 5.47 (s, 1H, CH benzylidene), 5.17 (bd, 2H, J=17.0 Hz, CH$_2$Cbz), 5.04 (t, 1H, J=8.5 Hz, H2$^B$), 4.96 (d, 1H, J=10.5 Hz, CHHBn), 4.86 (d, 1H, J=12.0 Hz, CHHBn), 4.81 (bd, 2H, J=12.0 Hz, H1$^A$), 4.75 (d, 1H, J=10.5 Hz, CHHBn), 4.64 (d, 1H, J=12.0 Hz, CHHBn), 4.52-4.49 (m, 3H, H1$^B$, NCH$_2$Bn), 4.39 (dd, 1H, J=1.5 Hz, J=12.0 Hz, H6a$^A$), 4.29 (dd, 1H, J=4.0 Hz, J=10.5 Hz, H6b$^A$), 4.10 (dd, 1H, J=4.5 Hz, J=10.5 Hz, H6b$^B$), 3.98 (bd, 1H, J=9.5 Hz, H5$^A$), 3.92 (t, 1H, J=9.5 Hz, H3$^A$), 3.79 (t, 1H, J=9.0 Hz, H4$^A$), 3.72-3.66 (m, 3H, H3$^B$, H4$^B$, OCHH Linker), 3.38-3.21 (m, 6H, H2$^A$, H5$^B$, H6b$^B$, CH$_2$N Linker), 2.84-2.78 (m, 1H, CHH Lev), 2.64-2.52 (m, 2H, CH$_2$ Lev), 2.39-2.30 (m, 1H, CHH Lev), 2.10 (bd, 3H, J=12.5 Hz, CH$_3$ Lev), 2.08 (s, 3H, CH$_3$Ac), 1.70-1.51 (m, 4H, 2×CH$_2$ Linker), 1.39-1.25 (m, 2H, CH$_2$Linker). $^{13}$C NMR (75.5 MHz, CDCl$_3$): δ 205.7, 171.3, 170.6, 156.7, 156.1, 138.4, 1381, 137.9, 136.9, 129.0, 128.5, 128.4, 128.3, 128.2, 128.2, 127.9, 127.8, 127.7, 127.6, 127.5, 127.5, 127.2, 127.9, 101.5, 101.1, 97.4, 81.4, 78.8, 78.2, 77.7, 77.4, 77.0, 76.5, 75.1, 74.3, 73.4, 68.5, 68.3, 68.3, 68.1, 67.1, 66.2, 62.9, 62.3, 50.5, 50.2, 47.0, 46.1, 37.5, 29.7, 29.6, 28.9, 27.9, 27.6, 27.4, 23.2, 20.9. HRMS-MALDI: (M+Na$^+$) calcd. 1084.4682, found 1080.6445.

N-(Benzyl)-benzyloxycarbonyl-5-aminopentyl O-(2-O-acetyl-3-O-benzyl-4,6-O-benzylidene-β-D-glucopyranosyl)-(1→4)-O-2-azido-3-O-benzyl-6-O-levulinoyl-2-deoxy-α-D-glucopyranoside (S3)

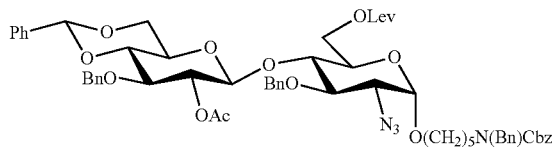

S3

Glycosyl donor 3 (1.51 g, 3.41 mmol) was coupled with acceptor 8 (2.0 g, 2.84 mmol) according to the general glycosylation procedure for synthesis of disaccharides to give disaccharide S3 (2.65 g, 85%). [α]$_D^{25}$ +31.5 (c=1.00, CHCl$_3$); $^1$H NMR (500 MHz, CDCl$_3$): δ 7.47-7.26 (m, 25H, CH Aromatic), 5.48 (s, 1H, CH benzylidene), 5.19 (bd, 2H, J=17.5 Hz, CH$_2$ Cbz), 5.05 (t, 1H, J=9.0 Hz, H2$^B$), 5.02 (d, 1H, J=11.0 Hz, CHHBn), 4.88 (d, 1H, J=12.0 Hz, CHHBn), 4.81 (bd, 2H, J=13.0 Hz, H1$^A$), 4.75 (d, 1H, J=11.0 Hz, CHHBn), 4.67 (d, 1H, J=8.0 Hz, H1$^B$), 4.65 (d, 1H, J=12.0 Hz, CHHBn), 4.51 (bs, 2H, NCH$_2$Bn), 4.29 (bs, 2H, H6a$_b$$^A$), 4.11 (dd, 1H, J=5.0 Hz, J=10.5 Hz, H6a$^B$), 3.90 (t, 1H, J=9.5 Hz, H3$^A$), 3.87-3.82 (m, 2H, H3$^B$, H4$^A$), 3.78-3.75 (m, 1H, H5$^A$), 3.70 (t, 1H, J=9.5 Hz, H4$^B$), 3.67-3.58 (m, 1H, OCHH Linker), 3.50 (ddd, 1H, J=4.5 Hz, J=9.5 Hz, J=14.0 Hz, H5$^B$), 3.44-3.23 [m, 5H, incl. H2$^A$: t, J=10.0 Hz, H6b$^B$: dd, J=3.0 Hz, J=10.0 Hz, CH$_2$N Linker and OCHH Linker], 2.89-2.82 (m, 1H, CHH Lev), 2.73-2.67 (m, 1H, CHH Lev), 2.64-2.58 (m, 1H, CHH Lev), 2.54-2.50 (m, 1H, CHH Lev), 2.17 (s, 3H, CH$_3$ Lev), 2.03 (s, 3H, CH$_3$Ac), 1.70-1.46 (m, 4H, 2×CH$_2$Linker), 1.38-1.22 (m, 2H, CH$_2$ Linker). $^{13}$C NMR (75.5 MHz, CDCl$_3$): δ 206.1, 172.4, 169.4, 168.5, 138.4, 138.2, 137.9, 137.2, 136.8, 128.9, 128.5, 128.4, 128.3, 128.2, 128.2, 127.8, 127.6, 127.6, 127.5, 127.4, 127.2, 125.9, 113.9, 101.4, 101.1, 97.5, 81.6, 78.8, 78.1, 77.7, 77.4, 77.0, 76.5, 75.0, 74.3, 73.3, 68.8, 68.4, 67.1, 65.9, 62.8, 62.1, 50.5, 50.2, 37.8, 29.7, 29.7, 29.3, 28.9, 27.8, 27.4, 23.2, 20.8. HRMS-MALDI: (M+NO calcd. 1084.4682, found 1080.644.

N-(Benzyl)-benzyloxycarbonyl-5-aminopentyl O-(2-O-levulinoyl-3-O-benzyl-4,6-O-benzylidene)-β-D-glucopyranosyl-(1→4)-O-2-azido-3-O-benzyl-6-O-levulinoyl-2-deoxy-α-D-glucopyranoside (S4)

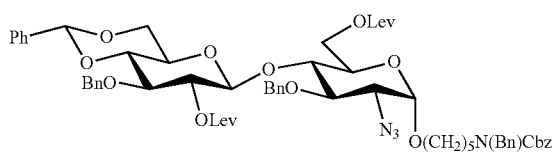

S4

Glycosyl donor 4 (85.1 mg, 0.170 mmol) was coupled with acceptor 8 (100 mg, 0.142 mmol) according to the general glycosylation procedure for synthesis of disaccharides to give disaccharide S4 (150 mg, 0.131 mmol, 92%). $[\alpha]_D^{25}$ +34.9 (c=1.00, CHCl$_3$); $^1$H NMR (500 MHz, CDCl$_3$): δ 7.44-7.24 (m, 25H, CH Aromatic), 5.47 (s, 1H, CH benzylidene), 5.17 (bd, 2H, J=16.5 Hz, CH$_2$ Cbz), 5.06-5.01 (m, 2H, H2$^B$, CHHBn), 4.85 (d, 1H, J=12.0 Hz, CHHBn), 4.81 (bd, 1H, J=11.0 Hz, H1$^A$), 4.73 (d, 1H, J=10.5 Hz, CHHBn), 4.68 (d, 1H, J=8.0 Hz, H1$^B$), 4.64 (d, 1H, J=12.0 Hz, CHHBn), 4.49 (bs, 2H, NCH$_2$Bn), 4.44 (dd, 1H, J=4.5 Hz, J=12.5 Hz, H6a$^A$), 4.33 (dd, 1H, J=2.0 Hz, J=12.5 Hz, H6b$^A$), 4.11 (dd, 1H, J=4.5 Hz, J=10.0 Hz, H6b$^B$), 4.00 (bd, 1H, J=9.5 Hz, H5$^A$), 3.92 (t, J=9.5 Hz, 1H, H3$^A$), 3.88-3.83 (m, 2H, H4$^A$, H3$^B$), 3.67 (t, 2H, J=9.5 Hz, H4$^B$, OCHH Linker), 3.54 (ddd, 1H, J=5.0 Hz, J=10.0 Hz, J=19.5 Hz, H5$^B$), 3.37-3.21 (m, 5H, incl.: H2$^A$: t, J=10.5 Hz, H6b$^B$: dd, J=3.5 Hz, J=10.5 Hz), CH$_2$N Linker and OCHH Linker), 2.90-2.78 (m, 2H, CH$_2$ Lev), 2.72-2.46 (m, 5H, 2×CH$_2$ Lev and CHH Lev), 2.39-2.30 (m, 1H, CHHLev), 2.16 (s, 3H, CH$_3$ Lev), 2.10 (bd, 3H, J=12.0 Hz, CH$_3$ Lev), 1.63-1.52 (m, 4H, 2×CH$_2$ Linker), 1.35-1.25 (m, 2H, CH$_2$ Linker). $^{13}$C NMR (75.5 MHz, CDCl$_3$): δ 206.2, 205.8, 172.5, 171.4, 138.5, 138.4, 137.9, 137.2, 136.7, 128.9, 128.5, 128.4, 128.2, 128.2, 127.9, 127.8, 127.6, 127.6, 127.5, 127.2, 126.0, 101.3, 101.1, 97.5, 81.6, 78.9, 78.1, 77.7, 77.4, 77.0, 76.6, 75.1, 74.3, 73.6, 68.5, 68.5, 68.1, 67.1, 65.9, 62.9, 62.5, 50.5, 50.2, 47.0, 46.1, 37.8, 37.6, 29.8, 29.7, 28.9, 27.9, 27.7, 23.9. HRMS-MALDI: (M+Na$^+$) calcd. 1140.4943, found 1136.6748.

N-(Benzyl)-benzyloxycarbonyl-5-aminopentyl O-(2-O-acetyl-3-O-benzyl-4,6-O-benzylidene-α-L-idopyranosyl)-(1→4)-O-2-azido-3-O-benzyl-6-O-acetyl-2-deoxy-α-D-glucopyranoside (S5)

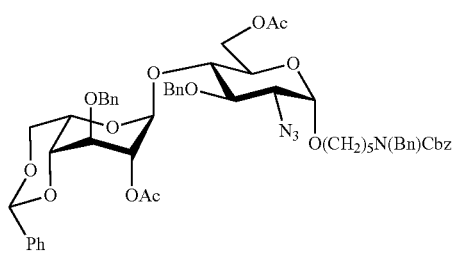

S5

Glycosyl donor 1 (82.1 mg, 0.185 mmol) was coupled with acceptor 7 (100 mg, 0.154 mmol) according to the general glycosylation procedure for synthesis of disaccharides to give disaccharide S5 (140 mg, 0.135 mmol, 88%). $[\alpha]_D^{24}$ +22.7 (c=1, CHCl$_3$); $^1$H NMR (500 MHz, CDCl$_3$): δ 7.44-7.25 (m, 25H, CH Aromatic), 5.28 (s, 1H, CH benzylidene), 5.17 (bd, 2H, J=15.0 Hz, CH$_2$Cbz), 5.00 (bs, 1H, H2$^B$), 4.98 (bs, 1H, H1$^B$), 4.86 (bd, 1H, J=12.5 Hz, H1$^A$), 4.80 (d, 1H, J=11.0 Hz, CHHBn), 4.75 (d, 1H, J=11.5 Hz, CHHBn), 4.65 (d, 1H, J=11.5 Hz, CHHBn), 4.62 (d, 1H, J=11.0 Hz, CHHBn), 4.50 (bd, 2H, J=7.0 Hz, NCH$_2$Bn), 4.46 (dd, 1H, J=12.0 Hz, H6a$^A$), 4.14 (d, 1H, J=12.5 Hz, H6b$^A$), 3.87-3.83 (m, 5H, H5$^A$, H3$^A$, H4$^A$, H4$^B$, H5$^B$), 3.77 (d, 1H, J=13.0 Hz, H6a$^B$), 3.71 (t, 1H, J=3.0 Hz, H3$^B$), 3.69-3.60 (m, 1H, OCHH Linker), 3.46-3.22 (m, 3H, CH$_2$N Linker, OCHHLinker), 3.36 (dd, 1H, J=3.0 Hz, J=9.5 Hz, H2$^A$), 3.09 (d, 1H, J=11.5 Hz, H6b$^B$), 2.09 (s, 3H, CH$_3$ Ac), 2.07 (s, 3H, CH$_3$Ac), 1.70-1.40 (m, 3×CH$_2$ Linker). $^{13}$C NMR (75.5 MHz, CDCl$_3$): δ 170.6, 170.2, 138.0, 137.9, 137.6, 128.9, 128.5, 128.4, 128.3, 128.1, 128.0, 127.8, 127.6, 127.4, 126.1, 100.4, 98.1, 97.5, 78.5, 77.4, 77.0, 76.6, 74.9, 74.6, 74.0, 73.8, 72.0, 69.4, 69.0, 68.2, 67.2, 67.1, 63.6, 62.3, 60.3, 29.7, 29.0, 23.3, 21.0. HRMS-MALDI: (M+Na$^+$) calcd. 1051.4316, found 1051.4595.

N-(Benzyl)-benzyloxycarbonyl-5-aminopentyl O-(2-O-levulinoyl-3-O-benzyl-4,6-O-benzylidene-α-L-idopyranosyl)-(1→4)-O-2-azido-3-O-benzyl-6-O-acetyl-2-deoxy-α-D-glucopyranoside (S6)

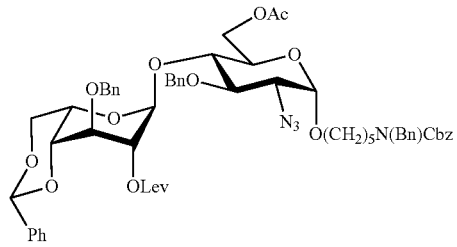

S6

Glycosyl donor 2 (92.6 mg, 0.185 mmol) was coupled with the acceptor 7 (100 mg, 0.154 mmol) according to the general glycosylation procedure for synthesis of disaccharides to give disaccharide S6 (140 mg, 83%) $[\alpha]_D^{25}$ +37.9 (c=1.00, CHCl$_3$); $^1$H NMR (500 MHz, CDCl$_3$): δ 7.44-7.24 (m, 25H, CH Aromatic), 5.29 (s, 1H, CH benzylidene), 5.17 (bd, 2H, J=14.5 Hz, CH$_2$ Cbz), 5.01 (bs, 1H, H2$^B$), 4.95 (bs, 1H, H1$^B$), 4.86 (bd, 1H, J=14.0 Hz, H1$^A$), 4.79 (d, 1H, J=10.5 Hz, CHHBn), 4.75 (d, 1H, J=12.0 Hz, CHHBn), 4.63 (d, 1H, J=11.5 Hz, CHHBn), 4.60 (d, 1H, J=11.0 Hz, CHHBn), 4.50 (bd, 2H, J=7.0 Hz, NCH$_2$Bn), 4.45 (dd, 1H, J=12.5 Hz, H6a$^A$), 4.17 (d, 1H, J=12.0 Hz, H6b$^A$), 3.85-3.82 (m, 5H, H5$^A$, H3$^A$, H4$^A$, H4$^B$, H5$^B$), 3.77 (d, 1H, J=13.0 Hz, H6a$^B$), 3.69 (t, 1H, J=3.0 Hz, H3$^B$), 3.69-3.60 (m, 1H, OCHH Linker), 3.46-3.22 (m, 3H, CH$_2$N Linker, OCHHLinker), 3.34 (dd, 1H, J=3.0 Hz, J=9.5 Hz, H2$^A$), 3.09 (d, 1H, J=11.5 Hz, H6b$^B$), 2.64-2.59 (m, 2H, CH$_2$ Lev), 2.56-2.50 (m, 2H, CH$_2$ Lev), 2.07 (s, 3H, CH$_3$ Lev), 2.01 (s, 3H, CH$_3$Ac), 1.70-1.40 (m, 3×CH$_2$Linker). $^{13}$C NMR (75.5 MHz, CDCl$_3$): δ 206.7, 171.9, 170.6, 138.1, 138.0, 137.9, 137.6, 128.9, 128.5, 128.4, 128.3, 128.1, 128.0, 127.8, 127.6, 127.4, 126.1, 100.4, 98.0, 97.5, 78.5, 77.4, 77.0, 76.6, 74.9, 74.6, 74.0, 73.8, 72.1, 69.3, 69.1, 68.2, 67.1, 67.1, 63.6, 62.3, 60.3, 50.5, 50.2, 37.9, 34.1, 32.1, 29.9, 29.8, 29.2, 28.3, 23.5, 22.9, 21.2, 14.3. HRMS-MALDI: (M+Na$^+$) calcd. 1084.4681. found 1080.4642.

N-(Benzyl)-benzyloxycarbonyl-5-aminopentyl O-(2-O-acetyl-3-O-benzyl-4,6-O-benzylidene-α-L-idopyranosyl)-(1→4)-O-2-azido-3-O-benzyl-6-O-levulinoyl-2-deoxy-α-D-glucopyranoside (S7)

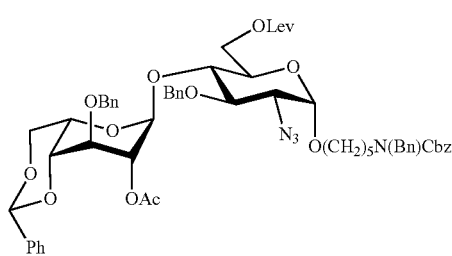

S7

Glycosyl donor 1 (100 mg, 0.22 mmol) was coupled with acceptor 8 (126.5 mg, 0.18 mmol) according to the general glycosylation procedure for synthesis of disaccharides to give disaccharide S7 (160 mg, 81%). [α]$_D^{25}$ +32.3 (c=1.00, CHCl$_3$); δ 7.45-7.27 (m, 25H, CH Aromatic), 5.30 (s, 1H, CH benzylidene), 5.19 (bd, 2H, J=16.0 Hz, CH$_2$ Cbz), 5.01 (bs, 1H, H2$^B$), 4.97 (s, 1H, H1$^B$), 4.87 (bd, 1H, J=12.5 Hz, H1$^A$), 4.80 (d, 1H, J=11.0 Hz, CHHBn), 4.77 (d, 1H, J=12.5 Hz, CHHBn), 4.66 (d, 1H, J=11.5 Hz, CHHBn), 4.63 (d, 1H, J=11.0 Hz, CHHBn), 4.52 (bd, 3H, J=11.0 Hz, NCH$_2$Bn, H6a$^A$), 4.15 (d, 1H, J=11.0 Hz, H6b$^A$), 3.89-3.78 (m, 5H, H5$^A$, H3$^A$, H4$^A$, H4$^B$, H5$^B$), 3.79 (d, 1H, J=13.0 Hz, H6$_a^B$), 3.73 (t, 1H, J=3.0 Hz, H3$^B$), 3.69-3.60 (m, 1H, OCHH Linker), 3.46-3.22 (m, 3H, CH$_2$N Linker, OCHH Linker), 3.36 (dd, 1H, J=3.0 Hz, J=9.0 Hz, H2$^A$), 3.13 (d, 1H, J=12.5 Hz, H6b$^B$), 2.77-2.74 (m, 2H, CH$_2$ Lev), 2.62-2.60 (m, 2H, CH$_2$ Lev), 2.15 (s, 3H, CH$_3$ Lev), 2.08 (s, 3H, CH$_3$Ac), 1.70-1.40 (m, 3×CH$_2$ Linker). $^{13}$C NMR (75.5 MHz, CDCl$_3$): δ 206.3, 172.2, 170.2, 138.0, 138.0, 137.9, 137.6, 136.8, 128.9, 128.5, 128.3, 128.2, 128.0, 128.0, 127.9, 127.8, 127.6, 127.3, 127.2, 126.1, 100.4, 97.9, 97.4, 78.5, 77.4, 77.0, 76.6, 75.0, 74.8, 74.6, 73.7, 72.0, 70.0, 69.3, 69.0, 68.1, 67.1, 66.9, 63.6, 62.7, 62.4, 60.2, 50.5, 50.2, 47.1, 46.1, 37.8, 29.7, 29.6, 29.0, 27.9, 27.4, 23.3, 20.9. HRMS-MALDI: (M+Na$^+$) calcd. 1084.4681, found 1080.4642.

N-(Benzyl)-benzyloxycarbonyl-5-aminopentyl O-(2-O-levulinoyl-3-O-benzyl-4,6-O-benzylidene-α-L-idopyranosyl)-(1→4)-O-2-azido-3-O-benzyl-6-O-levulinoyl-2-deoxy-α-D-glucopyranoside (S8)

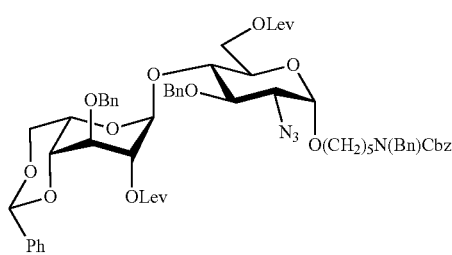

S8

Glycosyldonor 2 (100 mg, 0.199 mmol) was coupled with the acceptor 8 (116.6 mg, 0.166 mmol) according to the general glycosylation procedure for synthesis of disaccharides to give disaccharide S8 (180 mg, 95%). [α]$_D^{25}$ +37.3 (c=1.00, CHCl$_3$); $^1$H NMR (300 MHz, CDCl$_3$): δ 7.38-7.16 (m, 25H, CH Aromatic), 5.21 (s, 1H, CH benzylidene), 5.09 (bs, 2H, CH$_2$ Cbz), 4.93 (t, 1H, J=2.4 Hz, H2$^B$), 4.85 (bs, 1H, H1$^B$), 4.79 (bs, 1H, H1$^A$), 4.72 (d, 1H, J=10.8 Hz, CHHBn), 4.70 (d, 1H, J=11.7 Hz, CHHBn), 4.58 (d, 1H, J=11.4 Hz, CHHBn), 4.55 (d, 1H, J=11.1 Hz, CHHBn), 4.43 (t, 3H, J=3.0 Hz, NCH$_2$Bn, H6a$^A$), 4.15 (d, 1H, J=12.6 Hz, H6b$^A$), 3.78-3.73 (m, 5H, H5$^A$, H3$^A$, H4$^A$, H4$^B$, H5$^B$), 3.68 (s, 1H, H6a$^B$), 3.73 (t, 1H, J=3.0 Hz, H3$^B$), 3.63-3.52 (m, 1H, OCHH Linker), 3.42-3.12 (m, 3H, CH$_2$N Linker, OCHHLinker), 3.36 (dd, 1H, J=3.3 Hz, J=9.3 Hz, H2$^A$), 3.02 (d, 1H, J=11.7 Hz, H6b$^B$), 2.77-2.74 (m, 2H, CH$_2$ Lev), 2.62-2.60 (m, 2H, CH$_2$ Lev), 2.15 (s, 3H, CH$_3$ Lev), 2.08 (s, 3H, CH$_3$Ac), 1.70-1.40 (m, 6H, 3×CH$_2$ Linker). $^{13}$C NMR (75.5 MHz, CDCl$_3$): δ 206.4, 206.3, 172.1, 171.9, 138.0, 138.0, 137.8, 137.6, 136.8, 128.8, 128.5, 128.3, 128.2, 128.0, 127.9, 127.8, 127.8, 127.5, 127.3, 127.2, 126.1, 100.4, 97.7, 97.4, 78.4, 77.4, 77.2, 77.0, 76.5, 74.8, 74.5, 73.7, 73.6, 72.0, 69.3, 69.0, 68.1, 67.1, 66.9, 63.6, 62.4, 60.1, 50.5, 50.2, 47.0, 46.1, 37.8, 37.7, 30.8, 29.7, 29.6, 29.5, 29.0, 28.1, 27.9, 27.4, 23.2. HRMS-MALDI: (M+Na$^+$) calcd. 1140.4943, found 1136.6748.

Dimethylthexylsilyl O-(2-O-acetyl-β-O-benzyl-(3-D-glucopyranosyl)-(1→4)-O-2-azido-3-O-benzyl-6-O-levulinoyl-2-deoxy-β-D-glucopyranoside (S9)

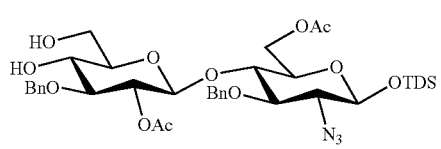

S9

Disaccharide 37 (0.427 g, 0.495 mmol) was dissolved in DCM:TFA:H$_2$O (0.06 M) (10/1/0.1, v/v) and treated according to the general procedure for benzylidene acetal cleavage to give S9 (0.290 g, 75%). [α]$_D^{25}$ +16.20 (c=1.00, CHCl$_3$); $^1$H NMR (500 MHz, CDCl$_3$): δ 7.37-7.25 (m, 10H, CH Aromatic), 4.97 (t, 1H, J=9.5 Hz, H2$^B$), 4.87 (d, 1H, J=10.0 Hz, CHHBn), 4.78 (d, 1H, J=15.0 Hz, CHHBn), 4.72 (d, 1H, J=10.0 Hz, CHHBn), 4.64 (d, 1H, J=10.0 Hz, CHHBn), 4.58 (d, 1H, J=10.0 Hz, H1$^A$), 4.44 (dd, 1H, J=2.0 Hz, J=10.0 Hz, H6a$^A$), 4.39 (d, 1H, J=10.0 Hz, H1$^B$), 4.06 (dd, 1H, J=7.0 Hz, J=12.0 Hz, H6b$^A$), 3.64-3.54 (m, 3H, H4$^B$, H4$^A$,H6a$^B$), 3.48-3.42 (m, 2H, H5$^A$, H3$^B$), 3.35-3.28 (m, 3H, H2$^A$, H3$^A$,H6b$^B$), 3.20-3.16 (m, 1H, H5$^A$), 2.06 (s, 3H, CH$_3$Ac), 2.00 (s, 3H, CH$_3$Ac), 1.65-1.61 [m, 1H, CH(CH$_3$)$_2$], 0.88-0.86 [4s, 12H, C(CH$_3$)$_2$ and CH(CH$_3$)$_2$], 0.17-0.15 [2s, 6H, Si(CH$_3$)$_2$]. $^{13}$C NMR (75.5 MHz, CDCl$_3$): δ 170.5, 169.4, 138.3, 137.9, 128.7, 128.4, 128.1, 127.8, 127.7, 127.1, 101.0, 96.7, 82.8, 80.6, 78.0, 77.4, 77.0, 76.6, 75.4, 75.1, 74.7, 73.3, 72.9, 70.5, 68.5, 62.4, 62.1, 33.9, 24.8, 20.8, 20.8, 19.9, 19.8, 18.4, 18.3, −2.2, −3.3. HRMS-MALDI: (M+Na$^+$) calcd. 796.34527, found 796.3431.

Dimethylthexylsilyl O-(2-O-levulinoyl-3-O-benzyl-β-D-glucopyranosyl)-(1→4)-O-2-azido-3-O-benzyl-6-O-levulinoyl-2-deoxy-β-D-glucopyranoside (S10)

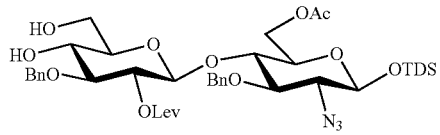

Disaccharide 38 (0.255 g, 0.277 mmol) was dissolved in DCM:TFA:H$_2$O (0.06 M) (10/1/0.1, v/v) and treated according to the general procedure for benzylidene acetal cleavage to give S10 (0.20 g, 87%). $^1$H NMR (500 MHz, CDCl$_3$): δ 7.36-7.25 (m, 10H, CH Aromatic), 4.97 (t, 1H, J=8.5 Hz, H2$^B$), [α]$_D^{25}$ +27.1 (c=0.024, CHCl$_3$); 4.87 (d, 1H, J=11.0 Hz, CHHBn), 4.79 (d, 1H, J=12.0 Hz, CHHBn), 4.76 (d, 1H, J=11.0 Hz, CHHBn), 4.62 (d, 1H, J=11.5 Hz, CHHBn), 4.50-4.48 (m, 2H, H1$^A$, H6a$^A$), 4.40 (d, 1H, J=7.5 Hz, H1$^B$), 4.11 (dd, 1H, J=6.0 Hz, J=12.0 Hz, H6b$^A$), 3.61-3.56 (m, 2H, H4$^B$, H6a$^B$), 3.53 (t, 1H, J=9.0 Hz, H5$^A$), 3.47 (t, 1H, J=9.0 Hz, H3$^B$), 3.36-3.27 (m, 3H, H2$^A$, H3$^A$, H6b$^B$), 3.20-3.17 (m, 1H, H5$^B$), 2.81-2.58 (m, 3H, CH$_2$ Lev, CHH Lev), 2.47-2.41 (m, 1H, CHH Lev), 2.17 (s, CH$_3$ Lev), 2.08 (s, 1H, CH$_3$Ac), 1.68-1.62 [m, 1H, CH(CH$_3$)$_2$], 0.89-0.86 [4s, 12H, C(CH$_3$)$_2$ and CH(CH$_3$)$_2$], 0.18-0.16 [2s, 6H, Si(CH$_3$)$_2$]. $^{13}$C NMR (75.5 MHz, CDCl$_3$): δ 206.1, 171.5, 170.6, 138.3, 138.1, 128.6, 128.4, 128.0, 127.7, 127.2, 100.9, 96.7, 82.9, 80.7, 77.9, 77.4, 77.0, 76.5, 75.4, 75.2, 74.7, 73.6, 72.7, 70.5, 68.5, 62.6, 62.1, 37.5, 33.9, 29.8, 27.7, 24.8, 20.8, 19.9, 19.8, 18.4, 18.3, -2.1, -3.2. HRMS-MALDI: (M+Na$^+$) calcd. 852.3714, found 852.5162.

Dimethylthexylsilyl O-(2-O-acetyl-3-O-benzyl-β-D-glucopyranosyl)-(1→4)-O-2-azido-3-O-benzyl-6-O-levulinoyl-2-deoxy-β-D-glucopyranoside (S11)

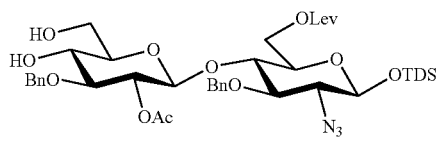

Disaccharide 39 (3.65 g, 3.97 mmol) was dissolved in DCM:TFA:H$_2$O (10/1/0.1, v/v/v) (0.06 M) and treated according to the general procedure for benzylidene acetal cleavage to give S11 (2.8 g, 85%). [α]$_D^{25}$ +30.6 (c=1.00, CHCl$_3$); $^1$H NMR (500 MHz, CDCl$_3$): δ 7.38-7.26 (m, 10H, CH Aromatic), 4.97 (t, 1H, J=9.0 Hz, H2$^B$), 4.90 (d, 1H, J=11.0 Hz, CHHBn), 4.77 (d, 1H, J=11.0 Hz, CHHBn), 4.72 (d, 1H, J=11.5 Hz, CHHBn), 4.65 (d, 1H, J=11.5 Hz, CHHBn), 4.47 (d, 1H, J=8.0 Hz, H1$^A$), 4.46 (d, 1H, J=7.0 Hz, H1$^B$), 4.35 (dd, 1H, J=1.5 Hz, J=11.5 Hz, H6a$^A$), 4.17 (dd, 1H, J=5.0 Hz, J=11.5 Hz, H6b$^A$), 3.71 (t, 1H, J=9.5 Hz, H4$^B$), 3.64-3.59 (m, 2H, H4$^B$, H3$^B$), 3.56 (ddd, 1H, J=3.5 Hz, J=9.0 Hz, J=18.0 Hz, H6$^B$), 3.45-3.41 (m, 1H, H5$^A$), 3.37-3.27 (m, 4H, H2$^A$, H6B, H5$^B$), 2.85-2.81 (m, 1H, CHH Lev), 2.75-2.67 (m, 1H, CHHLev), 2.65-2.52 (m, 2H, 2×CH$_2$ Lev), 2.06 (s, 3H, CH$_3$ Ac), 2.19 (s 3H, CH$_3$Lev), 2.04 (s, 3H, CH$_3$Ac), 1.65-1.61 [m, 1H, CH(CH$_3$)$_2$], 0.90-0.87 [4s, 12H, C(CH$_3$)$_2$ and CH(CH$_3$)$_2$], 0.17-0.16 [2s, 6H, Si(CH$_3$)$_2$]. $^{13}$C NMR (75.5 MHz, CDCl$_3$): δ 206.5, 172.4, 169.5, 138.3, 138.1, 128.6, 128.4, 128.0, 127.8, 127.7, 127.3, 100.8, 96.8, 82.9, 80.6, 77.4, 77.0, 76.6, 75.5, 75.2, 74.6, 73.3, 72.8, 70.8, 68.5, 62.3, 37.7, 33.9, 29.8, 29.7, 27.8, 24.8, 20.9, 19.9, 19.8, 18.5, 18.4, -2.1, -3.2. HRMS-MALDI: (M+Na$^+$) calcd. 852.3714, found 852.5162.

Dimethylthexylsilyl O-(2-O-levulinoyl-3-O-benzyl-β-D-glucopyranosyl)-(1→4)-O-2-azido-3-O-benzyl-6-O-levulinoyl-2-deoxy-β-D-glucopyranoside (S12)

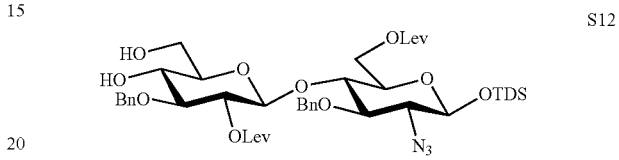

Disaccharide 40 (0.377 g, 0.387 mmol) was dissolved in DCM:TFA:H$_2$O (10/1/0.1, v/v) (0.06 M) and treated according to the general procedure for benzylidene acetal cleavage to give S12 (0.297 g, 87%). [α]$_D^{25}$ -9.1 (c=1.00, CHCl$_3$); $^1$H NMR (500 MHz, CDCl$_3$): δ 7.39-7.26 (m, 10H, CH Aromatic), 4.96 (t, 1H, J=8.5 Hz, H2$^B$), 4.90 (d, 1H, J=10.5 Hz, CHHBn), 4.75 (d, 2H, J=11.5 Hz, CHHBn and CHHBn), 4.65 (d, 1H, J=12.0 Hz, CHHBn), 4.489 (t, 2H, J=7.5 Hz, H1$^B$ and H1$^A$), 4.38, (dd, 1H, J=1.5 Hz, J=11.5 Hz, H6a$^A$), 4.25 (dd, 1H, J=4.5 Hz, J=12.0 Hz, H6b$^A$), 3.73 (t, 1H, J=9.5 Hz, H4$^A$), 3.62-3.57 (m, 3H, H3$^B$, H5$^A$,H6a$^B$), 3.51 (t, 1H, J=9.0 Hz, H4$^B$), 3.365-3.271 (m, 4H, H2$^A$, H3$^A$, H5$^B$, H6b$^B$), 3.56-3.58[m, 6H, 3×CH$_2$ Lev], 2.43-2.38 (m, 2H, CH$_2$ Lev), 2.38-2.18 (2s 3H, CH$_3$ Lev), 1.80-1.62 [m, 1H, CH(CH$_3$)$_2$], 0.89-0.87 [4s, 12H, C(CH$_3$)$_2$ and CH(CH$_3$)$_2$], 0.17-0.16 [2s, 6H, Si(CH$_3$)$_2$]. $^{13}$C NMR (75.5 MHz, CDCl$_3$): δ 206.6, 206.1, 172.4, 171.5, 138.4, 138.3, 128.6, 128.3, 127.9, 127.7, 127.3, 100.7, 96.7, 82.9, 80.6, 77.4, 77.0, 76.6, 75.4, 75.2, 74.6, 73.6, 72.6, 70.9, 68.5, 62.7, 62.3, 37.7, 37.6, 33.9, 29.9, 29.8, 27.8, 24.8, 19.9, 19.8, 18.4, 18.4, -2.1, -3.2. HRMS-MALDI: (M+NO calcd. 908.3977, found 908.5037.

Dimethylthexylsilyl O-(2-O-acetyl-3-O-benzyl-α-L-idopyranosyl)-(1→4)-O-2-azido-3-O-benzyl-6-O-acetyl-2-deoxy-β-D-glucopyranoside (49)

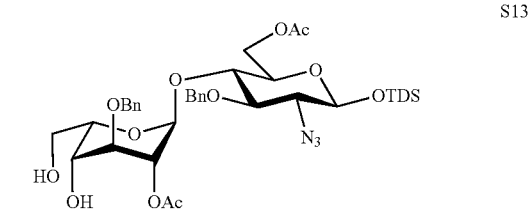

Disaccharide 49 (120 mg, 0.131 mmol) was dissolved in DCM and treated according to the general procedure for benzylidene acetal cleavage. Silica gel column chromatography of the residue (Toluene/EtOAc, 9/1→65/35, v/v) afforded 49 (116 mg, 65%). [α]$_D^{25}$ -21(c=1, CHCl$_3$); $^1$H NMR (500 MHz, CDCl$_3$): δ 7.33-7.07 (m, 10H, CH Aromatic), 4.79 (t, 1H, J=1.2 Hz, H2$^B$), 4.70 (bs, 1H, H1$^B$), 4.65 (d, 1H, J=10.0 Hz, CHHBn), 4.61 (d, 1H, J=11.3 Hz, CHHBn), 4.46 (d, J=11.3, 1H, CHHBn), 4.39 (d, J=7.6 Hz, 1H, H1$^A$), 4.36 (d, 1H, J=10.0 Hz, CHHBn), 4.33 (dd, 1H, J=2.3 Hz, J=12.2 Hz, H6a$^A$), 4.10 (bt, 1H, J=5.2 Hz, H5$^B$), 4.97 (dd, 1H, J=5.6 Hz, J=12.0 Hz, H6b$^A$), 3.67 (t, 1H, J=9.5 Hz, H4$^A$), 3.50 (t, 1H, J=2.6 Hz, H3$^B$), 3.45 (bd, 1H, J=9.6 Hz, H4$^B$), 3.34 (ddd, 1H, J=2.3 Hz, J=5.4 Hz, J=9.5 Hz, H5$^A$), 3.22 (dd, 1H, J=7.6 Hz, J=10.0 Hz, H2$^A$), 3.18 (d, 1H, J=6.0 Hz, J=12.0 Hz, H6a$^B$), 3.10 (t, 1H, J=9.7 Hz, H3$^A$), 3.05 (m, 1H, H6b$^B$), 2.40 (d, 1H, J=9.6, OH), 1.94-1.92 (2s, 6H, 2×CH$_3$Ac), 1.52-1.43[m, 1H, CH(CH$_3$)$_2$], 0.76-0.73 [4s, 12H, C(CH$_3$)$_2$ and CH(CH$_3$)$_2$], 0.05-0.03 [2s, 6H, Si(CH$_3$)$_2$]. $^{13}$C NMR (75.5 MHz, CDCl$_3$): δ 170.45, 169.48, 137.59, 137.47, 128.5, 128.14, 128.11, 128.03, 127.92, 97.8, 97.04, 81.30, 75.43, 75.09, 73.50, 73.43, 72.24, 69.2, 67.72, 67.50, 67.0, 62.71, 62.37, 33.95, 24.80, 20.99, 20.83, 19.94, 19.83, 18.50, 18.36, −2.21, −3.31. HRMS-MALDI: (M+Na$^+$) calcd. 796.3447, found 796.3451.

Dimethylthexylsilyl O-(2-O-levulinoyl-3-O-benzyl-α-L-idopyranosyl)-(1→4)-O-2-azido-3-O-benzyl-6-O-acetyl-2-deoxy-β-D-glucopyranoside (S14)

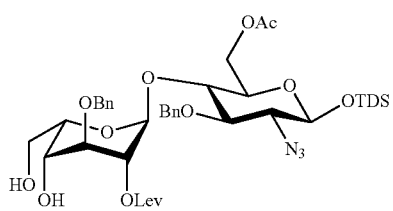

Disaccharide 50 (170 mg, 0.137 mmol) was dissolved in DCM:TFA:H$_2$O (10/1/0.1, v/v/v) (0.06 M) and treated according to the general procedure for benzylidene acetal cleavage to give S14 (71.5 mg, 55%). [α]$_D^{25}$ +45.6 (c=0.8, CHCl$_3$); $^1$H NMR (500 MHz, CDCl$_3$): δ 7.25-7.07 (m, 10H, CH Aromatic), 4.79 (t, 1H, J=1.1 Hz, H2$^B$), 4.70 (bs, 1H, H1$^B$), 4.64 (d, 1H, J=10.3 Hz, CHHBn), 4.61 (d, 1H, J=11.3 Hz, CHHBn), 4.46 (d, 1H, J=11.3 Hz, CHHBn), 4.39 (d, 1H, J=7.6 Hz, H1$^A$), 4.36 (d, 1H, J=10.3 Hz, CHHBn), 4.32 (dd, 1H, J=2.3 Hz, J=12.0 Hz, H6a$^A$), 4.08 (t, 1H, J=5.1 Hz, H5$^B$), 3.96 (dd, 1H, J=5.2 Hz, J=12.0 Hz, H6b$^A$), 3.70 (t, 1H, J=9.4 Hz, H4$^A$), 3.51 (t, 1H, J=2.4 Hz, H3$^B$), 3.46 (bs, 1H, H4$^A$), 3.33 (ddd, 1H, J=2.3 Hz, J=5.1 Hz, J=9.5 Hz, H5$^A$), 3.24-3.18 (m, 2H, H2$^A$, H6a$^B$), 3.10 (t, 1H, J=9.4 Hz, H3$^A$), 3.05-3.04 (m, 1H, H6b$^B$), 2.61 (t, 2H, CH$_2$ Lev), 2.56 (bd, 1H, J=6.4 Hz, OH), 2.42 (t, 2H, CH$_2$ Lev), 2.03-1.93 (2s, 6H, CH$_3$Ac, CH$_3$ Lev), 1.52-1.43[m, 1H, CH(CH$_3$)$_2$], 0.76-0.74[4s, 12H, C(CH$_3$)$_2$ and CH(CH$_3$)$_2$], 0.05-0.03 [2s, 6H, Si(CH$_3$)$_2$]. $^{13}$C NMR (75.5 MHz, CDCl$_3$): δ 170.45, 169.48, 137.59, 137.47, 128.5, 128.14, 128.11, 128.03, 127.92, 97.8, 97.04, 81.30, 75.43, 75.09, 73.50, 73.43, 72.24, 69.2, 67.72, 67.50, 67.0, 62.71, 62.37, 33.95, 24.80, 20.99, 20.83, 19.94, 19.83, 18.50, 18.36, −2.21, −3.31. HRMS-MALDI: (M+Na+) calcd. 852.3714, found 852.5162.

Dimethylthexylsilyl O-(2-O-acetyl-3-O-benzyl-α-L-idopyranosyl)-(1→4)-O-2-azido-3-O-benzyl-6-O-levulinoyl-2-deoxy-β-D-glucopyranoside (S15)

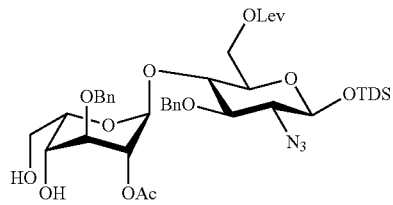

Disaccharide 51 (120 mg, 0.13 lmmol) was dissolved in DCM:TFA:H$_2$O (10/1/0.1, v/v)(0.06 M) and treated according to the general procedure for benzylidene acetal cleavage to give S15 (90 mg, 82%). [α]$_D^{25}$ +24 (c=1, CHCl$_3$): $^1$H NMR (500 MHz, CDCl$_3$): δ 7.31-7.15 (m, 10H, CH Aromatic), 4.86 (bs, 1H, H2$^B$), 4.74 (s, 1H, H1$^B$), 4.71 (d, 1H, J=10.5 Hz, CHHBn), 4.67 (d, 1H, J=11.0 Hz, CHHBn), 4.53 (d, 1H, J=11.0 Hz, CHHBn), 4.47-4.43 (m, 2H, CHHBn, H1$^A$), 4.39 (dd, 2H, J=2.0 Hz, J=12.0 Hz, H6a$^A$), 4.16 (t, 1H, J=2.0 Hz, H5$^B$), 4.06 (dd, 1H, J=5.0 Hz, J=12.5 Hz, H6b$^A$), 3.78 (t, 1H, J=9.5 Hz, H4$^A$), 3.57 (bs, 1H, H3$^B$), 3.57 (bs, 1H, H4$^B$), 3.42-3.39 (m, 1H, H5$^A$), 3.30-3.26 (m, 2H, H2$^A$, H6a$^B$), 3.19-3.12 (m, 1H, H3$^A$, H6b$^B$), 2.68-2.67 (m, 2H, CH$_2$ Lev), 2.52-2.50 (m, 2H, CH$_2$Lev), 2.10 (s, 3H, CH$_3$ Lev), 2.03 (s, 3H, CH$_3$Ac), 1.49-1.45 [m, 1H, CH(CH$_3$)$_2$], 0.72-0.70 [4s, 12H, C(CH$_3$)$_2$ and CH(CH$_3$)$_2$], 0.018-0.00 [2s, 6H, Si(CH$_3$)$_2$]. HRMS-MALDI: (M+NO calcd. 852.3714, found 852.5162.

Dimethylthexylsilyl-O-(2-O-levulinoyl-3-O-benzyl-α-L-idopyranosyl)-(1→4)-O-2-azido-3-O-benzyl-6-O-levulinoyl-2-deoxy-β-D-glucopyranoside (S16)

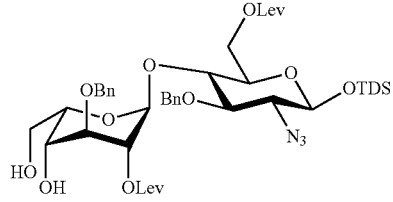

Disaccharide 52 (140 mg, 0.195 mmol) was dissolved in DCM:TFA:H$_2$O (10/1/0.1, v/v/v) (0.06 M) and treated according to the general procedure for benzylidene acetal cleavage to give S16 (50 mg, 30%), [α]$_D^{25}$ +24 (c=1, CHCl$_3$); $^1$H NMR (500 MHz, CDCl$_3$): δ 7.31-7.15 (m, 10H, CH Aromatic), 4.93 (bs, 1H, H2$^B$), 4.80 (s, 1H, H1$^B$), 4.77-4.43 (m, 2H, CHHBn, CHHBn), 4.59 (d, 1H, J=11.0 Hz, CHHBn), 4.53-4.49 (m, 2H, CHHBn, H1$^A$), 4.45 (dd, 2H, J=2.5 Hz, J=12.5 Hz, H6a$^A$), 4.20 (t, 1H, J=2.0 Hz, H5$^B$), 4.14 (dd, 1H, J=4.5 Hz, J=12.5 Hz, H6b$^A$), 3.86 (t, 1H, J=9.5 Hz, H4$^A$), 3.65 (bs, 1H, J=3 Hz, H3$^B$), 3.60 (bs, 1H, H4$^B$), 3.48-3.45 (m, 1H, H5$^A$), 3.38-3.33 (m, 2H, H2$^A$, H6a$^B$), 3.25-3.19 (m, 1H, H3$^A$, H6b$^B$), 2.78-2.71 (m, 2H, CH$_2$Lev), 2.65-2.54 (m, 2H, CH$_2$Lev), 2.17-2.16 (2s, 6H, 2×CH$_3$ Lev), 1.65-1.59[m, 1H, CH(CH$_3$)$_2$], 0.90-0.87 [4s, 12H, C(CH$_3$)$_2$ and CH(CH$_3$)$_2$], 0.019-0.018 [2s, 6H, Si(CH$_3$)$_2$]. $^{13}$C NMR (75.5 MHz, CDCl$_3$): δ 206.5, 206.5, 172.0, 171.6, 137.6, 137.5, 128.4, 128.3, 128.1, 128.1, 127.9, 97.4, 97.0, 81.2, 77.4, 77.0, 76.6, 75.4, 75.3, 73.3, 72.9, 72.3, 69.2, 67.8, 67.1, 62.7, 62.5, 37.8, 37.9, 33.9, 29.8, 29.7, 28.0, 27.9, 24.8, 19.9, 19.8, 18.5, 18.4, −2.1, −3.2. HRMS-MALDI: (M+Na$^+$) calcd. 908.3977, found 908.5037.

N-(Benzyl)-benzyloxycarbonyl-5-aminopentyl O-(2-O-acetyl-3-O-benzyl-β-D-glucopyranosyl)-(1→4)-O-2-azido-3-O-benzyl-6-O-acetyl-2-deoxy-α-D-glucopyranoside (S17)

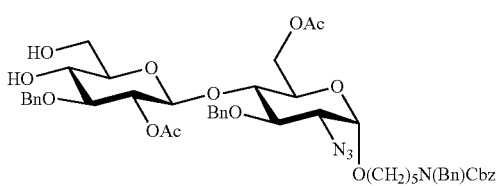

Disaccharide S1 (120 mg, 0.116 mmol) was dissolved in DCM:TFA:H$_2$O (10/1/0.1, v/v/v) (0.06M) and treated according to the general procedure for benzylidene acetal cleavageto give S17 (85 mg, 78%). [α]$_D^{23}$ +21.1 (c=1, CHCl$_3$); $^1$H NMR (500 MHz, CDCl$_3$): δ 7.31-7.07 (m, 25H, CH Aromatic), 5.12-5.1 (bd, 2H, J=17.5 Hz, CH$_2$Cbz), 4.94-4.88 (m, 2H, H2$^B$, CHHBn), 4.66 (d, 1H, J=12.0 Hz, CHHBn), 4.60 (d, 1H, J=11.5 Hz, CHHBn), 4.44 (bd, 2H, J=7.5 Hz, NCH$_2$Bn), 4.35-4.31 (m, 2H, H1$^A$, H6a$^A$), 4.07 (bd, 1H, J=12.0 Hz, H6b$^A$), 3.81 (bt, 1H, J=8.5 Hz, H3$^A$), 3.75-3.69 (bm, 1H, 5H$^A$), 3.64 (t, 1H, J=9.0 Hz, 4H$^A$), 3.56-3.44 (m, 3H, OCHH Linker, H6a$^B$, H4$^B$), 3.41-3.11 (m, 7H, H3$^B$, OCHHLinker, H2$^A$, NCH$_2$ Linker, H6b$^B$, H5$^B$), 2.35 (bs, 1H, OH), 2.02 (s, 3H, CH$_3$ Ac), 1.97 (s, 3H, CH$_3$ Lev), 1.35-1.17 (m, 6H, 3×CH$_2$ Linker). $^{13}$C NMR (75.5 MHz, CDCl$_3$): δ 170.5, 169.4, 138.3, 137.9, 137.8, 136.7, 129.0, 128.7, 128.5, 128.4, 128.2, 128.1, 127.9, 127.8, 127.7, 127.7, 127.3, 127.1, 125.3, 101.0 (C1$^B$), 97.5 (C1$^A$), 83.0, 78.1, 77.7, 77.4, 77.0, 76.6, 75.5, 74.9, 74.7, 73.3, 70.7, 68.8, 68.3, 67.2, 63.0, 62.1, 50.5, 50.2, 47.0, 46.1, 29.7, 28.9, 27.8, 27.4, 23.3, 20.9, 20.8. HRMS-MALDI: (M+Na$^+$) calcd. 940.4106, found 940.4055.

N-(Benzyl)-benzyloxycarbonyl-5-aminopentyl O-(2-O-levulinoyl-3-O-benzyl-β-D-glucopyranosyl)-(1→4)-O-2-azido-3-O-benzyl-6-O-acetyl-2-deoxy-α-D-glucopyranoside (S18)

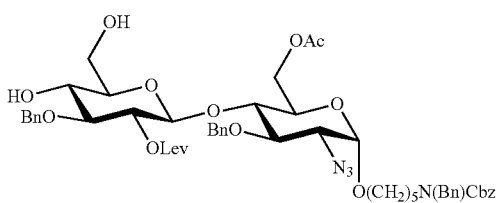

Disaccharide S2 (40 mg, 0.037 mmol) was dissolved in DCM:TFA:H$_2$O (10/1/0.1, v/v/v) (0.06 M) and treated according to the general procedure for benzylidene acetal cleavage to give S18 (35 mg, 94%). [α]$_D^{25}$ +47.0 (c=1.00, CHCl$_3$); $^1$H NMR (500 MHz, CDCl$_3$): δ 7.39-7.25 (m, 20H, CH Aromatic), 5.17 (bd, 2H, CH$_2$Cbz), 5.01-4.95 (m, 2H, H2$^B$, CHHBn), 4.83-4.81 (bd, 1H, J=11.0 Hz, H1$^A$), 4.78 (d, 2H, J=11.0 Hz,CHHBn, CHHBn), 4.62 (d, 1H, J=11.5 Hz,CHHBn), 4.51-4.49 (m, 2H, NCH$_2$Bn), 4.46 (dd, 1H, J=2.00 Hz, J=12.5 Hz, H6a$^A$), 4.39 (d, 1H, J=8.0 Hz, H1$^B$), 4.29 (dd, 1H, J=4.5 Hz, J=12.5 Hz, H6b$^A$), 3.98 (d, 1H, J=9.0 Hz, H5$^A$), 3.91 (t, 1H, J=9.5 Hz, H3$^A$), 3.75-3.66 (m, 2H, H4$^A$, OCHH Linker), 3.60 (dd, 1H, J=3.0 Hz, J=12.0 Hz, H6a$^B$), 3.53-3.45 (m, 2H, H3$^B$, H4$^B$), 3.30-3.16 (m, 4H, H5$^B$, H2$^A$,H6b$^B$, CH$_2$N Linker, OCHH Linker), 2.81-2.78 (m, 1H, CHH Lev), 2.65-2.59 (m, 2H, CH$_2$ Lev), 2.42-2.39 (m, CHHLev), 1.63-1.21 (2m, 6H, 3×CH$_2$ Linker). $^{13}$C NMR (75.5 MHz, CDCl$_3$): δ 205.7, 171.5, 170.6, 156.7, 156.1, 138.4, 138.1, 137.9, 128.6, 128.5, 128.4, 128.0, 127.9, 127.8, 127.7, 127.3, 127.0, 101.0, 97.4, 83.0, 78.1, 77.7, 77.4, 77.0, 76.6, 75.4, 74.9, 74.8, 73.6, 70.6, 68.6, 68.1, 67.1, 63.1, 62.4, 62.2, 50.5, 50.2, 46.5, 46.1, 37.5, 29.7, 29.7, 28.9, 27.8, 23.3, 20.9. HRMS-MALDI: (M+Na$^+$) calcd. 996.43682, found 996.4386.

N-(Benzyl)-benzyloxycarbonyl-5-aminopentyl O-(2-O-acetyl-3-O-benzyl-β-D-glucopyranosyl)-(1→4)-O-2-azido-3-O-benzyl-6-O-levulinoyl-2-deoxy-α-D-glucopyranoside (S19)

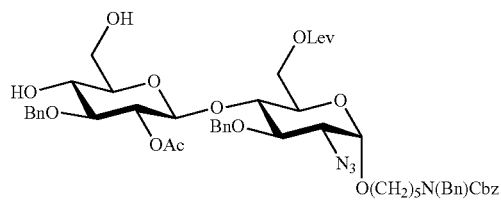

Disaccharide S3 (2.65 g, 2.44 mmol) was dissolved in DCM:TFA:H$_2$O (10/1/0.1, v/v/v) (0.06 M) and treated according to the general procedure for benzylidene acetal cleavage to give S19 (1.79 g, 88%). [α]$_D^{25}$ +23.0 (c=1.00, CHCl$_3$); $^1$H NMR (500 MHz, CDCl$_3$): δ 7.32-7.18 (m, 20H, CH Aromatic), 5.10 (bd, 2H, J=17.5 Hz, CH$_2$Cbz), 4.94-4.90 (m, 2H, H2$^B$, CHHBn), 4.74 (bd, 1H, J=13.0 Hz, H1$^A$), 4.70 (d, 1H, J=11.0 Hz, H1$^B$) 4.65 (d, 1H, J=12.0 Hz, CHHBn,), 4.60 (d, 1H, J=12.0 Hz, CHHBn), 4.45-4.42 (m, 2H, CHHBn, NCH$_2$Bn), 4.25 (bd, 1H, J=12.0, H6a$^A$), 4.17 (d, 1H, J=12.5 Hz, H6b$^A$), 3.83-3.81 (m, 1H, H4$^A$), 3.72-3.61 (bd, 2H, incl. H5$^A$: J=5.0 Hz, OCHH Linker), 3.59-3.52 (m, 2H, incl. H3$^B$: t, 1H, J=9.0 Hz, H6a$^B$: dd, 1H, J=3.0 Hz, J=12.0 Hz), 3.45 (m, 1H, H4$^B$), 3.36-3.34 (m, 1H, H5$^B$), 3.24-3.14 (m, 4H, H2$^A$,H3$^A$, H6b$^B$, CH$_2$N Linker), 2.81-2.78 (m, 1H, CHH Lev), 2.65-2.59 (m, 2H, CH$_2$ Lev), 2.42-2.39 (m, CHH Lev), 1.65-1.21 (m, 6H, 3×CH$_2$ Linker). $^{13}$C NMR (75.5 MHz, CDCl$_3$): δ 206.6, 172.4, 169.6, 138.3, 138.1, 137.8, 128.6, 128.5, 128.4, 127.9, 127.8, 127.7, 127.2, 100.8, 97.6, 82.9, 77.7, 77.6, 77.4, 77.0, 76.5, 75.5, 75.0, 74.6, 73.3, 71.1, 68.8, 68.3, 67.1, 63.0, 62.3, 62.2, 50.5, 50.2, 47.0, 46.1, 37.7, 29.8, 28.9, 27.7, 27.4, 23.2, 20.9. HRMS-MALDI: (M+Na$^+$) calcd. 996.43682. found 996.4386.

N-(Benzyl)-benzyloxycarbonyl-5-aminopentyl O-(2-O-levulinoyl-3-O-benzyl-β-D-glucopyranosyl)-(1→4)-O-2-azido-3-O-benzyl-6-O-levulinoyl-2-deoxy-α-D-glucopyranoside (S20)

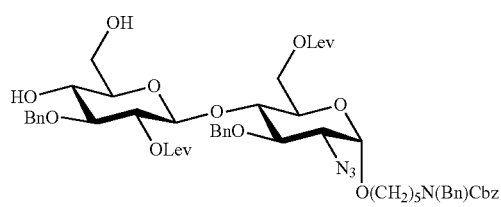

Disaccharide S4 (140 mg, 0.123 mmol) DCM:TFA:H$_2$O (10/1/0.1, v/v/v) (0.06 M) and treated according to the general procedure for benzylidene acetal cleavage to give S20 (100 mg, 77%). [α]$_D^{25}$ +52.1 (c=1.00, CHCl$_3$); $^1$H NMR (500 MHz, CDCl$_3$): δ 7.39-7.26 (m, 20H, CH Aromatic), 5.17 (bd, 2H, J=17.0 Hz, CH$_2$Cbz), 5.02-4.97 (m, 2H, H2$^B$, CHHBn), 4.83 (d, 1H, J=9.5 Hz, H1$^A$), 4.78 (d, 1H, J=10.5 Hz, CHHBn), 4.77 (d, 1H, J=11.5 Hz, CHHBn), 4.65 (d, 1H, J=12.0 Hz, CHHBn), 4.53 (d, 1H, J=8.0 Hz, H1$^B$), 4.48 (m, 2H, H6a$^A$, NCH$_2$Bn), 4.28 (d, 1H, J=10.5 Hz, H6b$^A$), 4.00 (d, 1H, J=10.0 Hz, H5$^A$), 3.92 (t, 1H, J=10.0 Hz, H3$^A$), 3.80 (t, 1H, J=9.5 Hz, H4$^A$), 3.68 (m, 2H, H3$^B$, OCHH Linker), 3.60 (dd, 1H, J=2.5 Hz, J=10.5 Hz, H6a$^B$), 3.53 (ddd, 1H, J=4.0 Hz, J=9.5 Hz, J=18.5 Hz, H4$^B$), 3.46-3.43 (ddd, 1H, J=3.0 Hz, J=6.0 Hz, J=15.5 Hz, H6b$^B$), 3.34-3.21 (m, 4H, H5$^B$, H2$^A$, CH$_2$N Linker), 2.92-2.79 (m, 2H, CH$_2$ Lev), 2.71-2.61 (m, 4H, 2×CH$_2$ Lev), 2.56-2.36 (m, 2H, CH$_2$ Lev), 2.18 (s, 3H, CH$_3$ Lev), 2.11 (bd, 3H, J=10.0 Hz, CH$_3$ Lev), 1.61-1.25 (2m, 6H, 3×CH$_2$ Linker). $^{13}$C NMR (75.5 MHz, CDCl$_3$): δ 206.7, 205.8, 172.5, 171.5, 138.5, 138.3, 137.9, 136.7, 128.6, 128.5, 128.4, 127.9, 127.8, 127.7, 127.3, 127.1, 100.8, 97.6, 83.0, 77.9, 77.7, 77.4, 77.0, 76.5, 75.3, 75.0, 74.6, 73.7, 71.1, 68.6, 68.1, 67.1, 63.1, 62.6, 62.4, 50.5, 50.2, 46.5, 46.1 37.7, 37.6, 29.9, 29.7, 29.7, 28.9, 27.8, 23.2. HRMS-MALDI: (M+NO calcd. 1052.4630, found 1052.4660.

N-(Benzyl)-benzyloxycarbonyl-5-aminopentyl O-(2-O-acetyl-3-O-benzyl-α-L-idopyranosyl)-(1→4)-O-2-azido-3-O-benzyl-6-O-acetyl-2-deoxy-α-D-glucopyranoside (S21)

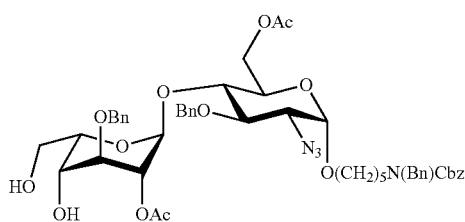

S21

Disaccharide S5 (130 mg, 0.135 mmol) was dissolved in DCM:TFA:H$_2$O (10/1/0.1, v/v/v) (0.06 M) and treated according the general procedure for benzylidene acetal cleavage to give S21 (80 mg, 67%). [α]$_D^{24}$ +51.0 (c=1, CHCl$_3$); $^1$H NMR (500 MHz, CDCl$_3$): δ 7.44-7.26 (m, 25H, CH Aromatic), 5.18 (bd, 2H, J=15.0 Hz, CH$_2$Cbz), 4.97 (bs, 1H, H2$^B$), 4.89-4.85 (m, 2H, H1$^A$, H1$^B$), 4.77-4.75 (m, 2H, CHHBn, CHHBn), 4.61 (d, 1H, J=11.5 Hz, CHHBn), 4.57 (d, 1H, J=12.5 Hz, CHHBn), 4.50 (bd, 2H, J=6.5 Hz, NCH$_2$Bn), 4.40 (d, 1H, J=12.5 Hz, H6), 4.22-4.20 (m, 2H, H5$^A$, H6a$^B$), 3.86-3.81 (m, 3H, H5$^A$,H4$^A$, H3$^A$), 3.70-3.58 (m, 3H, OCHH Linker, H3$^B$, H4$^B$), 3.44-3.16 (m, 5H, OCHH Linker, incl. H2$^A$: dd, J=3.0 Hz, J=9.5 Hz at 3.34, H6a$^B$, CH$_2$N Linker), 2.09 (s, 3H, CH$_3$ Ac), 2.08 (s, 3H, CH$_3$ Ac), 1.68-1.26 (m, 6H, 3×CH$_2$ Linker). $^{13}$C NMR (75.5 MHz, CDCl$_3$): δ 170.5, 169.4, 156.2, 137.8, 137.5, 137.4, 136.7, 128.5, 128.4, 128.4, 128.2, 128.0, 127.9, 127.8, 127.3, 97.8, 97.5, 78.8, 77.4, 77.0, 76.5, 75.1, 74.9, 73.6, 72.1, 69.2, 69.2, 68.2, 67.6, 67.4, 67.1, 67.0, 63.8, 62.9, 62.6, 62.2, 50.5, 50.2, 47.0, 46.1, 29.6, 29.0, 27.8, 27.4, 23.3, 20.9, 20.8. HRMS-MALDI: (M+Na$^+$) calcd. 940.4106, found 940.4123.

N-(Benzyl)-benzyloxycarbonyl-5-aminopentyl O-(2-O-levulinoyl-3-O-benzyl-α-L-idopyranosyl)-(1→4)-O-2-azido-3-O-benzyl-6-O-acetyl-2-deoxy-α-D-glucopyranoside (S22)

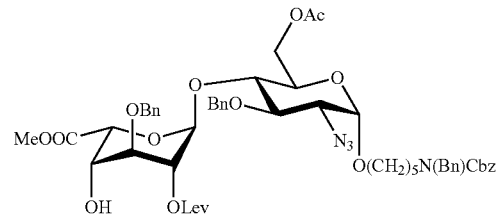

22

Disaccharide S6 (140 mg, 0.129 mmol) was dissolved in DCM:TFA:H$_2$O (10/1/0.1, v/v/v) (0.06 M) and treated according to the general procedure for benzylidene acetal cleavage to give S22 (84.7 mg, 60%). [α]$_D^{25}$ +53.3 (c=1, CHCl$_3$). $^1$H NMR (500 MHz, CDCl$_3$): δ 7.34-7.11 (m, 20H, CH Aromatic), 5.12-5.1 (bd, 2H, J=15.0 Hz, CH$_2$Cbz), 4.89 (bs, 1H, H2$^B$), 4.81-4.77 (m, 2H, H1$^A$, H1$^B$), 4.70-4.66 (m, 2H, 2×CHHBn), 4.54 (d, 1H, J=11.3 Hz, CHHBn), 4.50 (d, 1H, J=10.5 Hz, CHHBn), 4.45 (bd, 1H, J=6.9 Hz, NCH$_2$Bn), 4.34 (bd, 1H, J=12.2 Hz, H6a$^A$), 4.14-4.11 (m, 2H, H6b$^A$, H5$^B$), 3.83-3.73 (m, 3H, H4$^A$, H5$^A$, H3$^A$), 3.58-3.51 (m, 3H, OCHH Linker, H3$^B$, H4$^B$), 3.38-3.07 (m, 6H, OCHH Linker, H6a$^B$, NCH$_2$ Linker, H3$^B$, H6b$^B$), 2.70 (t, 2H, J=5.5 Hz, CH$_2$ Lev), 2.53-2.47 (m, 3H, CH$_2$ Lev, OH), 2.1 (s, 3H, CH$_3$ Ac), 2.01 (s, 3H, CH$_3$ Lev), 1.61-1.15 (m, 6H, 3×CH$_2$ Linker). $^{13}$C NMR (75.5 MHz, CDCl$_3$): δ 206.3, 171.6, 170.6, 137.9, 137.6, 137.5, 128.5-127.3, 97.7, 97.5, 78.8, 75.2, 75.0, 73.5, 72.2, 69.2, 68.2, 67.6, 67.5, 67.2, 67.0, 63.8, 63.0, 62.3, 50.6, 50.2, 47.0, 37.9, 29.7, 29.6, 29.1, 28.0, 23.3, 20.9. HRMS-MALDI: (M+Na$^+$) calcd. 996.43682, found 996.4386.

N-(Benzyl)-benzyloxycarbonyl-5-aminopentyl O-(2-O-acetyl-3-O-benzyl-α-L-idopyranosyl)-(1→4)-O-2-azido-3-O-benzyl-6-O-levulinoyl-2-deoxy-α-D-glucopyranoside (S23)

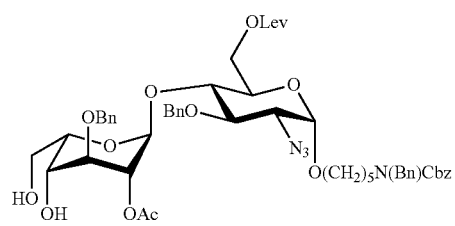

S23

Disaccharide S7 (160 mg, 0.147 mmol) was dissolved in DCM:TFA:H$_2$O (10/1/0.1, v/v/v) (0.06 M) and treated according to the general procedure for benzylidene acetal cleavage to give S23 (110 mg, 75%). [α]$_D^{24}$ +42 (c=1, CHCl$_3$); $^1$H NMR (500 MHz, CDCl$_3$): δ 5.11 (bd, 2H, J=16.0 Hz, CH$_2$Cbz), 4.90 (bs, 1H, H2$^B$), 4.80 (bd, 2H, J=11.5 Hz, H1$^A$), 4.75 (bs, 1H, H1$^B$), 4.70-4.66 (m, CHHBn, CHHBn), 4.55-4.51 (m, 2H,CHHBn, CHHBn), 4.47-4.41 (bd, 2H, J=7.0 Hz, NCH$_2$Bn), 4.32 (d, 1H, J=12.0 Hz, H6a$^A$), 4.18 (bd, 1H, J=12.0 Hz, H6b$^A$), 4.11 (t, 1H, J=5.0 Hz, H5$^B$), 3.84-3.74 (m, 3H, H5$^A$, H4$^A$, H3$^A$), 3.68-3.50 (m, 3H, H3$^B$, OCHH Linker, H4$^B$), 3.38-3.16 (m, 4H, OCHH Linker, H2$^A$, CH$_2$N Linker), 3.12 (dd, 1H, J=4.5 Hz, J=12.0 Hz, H6b$^B$), 2.74-2.45 (m, 4H, 2×CH$_2$ Lev), 2.10 (s, 3H, CH$_3$ Lev), 1.88 (s, 3H, CH$_3$Ac), 1.60-1.16 (m, 6H, 3×CH$_2$ Linker). HRMS-MALDI: (M+Na$^+$) calcd. 996.43682, found 996.4386.

Fully Protected Tetrasaccharides 70-75

N-(Benzyl)-benzyloxycarbonyl-5-aminopentyl O-[(methyl-2-O-acetyl-3-O-benzyl-4-O-(9-fluorenylmethoxycarbonyl)-β-D-glucopyranosyluronate)-(1→4)-O-(2-azido-3-O-benzyl-2-deoxy-6-O-levulinoyl-α-D-glucopyranoside)-(1→4)-O-(methyl-2-O-acetyl-3-O-benzyl-β-D-glucopyranosyluronate)]-(1→4)-O-(2-azido-3-O-benzyl-2-deoxy-6-O-levulinoyl-α-D-glucopyranoside (70)

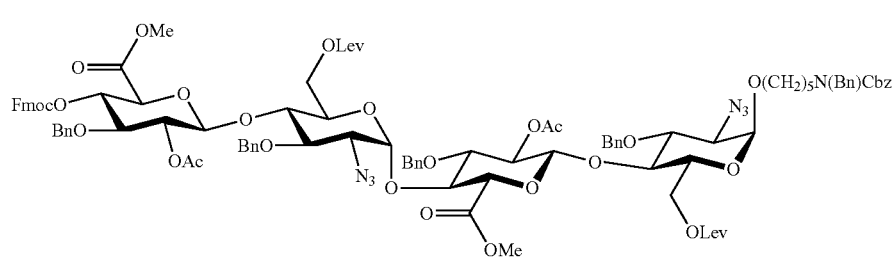

70

Glycosylation of disaccharide acceptor 19 (93.0 mg, 0.086 mmol) with disaccharide donor 47 (73.4 mg, 0.072 mmol) according to the general procedure for preparation of tetrasaccharides followed by silica gel chromatography (toluene/EtOAc, 60/40, v/v) provided tetrasaccharide 71 (85 mg, 61%). $[\alpha]_D^{25}$ +27.8 (c=0.93, CHCl$_3$); $^1$H NMR (500 MHz, CDCl$_3$): δ 7.75-7.73 (m, 2H, CH Aromatic), 7.56-7.53 (m, 2H, CH Aromatic), 7.41-7.17 (m, 34H, CH Aromatics), 5.35 (d, 1H, J=3.6 Hz, H1$^C$), 5.21 (d, 1H, J=11.4 Hz, CHHBn), 5.16 (bd, 2H, J=15.0 Hz, CH$_2$ Cbz), 5.10-5.05 (m, 3H, H2$^B$, H2$^D$, H4$^D$), 4.80-4.77 (m, 2H, H1$^A$, CHHBn), 4.74 (d, 1H, J=7.9 Hz, H1$^B$), 4.73 (d, 1H, J=7.6 Hz, H1$^D$), 4.67-4.54 (m, 6H, 3×CH$_2$Bn), 4.47 (m, 2H, NCH$_2$Bn), 4.41-4.34 (m, 4H, CHH Fmoc, H6a$^A$, H6a$^C$, H5$^D$), 4.27 (dd, 1H, J=7.6 Hz, J=10.4 Hz, CHHFmoc), 4.20-4.12 (m, 5H, CH Fmoc, H6b$^A$, H6b$^C$, H4$^B$, H5$^B$), 3.98 (t, 1H, J=9.5 Hz, H3$^B$), 3.94 (t, 1H, J=9.0 Hz, H3$^D$), 3.92-3.83 (m, 3H, H4$^A$, H4$^C$, H3$^A$), 3.72-3.68 (m, 3H, H5$^A$, H3$^A$, OCHH Linker), 3.59-3.55 (bm, 2H, OCHH Linker, H5$^C$), 3.44 (s, 3H, CO$_2$CH$_3$), 3.42 (s, 3H, CO$_2$CH$_3$), 3.27-3.19 (m, 4H incl. H2: dd, J=3.6 Hz, J=10.3 Hz at 3.25, H2$^A$, CH$_2$N Linker), 2.97-2.91 (m, 2H, 2×CH$_2$ Lev), 2.76-2.56 (m, 4H, 2×CH$_2$ Lev), 2.48-2.37 (m, 2H, CH$_2$ Lev), 2.20, 2.19, 2.00, 1.98 (4s, 12H, 2×CH$_3$ Ac, 2×CH$_3$ Lev), 1.58-1.24 (m, 6H, 3×CH$_2$ Linker). $^{13}$C NMR (75.5 MHz, CDCl$_3$): δ 206.1, 205.8, 172.3, 171.7, 171.5, 168.2, 168.3, 167.4, 166.5, 166.4, 153.1, 153.0, 142.7, 142.6, 142.4, 141.7, 141.6, 141.4, 140.3 128.7-127.5, 125.4, 125.3, 120.3, 101.4 (C1$^D$), 101.0 (C1$^B$), 98.1 (C1$^A$), 97.5 (C1$^C$), 79.7, 78.6, 78.4, 78.0, 77.7, 75.7, 75.6, 75.0, 74.7, 74.4, 73.3, 72.7, 72.6, 70.5, 69.3, 68.9, 68.7, 67.4, 63.0, 62.3, 61.8, 52.8, 50.7, 50.6, 38.2, 30.0, 29.2, 28.2, 23.5, 21.0, 20.9. HRMS-MALDI: (M+Na$^+$) calcd. 1966.7373, found 1943.7335.

N-(Benzyl)-benzyloxycarbonyl-5-aminopentyl O-[(methyl-2-O-acetyl-3-O-benzyl-4-O-(9-fluorenylmethoxycarbonyl)-(3-D-glucopyranosyluronate)-(1->4)-(2-azido-3-O-benzyl-2-deoxy-6-O-levulinoyl-α-D-glucopyranoside)-(1->4)-(methyl-2-O-acetyl-3-O-benzyl-α-L-idopyranosyluronate)]-(1→4)-O-2-azido-3-O-benzyl-2-deoxy-6-O-levulinoyl-α-D-glucopyranoside (71)

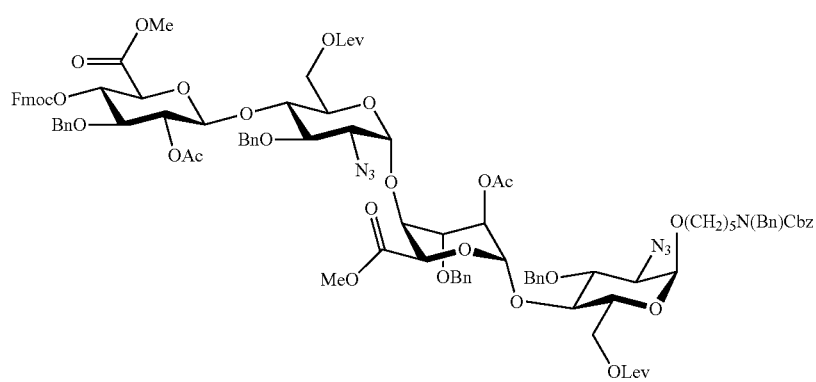

71

Glycosylation of disaccharide acceptor 23 (112 mg, 0.103 mmol) with disaccharide donor 47 (127 mg, 0.124 mmol) according to the general procedure for preparation of tetrasaccharides followed by silica gel chromatography (hexane/EtOAc, 60/40, v/v) provided tetrasaccharide 71

(125 mg, 62%). $[\alpha]_D^{25}$ +26 (c=1, CHCl$_3$); $^1$H NMR (500 MHz, CDCl$_3$): δ 7.73-7.71 (m, 2H, CH Aromatic), 7.55-7.50 (m, 2H, CH Aromatic), 7.42-7.14 (m, 34H, CH Aromatics), 5.23-5.18 (m, 2H, H1$^B$, CHHBn), 5.18-5.13 (m, 2H, CH$_2$ Cbz), 5.11-5.04 (m, 2H, H2$^D$, H4$^D$), 4.93-4.89 (m, 2H, H1$^C$, H2$^B$), 4.83-4.77 (m, 2H, CH$_2$Bn, H1$^A$), 4.73 (d, 1H, J=8.1 Hz, H1$^D$), 4.55-4.70 (m, 6H, 2×CH$_2$Bn, CHHBn, H5$^B$ at 4.61), 4.51-4.46 (m, 2H, NCH$_2$Bn), 4.43-4.37 (m, 5H, CH$_2$ Fmoc, H6a$^A$, H6a$^C$, H5$^D$ at 4.28), 4.21-4.14 (m, 3H, 2×H6, CH Fmoc), 3.99-3.94 (m, 2H, H4$^B$, H3$^D$), 3.92-3.86 (m, 2H, H4$^C$, H3$^B$), 3.83-3.75 (m, 3H, H3$^A$, H5$^A$, H5$^C$), 3.67-3.57 (m, 2H, incl. OCHH Link, H3$^C$: dd at 3.65 J=8.7 Hz, J=10.5 Hz), 3.52 and 3.43 (2s, 6H, 2×CO$_2$CH$_3$), 3.43-3.17 (m, 5H, incl. H2$^A$, H2$^C$: dd at 3.23 J=3.5 Hz, J=10.5 Hz, OCHH Linker, CH$_2$N Linker), 2.30-3.00 (m, 8H, 4×CH$_2$ Lev), 2.20-1.96 (4s, 12H, 2×CH$_3$ Ac, 2×CH$_3$ Lev), 1.72-1.40 (m, 4H, 2×CH$_2$ Linker), 1.40-1.20 (m, 2H, CH$_2$ Linker). $^{13}$C NMR (75.5 MHz, CDCl$_3$): δ 206.8, 206.3, 172.5, 172.3, 170.0, 169.6, 169.0, 167.4, 154.0, 143.3, 143.0, 141.3, 141.2, 138.1, 138.0, 137.9, 137.7, 137.4, 128.5-127.1, 125.1, 125.0, 120.0, 100.5 (C1$^B$), 98.0 (C1$^C$), 97.5 (C1$^A$), 97.4 (C1$^D$), 79.3, 78.2, 77.6, 77.2, 75.8, 75.4, 75.3, 74.7, 74.3, 74.2, 73.5, 72.9, 72.4, 72.8, 70.3, 69.7, 69.1, 69.0, 68.2, 67.0. HRMS-MALDI: (M+Na$^+$) calcd. 1966.7373, found 1966.7442.

N-(Benzyl)-benzyloxycarbonyl-5-aminopentyl O-[(methyl-2-O-acetyl-3-O-benzyl-4-O-(9-fluorenyl-methoxycarbonyl)-α-L-idopyranosyluronate)-(1→4)-O-(2-azido-3-O-benzyl-2-deozy-6-O-levu-linoyl-α-D-glucopyranoside)-(1→4)-O-(methyl-2-O-acetyl-3-O-benzyl-(3-D-glucopyranosyluronate)]-(1→4)-O-2-azido-3-O-benzyl-2-deoxy-6-O-levulinoyl-α-D-glucopyranoside (72)

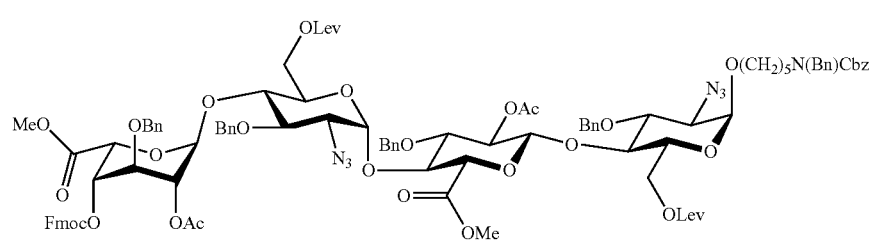

Glycosylation of disaccharide acceptor 19 (90 mg, 0.083 mmol) with donor 59 (107 mg, 0.100 mmol) was performed according to the general procedure for preparation of tetrasaccharides followed by chromatography (toluene/EtOAc, 75/25, v/v) providing tetrasaccharide 72 (104 mg, 64%). $[\alpha]_D^{25}$ +19 (c=1, CHCl$_3$); $^1$H NMR (500 MHz, CDCl$_3$): δ 7.73-7.70 (m, 2H, CH Aromatics), 7.54-7.50 (m, 2H, CH Aromatics), 7.42-7.14 (m, 36H, CH Aromatics), 5.36 (d, 1H, J=3.6 Hz, H1$^C$), 5.19-5.13 (m, 2H, CH$_2$ Cbz,), 5.13-5.08 (m, 3H, H1$^D$, H2$^B$, CHHBn), 4.94 (t, 1H, J=4.0 Hz, H4$^D$), 4.86-4.82 (m, 3H, H2$^D$, H5$^D$, CHHBn), 4.82-4.76 (m, 1H, H1$^A$), 4.75-4.58 (m, 7H, 2 CHHBn, 4×CHHBn, and H1$^B$ at 4.71), 4.51-4.45 (m, 2H, CH$_2$NBn), 4.45-4.38 (m, 2H, H6a$^C$, CHH Fmoc), 4.38-4.32 (m, 2H, H6a$^A$, CHHFmoc), 4.23-4.16 (m, 4H, CH$_2$CHFmoc, H6b$^A$, H4$^B$, H5$^B$), 4.10 (dd, 1H, J=11.2 Hz, J=3.3 Hz, H6b$^C$), 3.95-3.91 (m, 1H, H3$^B$), 3.90-3.82 (m, 4H, H3$^A$, H3$^B$, H3$^D$, H4$^C$), 3.76-3.70 (m, 1H, H5$^A$), 3.67 (dd, 1H, J=9.1 Hz, J=9.0 Hz, H3$^C$), 3.64-3.56 (m, 2H, H5$^C$, OCHH Linker), 3.48 (s, 3H, CO$_2$CH$_3$), 3.42-3.16 (m, 8H, incl. CO$_2$CH$_3$: s at 3.42, H2$^C$: dd J=3.8 Hz, J=10.3 Hz at 3.31, OCHH Linker, CH$_2$N Linker, H2$^A$), 2.80-2.45 (m, 8H, 4×CH$_2$ Lev), 2.20-1.95 (4s, 12H, 2×CH$_3$ Ac, 2×CH$_3$ Lev), 1.74-1.44 (m, 6H, 3×CH$_2$Linker). $^{13}$C NMR (75.5 MHz, CDCl$_3$): δ 206.7, 206.6, 171.5, 172.1, 171.4, 170.8, 169.8, 169.2, 168.4, 168.1, 154.1, 143.1, 142.9, 141.2, 138.3, 137.8, 137.6, 137.5, 137.1, 136.8, 128.5-127.0, 125.0, 124.9, 120.0, 101.0 (C1$^B$), 97.7 (C1$^D$), 97.4 (C1$^B$), 97.2 (C1$^A$), 81.9, 78.3, 78.1, 77.7, 77.2, 75.5, 75.3, 74.8, 74.5, 74.4, 74.3, 73.0, 72.0, 71.6, 70.8, 70.1, 69.5, 68.6, 68.3, 68.1, 67.3, 67.1, 63.4, 62.8, 62.0, 61.4, 55.7, 52.4, 52.1, 50.5, 50.2, 47.0, 46.5, 46.0, 37.9, 37.5, 34.8, 29.7, 29.6, 25.4, 25.2, 24.8, 24.6, 23.2. HRMS-MALDI: (M+Na$^+$) calcd. 1966.7373, found 1966.7372.

N-(Benzyl)-benzyloxycarbonyl-5-aminopentyl
O-[(methyl-2-O-acetyl-3-O-benzyl-4-O-(9-fluore-
nylmethoxycarbonyl)-α-L-idopyranosyluronate)-
(1→4)-O-(2-azido-3-O-benzyl-2-deoxy-6-O-levu-
linoyl-α-D-glucopyranoside)-(1→4)-O-(methyl-2-O-
acetyl-3-O-benzyl-α-L-idopyranosyluronate)-
(1→4)-O-2-azido-3-O-benzyl-2-deoxy-6-O-
levulinoyl-α-D-glucopyranoside (73)

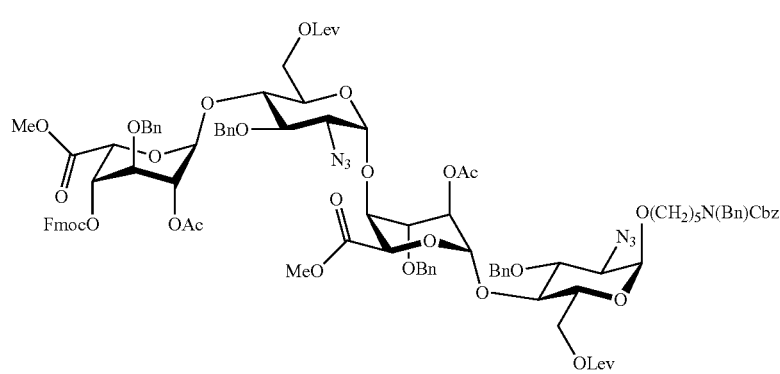

73

Glycosylation of disaccharide acceptor 23 (123.4 mg, 0.1140 mmol) with donor 59 (97.4 mg, 0.0950 mmol) was performed according to the general procedure for preparation of tetrasaccharides followed by silica chromatography (hexanes/EtOAc, 60/40 to 50/50, v/v) providing tetrasaccharide 73 (114.6 mg, 62%). $[\alpha]_D^{23}$ +30.4 (c=1, CHCl$_3$); $^1$H NMR (500 MHz, CDCl$_3$): δ 7.68-7.65 (m, 2H, CH Aromatic), 7.48-7.42 (m, 2H, CH Aromatic), 7.32-7.15 (m, 34H, CH Aromatic), 5.17-5.10 (m, 3H incl. H1$^B$: d, J=2.9 Hz at 5.16, CH$_2$ Cbz), 5.1 (d, 1H, J=2.7 Hz, H1$^D$), 4.95 (t, 1H, J=3.9 Hz, H4$^D$), 4.91 (t, 1H, J=3.8 Hz, H2$^B$), 4.88 (d, 1H, J=3.4 Hz, H1$^C$), 4.86 (d, 1H, J=3.4 Hz, H5$^D$), 4.83 (t, 1H, J=3.4 Hz, H2$^D$), 4.80-4.57 (m, 10H incl. H1$^A$: 4.79, H5$^B$: d, J=3.2 Hz at 4.75, 4×CH$_2$Bn), 4.48-4.40 (m, 5H, NCH$_2$Bn, H6a$^A$, H6a$^C$, CHH Fmoc), 4.35 (dd, 1H, J=7.6 Hz, J=10.5 Hz, CHH Fmoc), 4.2-7.17 (m, 2H, H6b$^A$, CH Fmoc), 4.11 (dd, 1H, J=2.44 Hz, J=12.7 Hz, H6b$^C$), 3.96 (t, 1H, J=3.9 Hz, H4$^B$), 3.92-3.88 (m, 2H, H4$^C$, H3$^B$), 3.86-3.74 (m, 5H, H3$^D$, H4$^A$, H5$^A$, H3$^A$, H5$^C$), 3.65-3.6 (m, 2H, incl. OCHH Linker, H3$^C$: t, J=9.7 Hz at 3.62), 3.45 and 3.44 (2s, 6H, 2×CO$_2$CH$_3$), 3.33-3.17 (bm, 1H, OCHH Linker), 3.29-3.27 (m, 2H incl. H2$^A$: dd, J=2.4 Hz, J=12.4 Hz at 3.28), 3.20-3.10 (bm, 2H, CH$_2$N Linker), 2.83-2.69 (m, 4H, 2×CH$_2$ Lev), 2.66-2.52 (m, 4H, 2×CH$_2$ Lev), 2.15-1.98 (4s, 12H, 2×CH$_3$ Ac, 2×CH$_3$ Lev), 1.34-1.23 (m, 6H, 3×CH$_2$ Linker). $^{13}$C NMR (75.5 MHz, CDCl$_3$): δ 206.9, 206.7, 172.6, 172.4, 170.3, 170.0, 169.5, 168.7, 143.4, 143.2, 141.5, 138.1, 137.7, 137.4, 137.3, 128.8-127.4, 125.2, 120.4, 98.2 (C1$^B$), 97.8 (C1$^D$), 97.5 (C1$^A$), 97.3 (C1$^C$), 78.5, 78.3, 77.7, 77.5, 77.2, 76.8, 75.6, 74.9, 74.8, 74.5, 73.7, 73.6, 73.4, 72.7, 71.8, 70.4, 69.9, 69.3, 69.1, 68.6, 68.4, 67.5, 67.4, 63.5, 62.6, 62.1, 52.4, 52.1 46.8, 38.1, 38.0, 30.0, 29.9, 29.3, 28.3, 28.2, 23.5, 21.1, 21.0. HRMS-MALDI: (M+Na$^+$) calcd. 1966.7373, found 1966.7362.

N-(Benzyl)-benzyloxycarbonyl-5-aminopentyl
O-[(methyl-2-O-acetyl-3-O-benzyl-4-O-(9-fluore-
nylmethoxycarbonyl)-α-L-idopyranosyluronate)-
(1→4)-O-(2-azido-3-O-benzyl-2-deozy-6-O-levu-
linoyl-α-D-glucopyranoside)-(1→4)-O-(methyl-3-O-
benzyl-2-O-levulinoyl-α-L-idopyranosyluronate)]-
(1→4)-O-2-azido-3-O-benzyl-2-deoxy-6-O-
levulinoyl-α-D-glucopyranoside (74)

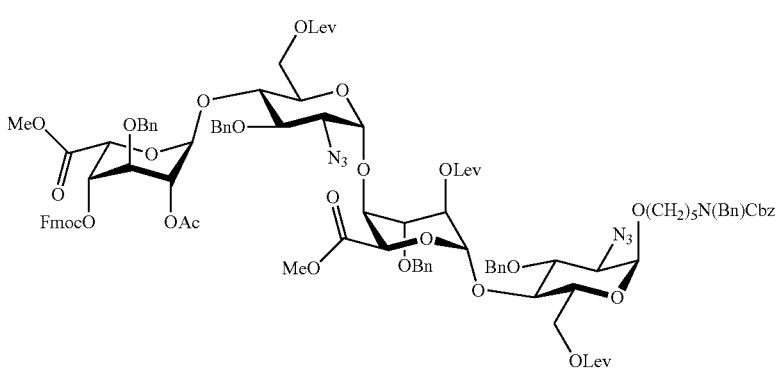

74

Glycosylation of disaccharide acceptor 19 (107 mg, 0.099 mmol) with donor 59 (128 mg, 0.119 mmol) was performed according to the general procedure for preparation of tetrasaccharides followed by silica gel chromatography (hexanes/EtOAc, 60/40 to 50/50, v/v) providing tetrasaccharide 72 (80 mg, 51%). $[\alpha]_D^{25}$ +30 (c=1, CHCl$_3$); $^1$HNMR (500 MHz, CDCl$_3$): δ 7.78-7.73 (m, 2H, CH Aromatics), 7.59-7.53 (m, 2H, CH Aromatics), 7.35-7.12 (m, 34H, CH Aromatic), 5.19-5.13 (m, 3H incl. H1$^B$: d, J=3.4 Hz at 5.18, CH$_2$ Cbz), 5.12 (d, 1H, J=3.0 Hz, H1$^D$), 5.02 (d, 1H, J=3.5 Hz, H1$^C$), 4.96-4.91 (m, 2H, H2$^B$, H4$^D$), 4.86 (d, 1H, J=3.6 Hz, H5$^D$), 4.82 (t, 1H, J=3.6 Hz, H2$^D$), 4.81-4.59 (m, 10H, incl. H1$^A$ at 4.80, H5$^B$ at 4.70, 4×CH$_2$Bn), 4.50-4.46 (m, 2H, CH$_2$NBn), 4.46-4.38 (m, 3H, H6a$^A$, H6a$^C$, CHH Fmoc), 4.35 (dd, 1H, J=7.5 Hz, J=8.3 Hz, CHHFmoc), 4.13 (bd, J=12.5 Hz, H6b$^A$), 4.18 (t, 1H, J=7.3 Hz, CH Fmoc), 4.12 (dd, 1H, J=3.1 Hz, J=12.5 Hz, H6b$^C$), 3.98 (t, 1H, J=4.4 Hz, H4$^B$), 3.94 (t, 1H, J=4.4 Hz, H3$^B$), 3.92-3.83 (m, 5H, H3$^A$, H3$^D$, H4$^A$, H4$^C$, H5$^A$), 3.76-3.20 (m, 1H, H5$^C$), 3.67-3.55 (m, 2H, incl. H3$^C$: t at 3.61 J=9.0 Hz, OCHH Linker), 3.56 (s, 3H, CO$_2$CH$_3$), 3.45 (s, 3H, CO$_2$CH$_3$), 3.43-3.17 (m, 5H, incl. H2$^C$: dd at 3.27, OCHH Linker, H2$^A$, CH$_2$N Linker), 2.76-2.42 (m, 8H, 4×CH$_2$ Lev), 2.10, 2.09, 2.05, 2.94 (4s, 12H, 1×CH$_3$ Ac, 3×CH$_3$ Lev), 1.72-1.20 (m, 6H, 3×CH$_2$ Linker). $^{13}$C NMR (75.4 MHz, CDCl$_3$): δ 206.5, 206.4, 206.1, 172.3, 172.1, 169.7, 169.3, 168.5, 154.1, 143.1, 143.0, 141.3, 141.2, 137.8, 137.5, 137.4, 137.1, 136.8, 128.5, 128.4, 128.2, 128.1, 127.9, 127.8, 127.6, 127.5, 127.4, 127.3, 127.1, 124.9, 120.0, 97.8 (C1$^B$), 97.5 (C1$^D$), 97.3 (C1$^C$), 96.6 (C1$^A$), 78.2, 78.0, 77.0, 75.4, 74.6, 74.3, 73.5, 73.3, 73.2, 72.9, 72.4, 71.8, 71.6, 71.4, 70.5, 70.2, 69.5, 69.3, 69.0, 68.9, 68.8, 68.3, 68.1, 67.3, 67.1, 64.3, 63.2, 62.4, 61.8, 52.1, 51.8, 50.5, 50.2, 47.0, 46.5, 46.2, 37.8, 37.7, 29.8, 29.7, 29.6, 28.9, 28.0, 27.9, 27.6, 23.2, 20.8. HRMS-MALDI: (M+NO calcd. 2022.7743, found 2022.7783.

N-(Benzyl)-benzyloxycarbonyl-5-aminopentyl O-[(methyl-2-O-acetyl-3-O-benzyl-4-O-(9-fluorenylmethoxycarbonyl)-(3-D-glucopyranosyluronate))-(1→4)-O-(2-azido-3-O-benzyl-2-deoxy-6-O-levulinoyl-α-D-glucopyranoside)-(1→4)-O-(methyl 2-O-levulinoyl-3-O-benzyl-α-L-idopyranosyluronate)]-(1→4)-O-2-azido-3-O-benzyl-2-deoxy-6-O-levulinoyl-α-D-glucopyranoside) (75)

Glycosylation of disaccharide acceptor 24 (274 mg, 0.254 mmol) with donor 47 (329 mg, 0.305 mmol) was performed according to the general procedure for preparation of tetrasaccharides followed by silica gel chromatography (Hexanes/EtOAc 60/40 to 50/50) providing tetrasaccharide 75 (282 mg, 59%). $[\alpha]_D^{25}$ +19 (c=1, CHCl$_3$); $^1$H NMR (500 MHz, CDCl$_3$): δ 7.75-7.71 (m, 2H CH Aromatics) 7.58-7.52 (m, 2H, CH Aromatics), 7.42-7.16 (m, 34H, CH Aromatics), 5.23 (d, 1H, J=4.4 Hz, H1$^B$), 5.20 (d, 1H, J=11.1 Hz, CHHBn), 5.18-5.12 (m, 2H CH$_2$ Cbz), 5.10-5.04 (m, 2H, H2$^D$, H4$^D$), 5.02 (d, 1H, J=3.5 Hz, H1$^C$), 4.92 (t, 1H, J=3.0 Hz, H2$^B$), 4.82-4.77 (m, 2H, H1$^A$, CHHBn), 4.74-4.55 (m, 9H, incl. H5$^B$ at 4.57, 4×CH$_2$Bn), 4.50-4.45 (m, 2H, CH$_2$NBn), 4.43-4.14 (m, 8H, incl. H5$^D$ at 4.31, H6a$^A$, H6b$^A$, H6a$^C$, H6b$^C$, CH$_2$ Fmoc, CHFmoc), 3.99-3.80 (m, 8H, H3$^A$, H3$^B$, H3$^D$, H4$^A$, H4$^B$, H4$^C$, H5$^A$, H5$^C$), 3.67-3.57 (m, 2H, incl. H3$^C$: dd at 3.64 J=8.5 Hz, J=10.2 Hz, OCHH Linker), 3.53 (s, 3H, CO$_2$CH$_3$), 3.45-3.18 (m, 8H incl. CO$_2$CH$_3$: s at 3.43, H2$^C$: dd at 3.24 J=3.5 Hz, J=10.4 Hz, H2$^A$, OCHH Linker, CH$_2$N Linker), 12.80-2.40 (m, 8H, 4×CH$_2$ Lev), 2.20-1.95 (4s, 12H, 1×CH$_3$ Ac, 3×CH$_3$ Lev), 1.64-1.24 (m, 6H, 3×CH$_2$ Linker). $^{13}$C NMR (75.5 MHz, CDCl$_3$): δ 206.8, 206.4, 206.1, 172.5, 172.4 172.0, 169.6, 169.0, 167.4, 156.6, 156.1, 154.0, 143.3, 143.0, 141.2, 138.2, 138.0, 137.9, 137.7, 137.5, 136.8, 128.5, 128.4, 128.3, 128.2, 128.1, 128.0, 127.8, 127.7, 127.5, 127.4, 127.2, 127.1, 125.1, 125.0, 124.0, 122.9, 120.0, 100.5 (C1$^B$), 97.9 (C1$^C$), 97.4 (C1$^A$), 97.1 9 (C1$^D$), 79.3, 78.1, 77.6, 75.9, 75.3, 74.8, 74.3, 73.6, 72.6, 72.4, 72.3, 70.3, 70.0, 69.6, 69.0, 68.9, 68.0, 67.1, 63.1, 62.5, 62.3, 61.7, 52.5, 52.1, 50.5, 50.2, 47.0, 46.5, 46.1, 38.0, 37.8, 376, 29.7, 29.6, 28.9, 27.8, 27.6, 23.2, 20.6. HRMS-MALDI: (M+Na$^+$) calcd. 2022.7743, found 2022.7982.

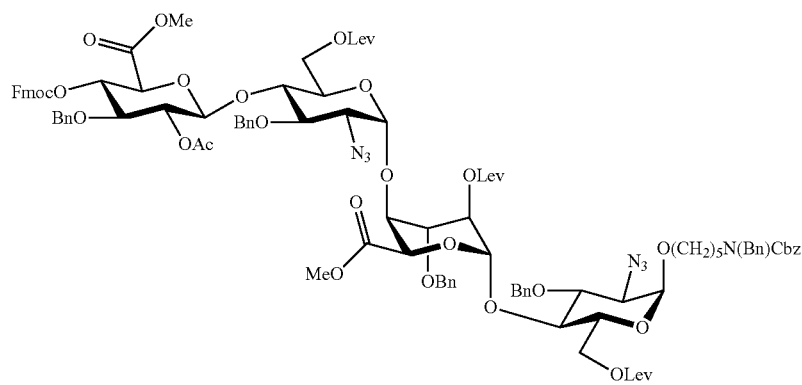

75

Hexasaccharides 63-69

N-(Benzyl)-benzyloxycarbonyl-5-aminopentyl O-[(methyl-2-O-acetyl-3-O-benzyl-4-O-(9-fluorenylmethoxycarbonyl)-β-D-glucopyranosyluronate)-(1→4)-O-(2-azido-3-O-benzyl-2-deoxy-6-O-levulinoyl-α-D-glucopyranoside)-(1→4)-O-(methyl-2-O-acetyl-3-O-benzyl-α-L-idopyranosyluronate)-(1→4)-O-(2-azido-3-O-benzy-2-deoxy-6-O-levulinoyl-α-D-glucopyranoside)-(1→4)-O-(methyl-2-O-acetyl-3-O-benzyl-β-D-glucopyranosyluronate)]-(1→4)-O-2-azido-3-O-benzyl-2-deoxy-6-O-levulinoyl-α-D-glucopyranoside (63)

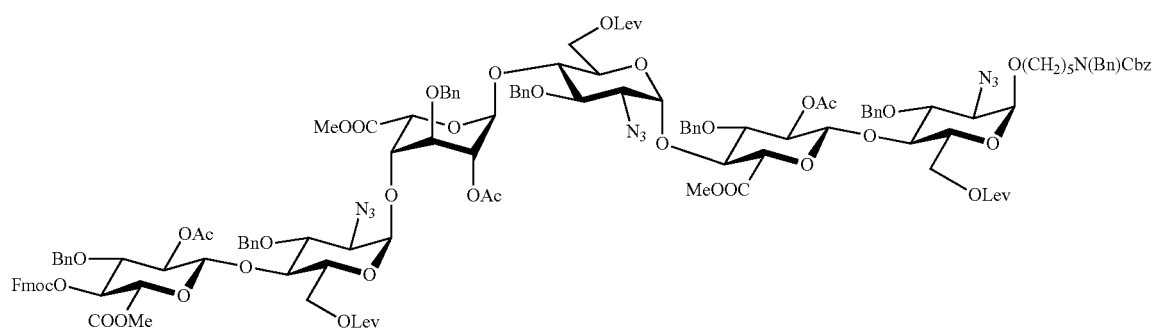

63

Trichloroacetimidate donor 59 (221.8 mg, 0.2052 mmol) was coupled with the acceptor 19 (174.9 mg, 0.1710 mmol) in the presence of TMSOTf (0.0257 mmol, 4.63 μL) according to the general procedure to give tetrasaccharide 61 (289 mg, 64%). Tetraaccharide 61 was subjected to Fmoc cleavage according to the general procedure to obtain acceptor 62 (209.9 mg, 82%). Acceptor 62 (209.9 mg, 0.1219 mmol) was coupled with the donor 47 (171 mg, 0.1585 mmol) according to the general procedure to obtain hesxasaccharide 63 (209.3 mg, 65%). $[\alpha]_D^{25}$ +167 (c=0.22, CHCl$_3$); $^1$H NMR (500 MHz, CDCl$_3$): δ 7.74-7.71 (m, 2H, CH Aromatics), 7.56-7.52 (m, 2H, CH Aromatics), 7.40-7.17 (m, 40H, CH Aromatics), 5.34 (d, 1H, J=3.7 Hz, H1$^C$), 5.25 (d, 1H, J=4.9 Hz,H1$^D$), 5.20-5.039 (m, 7H, CH$_2$Bn, CH$_2$ Cbz, H2$^B$, H2$^F$, H4$^F$), 4.97 (d, 1H, J=3.4 Hz, H1$^E$), 4.87 (t, 1H, J=5.6 Hz, H2$^D$), 4.83-4.77 (m, 3H incl.CH$_2$Bn, H1$^A$ at 4.80), 4.73-4.7 (m, 3H incl. H1$^F$ at 4.73, H1$^B$ at 4.72, CH$_2$Bn), 4.68-4.55 (m, 7H, CH$_2$Bn), 4.47-4.45 (m, 4H incl. NCH$_2$Bn, H5$^B$ at 4.56, CHH Fmoc), 4.41-4.25 (m, 5H, H6a$^A$, H6a$^E$, H6a$^C$, H5$^F$ at 4.28, CHH Fmoc), 4.19-4.11 (m, 6H, H6b$^E$, H6b$^A$, H6b$^C$, H5$^B$, H4$^B$), 3.98-3.92 (m, 3H, H3$^F$, H3$^B$, H4$^D$), 3.91-3.80 (m, 5H, H3$^D$, H4$^E$, H4$^A$, H3$^A$, H5$^E$), 3.79 (t, 1H, J=9.5 Hz, H4$^C$), 3.73-3.70 (bm, 1H, H5$^A$), 3.68-3.60 (m, 2H incl. H3$^C$: t, J=9.52 Hz, J=10.3 Hz at 3.7, H3$^E$: t, J=8.79 Hz at 3.64), 3.58-3.51 (m, 5H incl. CO$_2$CH$_3^D$: s at 3.56, H5$^C$ at 3.54, OCHH Linker), 3.43 (s, 3H, CO$_2$CH$_3^F$), 3.39 (s, 3H, CO$_2$CH$_3^B$), 3.28-3.19 (m, 6H, H2$^C$: dd, J=3.6 Hz, J=10.3 Hz at 3.28, H2$^E$, H2$^A$, OCHH Linker, CH$_2$N Linker), 2.75-2.54 (m, 6H, 3×CH$_2$ Lev), 2.49-2.39 (m, 6H, 3×CH$_2$ Lev), 2.19-1.94 (6s, 36H, 3×CH$_3$ Lev, 3×CH$_3$ Ac), 1.65-1.23 (m, 6H, 3×CH$_2$Linker). $^{13}$C NMR (150.8 MHz, CDCl$_3$): δ 206.8, 206.7, 206.5, 172.6, 172.5, 172.4, 169.9, 169.8, 169.3, 169.0, 168.2, 167.44, 154.0, 143.3, 143.0, 141.3, 141.2, 138.4, 138.1, 137.7, 137.6, 137.4, 128.5-127.1, 125.1, 125.0, 120.0, 101.1, 100.5 (C1$^F$), 98.0 (C1$^D$), 97.8 (C1$^E$), 97.7, 97.2 (C1$^C$), 82.0, 79.3, 78.4, 78.0, 77.7, 77.6, 77.4, 75.7, 75.5, 75.4, 75.3, 75.0, 74.5, 74.4, 74.3, 74.2, 73.3, 73.1, 72.4, 72.3, 70.5, 70.3, 70.2, 69.5, 69.2, 68.6, 67.2, 63.1, 62.8, 62.5, 62.1, 61.7, 61.6, 52.6, 52.4, 52.2, 50.6, 50.3, 47.1, 46.6, 46.2, 38.1, 38.0, 37.9, 37.8, 31.9, 29.8, 29.7, 29.6, 29.4, 28.9, 27.9, 27.8, 27.7, 27.4, 23.2, 22.7, 20.8, 20.7, 20.6. HRMS-MALDI: (M+Na$^+$) calcd. 2663.9856. found 2663.9900.

Hexasaccharide Deprotection

Synthesis of Hexasaccharide (69): Cleavage of Lev esters: Hexasaccharide 63 (73.5 mg, 0.028 mmol) was de-levulinoylated according to the general procedure for cleavage of levulinoyl ester to give 64 as a colorless oil (59.2 mg, 90%). $^1$H NMR (500 MHz, CD$_3$OCD$_3$): δ 7.72-7.70 (m, 2H, CH Aromatic), 7.57-7.55 (m, 2H, CH Aromatics), (m, 40H, CH Aromatics), 5.47 (d, 1H, J=3.7 Hz, H1$^C$), 5.38 (d, 1H, J=4.0 Hz, H1$^D$), 5.22-512 (m, 4H, CH$_2$ Cbz, 2×CHHBn), 5.09-5.06 (m, 3H incl. H1$^E$ at 5.02, H2$^B$, H2$^F$), 5.04-4.91 (m, 5H, H2$^D$, H4$^F$, H1$^F$, H1$^B$, CHHBn), 4.87-4.75 (m, 6H incl. 4×CH$_2$Bn, H1$^A$ at 4.80), 4.64-4.49 (m, 7H, 5×CH$_2$Bn, CH$_2$ Fmoc, NCH$_2$Bn), 4.30 (t, 1H, J=6.6 Hz, CH Fmoc), 4.21-4.12 (m, 3H, H5$^F$, H4$^B$, H5$^B$), 4.07 (t, 1H, J=5.2 Hz, H3$^D$), 4.03-3.92 (m, 5H, H3$^F$, H3$^B$, H4$^C$, H4$^E$, H4$^A$), 3.88-3.71 (m, 10H, H3$^A$, H3$^E$, H3$^C$, H6a$^A$, H6a$^E$, H6a$^C$, H6b$^E$, H6b$^A$, H6b$^C$, H5$^E$), 3.62 (m, 5H incl. s at 3.62: CO$_2$CH$_3$, OCHH Linker, H5$^A$), 3.53, 3.51 (2s, 6H, CO$_2$CH$_3^B$ or $^D$, CO$_2$CH$_3^B$ or $^D$), 3.46-3.43 (m, 2H, H2$^C$, H5$^C$), 3.43-3.38 (bm, 1H, OCHH Linker), 3.45 (dd, 1H, J=3.7 Hz, J=10.4 Hz, H2$^C$), 3.30 (dd, 1H, J=3.3 Hz, J=10.4 Hz, H2$^E$), 3.25-3.23 (m, 3H incl. H2$^A$: dd, J=3.0 Hz, J=10.2 Hz at 3.25, CH$_2$N Linker), 2.10-2.05 (3s, 9H, 3×CH$_3$ Ac), 1.56-1.28 (m, 6H, 3×CH$_2$ Linker). HRMS-MALDI: (M+Na$^+$) calcd. 2369.8753, found 2369.8722.

O-sulfation: Hexasaccharide 64 (59.2 mg, 0.025 mmol) was dissolved in DMF (1.76 mL) and O-sulfated according to the general procedure for O-sulfation providing 65 as sodium salt (53.3 mg, 80%). $[\alpha]_D^{23}$ −32.1 (c=1.3, CHCl$_3$); $^1$H NMR (500 MHz, CD$_3$OCD$_3$): δ7.85-7.80 (m, 2H, CH Aromatic), 7.66-7.60 (m, 2H, CH Aromatics), 7.50-7.21 (m, 40H, CH Aromatic), 5.42 (bs, 1H, H1$^D$), 5.36 (d, 1H, J=3.8 Hz, H1$^C$), 5.33 (d, 1H, J=8.2 Hz, H1$^E$), 5.25 (d, 1H, J=8.2 Hz, H1$^F$), 5.18-5.15 (m, 3H, CH$_2$ Cbz, CHHBn), 5.11-5.09 (m, 2H, H2$^D$, CHHBn), 5.03-4.99 (m, 4H, CHHBn, H2$^E$, H2$^F$, H1$^E$), 4.95 (t, 1H, J=9.6 Hz, H4$^F$), 4.92 (d, 1H, J=1.8 Hz, H5$^D$), 4.87-4.48 (m, 12H incl. H1$^A$: bs at 4.87, 8×CHHBn, NCH$_2$Bn, CHH Fmoc,), 4.42 (dd, 1H, J=6.8 Hz, J=10.5 Hz, CHHFmoc), 4.36-4.32 (m, 5H, H5$^B$, H6a$^A$, H6a$^E$, H6a$^C$, H5$^F$), 4.27 (t, 1H, J=6.8 Hz, CH Fmoc), 4.23-4.4.16 (m, 4H, H6b$^E$, H6b$^A$, H6b$^C$, H4$^E$), 4.10-4.01 (m, 6H, H3$^E$, H4$^D$, H3$^F$, H3$^D$, H4$^E$, H4$^A$), 3.94 (t, 1H, J=9.6 Hz, H4$^C$), 3.85-3.81 (bm, 9H, H5$^E$, H3$^A$, H5$^C$, H3$^C$, H3$^E$, OCHH Linker, CO$_2$CH$_3^D$), 3.59 (dd, 1H, J=3.6 Hz, J=10.4 Hz, H2$^C$), 3.53, 3.52 (2s, 6H, CO$_2$CH$_3^F$, CO$_2$CH$_3^B$), 3.37-3.35 (m, 2H incl. H2$^C$: dd, J=3.5 Hz, J=10.4 Hz at 3.36, H2$^E$, OCHH Linker), 3.29-3.20 (bm, 3H, H2$^A$, CH$_2$N Linker), 2.15, 2.11, 2.00 (3s, 9H, 3×CH$_3$ Ac), 1.56-1.25 (m, 6H, 3×CH$_2$ Linker). ESI-MS: m/z: calcd. for C$_{122}$H$_{128}$N$_{10}$Na$_3$O$_{47}$S$_3$: 1292.3710, found: 1292.3712 [M−2H]$^{2-}$; calcd. C$_{122}$H$_{127}$N$_{10}$Na$_3$O$_{47}$S$_3$: 861.2449, found: 861.2446 [M−3H]$^{3-}$.

Fmoc cleavage and saponification of methyl esters and de-O-Acetylation:

Hexasaccharide 65 (53.3 mg, 0.020 mmol) was dissolved in DMF (1.25 mL) and subjected to Fmoc cleavage according to the general procedure. The resulting product was directly used in the next step. The compound (33.0 mg, 0.0124 mmol) was dissolved in THF (1.4 mL) and subjected to saponification and de-O-acetylation according to the general procedure of saponification of methyl ester and de-O-acetylation to give 66 as sodium salt (23.9 mg, 82%). [α]$_D^{23}$ +36.9 (c=0.48, CH$_3$OH); $^1$H NMR (500 MHz, CD$_3$OCD$_3$): δ 7.47-7.19 (m, 40H, CH Aromatic), 5.53 (d, 1H, J=3.5 Hz, Fin, 5.30 (bs, 1H, H1$^E$), 5.17-4.56 (m, 18H incl. H1$^E$ at 5.14, H1$^E$ at 4.90, H1$^A$ at 4.82, H1$^F$ at 4.8, H5$^D$, CH$_2$ Cbz, 6×CH$_2$Bn), 4.51-4.31 (m, 8H, NCH$_2$Bn, H6a$^A$, H6a$^C$, H6a$^E$, H6b$^A$, H6b$^E$, H6b$^C$), 4.27-4.20 (m, 4H, H3$^D$, H4$^D$, H5$^A$, H5$^E$), 4.08-3.82 (m, 8H, H4$^E$, H4$^C$, H4$^A$, H5$^E$, H3$^E$, H3$^C$, H3$^A$, H2$^D$, H3$^D$), 3.72 (t, 1H, J=8.9 Hz, H3$^B$), 3.59-3.47 (m, 5H, OCH$_2$ Linker, H4$^A$, H4$^F$, H2), 3.51-3.47 (m, 2H incl. H2$^E$: dd, J=3.2 Hz, J=9.8 Hz at 3.50, H3$^F$), 3.89 (t, 1H, J=9.8 Hz, H2$^B$), 3.34-3.24 (m, 2H, CH$_2$N Linker), 3.18 (m, 1H, H2$^A$), 3.14 (dd, 1H, J=3.5 Hz, J=9.8 Hz, H2$^C$), 1.57-1.28 (m, 6H, 3×CH$_2$ Linker). ESI-MS:m/z: calcd. for C$_{98}$H$_{104}$N$_{10}$Na$_6$O$_{42}$S$_3$: 1097.2976, found: 1097.2973 [M−2H]$^{2-}$; calcd. C$_{98}$H$_{103}$N$_{10}$Na$_6$O$_{42}$S$_3$: 731.1960, found: 731.1951 [M−3H]$^{3-}$.

Reduction of azide group: Hexasacharide 66 (23.9 mg, 0.0102 mmol) was dissolved in 1:1 mixture of THF and (0.1 M) NaOH (0.102 mL, 0.102 mmol, 10 eq. per azido group) and subjected to azide reduction to obtain hexasaccharide 67 (17.3 mg, 65%). $^1$HNMR (500 MHz, CD$_3$OCD$_3$): δ 7.50-7.18 (m, 40H, CH Aromatics), 5.49 (d, 1H, J=3.1 Hz, Fin, 5.24 (d, 1H, J=3.7 Hz, H1$^D$), 5.18-5.00 (m, 7H, CH$_2$Cbz, 2×CH$_2$Bn, H1$^E$ at 5.10), 4.82-4.61 (m, 11H incl. H1$^F$ at 4.76, H1$^B$ at 4.68, H1$^A$ at 4.66, H5$^D$ at 4.72, 3×CH$_2$Bn, CHHBn), 4.56-4.33 (m, 6H, NCH$_2$Bn, H6a$^A$, H6a$^C$, H6a$^E$, CHHBn), 4.32-4.22 (m, 4H, H4$^D$, H6b$^A$, H6b$^E$, H6b$^C$), 4.16-4.03 (m, 5H, H5$^C$, H5$^E$, H4C, H4$^E$, H4$^B$), 3.93 (t, 1H, J=9.3 Hz, H3$^E$), 3.90-3.75 (m, 5H, H2$^D$, H5$^B$, H3$^C$, H3$^D$, H3$^B$), 3.66-3.56 (m, 4H, OCHH Linker, H2$^B$, H4$^F$, H3$^A$), 3.51 (t, 1H, J=8.9 Hz, H3$^F$), 3.40 (t, 1H, J=9.1 Hz, H2$^F$), 3.32-3.23 (m, under CD$_2$HOD OCHH Linker, CH$_2$N Linker), 3.00 (bd, 1H, J=8.9 Hz, H2$^E$), 2.80-2.72 (m, 2H incl. H2$^C$ at 2.79, H2$^A$ at 2.74), 1.55-1.21 (m, 6H, 3×CH$_2$ Linker). ESI-MS:m/z: calcd. for C$_{98}$H$_{110}$N$_4$Na$_6$O$_{42}$S$_3$: 1058.3119, found: 1058.3131 [M−2H]$^{2-}$; calcd. for C$_{98}$H$_{109}$N$_4$Na$_6$O$_{42}$S$_3$: 705.2055 found: 705.2047 [M−3H]$^{3-}$.

Selective N-sulfation[2]: Hexasaccharide 67 (17.3 mg, 0.008 mmol) was subjected to selective N-sulfation to obtain hexasaccharide 68 (10.2 mg, 50 µmol). [α]$_D^{23}$ +59.9 (c=0.47, CH$_3$OH). $^1$H NMR (500 MHz, CD$_3$OCD$_3$): δ7.53-7.15 (m, 40H, CH Aromatics), 5.65 (d, 1H, J=3.1 Hz, Fin, 5.33 (bs, 1H, H1$^E$), 5.25 (bs, 1H, H1$^E$), 5.18-5.08 (m, 4H incl. H1$^A$ at 5.10, CH$_2$Cbz, CHHBn), 4.94-4.58 (m, under CD$_3$OH peak, 14H incl. H5$^D$ at 4.82, H1$^F$ at 4.83, H5$^D$ at 4.76, eleven CHHBn), 4.51-4.19 (m, 9H, NCH$_2$Bn, H6a$^A$, H6a$^C$, H6a$^E$, H6b$^A$, H6b$^E$, H6b$^C$, H4$^D$), 4.11-3.79 (m, 6H, H5$^C$, H4$^B$, H5$^E$, H5$^B$, H4$^E$, H2$^D$), 3.90-3.79 (m, 5H, H5$^A$, H4$^A$, H3$^C$, H3$^B$, H3$^E$), 3.70-3.54 (m, 6H, H5$^F$, OCHH Linker, H3$^A$, H4$^F$, H2$^B$, H3$^F$), 3.47-3.23 (m, 7H, H2$^C$, H2$^E$, H2$^A$, H2$^B$, OCHH Linker, CH$_2$N Linker), 1.67-1.28 (m, 6H, 3×CH$_2$ Linker). ESI-MS: m/z: calcd. for C$_{98}$H$_{107}$N$_4$Na$_9$O$_{51}$S$_6$: 1178.2471, found: 1178.2475 [M−2H]$^{2-}$; calcd. for C$_{98}$H$_{106}$N$_4$Na$_9$O$_{51}$S$_6$: 705.2055, found 705.2047 [M−3H]$^{3-}$.

Global debenzylation: A solution of the hexasaccharide 68 (10.2 mg, 0.004 mmol) in (CH$_3$OH/H$_2$O 1:1, v/v) (1 mL) was subjected to debenzylation according to the general procedure for global debenzylation to give hexasaccharide 69 (4.8 mg, 67%). NMR data reported in Example I.

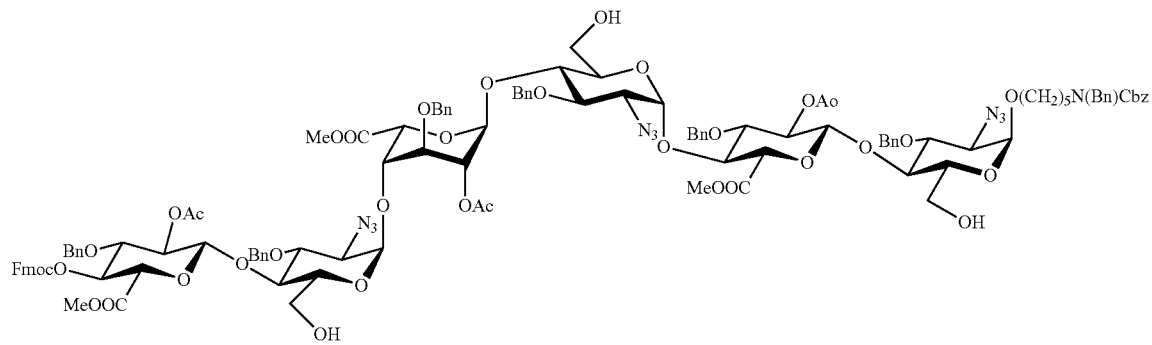

64

-continued
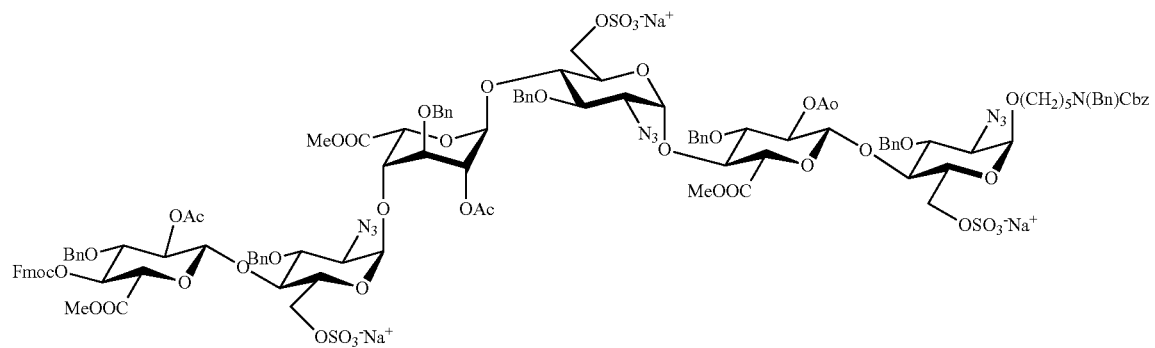
65
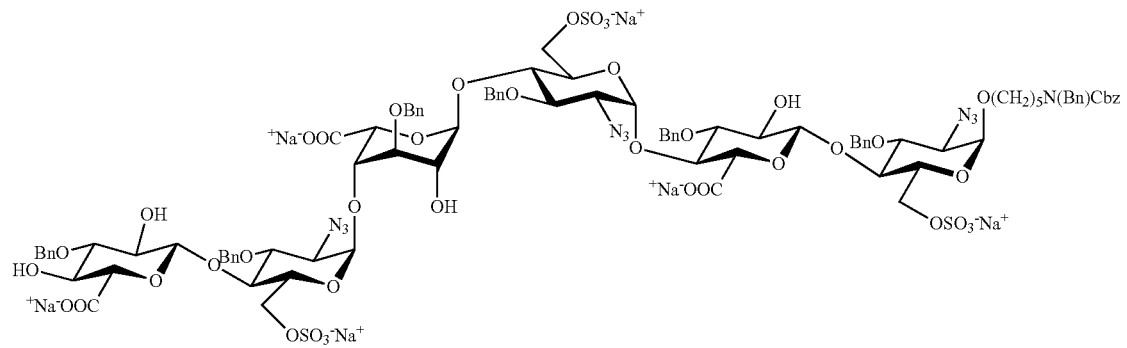
66
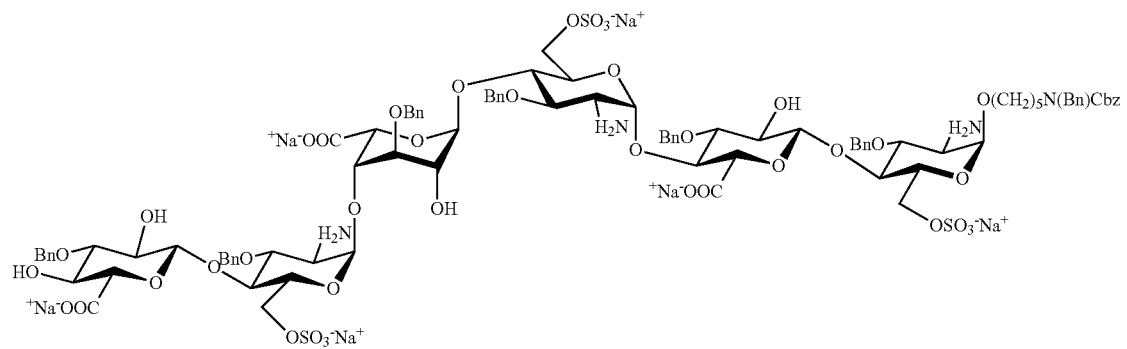
67
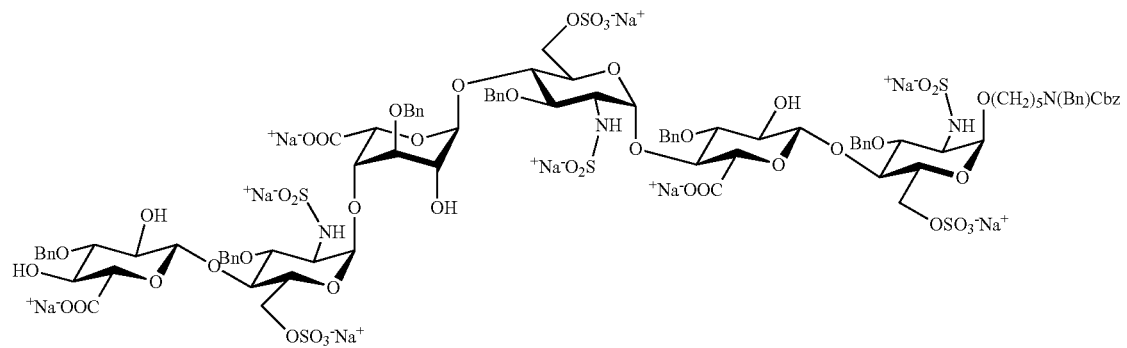
68

-continued

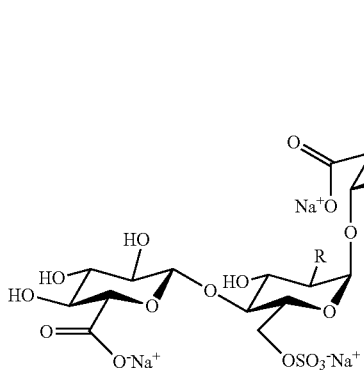
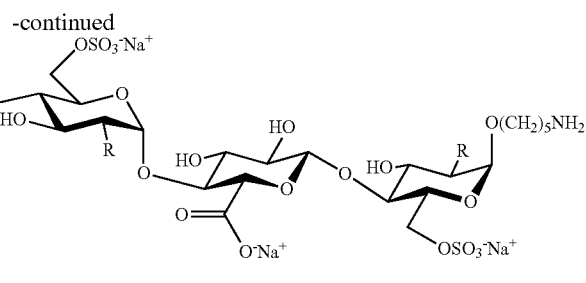

69: R = NHSO$_3^-$Na$^+$

NMR spectra of synthetic intermediates and final products, and synthetic procedures and NMR assignments for intermediates are available in the supporting information for Arungundram et al., 2009, *J. Amer. Chem. Soc.* 131:17394-17405. The supporting information is available on the world wide web at pubs.acs.org/doi/suppl/10.1021/ja907358k.

Example III

Synthesis and Use of Libraries of Heparan Sulfate Derivatives

Heparan Sulfates as Regulators of Protein Function

Heparan sulfate (HS) is required for many biological events and is structurally very diverse. Specific glycan sequences confer selective protein-binding properties to HS. However, ligand identification for specific GAG binding proteins is a major challenge in glycobiology.

Figure 5:
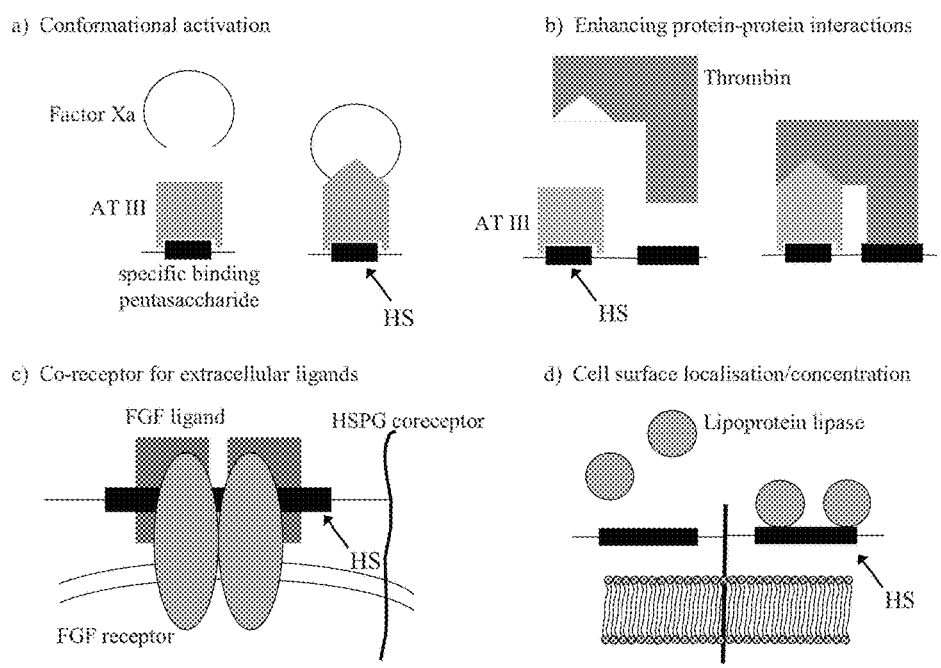
FIG. 5 shows a schematic representation of some of the activities of heparan sulfate.

Activities of HS include stabilizing proteins, restricting protein mobility and localization, altering protein conformation, and acting as a template for assembly of multiprotein complexes. Schematic representations of some of the activities of HS are shown in FIG. 5.

Chemical Synthesis of Oligosaccharides

Figure 7:
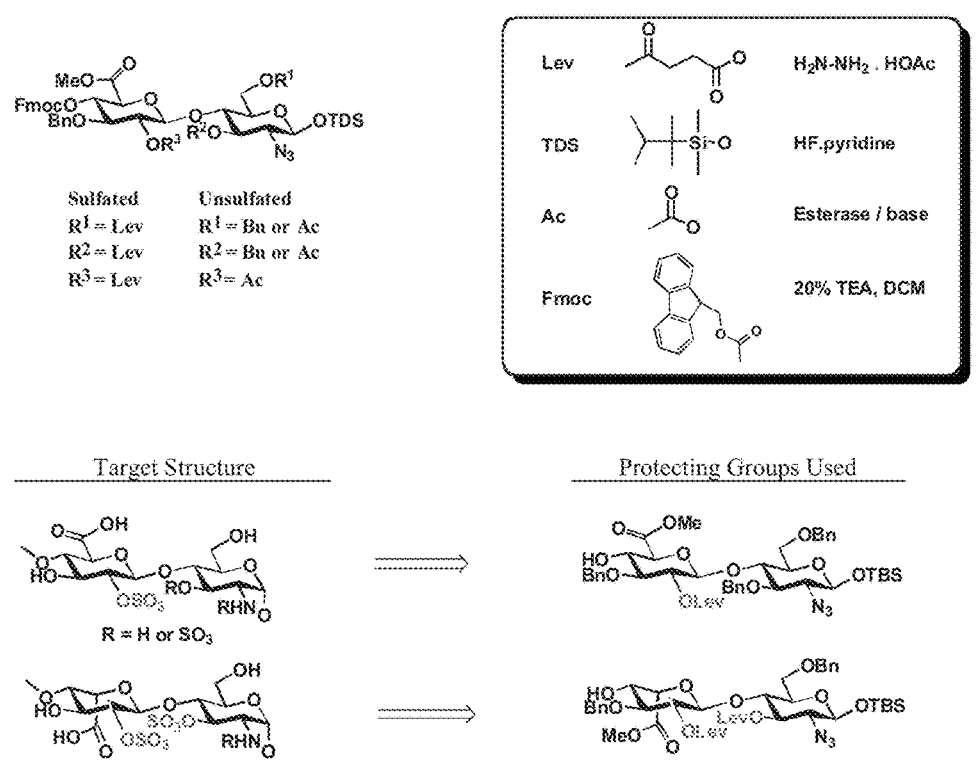
FIG. 7 shows a schematic representation of a modular approach for heparan sulfate oligosaccharide synthesis.
Figure 8:
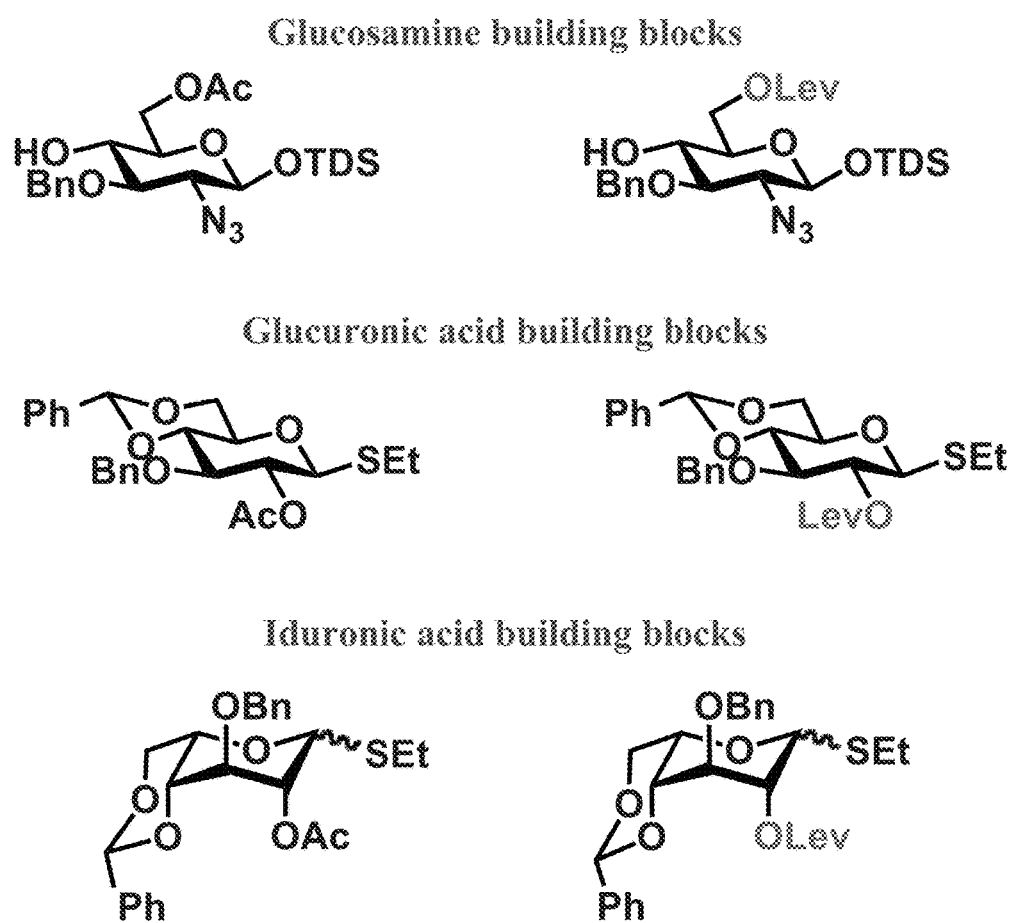
FIG. 8 shows examples of monosaccharide building blocks for use in heparan sulfate oligosaccharide synthesis.
Figure 9:
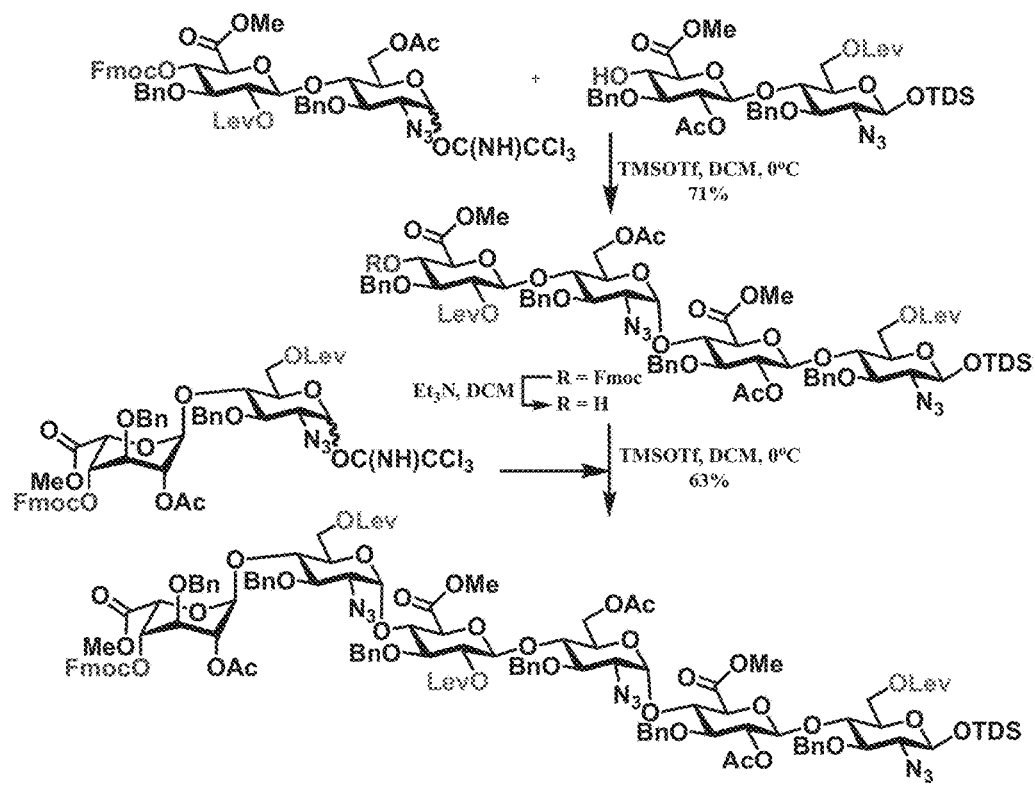
FIG. 9 shows an exemplary synthesis of an orthogonally protected heparan sulfate hexasaccharide from orthogonally protected disaccharide building blocks.
Figure 10:
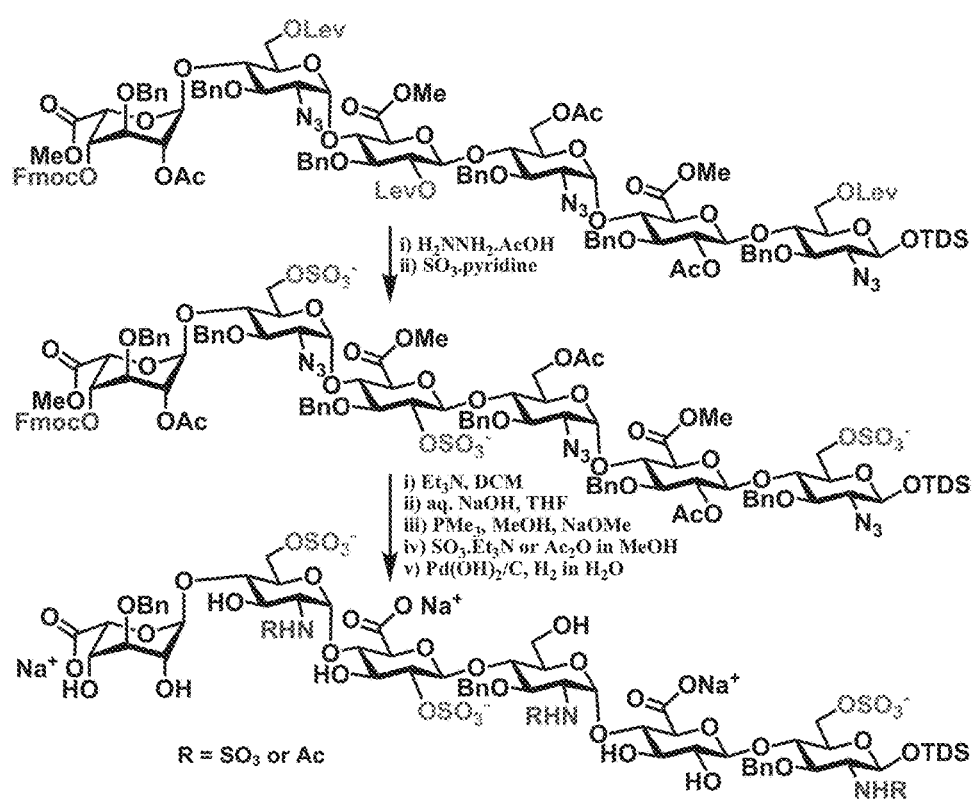
FIG. 10 shows selective sulfation and deprotection.

Until now the chemical synthesis of a wide range of HS oligosaccharides has been an elusive goal. Anomeric control has been often problematic, the outcome of glycosylation has been unpredictable, and the preparation of glycosyl donor and acceptor molecules has proven very time consuming. Here we demonstrate the use of a modular approach in which key building blocks are repeatedly used in the synthesis of oligosaccharides. Heparan sulfate constituent disaccharides can contain varying levels of sulfation. FIG. 6A shows a range of sulfation levels, from unsulfated to triply sulfated. Heparan sulfate disaccharides with different levels of sulfation are shown in FIG. 6B. A modular synthesis of HS oligosaccharides is described in more detail in Example I and is also exemplified in FIG. 7. Selected monosaccharide building blocks are shown in FIG. 8. An exemplary synthesis of an orthogonally protected HS hexasaccharide from disaccharide building blocks is shown in FIG. 9. Deprotection and sulfation of a hexasaccharide is shown in FIG. 10.

Generation of Anti-HS Antibodies

Cleavage of amyloid precursor protein (APP) by BACE-1 is a key step in amyloid plaque formation. HS interacts with the β-site of BACE-1 and can inhibit the cleavage of APP. Studies with fractionated and modified HS fragments have indicated that the active structures contain 6-O-sulfate and NHAc groups. Synthetic tetrasaccharides have been prepared to probe interactions of Bace-1 with HS fragments (see Example I).

Our previous work has demonstrated that a three-component vaccine composed of a TLR2 or TLR6 agonist, a promiscuous peptide T-helper epitope and a tumor-associated glycopeptide can elicit in mice exceptionally high titers of IgG antibodies that can recognize cancer cells expressing the tumor-associated carbohydrate (Ingale, Nat. Chem. Biol. 2007, 3, 663-667; US Patent Application Publication 2009/0041836; and WO 2010/002478). The superior properties of the vaccine candidate are attributed to the local production of cytokines, upregulation of co-stimulatory proteins, enhanced uptake by macrophages and dendritic cells and avoidance of epitope suppression.

Figure 11:
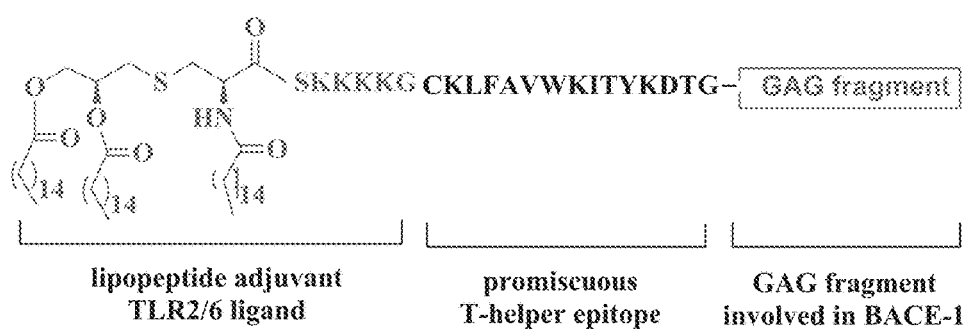
FIG. 11 shows an example of a three-component vaccine construct.
Figure 12:
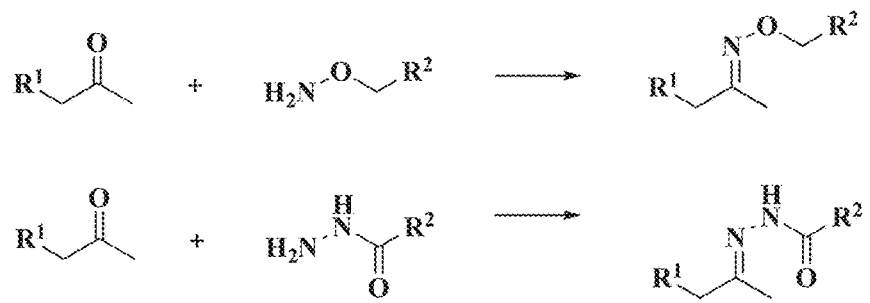
FIG. 12 shows conjugation chemistry to attach HS to the lipopeptide of the three-component vaccine construct.

We will use the three-component immunogen technology (Ingale et al., 2006. *Org. Lett.* 8(25): 5785-5788; WO 2007/146070; and US Patent Application Publication 2009/0196916) to generate monoclonal antibodies (MAbs) against heparan sulfate oligosaccharides (including disaccharides, tetrasaccharides, hexasaccharides, and higher order oligosaccharides) (FIG. 11). Development of appropriate conjugation chemistry to attach various HS oligosaccharides to the lipopeptide component is shown in FIG. 12.

Example IV

Preparation of Heparan Sulfate Disaccharide Building Blocks Modified by Orthogonal Amino Protecting Groups We envisaged that HS-oligosaccharides having both N-acetyl and N-sulfates could be obtained by employing disaccharide building blocks that are modified by orthogonal amino protecting groups. The lack of non-participating amino protecting groups however complicates such an approach. To address this difficulty, the previously employed disaccharide building blocks that have an azido-protecting group at C-2 were employed as glycosyl donors for oligosaccharide assembly. The azido group on a glycosylated acceptor is reduced to an amine and then protected as an Fmoc function. Subsequent glycosylation with an azido containing building block provides a tetrasaccharide that is modified by orthogonal amino-protecting groups (azido and Fmoc).

Scheme 6. Preparation of a tetrasaccharide having orthonal amino-protecting groups.

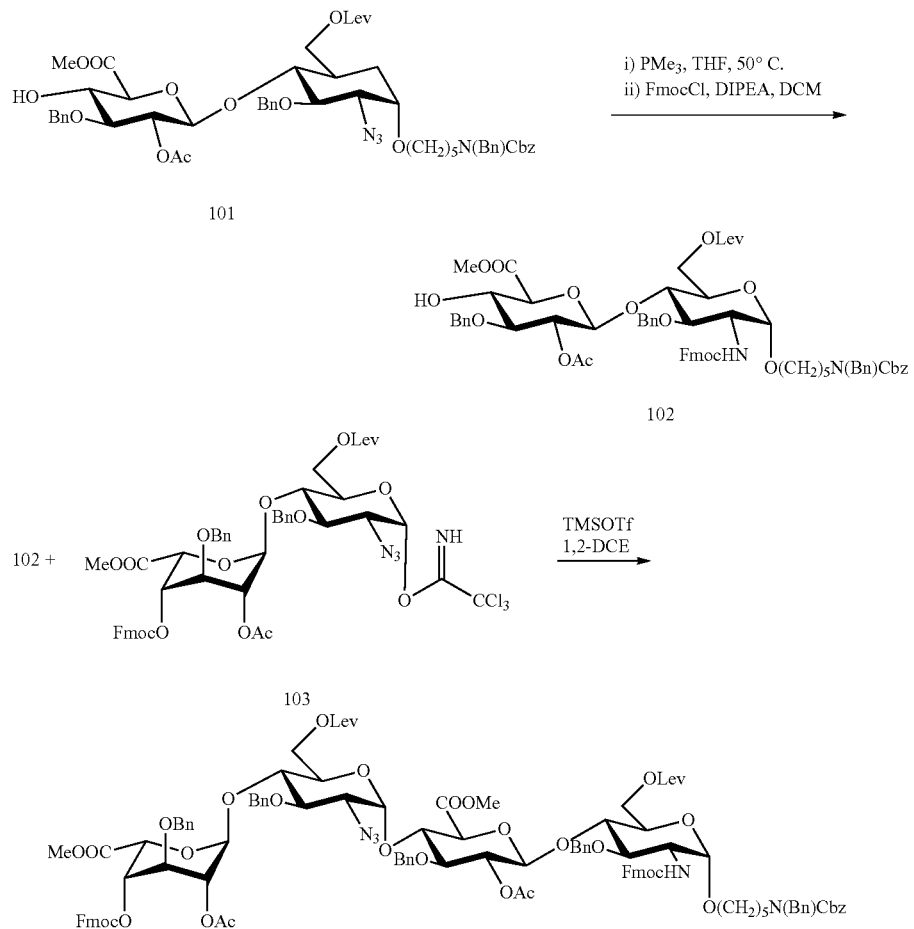

To demonstrate the feasibility of the methodology, the azido function of the previously synthesized disaccharide 101 was reduced with trimethyl phosphine and the resulting amine protected as a Fmoc carbamate to give compound 102. A TMSOTf mediated glycosylation of 102 with previously prepared glycosyl donor 103 give tetrasaccharide 104 as only the α-anomer in a yield of 65% (Scheme 6).

Compound 104 was the starting material for the preparation of differentially modified tetrasaccharide 110 (Scheme 7) and 116 (Scheme 8). The sequence of amino functionalization was important in the preparation of these two derivatives, and it was found that the acetamido moiety needed to be installed prior to the N-sulfate.

Scheme 7. Synthesis of an N-sulfate and N-acetyl modified tetrasaccharide

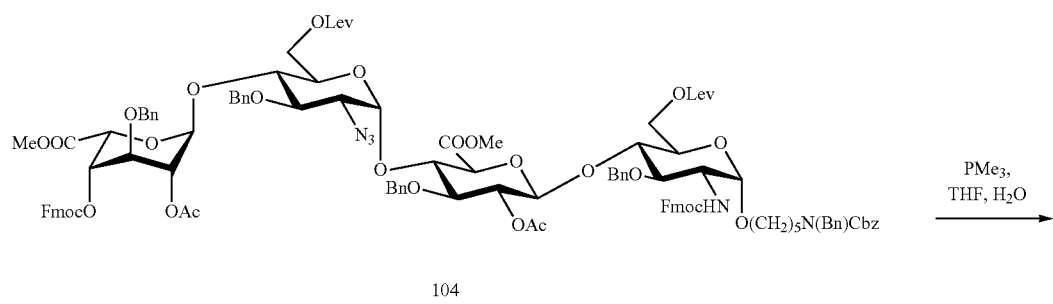

-continued
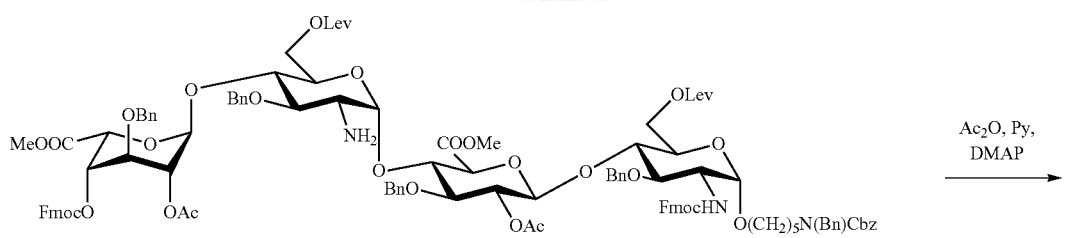
105
Ac₂O, Py, DMAP →
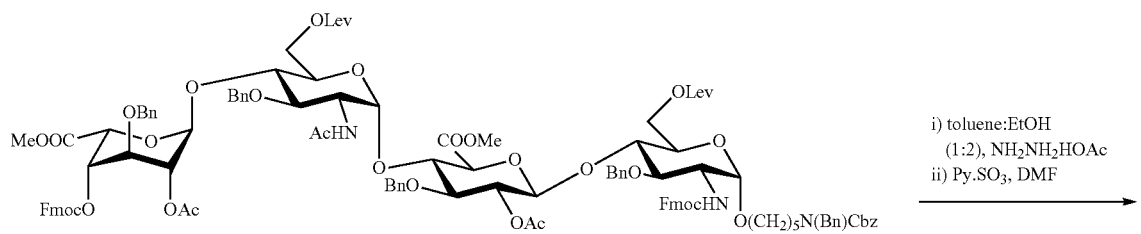
106
i) toluene:EtOH (1:2), NH₂NH₂·HOAc
ii) Py·SO₃, DMF →
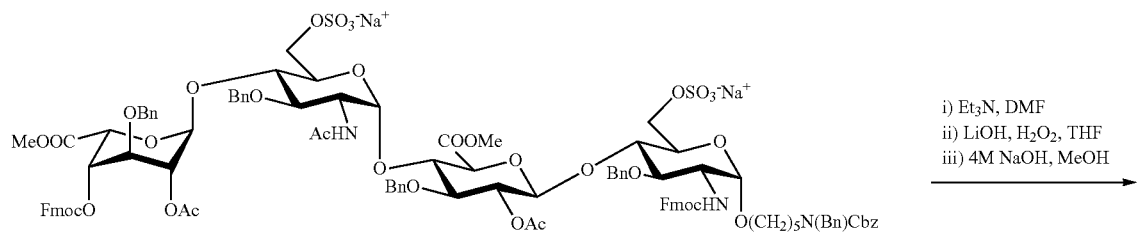
107
i) Et₃N, DMF
ii) LiOH, H₂O₂, THF
iii) 4M NaOH, MeOH →
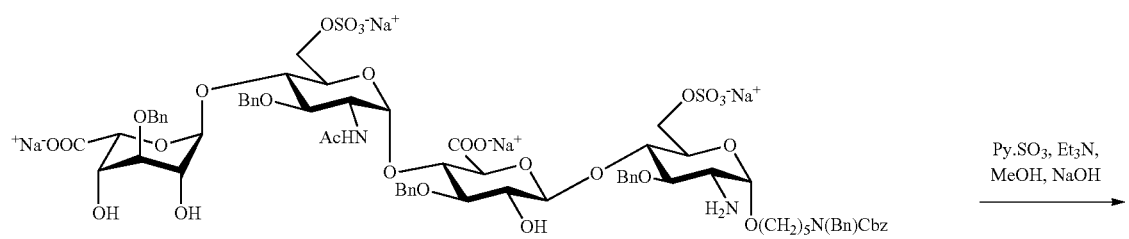
108
Py·SO₃, Et₃N, MeOH, NaOH →
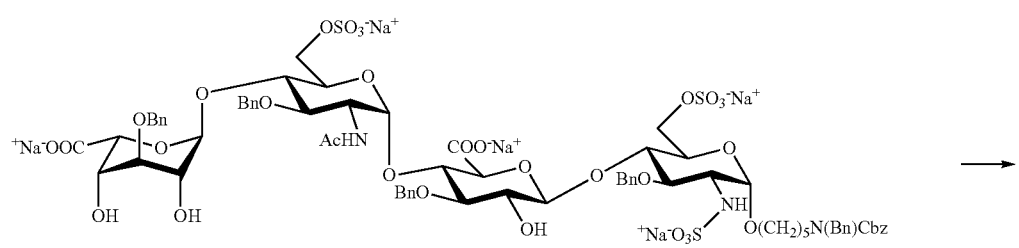
109

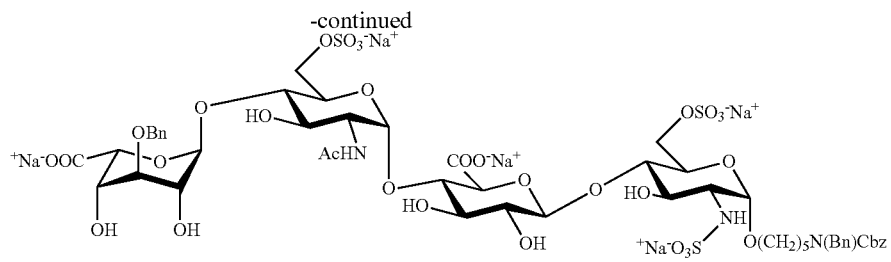

110

The preparation of tetrasaccharide 110 commenced with the reduction of the azido moiety of 104 with trimethyl phosphine followed by acetylation of the resulting amine 105 with acetic anhydride in pyridine to give compound 106. The Lev esters of 106 were removed by treatment by hydrazine acetate in toluene and the resulting hydroxyls modified as sulfate esters by treatment with pyridinium sulfur trioxide to give compound 107. Next, the Fmoc groups were removed by treatment with triethylamine and the acetyl and methyl esters of the resulting compound were saponified by a two-step procedure employing first LiOH in a mixture of hydrogen peroxide and THF and then sodium hydroxide in methanol to give partially deprotected 108. The amine of 108 was selectively sulfated with pyridinium sulfur trioxide in the presence of triethylamine in methanol to give N-sulfate 109. Finally, the benzyl ethers and benzyloxycarbamate of 109 were removed by a two-step procedure involving hydrogenation over Pd/C in a mixture of MeOH/$H_2O$ which led to the removal of the spacer protecting groups followed by hydrogenation over $Pd(OH)_2$ which led to the removal of the benzyl ethers to give HS oligosaccharides 110 (Scheme 7).

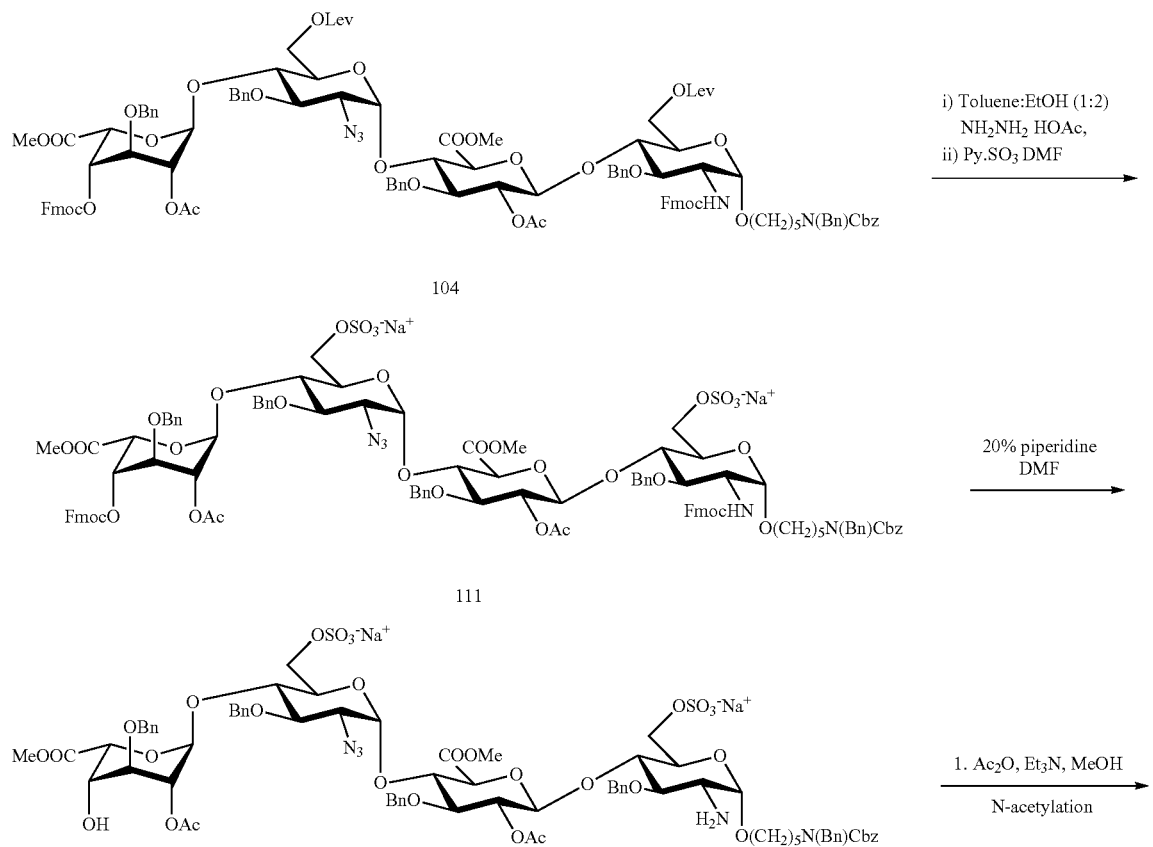

Scheme 8. Synthesis of an N-sulfate and N-acetyl modified tetrasaccharide

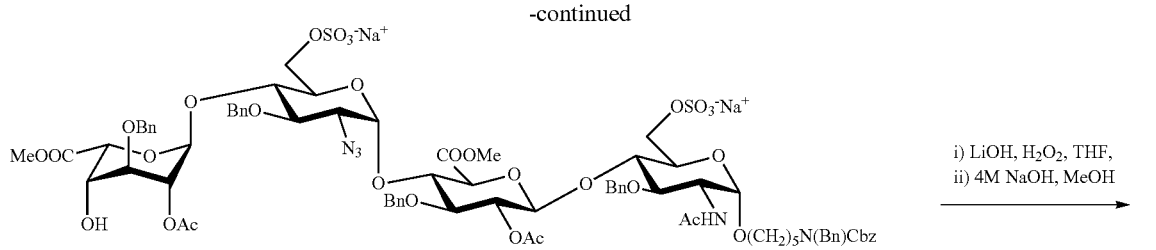

113

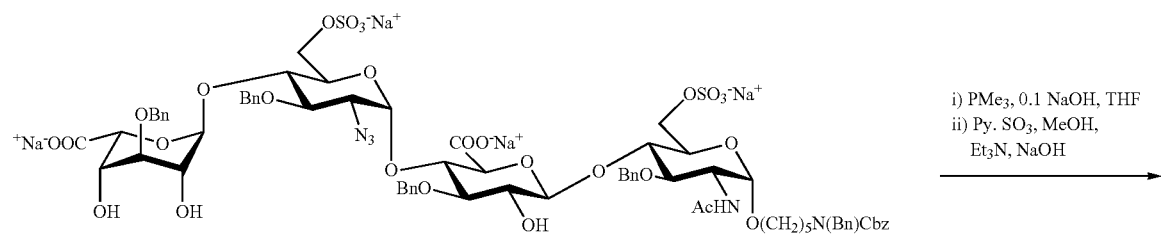

114

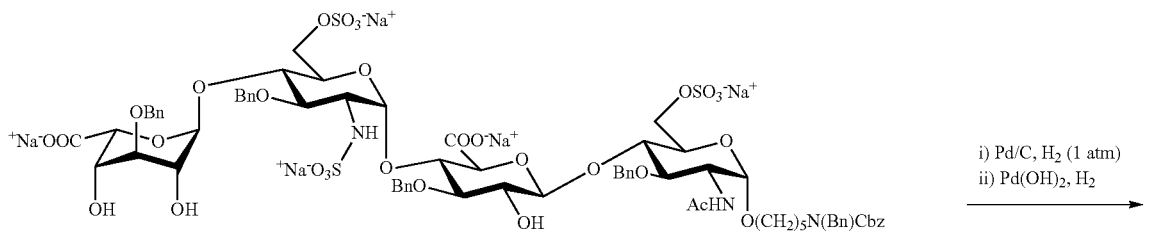

115

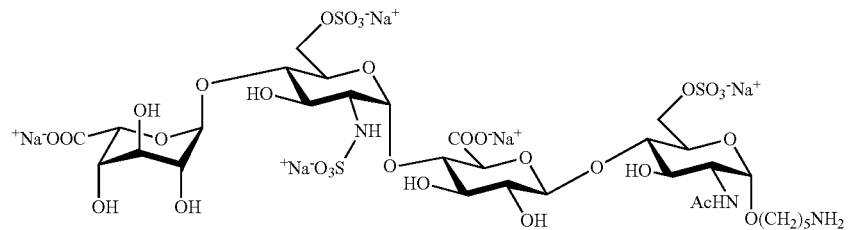

116

Next, attention was focused on the preparation of tetrasaccharide 116. Thus, the Lev esters of 104 were removed by treatment by hydrazine acetate in toluene and the resulting hydroxyls modified as sulfate esters by treatment with pyridinium sulfur trioxide to give compound 111. Next, the Fmoc groups of 111 were removed by treatment with piperidine in DMF and the amine of the resulting compound 112 selective acetylated by reaction with acetic anhydride in the presence of triethylamine in methanol to give 113. Next, the acetyl and methyl esters of 113 were saponified by a two-step procedure employing first LiOH in a mixture of hydrogen peroxide and THF and then sodium hydroxide in methanol to give partially deprotected 114. The azido moiety of 114 was reduced with trimethyl phosphine in THF in the presence of NaOH and the resulting amine was immediately sulfated with pyridinium sulfur trioxide in the presence of triethylamine in methanol to give N-sulfate 115. The benzyl ethers and benzyloxycarbamate of 115 were removed by a two-step procedure involving hydrogenation over Pd/C in a mixture of MeOH/H$_2$O which led to the removal of the spacer protecting groups followed by hydrogenation over Pd(OH)$_2$ which led to the removal of the benzyl ethers to give HS oligosaccharide 116 (Scheme 8).

Example V

Preparation of a Hexasaccharide Having an N-acetyl, N-sulfate and a Free Amino Moiety The modular disaccharide building blocks for HS-oligosaccharide synthesis gave access to compounds that have either N-acetyl or N-sulfates at the amino groups of the glucosamine moieties. We envisaged that HS-oligosaccharides having a combination of free amine, N-acetyl or N-sulfates could be obtained by employing disaccharide building blocks that are modified by orthogonal amino protecting groups. The lack of non-participating amino protecting groups complicated, however, such an approach.

To address this difficulty, the previously employed disaccharide building blocks that have an azido-protecting group at C-2 were employed as glycosyl donors for oligosaccharide assembly. After a glycosylation, the azido group is reduced to an amine and then protected as a fluorenylmethyloxycarbonyl (Fmoc) or benzyloxycarbonyl (CBz) function. Subsequent glycosylation with an azido containing building block will provide a hexasaccharide that is modified by orthogonal amino-protecting groups.

To demonstrate the feasibility of the methodology, hexasaccharides 142 (Scheme 10) was prepared from disaccharide acceptor 126, and disaccharide donors 130 and 134 (Scheme 9). The latter three compounds were prepared from the previously described modular disaccharides. Thus, the TDS protecting group of disaccharide 121 was removed by HF in pyridine and the resulting lactol 122 was converted into glycosyl donor 123 using conventional conditions. A glycosylation of 123 with benzyl alcohol in the presence of TMSOTf gave mainly benzyl glycoside 124. Next, the azido function of 124 was reduced with trimethyl phosphine and the resulting amine 125 was protected as a Fmoc carbamate to give compound 126.

Glycosyl donor 130 was prepared from previously described disaccharide 127 by protection of the C-4 hydroxyl as an allyloxycarbonyl carbonate to give fully protected 128. The anomeric center of the resulting compound was converted into an imidate by conventional manipulations to give glycosyl donor 130. Glycosyl donor 134 was prepared in a similar fashion however, in this case the C-4' hydroxyl was protected as an acetyl ester because it does not require selective removal at the end of the synthetic sequence.

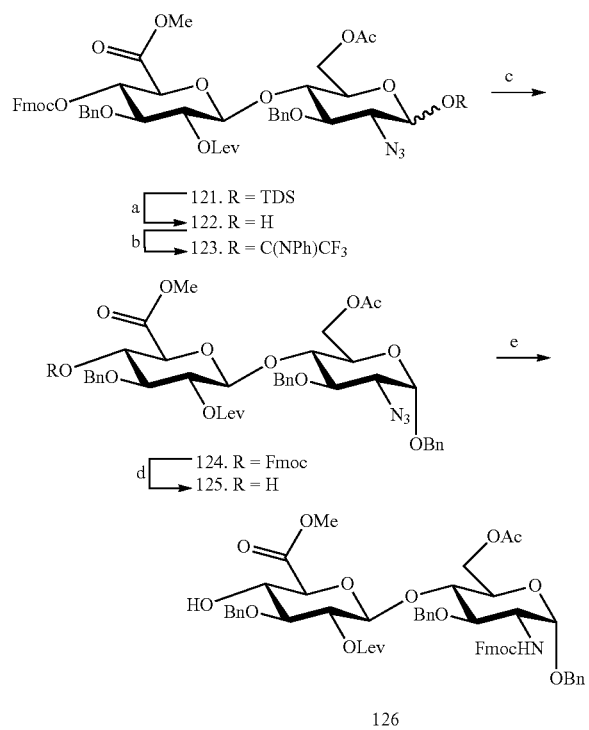

Scheme 9. Chemical synthesis of disacchardie building blocks.

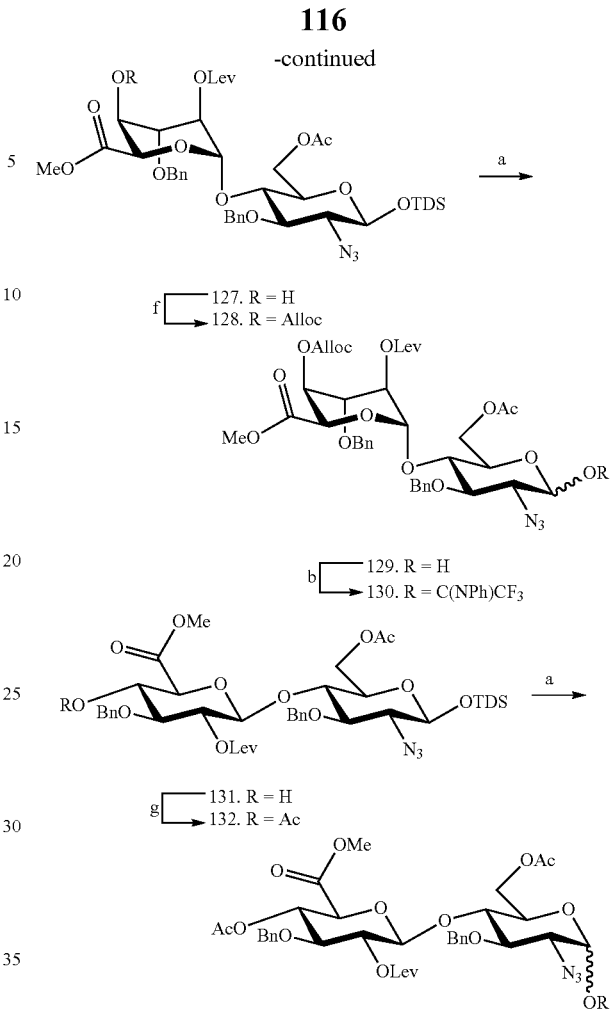

Reagents and conditions: a) HF pyridine; b) PhNC(CF$_3$)Cl, K$_2$CO$_3$, acetone; c) BnOH, TMSOTf, DCM; d) Et$_3$N, DCM; e) PMe$_3$, THF then FmocCl, Na$_2$CO$_3$: f) AllocCl, pyridine, DCM; g) Ac$_2$O, pyridine A TMSOTf mediated glyosylation of 126 with 130 give tetrasaccharide 135 as only the α-anomer in a yield of 65%. Reduction of the azido moiety of 135 with trimethyl phosphine gave an amine, which was protected as a benzyloxycarbamate using standard conditions to give 136. The allyloxycarbonate of 136 was removed by using a Pd(0) catalyst to give glycosyl acceptor 137, which was coupled with glycosyl donor 134 to provide hexasaccharide 138. This compound has amines masked as Fmoc, CBz and azide moieties, which can be selectively removed allowing unique functionalization of each amine. Thus, the Fmoc group of 138 was removed by hindered base and the resulting amine acetylated with acetic anhydride in methanol to give hexasaccharide 139. The Lev esters of 139 were removed by treatment by hydrazine acetate in toluene and the resulting hydroxyls modified as sulfate esters by treatment with pyridinium sulfur trioxide Next, the ester of the resulting compound were saponified by a two-step procedure employing first LiOH in a mixture of hydrogen peroxide and THF and then sodium hydroxide in methanol to give a partially deprotected compound 140. The latter compound was subjected to trimethyl phophine to reduce the azide to an amine, which was selectively sulfated with pyridinium sulfur trioxide in the presence of triethylamine in methanol to provide N-sulfate 141. Finally, the benzyl ethers and benzy-lozycarbamate of 141 were removed by hydrogenation over Pd/C in a mixture of MeOH/H$_2$O to give HS oligosaccharides 142.
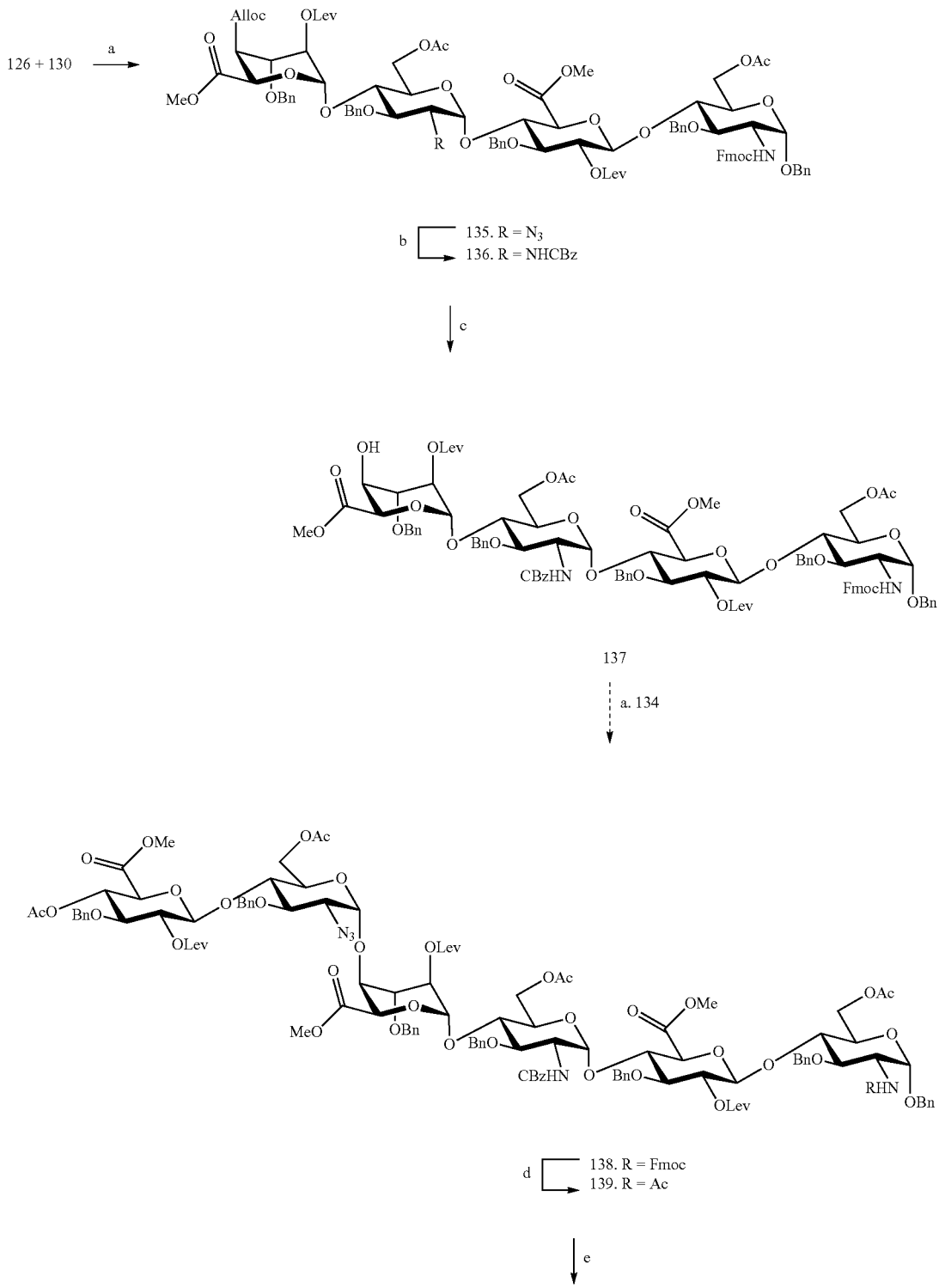
Scheme 10. Chemical synthesis of hexasacchardie 142.

-continued
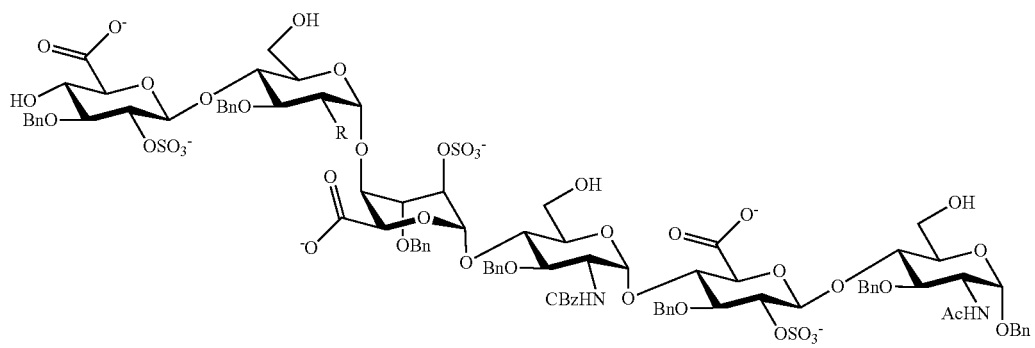
f ⌈ 140. R = N₃
  ⌊ 141. R = NHSO₃
g ↓
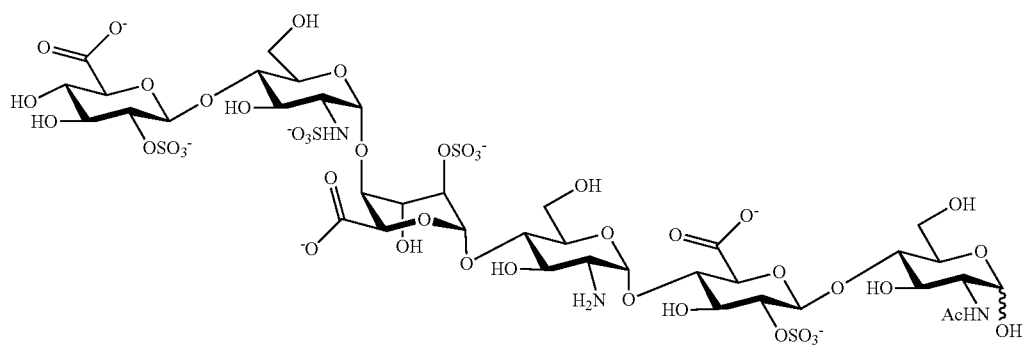
142
Reagents and conditions: a) TMSOTf, DCM; b) PMe₃, THF then CBzCl, Na₂CO₃; c) Pd[P(C₆H₅)₃]₄, Et₂HN; d) Et₃N, DCM then Ac₂O, MeOH; e) NH₂NH₂·HOAc, toluene/EtOH, then Py·SO₃, DMF, then LiOH, H₂O₂, then NaOH, MeOH; f) PMe₃, THF, NaOH, then Py·SO₃, MeOH, Et₃N; g) Pd on C, H₂, MeOH:H₂O, 3 hrs; ii) Pd(OH)₂ on C, H₂, H₂O, 8 hrs, 67%

Example VI

Diversification of Heparan Sulfate Oligosaccharides Obtained by Modular Synthesis Modular disaccharides have been employed for the preparation of libraries of heparan sulfate oligosaccharides. Each intermediate such as tetrasaccharide 162 can be employed for the preparation of two target compounds that have N-sulfate (171) or acetamido (170) moieties. We now demonstrate that by late stage selective derivatization of a single tetrasaccharide such as compound 162, six additional tetrasaccharides (172, 179, 180, 181, 188, 189) having variations in O- and N-sulfations, can be obtained.

Starting Tetrasaccharide

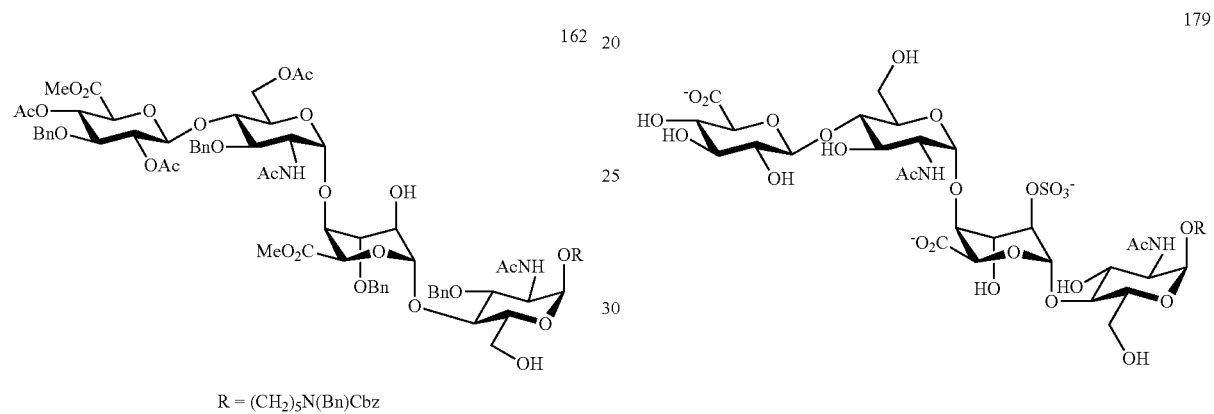

R = (CH$_2$)$_5$N(Bn)Cbz

Final Deprotected Tetrasaccharides

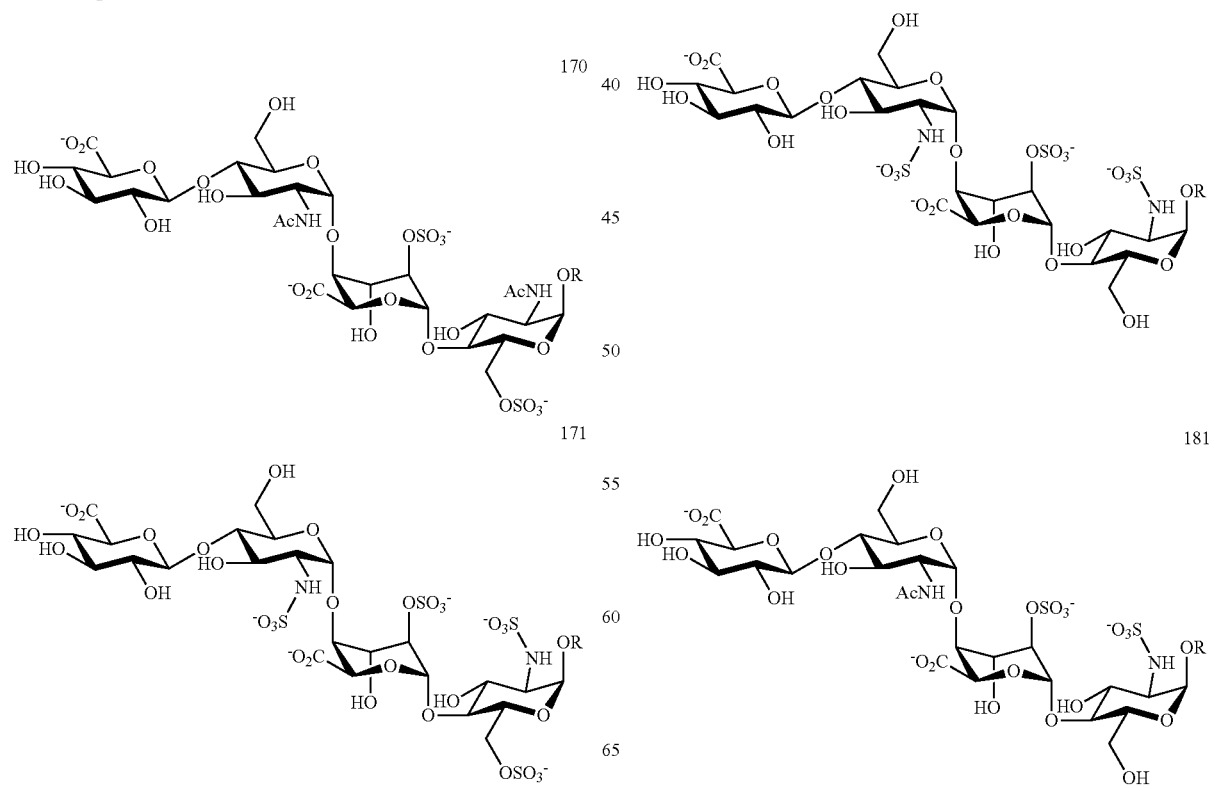

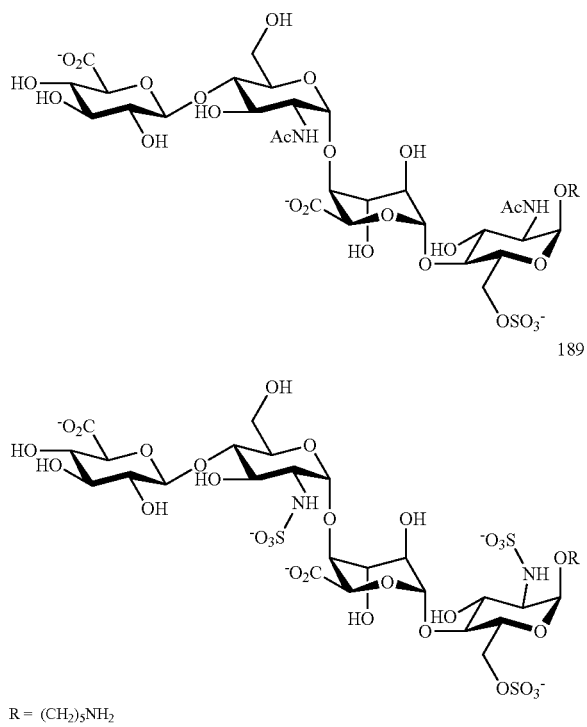

R = (CH$_2$)$_5$NH$_2$

In addition to the standard deprotection sequence, which leads to tetrasaccharides 170 and 171, other derivatization reactions can additionally or alternatively be performed at an appropriate stage of synthesis. For example, selective sulfation of the amino group of the reducing GlcNH$_2$ unit (also referred to herein as selective N-sulfation), followed by acetylation of the unmodified GlcNH$_2$ leads to tetrasaccharides such as 172 and 181. As another example, selective O-desulfation of primary O-sulfate groups (also referred to herein as selective 6-O-desulfation) leads to compounds such as 179 and 180. As another example, selective sulfation of a primary hydroxyl groups (also referred to herein as selective 6-O-sulfation) leads to compounds 188 and 189.

Prior Selective O-desulfation. As the sulfation using SO$_3$.Py is reversible (Harris et al., 1969 Carbohydr. Res. 9:397), solvolytic desulfation of Methyl 2,3,6-tri-O-benzoyl α-D-galactopyranoside 4 sulfate, Methyl 2,3,4-tri-O-acetyl-α-D-glucopyranoside 6-sulfate and of 1,2:3,4-Di-O-isopropylidene-α D-galactopyranose 6-sulfate, has been reported to proceed by heating the pyridinium salts in DMF, dioxane and better in DMSO (Usov et al., 1971 Carbohydr. Res. 18:336-338). However, this procedure does not seem to show selectivity.

Later, it was reported that heating Gal 2-, 3-, 4- or 6-sulfates (Py salts) in the presence of a large excess N,O-bis(trimethylsilyl)acetamide (BTSA) or N,O-bis(trimethylsilyl)trifluoroacetamide (BTSTFA) led to regioselective desulfation of the 6-sulfate (Takano et al., 1992 Biosci. Biotech. Biochem. 56:1577-1580; Matsuo et al., 1993 Carbohydr. Res. 241:209-215; Takano et al., 1995 J. Carb. Chem. 14:885-888). Other silylating reagents were further investigated later on (Horide et al., Bull. Chem. Soc. Jpn. 74:181-182). The reaction mechanism is different from solvolytic desulfation and different silylated intermediates have been proposed (Takano et al., 1995 J. Carb. Chem. 14:885-888; Horide et al., Bull. Chem. Soc. Jpn. 74:181-182).

The selective desulfation at the primary position has successfully been applied to heparin (Py salt) (Kariya et al., 2000 J. Biol. Chem. 275:25949-25958) and recently to fragments of heparin (Roy et al., 2011 Glycobiology 21:1194-1205). However, there have been no reports of selective O-desulfation applied to synthetic and protected oligosaccharides.

Previous selective O-sulfation and diversification. Previous resulfation of chondroitin 4-sulfate and chondroitin 6-sulfate using SO$_3$.Py/DMF indicated that it is more difficult to re-sulfate C-6 than C-4. It was concluded that O-sulfation proceeds according to the order of reactivity of the hydroxyl groups (Nagasawa et al., 1986 Carbohydr. Res. 158:183-190). Similar results have been reported for the re-sulfation of de-sulfated heparin, the authors concluded that O-sulfation proceeded according to the order of reactivity of the hydroxyl groups: 6-OH in GlcN>>2-OH in IdoA (Ogamo et al., Carbohydr. Res. 193:165-172).

Selective sulfation using SO$_3$.Me$_3$N (DMF 50° C.) allowed the selective sulfation of the 6-OH of the Gal 4,6-diol unit of a synthetic and protected chondroitin derived disaccharide (Jacquinet et al., Carbohydr. Res. 314:283-288). The same authors then expanded this procedure to the selective 6-O-sulfation of tri-, tetra-, and pentasaccharides (Belot et al., 2000 Carbohydr. Res. 325:93-106; Jacquinet, 2004 Carbohydr. Res. 339:349-359; Lopin et al., 2006 Angew. Chem. 45:2574-2578; Jacquinet et al., 2009 Chem. Eur. J. 15:9579-9595). The same group has also reported that during the synthesis of β-D-GlcA(2S)-(1-3)-D-GalNAc (6S), sulfation of the 2-OH of the GlcA unit required longer reaction time and larger excess of reagent (Karst et al., 2000 J. Chem. Soc., Perkin Trans. 1:2709-2717). The same procedure has been used and expanded by Gama et al. (Gama et al., 2006 Nature Chem. Biol. 2:467-473) in order to synthesize 4 sulfated forms of single synthetic chondroitin tetrasaccharide to allow for some diversity for biological testing.

Diversity in the modification of size-defined sulfated heparin derivatives (obtained from a natural source) has been reported in Roy et al., (Roy et al., 2011 Glycobiology 21:1194-1205; see FIG. 1) and the derivatives have been used for biological screening.

Results

Synthesis of the Precursor Tetrasaccharide 162 (Scheme 11)

The synthesis of disaccharide 162 follows the synthetic pathway previously used. Glycosylation of acceptor 152 with donor 151 in the presence of NIS and TMSOTf provided disaccharide 155 (81%). Disaccharide 155 was then submitted to the usual sequence of reactions: (1) removal of the 4,6-benzylidene protecting group followed by (2) TEMPO catalyzed oxidation of the primary hydroxyle leading to an acid intermediate followed by (3) esterification using diazometnane leading to disaccharide 156 (65%). An acetyl group was then introduced at the 4' position leading to disaccharide 157. This is a difference with the previous syntheses in which a Fmoc group was introduced.

The disaccharide acceptor 160 was synthesized as previously described. Glycosylation of disaccharide acceptor 160 by the imidate donor 158 catalyzed by TMSOTf provided tetrasaccharide 161 (65%). Both Lev protecting groups were then removed using NH$_2$NH$_2$.AcOH leading to the tetrasaccharide diol 162.

Scheme 11. Synthesis of tetrasaccharide 162.

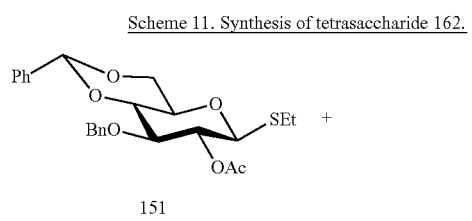

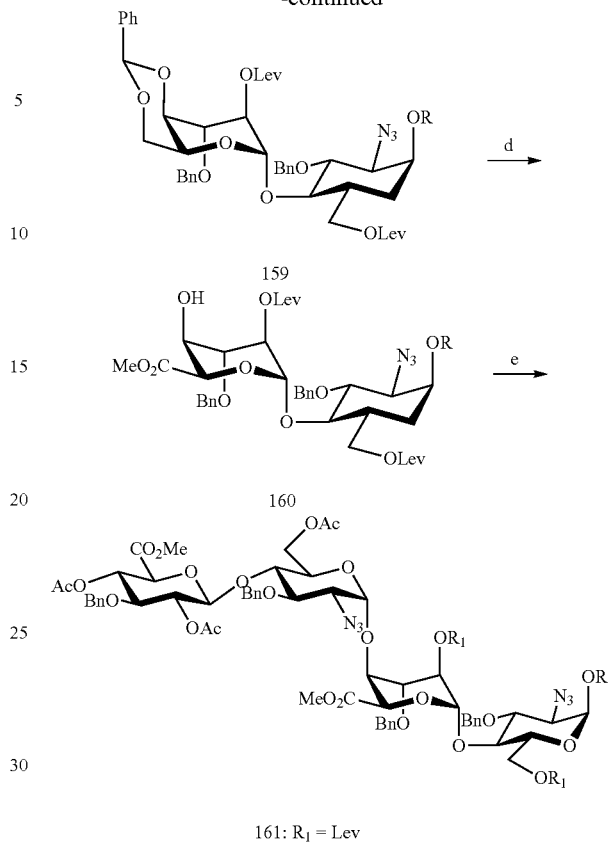

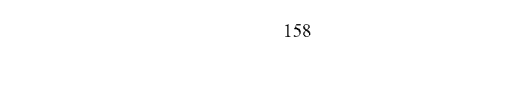

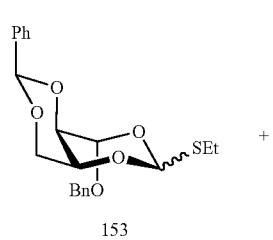

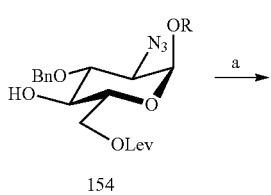

161: $R_1$ = Lev
162: $R_1$ = H
163a: $R_1$ = $SO_3^-Py^+$
163b: $R_1$ = $SO_3^-Na^+$

R = $(CH_2)_5N(Bn)CbZ$

Reagents and conditions: (a) NIS, TMSTTf, DCM, MS, 0° C., (81%); (b) (i) DCM: TFA:H$_2$O; (ii) TEMPO, BAIB, DCM, H$_2$O, 1 h: (iii) CH$_2$N$_2$, THF: (iv) Ac$_2$O, Py, DMAP (65%); (c) (i) HF.Py, 18 h; (ii) K$_2$CO$_3$, CCl$_3$CN, DCM (70%); (d) TEMPO, BAIB, DCM, H$_2$O, 1 h; (iii) CH$_2$N$_2$, THF, (80%); (e) (i) 158, DCM, TMSOTf, MS -30° C., (61%); (ii) NH$_2$NH$_2$.AcOH, toluene/ethanol, (92%), (iii) Py.SO$_3$, DMF, 82%

Tetrasaccharide diol 162 could then be (i) completely sulfated providing the disulfated tetrasaccharide as pyridinium salt 163a which will be later used for selective desulfation leading to intermediate 173, or as a sodium salt 163b used for the normal deprotection sequence or (ii) partially sulfated on the primary hydroxyle thus providing a monosulfate intermediate 183 derivative of starting tetrasaccharide.

Standard Deprotection Sequence of Tetrasaccharide 163b Leading to Tetrasaccharides 170 and 171 (Scheme 12)

Tetrasaccharide 163b was saponified providing intermediate 164 (75%) and both azido groups reduced leading to tetrasaccharide 165 (88%). A portion of tetrasaccharide 165 was di-Acetylated leading to intermediate 166 (77%), while another portion was di-N-sulfated leading to 167 (62%), as indicated in the general procedures. Final hydrogenolysis of intermediates 166 and 167 led to tetrasaccharides 170 (97%) and 171 (95%).

In addition, the di-amino intermediate tetrasaccharide 165 can be used in a selective NH$_2$ sulfation reaction leading to compound 168 as described later on.

Scheme 12. Deprotection of tetrasaccharide 163b

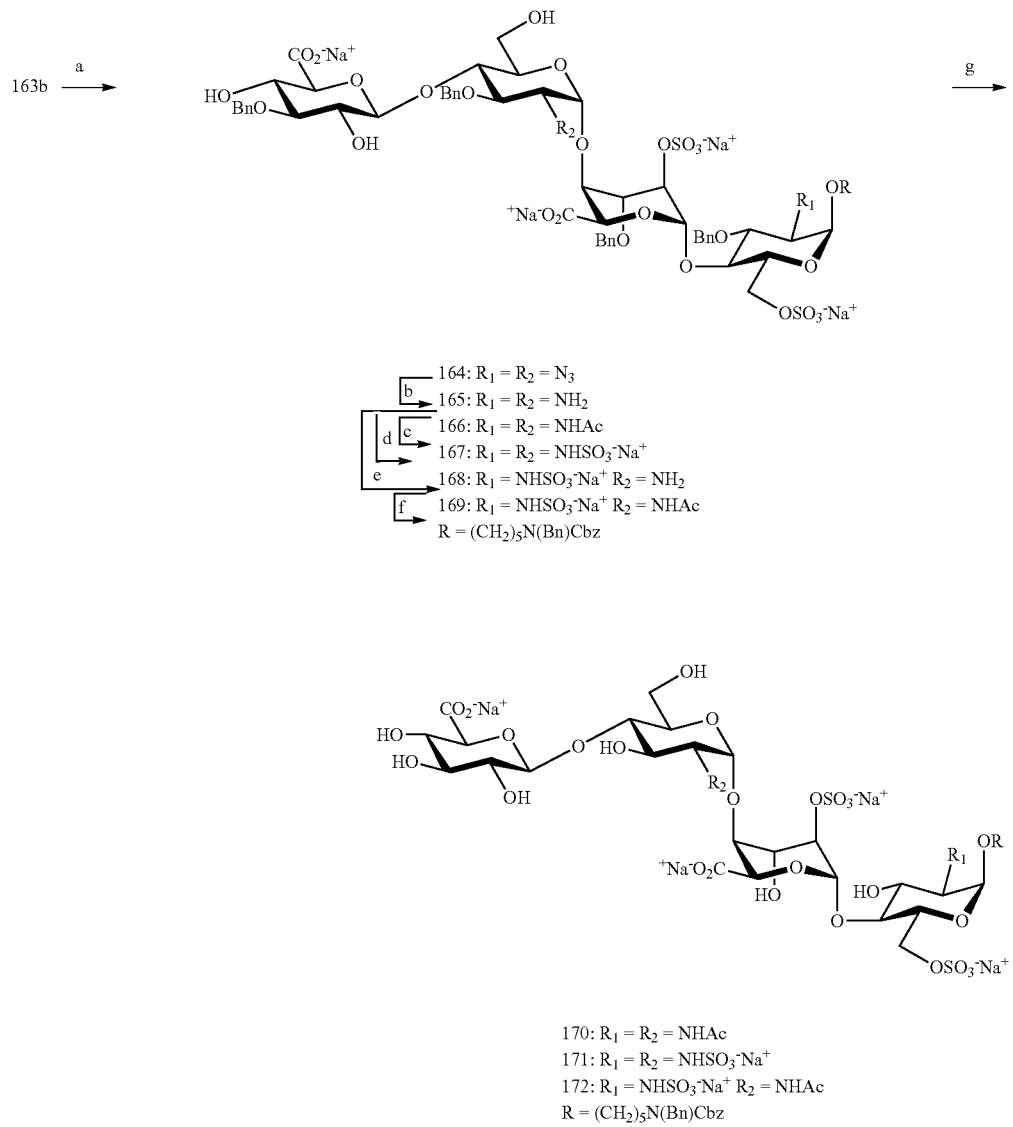

Reagents and conditions: (a) (i) LiOH, H$_2$O, THF, (ii) 4M NaOH, MeOH (75%); (b) PMe$_3$, THF, NaOH (91%); (c) Ac$_2$O, Et$_3$N, MeOH, (75%); (d) Py.SO$_3$ (excess), MeOH, Et$_3$N, 0.1 M NaOH (62%); (e) Py.SO$_3$ (6 equiv), MeOH, Et$_3$N, 0.1M NaOH, 0° C. (44%); (f) Ac$_2$O, Et$_3$N, MeOH, (70%); (g) (i) Pd/C, H$_2$, MeOH, H$_2$O; Pd(OH)$_2$, H$_2$, H$_2$O (170: 95%, 171: 88%, 172: 82%).

Selective 6-O-Desulfation of Tetrasaccharide 163a (Py Salt) (Scheme 13)

1) Synthesis of tetrasaccharide 173. Two parallel reactions were performed one using N,O-bis(trimethylsilyl) acetamide (BTSA, 80 equivalents) and the other using N,O-bis(trimethylsilyl)trifluoroacetamide (BTSTFA, 80 equivalents) in pyridine at 56-58° C., but no difference was observed by TLC. The starting material disappeared and two new spots appeared on the TLC. The solvents, and likely most of the excess of BTSA and BTSTFA were removed by evaporation in vacuo (which may be important since after desilylation, acetamide and trifluoroacetamide would be formed and may then complicate the isolation procedure). De-O-silylation was then done by repeated co-evaporation with CH$_3$OH. Tetrasaccharide 173 (90%) was purified by chromatography on Iatrobeads followed by ion exchange chromatography on Biorad 50×8, Na$^+$resin followed by reverse phase C18 chromatography. Selective position of de-O-sulfation at the is supported by the upfield move of the H6a and H6b protons on the 500 MHz NMR spectrum.

2) Standard deprotection sequence: synthesis of tetrasaccharides 180 and 181.

Tetrasaccharide 173 was submitted to the usual sequence of reactions: saponification (leading to 174, 87%), azide groups reduction leading to di-amino tetrasaccharide 175 (88%). Tetrasaccharide 175 was di-N-acetyalted leading to 176 (91%), and another portion was di-N-sulfated leading to 177 (77%). Both tetrasaccharides 176 and 177 were hydrogenolysed following the general procedure, providing tetrasaccharides 180 (80%) and 181 (77%).

Scheme 13. Selective 6-O-desulfation of tetrasaccharide 163a
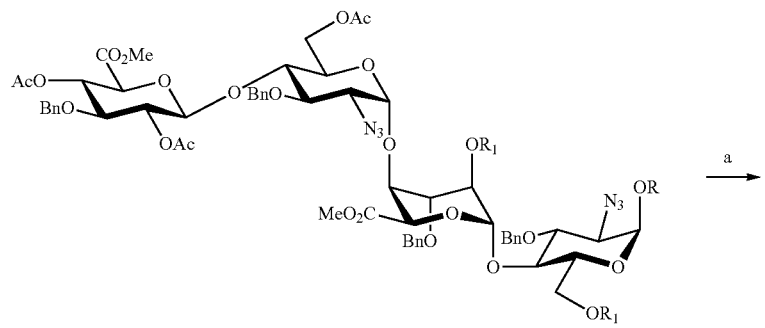
163a: R₁ = SO₃⁻Py⁺
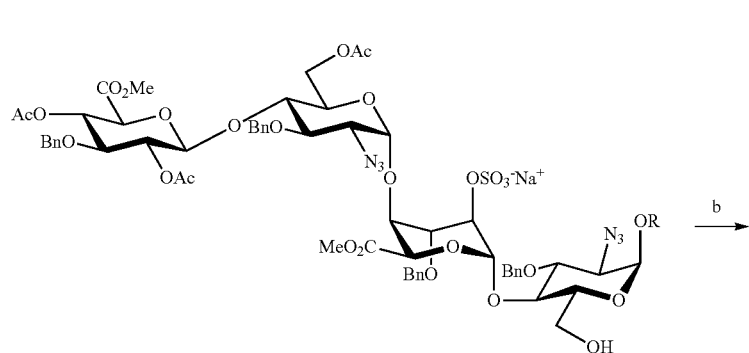
173
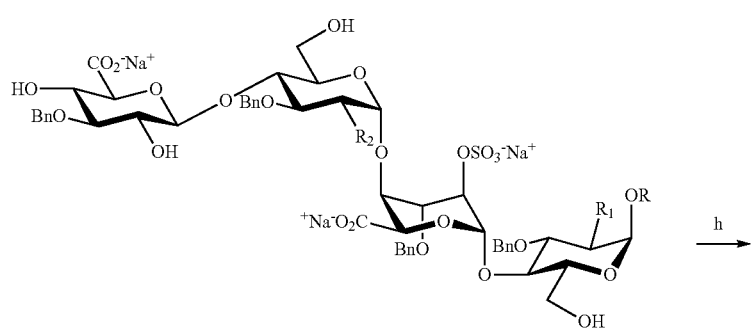
174: R₁ = R₂ = N₃
175: R₁ = R₂ = NH₂
176: R₁ = R₂ = NHAc
177: R₁ = R₂ = NHSO₃⁻Na⁺
178: R₁ = NHSO₃⁻Na⁺ R₂ = NH₂
179: R₁ = NHSO₃⁻Na⁺ R₂ = NHAc
R = (CH₂)₅N(Bn)Cbz -continued

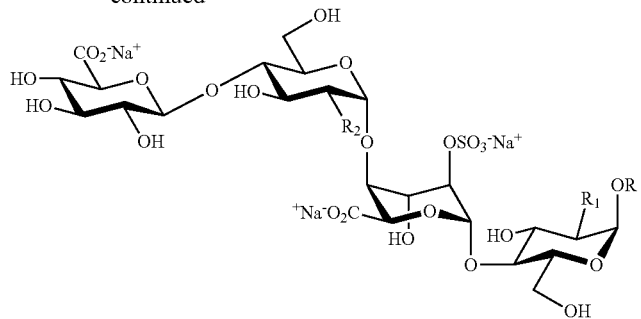

180: $R_1 = R_2 = NHAc$
181: $R_1 = R_2 = NHSO_3^-Na^+$
182: $R_1 = NHSO_3^-Na^+ R_2 = NHAc$
$R = (CH_2)_5NH_2$

Reagents and conditions: (a) BTSA, Py, 56-58° C., 6 h (93%); (b) (i) LiOH, H$_2$O, THF, (iii) 4M NaOH, MeOH (87%); (c) PMe$_3$, THF, NaOH (88%); (d) Ac$_2$O, Et$_3$N, MeOH, (91%); (e) Py.SO$_3$ (excess), MeOH, Et$_3$N, 0.1M NaOH (77%); (f) Py.SO$_3$ (6 equiv), MeOH, Et$_3$N, 0.1M NaOH, 0° C. (44%); (g) Ac$_2$O, Et$_3$N, MeOH, (70%); (h) Pd/C, H$_2$, MeOH, H$_2$O; Pd(OH)$_2$, H$_2$, H$_2$O (180: 95%, 181: 77%), 182: 95%.

Selective N-Sulfation of Tetrasaccharides 165 and 175 (Schemes 12 and 13)

1. Selective N-sulfation procedure of 165 and 175. Di-N-sulfation of a di-amino tetrasaccharide intermediate is usually achieved by addition of at least 6 equivalents of Py.SO$_3$ per OH, to the tetrasaccharide dissolved in a mixture of CH$_3$OH, Et$_3$N and 0.1M NaOH at room temperature, as indicated in the general procedures.

When the B unit of the tetrasaccharide is a Ido2S moiety (such as in tetrasaccharides 165 and 175), a more controlled addition of smaller portion of the reagent at 0° C. (see general procedures) leads to the formation of an intermediate mono-NH-sulfated tetrasaccharide, which can be isolated after the transformation of the starting material is stopped at ~50%. Reverse phase C18 chromatography using a gradient of H$_2$O and CH$_3$OH led to the isolation of the untransformed starting material, the intermediate product and a mixed fraction with the di-NH-sulfated tetrasaccharide. NMR spectra of the recovered intermediates indicated the presence of a NH-sulfated amino on unit B and an unsulfated NH$_2$ group on unit C of the tetrasaccharides. Tetrasaccharides 165 and 175 have thus been transformed into mono-N-sulfates derivatives 168 (44%, scheme 12) and 178 (47%, scheme 13).

2. Identification of the mono-N-sulfation site. Surprisingly, the sulfation takes place on the amino substituent of unit A of the tetrasaccharides 168 and 178. This is supported by the examination of the NMR data of compounds 165-169 and of tetrasaccharides 175-179 reported in the two tables below.

TABLE 2

NMR data of Tetrasaccharides 168 and 169 (Scheme 12).

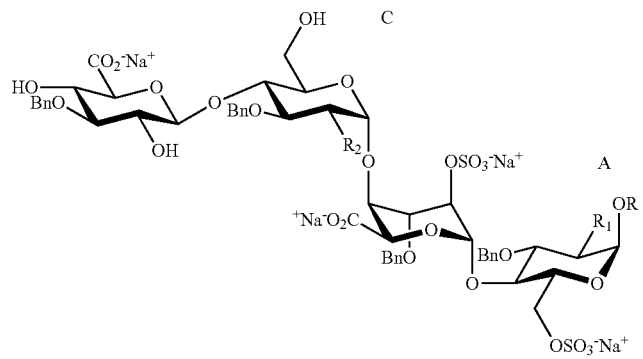

| | $R_2$ | $R_1$ | $H_1^C$ | $C_1^C$ | $H_2^C$ | $C_2^C$ | $H_1^A$ | $C_1^A$ | $H_2^A$ | $C_2^A$ |
|---|---|---|---|---|---|---|---|---|---|---|
| 165 | $NH_2$ | $NH_2$ | 5.05 | 94 | 2.90 | 54 | 4.53 | 98 | 2.45 | 54 |
| 166 | NHAc | NHAc | ~4.70 | 95 | 4.06 | 54 | 4.58 | 95 | ~4.06 | 54 |
| 167 | $NHSO_3^-$ | $NHSO_3^-$ | 5.29 | 95 | 3.46 | 58 | ~5.19 | 95 | 3.43 | 58 |

TABLE 2-continued

NMR data of Tetrasaccharides 168 and 169 (Scheme 12).

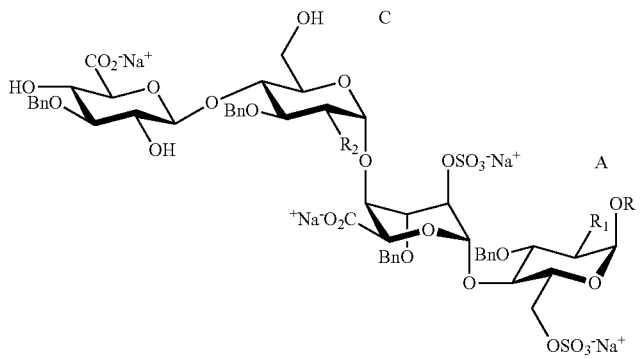

| | $R_2$ | $R_1$ | $H_1^C$ | $C_1^C$ | $H_2^C$ | $C_2^C$ | $H_1^A$ | $C_1^A$ | $H_2^A$ | $C_2^A$ |
|---|---|---|---|---|---|---|---|---|---|---|
| 168 | $NH_2$ | $NHSO_3^-$ | 5.26 | 92 | 3.22 | 54 | ~5.15 | 98 | 3.36 | 58 |
| 169 | NHAc | $NHSO_3^-$ | ~4.73 | 96 | 4.12 | 52 | 5.15 | 96 | 3.40 | 57 |

($^{13}$C values are from HSQC)

Compound 168 shows the same shifts for $H1^A$ and $H2^A$ of unit A as those of $H1^A$ and $H2^A$ of the di-N-sulfate 167 which would support the N-sulfation in this unit. A downshift shift of the anomeric proton is usually observed after the introduction of a sulfate group on the 2-amino of units A or C or the 2-hydroxyle of the idose unit.

N-acetylation of compound 168 leads to compound 169 in which $H1^A$ and $H2^A$ show the same shifts as those of $H1^A$ and $H2^A$ of the di-N-sulfated compound 167. Also in compound 169, the shifts of $H1^C$ and $H2^C$ match those of $H1^C$ and $H2^C$ of the di-N-acetylated compound 166. ($^{13}$C data for $C1^C$ obtained from HSQC are reported in the table, seem to support these conclusions, however, the differences are small).

Additionally, in the NMR spectrum of tetrasaccharide 166, the NHAc signal of unit C appears as a sharp singlet at 1.95 ppm while the NHAC signal of unit A appears as a think doublet at 1.58 ppm due to the presence of rotamers on the linker. The spectrum of tetrasaccharide 169 shows a sharp singlet at 2.02 ppm unaffected by the rotamers of the linker, and corresponding to the signal of NHAc of unit C.

TABLE 3

NMR data of Tetrasaccharides 178 and 179 (Scheme 13).

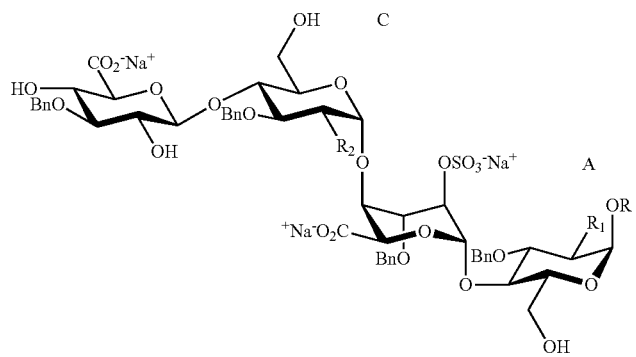

| | $R_2$ | $R_1$ | $H_1^C$ | $C_1^C$ | $H_2^C$ | $C_2^C$ | $H_1^A$ | $C_1^A$ | $H_2^A$ | $C_2^A$ |
|---|---|---|---|---|---|---|---|---|---|---|
| 175 | $NH_2$ | $NH_2$ | ~5.3 | 95 | 2.87 | 56 | ~4.6 | 99 | 2.48 | 56 |
| 176 | NHAc | NHAc | ~4.7 | 98 | 4.10 | 53 | 4.64 | 98 | ~4.14 | 53 |
| 177 | $NHSO_3^-$ | $NHSO_3^-$ | 5.30 | 99 | ~3.4 | 58 | ~5.15 | 95 | ~3.4 | 58 |
| 178 | $NH_2$ | $NHSO_3^-$ | ~5.3 | 91 | 3.2 | 54 | ~5.15 | 98 | 3.4 | 58 |
| 179 | NHAc | $NHSO_3^-$ | ~4.74 | 96 | 4.12 | 52 | ~5.15 | 96 | 3.42 | 57 |

$^{13}$C values are from HSQC

Identification of the mono-N-sulfation site to unit A of the tetrasaccharide by comparaison of the NMR data of $H1^C$ and $H1^A$ of compounds 175, 176, 177, 178 and 179 almost exactly follows what has been reported above for tetrasaccharides 168 and 169. The observations regarding the signals of the NHAc groups in tetrasaccharides 176 and 179 parallel those that have been described before for compounds 166 and 169.

Deprotection and Synthesis of Tetrasaccharides 172 (Scheme 12) and 182 (Scheme 13).

After the final hydrogenolysis deprotection procedure (see general procedures), tetrasaccharides 19 and 29 provided the deprotected tetrasaccharides 22 (82%) and 32 (95%).

Selective O-Sulfation of Tetrasaccharide 162 (Scheme 14)

Mono-sulfation of the primary hydroxyl of tetrasaccharide 162 is best achieved by rapid addition of 6 equiv of $Py.SO_3$ complex, which leaves part of the starting material untransformed, but gives a cleaner formation of the mono-O-sulfate 183 which was purified by reverse phase C18 chromatography. The result is in agreement with the order of reactivity of the GlcN 6OH>IdoA 2OH mentioned by Ogamo et al. (Ogamo et al., Carbohydr. Res. 193:165-172). Sulfation of the 6OH is supported by deshielding of the two H6a and H6b protons in the 500 MHz NMR spectrum of 183.

Scheme 14. Selective O-sulfation of tetrasaccharide 162

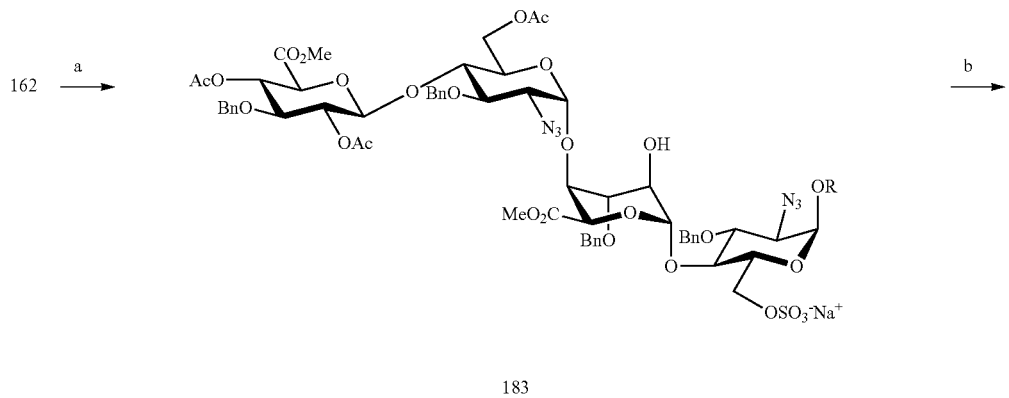

183

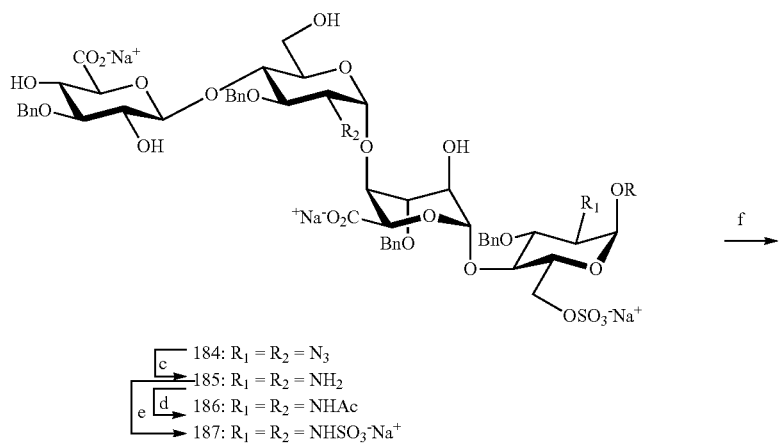

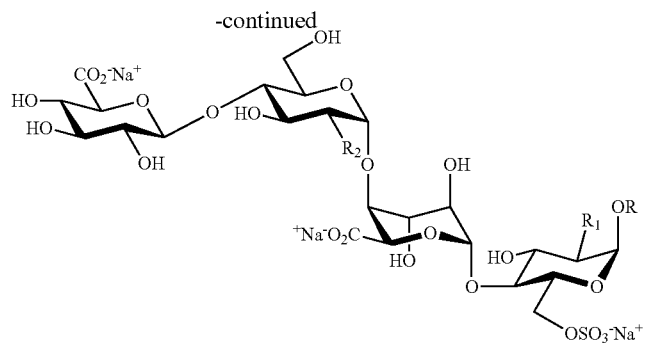

188: $R_1 = R_2 = NHAc$
189: $R_1 = R_2 = NHSO_3^-Na^+$
$R = (CH_2)_5NH_2$

Reagents and conditions: (a) Py.SO3 (6 equiv), DMF, RT, 40%;; (b) (i) LiOH, H$_2$O, THF, (ii) 4M NaOH, MeOH (72%);
(c) PMe$_3$, THF, NaOH (86%); (d) Ac$_2$O, Et$_3$N, MeOH, (78%); (e) Py.SO$_3$ (excess), MeOH, Et$_3$N, 0.1M NaOH (77%);
(f) Pd/C, H$_2$, MeOH, H$_2$O; Pd(OH)$_2$, H$_2$, H$_2$O (188: 95%, 189: 93%).

Deprotection and Synthesis of Tetrasaccharides 188 and 189 (Scheme 14)

Tetrasaccharide 183 was submitted to the usual sequence of reactions: saponification (leading to 184, 72%), azide groups reduction leading to di-amino tetrasaccharide 185 (86%). Tetrasaccharide 185 was di-N-acetyalted leading to 186 (78%), and another portion was di-N-sulfated leading to 187 (77%). Both tetrasaccharides 186 and 187 were hydrogenolysed following the general procedure, providing tetrasaccharides 188 (95%) and 189 (93%).

Experimental Section—General Procedures

HO-Sulfation. 1. Complete di-O-sulfation: SO$_3$.Py complex (12 equiv.) was added at once to the tetrasaccharide diol in anhydrous DMF (0.5 mL for 0.150 mml) at room temperature. Stirring was continued for 3 h until TLC (CHCl$_3$/CH$_3$OH 95:5, v/v) indicated completion of the reaction. Pyridine (0.4 mL) followed by CH$_3$OH (0.3 mL) were then added and stirring was continued for 0.5 h. The mixture was concentrated in vacuo (bath temperature 18° C.), and the residue vortexed with a small amount of CHCl$_3$ and immediately applied to a small column of Iatrobeads (2 g, packed with CHCl$_3$ containing a trace of pyridine), which was then eluted with a gradient of CHCl$_3$, CH$_3$OH (97:3 to 90:10, v/v). The fractions containing the product were evaporated in vacuo (bath temperature 18° C.), and the residue immediately run through a small column of Biorad 50×8 Na$^+$resin (0.8×5 cm) using CH$_3$OH as eluant. The fractions containing the product were evaporated in vacuo providing the product as Na$^+$salt.

2. Selective mono-O-sulfation of CH$_2$OH: similar procedure as above with the exception of the addition of a smaller amount of SO$_3$.Py complex (6 equiv.) to the tetrasaccharide diol in DMF. Stirring was continued for 1.5 h until TLC (CHCl$_3$/CH$_3$OH 95:5, v/v) indicated the clean formation of a spot of lower Rf, while some starting material remained untransformed. Pyridine (0.4 mL) followed by CH$_3$OH (0.3 mL) were then added and stirring was continued for 0.5 h. The mixture was concentrated in vacuo (bath temperature 18° C.), and the residue vortexed with a small amount of CHCl$_3$ and immediately applied to a small column of Iatrobeads (2 g, packed with CHCl$_3$ containing a trace of pyridine) which was then eluted with a gradient of CHCl$_3$, CH$_3$OH (98:2 to 93:7, v/v). The fractions containing the lower spot were evaporated in vacuo (bath temperature 18° C.). The recovered material was dry loaded on RP C-8 silicagel (130 mg) using CH$_3$OH, which was then vortexed with a small amount of H$_2$O:CH$_3$OH (70:30, v/v) and applied on top of small column of C18 silicagel (220 mg) which was eluted with a gradient of H$_2$O and CH$_3$OH (70:30 to 50:50). The fractions containing the product were evaporated in vacuo (bath temperature 18° C.).

Saponification of Methyl Esters and De-O-acetylation. A premixed solution of 30% solution of H$_2$O$_2$ in water (100 equiv. per CO$_2$Me) and 1 M LiOH (50 equiv per CO$_2$Me) were added to a solution of the starting material in THF (0.02 M). The reaction mixture was stirred at room temperature for 5 h to 8 h until TLC (CHCl$_3$/CH$_3$OH 75:25) showed the disappearance of the starting material. In the case where the starting material contained a 2-O-sulfate group on the iduronic moiety, stirring was continued an additional 12 h at 35° C. to complete the saponification. A 4N solution of NaOH was then added to pH 12-13 and the reaction mixture was stirred for 12-18 h at room temperature. The progress of the reaction checked by TLC. AcOH was then carefully added to the mixture until pH 8-8.5 and the mixture was concentrated in vacuo (bath temperature 18° C.). The residue was vortexed with a small amount of H$_2$O and applied on top of a small column RP-C18 column (8 times the weight of the starting material) which was then eluted with a gradient of H$_2$O and CH$_3$OH (from 90/10 to 40/60, v/v). The appropriate fractions were concentrated in vacuo (bath temperature 18° C.) and the residue was passed through a small column of Biorad 50×8 Na$^+$resin (0.6×5 cm) using CH$_3$OH as eluant providing the product.

Reduction of the Azide Group. A 1M solution of PMe$_3$ in THF (8 equiv per azide group) was added to a solution of the starting material dissolved in THF (1 mL for 0.013 mmol) and 0.1 M solution of NaOH (3 equiv per azido group). The mixture was stirred at room temperature for 3-5 h, while the progress of the reaction was checked by TLC (CHCl$_3$/CH$_3$OH/H$_2$O 70/30/5 or 65/35/5, v/v/v) and RP-C18 plates with H$_2$O/CH$_3$OH 40/60, v/v) The presence of amino groups was confirmed using ninhydrin as visualizing agent (in some cases an additional amount of PMe$_3$ solution was added to achieve completion of the reaction). The pH of the solution was then carefully adjusted to 8.5 by addition of AcOH, and the mixture concentrated in vacuo (bath temperature 18° C.). The residue was dry-loaded using CH$_3$OH on RP C18 silicagel (~5 times the amount of starting material), vortexed with water and applied to a small RP-C18 silicagel column (~8 times the weight of the starting material), which was then eluted with a stepwise gradient of $H_2O$ and $CH_3OH$ (from 90/10 to 40/60, v/v). The appropriate fractions were concentrated in vacuo, and the residue ran through a small column of Biorad 50×8, $Na^+$column (06×5 cm) using $CH_3OH$ as eluant providing the product.

$NH_2$ acetylation. Acetic anhydride (5 equiv per $NH_2$) was added to a solution of the starting material in a mixture of anhydrous $CH_3OH$ (1.5 mL for 0.010 mmol) and $Et_3N$ (10 equiv per $NH_2$) at 0° C. The reaction was then brought at room temperature for 1-1.5 h. The progress of the reaction was followed by TLC ($CHCl_3$, $CH_3OH$, $H_2O$ 70/30/3, v/v) or RP C18 silicagel, $H_2O/CH_3OH$ 40/60, v/v) and, if incomplete, another portion of $Et_3N$ and of $Ac_2O$ were added at 0° C. The mixture was brought at room temperature. The mixture was then co-evaporated with some toluene (bath temperature 18° C.) and the residue passed through a short column of Biorad 50×8, $Na^+$resin (0.8×5 cm) using a mixture of $CH_3OH$ and $H_2O$ (90/10, v/v). The appropriate fractions were concentrated in vacuo. The residue was dry-loaded using $CH_3OH$ on RP C18 silicagel (~5 times the amount of starting material), vortexed with water and applied on a small RP-C18 column (~8 times the amount of starting material) which was eluted with a stepwise gradient of $H_2O$ and $CH_3OH$ (from 90/10 to 40/60, v/v). The elution was monitored by TLC on silicagel plates. The recovered fractions were concentrated in vacuo and the residue was run through a small column of Biorad resin using $CH_3OH$ as solvent, as above. Evaporation in vacuo provided the expected product.

Di-N-sulfation. $SO_3.Py$ (5-6 equiv. per $NH_2$) was added to the starting material dissolved in a mixture of $CH_3OH$ (1 mL per 0.006 mmol), $(Et)_3N$ (0.2 mL) and 0.1M NaOH (2 equiv per $NH_2$) stirred at 0° C. The progress of the reaction was monitored by TLC (silicagel: EtOAc/pyridine/water/AcOH 8/5/3/1 v/v/v/v and RP-18 TLC: $H_2O/CH_3OH$ 50/50, v/v). Additional portions of $SO_3.Py$ were added at 0° C. after 1 and 2 h for completion of the reaction. After stirring for about 6-8 h, the mixture was co-evaporated with water under vacuum (bath temperature 18° C.), and the residue slowly run through a short column of Biorad 50×8 $Na^+$resin (0.8×5 cm) using $CH_3OH$ and $H_2O$ (90/10 v/v) as eluant. After evaporation in vacuum, the residue was dry-loaded on RP-C18 silicagel (~5 times the amount of starting material) using $CH_3OH$, vortexed with water and applied on top of a small RP-C18 column (~8 times the amount of starting material) which was eluted with a stepwise gradient of $H_2O$ and $CH_3OH$ (90/10 to 40/60, v/v). The elution was monitored by TLC on silicagel plates and the appropriate fractions were concentrated in vacuo and the residue was run through a small column of Biorad $Na^+$resin as above. Evaporation in vacuo provided the expected product.

Selective mono-N-sulfation. $SO_3.Py$ (3.5 equiv) was added to the starting material dissolved in a mixture of $CH_3OH$ (1 mL per 0.006 mmol), $(Et)_3N$ (0.2 mL) and 0.1M NaOH (2 equiv per $NH_2$) stirred at 0° C. The reaction was stirred at 0° C. for 0.5 h and at room temperature for 0.5 h. Two to 3 identical additions of $SO_3.Py$ were added to the reaction mixture in a similar way. The progress of the reaction was monitored by TLC (silicagel: EtOAc/pyridine/water/AcOH 10/5/3/1 or 8/5/3/1 v/v/v/v). The reaction was stopped before disappearance of the starting material, and before the lower spot of the di-N-sulfated material became strong). The reaction mixture was evaporated under vacuo (bath temperature 18° C.). The recovered crude product was slowly run through a column of Biorad 50×8 $Na^+$resin (3 g) using $CH_3OH$ as eluant and the fractions evaporated. The residue dry loaded on 0.350 g of RP C18 silicagel with $CH_3OH$, vortexed with $H_2O/CH_3OH$ (90/10 v/v, 0.300 mL) and applied on top of a short column of the same silicagel (~8 times the amount of starting material), and further eluted with a stepwise gradient of $H_2O/CH_3OH$ (90/10 to 45:35 v/v). The separation of the fractions was followed by TLC (silicagel $EtOAc/Py/H_2O/AcOH$ 10/5/3/1 or 8/5/3/1, v/v): the di-N-sulfate eluted first followed by the main product. The fractions of the main product were combined and evaporated in vacuo (bath temperature 18° C.). The residue was run through a small column (0.8 cm×5 cm) of BioRad 50×8 $Na^+$resin using $CH_3OH$ as eluant. Evaporation provided the expected tetrasaccharide.

Final debenzylation. Pd/C 10% (~1.5 times the weight of the starting material) was added to a solution of the starting material dissolved in a mixture of $CH_3OH$ and $H_2O$ (1/1, v/v, about 1 mL for 5 mg). The mixture was stirred under hydrogen and the progress of the reaction was followed by TLC (silicagel: EtOAc, Pyridine, $H_2O$, AcOH 8/5/3/1, v/v/v/v and $CHCl_3/CH_3OH/H_2O$, 60/40/10, v/v/v). The hydrogenation was stopped when the TLC indicated the disappearance of the starting material and the formation of a ninhydrin-positive spot (about 2 h). The mixture was filtered through a PTFE syringe filter (0.2 µm, 13 mm), washed with a mixture of $CH_3OH$ and water (1/1, v/v, 2 mL), and the solvents removed in vacuo (bath temperature 18° C.). The residue was dissolved in distilled water (1.0 mL for 5 mg of starting material) and palladium hydroxide on carbon (Degussa type, 20%, 1.0-1.5 times the weight of the starting material) was added. The mixture was stirred under hydrogen for about 12 h and the progress of the reaction was followed by when TLC (silicagel: Pyridine, $H_2O$, AcOH 3/5/3/1, v/v/v/v) and stopped when it indicated the completion of the reaction. The mixture filtered through a PTFE syringe filter (0.2 µm, 13 mm), and washed with distilled $H_2O$ (2 mL). The filtrate was freeze-dried and the residue passed through a short column of Biorad 50×8, $Na^+$resin (0.6×2.5 cm) using $H_2O$ as eluant. The recovered fractions were freeze dried to provide the final product.

Synthesis of Tetrasaccharides 162 (Scheme 11)

Dimethylhexylsilyl O-(methyl 2,4-di-O-acetyl-3-O-benzyl-β-D-glucopyranosylonate)-(1→4)-O-6-O-acetyl-2-azido-3-O-benzyl-2-deoxy-β-D-glucopyranoside (157)

Acetic anhydride (0.5 mL) was added to a solution of disaccharide 156 (0.560 g, 0.699 mmol), in pyridine containing a catalytic amount of dimethylamino pyridine. The mixture was stirred for 4 hours at room temperature and then quenched with $CH_3OH$, diluted with DCM, washed with a saturated solution of $CO_3HNa$, water and a saturated solution of NaCl. After drying over $SO_4Mg$, the solution was evaporated and the residue chromatographed on silicagel using a 75:25 mixture of hexanes and EtOAc providing the acetylated disaccharide 157 (481 mg, 82%); $^1H$ NMR (500 MHz, $CDCl_3$): δ 7.12-7.05 (m, 10H, CH aromatics), 5.02 (t, 1H, J=9.5 Hz, H-$4^B$), 4.80 (dd, 1H, J=8.1 Hz and J=9.1 Hz, H-$2^B$), 4.68 (d, J=11.7 Hz, CHHPh), 4.53 (d, J=11.7 Hz, CHHPh), 4.40-4.50 (m, 3H, $CH_2Ph$, H-$1^B$), 4.33 (d, 1H, J=7.3 Hz, H-$1^A$), 4.22 (dd, 1H, J=2.2 Hz and 11.7 Hz, H6$a^A$), 3.59 (dd, 1H, J=6.5 Hz and 11.7 Hz, H-6$b^A$), 3.62-33.46 (m, 3H, H-$3^B$, H-$4^A$, H-$5^B$), 3.78-3.40 (m, 5H, incl. $CO_2CH_3$: s at 3,76, H-$5^A$, and H-$3^A$: t at 3.50 J=8.3 Hz), 3.24 (dd, 1H, J=8.1 Hz and 9.1 Hz, H-$2^A$), 1.82, 1.64 and 1.61 (3s, 3H each, three CH₃ Ac), 1.47 (m, 1H, CH(CH₃)₂), 0.72 (m, 12H, two C(CH₃)₂, 0.00 (2s, 6H, Si(CH₃)₂.

O-(methyl 2,4-di-O-acetyl-3-O-benzyl-β-D-glu-copyranosylonate)-(1→4)-O-6-O-acetyl-2-azido-3-O-benzyl-2-deoxy-β-D-glucopyranoside trichloro-acetimidate (158)

A mixture of Disaccharide 157 (481 mg, 0.570 mmol) in THF (4 mL) and HF.pyridine (1.6 mL) was stirred for 18 h at room temperature. The reaction mixture was diluted with DCM and washed with saturated aqueous solution of CO₃HNa, water, a saturated solution of NaCl and dried over SO₄Mg. After evaporation the intermediate lactol was purified by chromatography using a 95:5 mixture of CHCl₃ and CH₃OH.

The obtained lactol 380 mg (0.542 mmol) was dissolved in DCM (5 mL), CCl₃CN (0.325 mL), and stirred with anhydrous CO₃Cs₂ (25 mg) for 30 minutes at room temperature. After filtration of the insoluble, the product was chromatographed using a 2:1 mixture of hexanes and EtOAc providing the imidate 158 (0.434 mg, 95%) as an α/β mixture which was directly used in the next step.

N-(Benzyl)-benzyloxycarbonyl-5-aminopentyl O-[(methyl 2,4-di-O-acetyl-3-O-benzyl-β-D-glu-copyranosluronate)-(1→4)-O-(6-O-acetyl-2-azido-3-O-benzyl-2-deoxy-α-D-glucopyranoside)-(1→4)-O-(methyl 2-O-levulinoyl-3-O-benzyl-α-L-idopyranosyl-uronate)]-(1→4)-O-2-azido-3-O-benzyl-2-deoxy-6-O-levulinoyl-α-D-glucopyranoside (161)

Imidate 158 (0.903 g, 1.07 mmol) and acceptor 160 (1.70 g, 1.57 mmol,) were co-evaporated three times with dry toluene (5 mL), the residue dissolved in DCM (15 mL) and stirred with crushed Molecular Sieves AW (2.50 g) for 30 minutes at room temperature. After cooling at −40° C., TMSOTf (18 μL, 22 mg, 0.107 mmol) was syringed in. The progress of the reaction was checked by TLC (60:40 hexanes/ETOAc). The reaction appeared finished after 20 minutes. The mixture was warmed up to −10° C., then quenched by pyridine (304), the mixture evaporated and the residue chromatographed on silicagel with a mixture of toluene and EtOAc (70:30 to 40:60) providing the tetrasaccharide 161 (1.27 g, 61%); $^1$H NMR (500 MHz, CDCl₃): δ 7.4-7.20 (m, 30H, CH aromatics), 5.22 (d, 1H, J=4.1 Hz, H1$^B$), 5.20-5.12 (m, 4H, H4$^D$, CHHPh, CH₂Cbz), 5.05 (dd, 1H, J=8.1 Hz and J=9.1 Hz, H-2$^D$), 5.00 (d, 1H, J=3.4 Hz, H1$^C$), 4.92 (bt, J=4.5 Hz, H2$^B$), 4.83-4.76 (m, 2H, CHHPh, H1$^A$), 4.73-4.59 (m, 7H, H5$^B$, six CHHPh), 4.51-4.45 (m, 3H, H1$^D$, NCH₂Ph), 4.42 (bd, 1H, J=11.4 Hz, H6a$^A$ or $^C$), 4.35 (bd, 1H, J=11.0 Hz, H6a$^C$or$^A$), 4.25 (dd, 1H, J=11.4 Hz and J=2.6 Hz, H6b$^A$ or $^C$), 4.16 (dd, 1H, J=3.2 Hz and J=11.0 Hz, H6b$^C$ or $^A$), 3.98 (bt, 1H, J=5.0 Hz, H4$^B$), 3.94 (bt, 1H, J=5.2 Hz, H3$^B$), 3.89-3.72 (m, 6H, H3$^A$, H4$^A$, H4$^C$, H5$^A$, H5$^C$, H5$^D$), 3.70-3.59 (m, 3H, H3$^C$, H3$^D$, OCHH linker), 3.54 (s, 3H, OCH₃), 3.47 (s, 3H, OCH₃), 3.42-3.17 (m, 5H, including OCHH linker, CH₂N, H2$^A$ and H2$^C$: dd, J=3.5 Hz and J=10.1 Hz at 3.20), 2.80-2.45 (m, 8H, four CH₂ Lev), 2.16, 2.10, 2.04, 1.96, 1.94 (5s, 3H each, three CH₃ Ac, two CH₃ Lev), 1.72-1.20 (m, 6H, three CH₂ linker).

N-(Benzyl)-benzyloxycarbonyl-5-aminopentyl O-[(methyl 2,4-di-O-acetyl-3-O-benzyl-β-D-glu-copyranosyluronate)-(1-4)-O-(6-O-acetyl-2-azido-3-O-benzyl-2-deoxy-α-D-glucopyranoside)-(1 4)-O-(methyl 3-O-benzyl-α-L-idopyranosyl-uronate)]-(1→4)-O-2-azido-3-O-benzyl-2-deoxy-α-D-glucopyranoside (162)

Anhydrous hydrazine acetate (140 mg, 1.60 mmol) was added to a solution of 162 (280 mg, 0,158 mmol), dissolved in a mixture of ethanol (9 mL) and toluene (4.5 mL). The reaction was followed by TLC (toluene:EtOAc 60:40) and stirred at room temperature for 4 h. The reaction mixture was then diluted with EtOAc (50 mL), washed with H₂O (3×25 mL), saturated solution of sodium chloride and dried over MgSO₄. After filtration, the residue was chromatographed using a mixture of hexanes and EtOAc (45:55) providing the product 162 (230 mg, 92%); $^1$H NMR (500 MHz, CDCl₃): δ 7.38-7.18 (m, 30H, CH aromatics), 5.28 (bs, 1H, H1$^B$), 5.20-5.12 (m, 4H, H4$^D$, CHHPh, CH₂Cbz), 5.06 (dd, 1H, J=8.0 Hz and J=9.0 Hz, H-2$^D$), 5.00 (bs, 1H, H1$^C$), 4.87-4.80 (m, 1H, H1$^A$), 4.80-4.70 (m, 3H, H5$^B$, two CHHPh), 4.64-4.56 (m, 5H, five CHHPh), 4.52-4.46 (m, 3H, NCH₂Ph, H1$^D$), 4.36 (bd, 1H, J=12.4 Hz, H6a$^C$), 4.20 (dd, 1H, J=3.0 Hz and J=12.4 Hz, H6b$^C$), 4.20 (bs, 1H, H4$^B$), 3.9-3.58 (m, 13H, H3$^A$, H4$^A$, H5$^A$, H6a$^A$, H6b$^A$, H2$^B$, H3$^B$, H3$^C$, H4$^C$, H5$^C$, H3$^D$, H5$^D$, OCHH linker), 3.50-3.28 (m, 11H, including: s, 3.44: two OCH₃, H2$^A$, H2$^C$, OCHH linker, CH₂N linker), 2.08, 1.05, 1.40 (3s, 3H each, three CH₃ Ac), 1.72-1.20 (m, 6H, three CH₂ linker).

Tetrasaccharide 162: Sulfation and Deprotection (Scheme 12)

Synthesis of tetrasaccharide 163a: Sulfur trioxide pyridine complex (25 mg, 0.152 mmol) was added at once to a solution of tetrasaccharide 162 (20 mg, 0.0127 mmol) in anhydrous DMF (0.5 mL). The mixture was stirred at room temperature for 3 h until TLC (CHCl₃/CH₃OH 96:4) and further processed as indicated in the general procedure providing tetrasaccharides 163a (Pyridinium salt) and 163b, Na⁺salt: 18.6 mg, 82%; $^1$H NMR (500 MHz, CD₃OD): δ 7.46-7.15 (m, 30H, CH aromatics), 5.40 (bs, 1H, H1$^B$), 5.19-5.11, (m, 3H, H1$^C$, CH₂Cbz, CHHPh), 5.09 (d, 1H, J=11.3 Hz, CHHPh), 5.03 (t, 1H, J=9.6 Hz, H4$^D$), 4.96-4.89 (m, 2H, H5$^B$, H2$^D$), 4.89-4.79 (m, OH, H-1$^A$, CHHPh), 4.76 (d, 1H, J=7.9 Hz, H1$^D$), 4.67 (d, 1H, J=11.3 Hz, CHHPh), 4.65-4.59 (m, 4H, H2$^B$, three CHHPh), 4.56-4.48 (m, 3H, CHHPh, NCH₂Ph), 4.44-4.38 (m, 2H, H6a$^C$, CHHPh), 4.36-4.27 (m, 3H, H4$^B$, H6a$^A$, H6b$^A$), 4.09 (dd, J=5.5 HZ and J=12.0 Hz, H6b$^C$), 4.40 (d, 1H, J=10.0 Hz, H5$^D$), 4.00-3.89 (m, 4H), 3.81-3.62 (m, 5H), 3.45 (s, 3H, CO₂CH₃), 3.35-3.22 (m, incl.H2$^A$, H2$^C$, CO₂CH₃ at 3.34, CH₃OH, OCHH linker, CH₂N linker), 2.40, 2.00, 1.94 (3s, 3H each, three CH₃ Ac), 1.72-1.20 (m, 6H, three CH₂ linker).

Synthesis of tetrasaccharide 164: Tetrasaccharide 163b (107 mg, 0.060 mmol) was dissolved in THF (2.80 mL) and subjected to saponification and de-O-acetylation according to the general procedure to provide compound 164 as sodium salt (76 mg, 75%); $^1$H NMR (500 MHz, CD₃OD): δ 7.46-7.08 (m, 30H, CH aromatics), 5.40 (bs, 1H, H1$^B$), 5.13 (d, 1H, J=3.5 Hz, H1$^C$), 5.11-5.03 (m, 2H, CH₂Cbz), 4.95 (d, 1H, J=10.8 Hz, CHHPh), 4.83-4.69 (m, incl. H1$^A$, H5$^B$ at 4.83, OH, four CHHPh), 4.58-4.52 (m, 3H, H1$^D$, H2$^B$, CHHPh), 4.43-4.38 (m, 2H, NCH₂Ph), 4.31 (dd, 1H, J=3.0 Hz and J=11.3 Hz, H6a$^A$), 4.26 (d, 1H, J=11.8 Hz, CHHPh), 4.21-4.15 (m, 3H, H3$^B$, H4$^B$, H6b$^A$), 3.98 (bt, 1H, J=9.1 Hz, H-4$^A$), 3.94-3.68 (m, 6H, H3$^A$, H5$^A$, H3$^C$, H4$^C$, H5$^C$, H6a$^C$, H6b$^C$), 3.66-3.50 (m, 2H, OCHH linker, H4$^D$), 3.41 (d, 1H, J=10.1 Hz, H5$^D$), 3.36 (dd, 1H, J=3.5 Hz and J=9.8 Hz, H2$^C$), 3.34-3.29 (m, 2H, H-2$^D$, H-3$^D$), 3.28-3.04 (m, OCHH linker, CH$_3$OH, CH$_2$N linker, H2$^A$), 1.60-1.20 (m, 6H, CH$_2$ linker).

Synthesis of tetrasaccharide 165: A 1M solution of PMe$_3$ in THF (0.731 mL) was added to tetrasaccharide 164 (76 mg, 0.046 mmol) in THF (4 mL) and 0.1M NaOH (0.280 mL) according to the general procedure, which provided tetrasaccharide 165 (67 mg, 91%); $^1$H NMR (500 MHz, CD$_3$OD): 7.53-7.12 (m, 30H, CH aromatics), 5.45 (bs, 1H, H1$^B$), 5.22-5.13 (m, 4H, H1$^C$, CHHPh, CH$_2$Cbz), 5.01 (bs, 1H, H-5$^B$), 4.99-4.89 (m, 3H, three CHHPh), 4.80 (d, 1H, J=11.2 Hz, CHHPh), 4.72 (d, 1H, J=10.6 Hz, CHHPh), 4.68 (d, 1H, J=11.2 Hz, CHHPh), 4.67-4.57 (m, 3H, H1$^A$, H1$^D$, H2$^B$), 4.57-4.50 (m, 2H, NCH$_2$Ph), 4.39-4.26 (m, 5H, H6a$^A$, H6b$^A$, H3$^B$, H4$^B$, CHHPh), 4.02-3.80 (m, 7H, H4$^A$, H5$^A$, H3$^C$, H4$^C$, H5$^C$, H6a$^C$, H6b$^C$), 3.62-3.48 (m, 2H, H4$^D$, OCHH linker), 3.44 (d, 1H, J=10.1 Hz, H5$^D$), 3.50-3.39 (m, 3H, H3$^A$, H2$^D$, H3$^D$), 3.24-3.10 (m, CH$_3$OH, OCHH linker, CH$_2$N linker) 3.10 (bd, 1H, J=6.8 Hz, H2$^C$), 2.55 (bd, J=7.3 Hz, H-2$^A$), 1.62-1.46 (m, 6H, CH$_3$ Ac, (CH$_2$)$_2$ linker, 1.38-1.22 (m, 2H, CH$_2$ Linker).

Synthesis of tetrasaccharide 166: Acetic anhydride (25 µL, 25 mg, 0.25 mmol) was syringed portionwise into a solution of the tetrasaccharide 165 (33 mg, 0.0205 mmol) in anhydrous CH$_3$OH (2.5 mL) and Et$_3$N (25 µL) stirred at 0° C. according to the general procedure, which provided tetrasaccharide 166 (26 mg, 75%); $^1$H NMR (500 MHz, CD$_3$OD): δ 7.48-7.16 (m, 30H, CH aromatics), 5.22-5.12 (m, 2H, CH$_2$Cbz), 5.01 (d, 1H, J=12.2 Hz, CHHPh), 4.95-4.82 (m, H-5$^B$, OH, three CHHPh), 4.82-4.77 (m, 2H, H1$^C$, CHHPh), 4.70-4.58 (m, 5H, H1$^A$, H2$^B$, H1$^D$, two CHHPh), 4.53 (bs, 2H, NCH$_2$Ph), 4.44 (bd, 1H, J=12.3 Hz, CHHPh), 4.40 (dd, 1H, J=4.2 Hz and J=10.8 Hz, H6a$^A$), 4.33 (bd, 1H, J=10.8 Hz, H6b$^A$), 4.21-4.13 (m, 2H, H4$^B$, H2$^C$), 4.12-3.97 (m, 4H incl. H2$^A$ and H3$^B$), 3.97-3.86 (m, 5H), 3.80-3.56 (m, 3H, incl. H4$^D$, OCHH linker), 3.54 (d, 1H, J=10.1 Hz, H-5$^D$), 3.45-3.35 (m, 2H, H2$^D$, H3$^D$), 3.35-3.20 (m, CH$_3$OH, OCHH linker, CH$_2$N linker), 2.09 (s, 3H, CH$_3$ Ac), 1.68-1.48 (m, 6H, CH$_3$ Ac, (CH$_2$)$_2$ linker, 1.40-1.22 (m, 2H, CH$_2$ Linker).

Synthesis of tetrasaccharide 167: Py.SO$_3$ (31 mg, 0.2 mmol) was added to tetrasaccharide 165 (32 mg, 0.020 mmol) dissolved in a mixture of CH$_3$OH (3 mL), (Et)$_3$N (0.6 mL) and 0.1M NaOH (0.4 mL) stirred at 0° C., according to the general procedure, which provided tetrasaccharide 167 (22.8 mg, 62%, some incompletely mono-N-sulfated product was also obtained); $^1$H NMR (500 MHz, CD$_3$OD): δ 7.53-7.09 (m 30H, CH aromatics), 5.52 (bs, 1H, H1$^B$), 5.29 (d, 1H, J=3.4 Hz, H1$^C$), 5.19-5.08 (m, 4H, H1$^A$, CHHPh, CH$_2$Cbz), 4.93-4.78 (m, five CHHPh, OH, H5$^B$ at 4.84), 4.76 (d, 1H, J=11.2 Hz, CHHPh), 4.71-4.66 (m, 2H, H2$^B$, CHHPh), 4.60 (bd, 1H, J=11.1 Hz, CHHPh), 4.58-4.54 (m, 1H, H1$^D$), 4.53-4.46 (m, 2H, NCH$_2$Ph), 4.41 (dd, 1H, J=3.6 Hz and J=11.1 Hz, H6a$^A$), 4.28-4.22 (m, 3H, H3$^B$, H4$^B$, H6b$^A$), 4.00 (m, 1H, H-5$^C$), 3.95-3.90 (m, 2H, incl H6a$^C$ at 3.91), (3.86-3.76 (m, 4H, including H6b$^C$ at 3.84), 3.65-3.49 (m, 4H, H3$^A$, H4$^D$, H5$^D$, OCHH linker), 3.46 (dd, 1H, J=3.4 Hz and J=10.5 Hz, H2$^C$), 3.43-3.32 (m, 4H, H2$^A$, H2$^D$, H3$^D$, OCHH linker), 3.30-3.20 (m, CH$_3$OH, CH$_2$N linker), 1.62-1.44 (m, 4H, two CH$_2$ linker), 1.36-1.20 (m, 2H, CH$_2$ linker).

5-Aminopentyl [(β-D-Glucopyranosyluronate)-(1→4)-O-(2-acetamido-2-deoxy-α-D-glucopyranoside)-(1→4)-O-(2-O-sulfonate-α-L-idopyranosyluronate)-(1→4)-O-2-acetamido-2-deoxy-6-O-sulfonate-α-D-glucopyranoside tetra-sodium salt (170)

Palladium on carbon 10% (25 mg]) was added to tetrasaccharide 166 (25.0 mg, 0.0147 mmol), dissolved in CH$_3$OH (2 mL) and distilled H$_2$O (2 mL). The mixture was stirred under H$_2$ and processed as indicated in the general debenzylation procedure providing tetrasaccharide 170 (16 mg, 95%); $^1$H NMR (800 MHz, 21° C., D$_2$O): 5.20 (d, 1H, J=1.9 Hz, H1$^B$), 5.13 (d, 1H, J=3.7 Hz, H1$^C$), 4.85 (d, 1H J=3.7 Hz, H-1$^A$), 4.79 (d, J=2.4 Hz, H-5$^B$), 4.50 (d, 1H, J=7.9 Hz, H-1$^D$), 4.39 (dd, 1H, J=2.0 Hz and J=11.4 Hz, H6a$^A$), 4.29 (ddd, J=1.7 Hz and J=3.4 Hz, H-2$^B$), 4.27 (dd, 1H, J=6.4 Hz and J=11.5 Hz, H6b$^A$), 4.20 (bt, J=3.4 Hz, H-3$^B$), 4.07-3.99 (m, 1H, H-5$^A$), 3.98 (bt, 1H, J=2.7 Hz, H4$^B$), 3.99 (dd, 1H, J=3.6 Hz and J=10.6 Hz, H2$^C$), 3.95 (dd, 1H, J=3.7 Hz and J=10.6 Hz, H2$^A$), 3.92-3.85 (m, 3H, H-5$^C$, H6a$^C$, H6b$^C$), 3.83 (dd, 1H, J=8.7 Hz and J=10.6 Hz, H3$^A$), 3.77 (dd, 1H, J=8.9 Hz and J=10.6 Hz, H3$^C$), 3.75-3.73 (m, 1H, H5$^D$), 3.73-3.70 (m, 3H, H4$^A$, H4$^C$, OCHH linker), 3.54-3.49 (m, 3H, H-3$^D$, H-4$^{D'}$ OCHH linker), 3.39-3.36 (m, 1H, H2$^D$), 3.00 (t, 2H, J=7.1 Hz, CH$_2$N linker), 1.64-1.50 (m, 4H, two CH$_2$ linker), 1.45-1.30 (m, 2H, CH$_2$linker).

5-Aminopentyl [(β-D-Glucopyranosyluronate)-(1-4)-O-(2-deoxy-2-sulfamino-α-D-glucopyranoside)-(1-4)-O-(2-O-sulfonate-α-L-idopyranosyluronate)-(1-4)-O-2-deoxy-2-sulfoamino-6-O-sulfonate-α-D-glucopyranoside hexa-sodium salt (171)

Palladium on carbon 10% (16 mg]) was added to tetrasaccharide 167 (14.9 mg, 0.0082 mmol), dissolved in CH$_3$OH (1mp and distilled H$_2$O (1 mL). The mixture was stirred under H$_2$ and processed as indicated in the general debenzylation procedure providing tetrasaccharide 171 (9 mg, 88%); $^1$H NMR (800 MHz, 28° C., D$_2$O): 5.38 (d, J=3.5 Hz, H-1$^C$), 5.24 (d, 1H, J=3.0 Hz, H-1$^B$), 5.12 (d, 1H, J=3.6 Hz, H-1$^A$), 4.71 (d, 1H, J=2.8 Hz, H-5$^B$), 4.50 (d, 1H, J=7.8 Hz, H-1$^D$), 4.35 (dd, 1H, J=1.8 Hz and J=11.2 Hz, H6a$^A$), 4.29-4.22 (m, 2H, H6b$^A$, H-2$^B$), 4.18 (dd, 1H, J=3.7 Hz and J=5.8 Hz H3$^B$), 4.06 (bt, 1H, J=3.4 Hz, H-3$^B$), 4.04-3.98 (m, 1H, H5$^A$), 4.02-3.89 (m, 1H, H5$^C$), 3.88-3.83 (m, 2H, H6a$^C$, H6b$^C$), 3.75-3.67 (m, 6H, H3$^A$, H4$^A$, H3$^C$, H4$^C$, H5$^D$, OCHH linker), 3.56-3.53 (m, 1H, OCHH linker), 3.52-3.47 (m, 2H, H3$^D$, H4$^D$), 3.36-3.35 (m, 1H, H-2$^D$), 3.27-3.23 (m, 2H, H2$^A$, H2$^C$), 3.00 (t, 2H, J=7.1 Hz, CH$_2$N linker), 1.64-1.50 (m, 4H, two CH$_2$ linker), 1.45-1.30 (m, 2H, CH$_2$ linker).

Synthesis of Partially N-Sulfated Tetrasaccharides (Schemes 12 and 13)

1. Selective N-Mono-Sulfation of O-Sulfated Tetrasaccharide 165

N-(Benzyl)-benzyloxycarbonyl-5-aminopentyl O-[(methyl→3-O-benzyl-β-D-glucopyranosyluronate)-(1→4)-O-(2-amino-3-O-benzyl-2-deoxy-α-D-gluco-pyranoside)-(1 4)-O-(methyl 3-O-benzyl-2-O-sulfonate-α-L-idopyranosyl-uronate)]-(1→4)-O-(3-O-benzyl-2-deoxy-2-sulfonamido-6-O-sulfonate-α-D-glucopyranoside) (168)

Four portions of SO$_3$.Py complex (11 mg, 3.2 mmol) were sequentially added to tetrasaccharide 165 (32 mg, 0.020 mmol) dissolved in CH$_3$OH (3.0 mL), Et$_3$N (0.60 mL) and 0.1M NaOH (0.41 mL, 0.041 mmol) and stirred at 0° C., as indicated in the general procedure. Purification of the mixture (as indicated in the general procedures for total NH$_2$ sulfation) provided the unreacted 165 (8.0 mg, 24%), followed by a mixed fraction and then tetrasaccharide 168 (15.0 mg, 44%). $^1$H NMR (500 MHz, CD$_3$OD): δ 7.48-7.10 (m, 30H, CH aromatics), 5.50 (bs, 1H, H1$^B$), 5.19-5.11 (m, 3H, H1$^A$, CH$_2$Cbz), 5.00 (bs, 1H, H5$^B$), 4.93-4.76 (m, OH, five CHHPh), 4.76-4.70 (m, 3H, H1$^C$, two CHCHPh), 4.65-4.57 (m, 5H, H1$^D$, H2$^B$ at 4.52, three CHHPh), 4.52 (bs, 2H, NCH$_2$Ph), 4.33-4.20 (m, 4H, H6a$^A$, H6b$^A$, H4$^B$: bs at 4.30, H3$^B$: bs at 4.27), 4.10 (t, 1H, J=9.2 Hz, H4$^C$), 4.20-3.78 (m, 6H incl. H6a$^C$ at 4.0 and H6b$^C$ at 3.88), 3.70-3.54 (m, 3H, H3$^A$, H4$^D$, OCHH linker), 3.46-3.34 (m, 5H, incl H2$^A$ at 3.46, H2$^D$, H3$^D$, H5$^D$ at 3.44, J=10.0 Hz, OCHH linker), 3.31-3.19 (m, CH$_3$OH, NCH$_2$ linker, H2$^C$ at 3.23), 1.70-1.59 (m, 4H, two CH$_2$ linker), 1.49-1.40 (m, 2H, CH$_2$ linker).

Synthesis of tetrasaccharide 169: Tetrasaccharide 168 (18 mg, 0.0105 mmol), was N-acetylated and isolated according to the general N-acetylation procedure providing tetrasaccharide 169 (13 mg, 70%); $^1$H NMR (500 MHz, CD$_3$OD):δ δ 7.48-7.10 (m, 30H, CH aromatics), 5.50 (bs, 1H, H1$^B$), 5.20-5.15 (m, 3H, H1$^A$, CH$_2$Cbz), 5.00 (bs, 1H, H5$^B$), 4.93-4.77 (m, OH, five CHHPh), 4.76-4.70 (m, 3H, H1$^C$ at 4.73, two CHHPh), 4.65-4.58 (m, 5H, including H1$^D$, H5$^B$, three CHHPh), 4.55-4.48 (bs, 2H, NCH$_2$Ph), 4.36-4.28 (m, 2H, H6a$^A$, H6b$^A$), 4.12 (m, 1H, H2$^C$), 4.06 (bs, 1H, H4$^B$), 4.00 (bs, 1H, H3$^B$), 3.97-3.80 (m, 7H, incl. H6a$^C$ at 3.90 and, H6b$^C$ at 3.84), 3.65-3.49 (m, 4H, including H4$^D$ and H5$^D$ at 3.61, OCHH linker), 3.48-3.32 (m, 4H, H2$^A$ at 3.43, H2$^D$, H3$^D$, OCHH linker), 3.32-3.23 (m, CH$_3$OH, NCH$_2$ linker), 2.02 (s, 3H, CH$_3$ Ac), 1.68-1.48 (m, 4H, two CH$_2$ linker), 1.44-1.26 (m, 2H, CH$_2$ linker).

5-Aminopentyl [((β-D-Glucopyranosyluronate)-(1→4)-O-(2-deoxy-2-acetamido-α-D-glucopyranoside)-(1→4)-O-(2-O-sulfonate-α-L-idopyranosyluronate)-(1→4)-O-2-deoxy-2-sulfoamino-6-O-sulfonate-α-D-glucopyranoside penta-sodium salt (172)

Palladium on carbon 10% (16 mg]) was added to tetrasaccharide 169 (13.0 mg, 0.0078 mmol), dissolved in CH$_3$OH (1 mL) and distilled H$_2$O (1 mL). The mixture was stirred under H$_2$ and processed as indicated in the general debenzylation procedure providing tetrasaccharide 172 (6.9 mg, 82%); $^1$H NMR (800 MHz, 21° C., D$_2$O): 5.19 (bs, 1H, H1$^B$), 5.12 (d, 1H, J=3.7 Hz, H1$^A$), 5.11 (d, 1H, J=3.7 Hz, H1$^C$), H1$^C$), 4.81 (d, 1H, J=2.3 Hz, H5$^B$), 4.49 (d, 1H, J=7.9 Hz, H1$^D$), 4.37 (dd, 1H, J=2.0 Hz and J=11.2 Hz, H6a$^A$), 4.27 (bt, 1H, H2$^B$), 4.23 (dd, 1H, J=5.3 Hz and J=11.2 Hz, H6b$^A$), 4.20 (bt, 1H, J=3.3 Hz, H3$^B$), 4.03-4.00 (m, 2H, incl. H4$^B$ at 4.02, H5$^A$), 3.97 (dd, 1H, J=3.5 Hz and J=10.6 Hz, H2$^C$), 3.90-3.85 (m, 3H, H-5$^C$, H6a$^C$, H6b$^C$), 3.77 (dd, 1H, J=8.2 Hz and J=10.5 Hz, H3$^C$), 3.75-3.67 (m, 5H, H3$^A$, H4$^A$, H4$^C$, H5$^D$, OCHH linker), 3.57-3.53 (m, 1H, OCHH linker), 3.52-3.48 (m, 2H, H3$^D$, H4$^D$), 3.38-3.35 (m, 1H, H2$^D$), 3.28-3.25 (m, 1H, H2$^A$), 3.00 (t, 2H, J=7.4 Hz, NCH$_2$ linker), 2.02 (s, 3H, CH$_3$ Ac), 1.70-1.59 (m, 4H, two CH$_2$ linker), 1.49-1.40 (m, 2H, CH$_2$ linker).

2. Selective N-Mono-Sulfation of O-Sulfated Tetrasaccharide 175 (Scheme 13)

N-(Benzyl)-benzyloxycarbonyl-5-aminopentyl O-[(methyl 3-O-benzyl-β-D-glucopyranosyluronate)-(1→4)-O-(2-amino-3-O-benzyl-2-deoxy-α-D-glucopyranoside)-(1→4)-O-(methyl 3-O-benzyl-2-O-sulfonate-α-L-idopyranosyl-uronate)]-(1→4)-O-2-sulfoamino-3-O-benzyl-2-deoxy-α-D-glucopyranoside (178)

Four portions of SO$_3$.Py complex (11 mg, 0.069 mmol each) were sequentially added to tetrasaccharide 175 (34 mg, 0.0206 mmol) dissolved in CH$_3$OH (3.20 mL), Et$_3$N (0.60 mL) and 0.1M NaOH (0.42 mL, 0.042 mmol) and stirred at 0° C., as indicated in the general procedure. Purification of the mixture (as indicated indicated in the general procedures for total NH$_2$ sulfation) provided the di N-sulfated tetrasaccharide 177 (8.0 mg, 24%), followed by tetrasaccharide 178 (17.0 mg, 47%) and a later fraction (8 mg). $^1$H NMR (500 MHz, CD$_3$OD): δ 5.40 (bs, 1H, H1$^B$), 5.32-5.27 (m, 2H, H1$^C$, CHHPh), 5.18-5.10 (m, 3H, H1$^A$, CH$_2$CBz,), 4.90 (bs, 1H, H5$^B$), 4.88-4.72 (m, OH, 5 CHHPh), 4.63-4.53 (m, 4H, H2$^B$, H1$^C$, two CHHPh), 4.49 (bs, 2H, NCH$_2$Ph), 4.28 (bs, 2H, H3$^B$, H4$^B$), 4.15 (bt, 1H, J=9.2 Hz, H4$^C$), 4.40-3.96 (m, 2H, incl. H3$^C$, H6a$^{A or C}$), 3.94-3.76 (m, 5H, incl. three H6$^{A and B}$), 3.70-3.55 (m, 5H), 3.48-3.36 (m, 5H, H2$^D$, H3$^D$, OCHH linker, H2$^A$ at 3.40, H5$^D$: d, J=9.9 Hz at 3.47), 3.30-3.18 (m, CH$_3$OH, H2$^C$, CH$_2$N linker), 1.65-1.40 (m, 4H, two CH$_2$ linker), 1.40-1.25 (m, 2H, CH$_2$ linker).

Synthesis of tetrasaccharide 179: Tetrasaccharide 178 (17 mg, 0.0105 mmol), was N-acetylated and isolated according to the general N-acetylation procedure providing tatrasaccharide 179 (13.0 mg, 75%); $^1$H NMR (500 MHz, CD$_3$OD): δ 7.44-7.10 (m, 30H, CH aromatics), 5.47 (bs, 1H, H1$^B$), 5.19-5.11 (m, 3H, H1$^A$, CH$_2$Cbz), 5.00 (bs, 1H, H-5$^B$), 4.92-4.90 (m, OH, five CHHPh), 4.80-4.73 (m, 3H, H1$^C$, two CHHPh), 4.67 (d, 1H, J=10.6 Hz, CHHPh), 4.64-4.57 (m, 4H, H1$^D$ and H2$^B$ at ~4.58, two CHHPh), 4.51 (bs, 2H, NCH$_2$Ph), 4.12 (m, 1H, H2$^C$), 4.02 (bs, 1H, H4$^B$), 3.98 (bs, 1H, H3$^B$), 3.96-3.76 (m, 9H, including H6$^A$ and H6$^B$ at 3.90 and 3.80), 3.70-3.48 (m, 5H), 3.48-3.35 (m, 4H, H2$^A$ at 3.43, H2$^D$, H3$^D$, OCHH linker), 3.38-3.32 (m, 2H, NCH$_2$ linker), 2.01 (s, 3H, CH$_3$ Ac), 1.68-1.48 (m, 4H, two CH$_2$ linker), 1.42-1.26 (m, 2H, CH$_2$ linker).

5-Aminopentyl [((β-D-Glucopyranosyluronate)-(1→4)-O-(2-acetamido-2-deoxy-α-D-glucopyranoside)-(1→4)-O-(2-O-sulfonate-α-L-idopyranosyluronate)-(1→4)-O-2-deoxy-2-sulfoamino-6-O-sulfonate-α-D-glucopyranoside tetra-sodium salt (182)

Palladium on carbon 10% (14 mg) was added to tetrasaccharide 179 (13.0 mg, 0.0078 mmol), dissolved in CH$_3$OH (0.8 mL) and distilled H$_2$O (0.8 mL). The mixture was stirred under H$_2$ and processed as indicated in the general debenzylation procedure providing tetrasaccharide 182 (6.9 mg, 82%); $^1$H NMR (800 MHz, 28° C., D$_2$O): 5.17 (bs, 1H, H1$^B$), 5.13 (d, 1H, J=3.8 Hz, H-1$^A$), 5.08 (d, 1H J=3.6 Hz, H1$^C$), 4.83 (d, 1H, J=2.1 Hz, H5$^B$), 4.49 (d, 1H, J=7.9 Hz, H1$^D$), 4.25 (bs, 1H, H2$^B$), 4.20 (bt, 1H, J=2.6/3.0 Hz, H4$^B$), 4.02 (bs, 1H, H4$^B$), 3.98 (dd, 1H, J=3.5 Hz and J=10.6 Hz, H2$^C$), 3.91-3.81 (m, 5H, H5$^A$ or C, H6a$^A$, H6b$^A$, H6a$^C$, H6b$^C$), 3.80-3.76 (m, 2H, H3$^B$, H5$^{C or A}$), 3.75-3.66 (m, 6H, H3$^A$, H4$^A$, H3$^C$, H4$^C$, H5$^D$, OCHH linker), 3.54-3.49 (m, 3H, C3$^D$, C4$^D$, OCHH linker), 3.37-3.35 (m, 1H, H2$^D$), 3.23 (dd, 1H, J=3.5 Hz and J=9.9 Hz, H2$^A$), 3.00 (t, 2H, J=7.5 Hz, NCH$_2$ linker), 2.01 (s, 3H, CH$_3$ Ac), 1.70-1.59 (m, 4H, two CH$_2$ linker), 1.49-1.40 (m, 2H, CH$_2$ linker).

Selective De-O-Sulfation of Di-O-Sulfated Tetrasaccharide 163 (Scheme 13)

N-(Benzyl)-benzyloxycarbonyl-5-aminopentyl O-[(methyl 2,4-di-O-acetyl-3-O-benzyl-β-D-glucopyranosyluronate)-(1→4)-O-(6-O-acetyl-2-azido-3-O-benzyl-2-deoxy-α-D-glucopyranoside)-(1→4)-O-(methyl 3-O-benzyl-2-O-sulfonate-α-L-idopyranosyl-uronate)]-(1→4)-O-2-azido-3-O-benzyl-2-deoxy-α-D-glucopyranoside (173)

Tetrasaccharide 163a (69 mg, 0.066 mmol) was di-O-sulfated according to the general procedure, which after Iatrobeads chromatography provides the intermediate 163a as Pyridinium salt. The fractions were evaporated (bath temperature 18° C.) and the residue immediately diluted in dry pyridine (4 mL). N,O-bis(trimethylsilyl)acetamide (BTSA) (714 mg, 3.36 mmol, 80 equiv) was added to the mixture which was then stirred at 56-58° C. for 6 h until TLC (CHCl$_3$/CH$_3$OH 93/7, v/v) indicated the disappearance of the starting material and the formation of two spots. Pyridine and most of the BTSA were evaporated in vacuo (bath temperature 18° C.), and the residue was co-evaporated with dry CH$_3$OH (5 mL×3 times), until TLC indicated the presence of a single spot of desilylated product. Pyridine (104) was added to the residue which was vortexed with CHCl$_3$ (0.2 mL) and applied to a column of Iatrobeads (5 g packed in CHCl$_3$ with 0.1% of pyridine) and eluted with a gradient of CHCl$_3$ and CH$_3$OH (from 100% to 95:5). The appropriate fractions were evaporated and the residue run through a short column of BioRad 50×8 Na$^+$(0.8×5 cm) using CH$_3$OH as eluant. The recovered material was dry loaded on RP C18 silicagel (500 mg) using methanol. The dry materiel was vortexed with a small amount of CH$_3$OH/H$_2$O 70/30, v/v) and applied on a short column of C18 silicagel (1 g) which was then eluted with a gradient of CH$_3$OH and H$_2$O (from 70/30 to 20/80, v/v). The appropriate fractions provided tetrasaccharide 173 (69 mg, 93%); $^1$H NMR (500 MHz, CD$_3$OD): δ 7.44-7.12 (m, 30H, CH aromatics), 5.32 (bs, 1H, H1$^B$), 5.17-5.10 (m, 2H, CH$_2$Cbz), 5.09-5.03 (m, 2H, H1$^C$, CHHPh), 5.02 (t, 1H, J=9.8 Hz, H4$^D$), 4.92 (dd, 1H, J=8.2 Hz andJ=9.1 Hz, H2$^D$), 4.87-4.79 (m, OH, H1$^A$, H1$^D$, H5$^B$, four CHHPh), 4.69 (d, 1H, J=11.4 Hz, CHHPh), 4.65-4.57 (m, 5H, H2$^B$ at 4.60, four CHHPh), 4.50 (bs, 2H, NCH$_2$Ph), 4.48-4.40 (m, 2H, H6a$^C$, CHHPh), 4.30 (bs, 1H, H4$^B$), 4.14-4.07 (m, 2H, H6b$^A$: dd J=5.2 Hz and J=11.9 Hz, H5$^D$: d, J=9.8 Hz), 3.99-3.68 (m, 10H), 3.50 (s, 3H, CO$_2$CH$_3$), 3.36-3.23 (m, CH$_3$OH, H2$^A$, CO$_2$CH$_3$, OCHH linker, NCH$_2$ linker), 3.19 (dd, 1H, J=3.2 Hz and J=9.9 Hz, H2$^C$), 2.04, 1.94, 1.92 (3s, 3H each, three CH$_3$ Ac), 1.69-1.50 (m, 4H, two CH$_2$ linker), 1.49-1.32 (m, 2H, CH$_2$ linker).

Synthesis of tetrasaccharide 174: Tetrasaccharide 173 (35 mg, 0.215 mmol) was dissolved in THF (1.0 mL) and subject to the saponification and de-O-acetylation according to the general procedure to provide tetrasaccharide 174 as a sodium salt (30 mg, 87%); $^1$H NMR (500 MHz, CD$_3$OD): δδ 7.44-7.12 (m, 30H, CH aromatics), 5.38 (bs, 1H, H1$^B$), 5.24 (d, 1H, J=3.4 Hz, H1$^C$), 5.18-5.12 (m, 2H, CH$_2$Cbz), 5.06 (d, 1H, J=10.7 Hz, CHHPh), 4.95-4.80 (m, OH, H5$^B$ at 4.91, H1$^A$ at 4.85, six CHHPh), 4.76 (d, 1H, J=11.3 Hz, CHHPh), 4.67-4.58 (m, 3H, CHHPh, H1$^D$ at 4.63, H2$^B$ at 4.60), 4.49 (s, 2H, NCH$_2$Ph), 4.44 (d, 1H J=11.7 Hz, CHHPh), 4.27 (bs, 1H, H4$^B$), 4.25 (bs, 1H, H3$^B$), 4.02-3.79 (m, 9H, incl. H6a$^A$, H6b$^A$, H6a$^C$, H6b$^C$), 3.70-3.57 (m, 3H, incl OCHH linker, H4$^D$), 3.49 (d, 1H, J=10.2 Hz, H5$^D$), 3.43 (dd, 1H, J=3.2 Hz and J=9.7 Hz, H2$^C$), 3.40-3.33 (m, 3H, H2$^D$, H3$^D$, OCHH linker), 3.28-3.19 (m, 2H, NCH$_2$ linker), 3.19-3.11 (m, 1H, H2$^A$), 1.64-1.42 (m, 4H, two CH$_2$ linker), 1.38-1.22 (m, 2H,CH$_2$ linker).

Synthesis of tetrasaccharide 175: A 1M solution of PMe$_3$ in THF (0.73 mL, 0.73 mmol) was added to a solution of tetrasaccharide 174 (76 mg, 0.047 mmol) in THF (4 mL) and 0.1 M NaOH (2.80 mL, 0.280 mmol) according to the general procedure, providing tetrasaccharide 175 (65.0 mg, 88%); $^1$H NMR (500 MHz, CD$_3$OD): 7.50-7.10 (m, 30H, CH aromatics), 5.42 (bs, 1H, H1$^B$), 5.20-5.12 (m, 2H, CH$_2$Cbz), 5.08-5.03 (m, 2H, H1$^C$, CHHPh), 4.98 (bs, 1H, H5$^B$), 4.95-4.80 (m, OH, six CHHPh), 4.78-4.71 (m, 2H, two CHHPh, 4.66 (d, 1H, J=11.3 Hz, CHHPh), 4.65-4.54 (m, 3H, H1$^A$, H2$^B$, H1$^D$ at 4.58), 4.50 (bs, 2H, NCH$_2$Ph), 4.36 (d, 1H, J=12.2 Hz, CHHPh), 4.30 (bs, 1H, H4$^B$), 4.20 (bs, 1H, H3$^B$), 3.97-3.85 (m, 6H, incl. H6a$^A$, H-6a$^C$, H6b$^{A or C}$), 3.83-3.75 (m, 2H, H3$^C$, H6$^{C or A}$), 3.66-3.55 (m, 3H, incl. H4$^A$, H4$^D$, OCHH linker), 3.52 (d, 1H, J=10.0 Hz, H-5$^D$) 3.44-3.36 (m, 3H, H3$^A$, H2$^D$, H3$^D$), 3.28-3.18 (m, 3H, OCHH linker, NCH$_2$ linker), 2.86 (bd, 1H, J=10.0 Hz, H2$^C$), 2.48 (bd, 1H, J=9.4 Hz, H2$^A$), 1.60-1.40 (m, 4H, two CH$_2$ linker), 1.34-1.18 (m, 2H, CH$_2$ linker).

Synthesis of tetrasaccharide 176: Tetrasaccharide 175 (15 mg, 0.0096 mmol) was treated according to the general N-acetylation procedure (the progress of the reaction was followed by TLC (silicagel, CHCl$_3$/CH$_3$OH 70:30, v/v) providing tetrasaccharide 176 (14.0 mg, 91%); $^1$H NMR (500 MHz, CD$_3$OD): 7.36-7.02 (m, 30H, CH aromatics), 5.50 (bs, 1H, H1$^B$), 5.18-5.08 (m, 2H, CH$_2$Cbz), 4.98-4.92 (m, 2H, CHHPh, H5$^B$), 4.89-4.72 (m, OH, H1$^C$ at 4.76, six CHHPh), 4.68-4.43 (m, 8H, incl. H1$^A$ at 4.67, H-1$^D$ and H5$^B$ at 4.60, NCH$_2$Ph at 4.50, three CHHPh), 4.18-4.06 (m, 2H, H2$^A$, H2$^C$), 4.02-3.66 (m, 14H), 3.66-3.56 (m, 1H, OCHH linker), 3.44-3.22 (m, H2$^D$ and H3$^D$ at 3.38, CH$_3$OH, OCHH linker, NCH$_2$ linker), 1.92 (s, 3H, CH$_3$ Ac), 1.61 (bd, 3H, CH$_3$ Ac), 1.56-1.38 (m, 4H, two CH$_2$ linker), 1.31-1.16 (m, 2H, CH$_2$ linker).

Synthesis of tetrasaccharide 177: SO$_3$.Py (17 mg, 0.106 mmol) was added to the solution of tetrasaccharide 175 (16 mg, 0.0106 mmol) in CH$_3$OH (2.0 mL), Et$_3$N (0.300 mL) and 0.1 M NaOH (0.424 mL, 0.0424 mmol at 0° C. as indicated in the general procedure for di-N-sulfation which provided tetrasaccharide 177 (13.0 mg, 77%); $^1$HNMR (500 MHz, CD$_3$OD): δ 7.54-7.10 (m, 30H, CH aromatics), 5.55 (bs, 1H, H1$^B$), 5.30 (d, 1H, J=2.9 Hz, H1$^C$), 5.19-5.11 (m, 3H, H-1$^A$, CH$_2$Cbz), 5.09 (d, 1H, J=11.3 Hz, CHHPh), 4.95 (bs, 1H, C2$^B$), 4.91-4.76 (m, OH, four CHHPh), 4.72 (d, 1H, J=11.0 Hz, CHHPh), 4.68 (m, 3Hm two CHHPh, H5$^B$ at 4.64), 4.58 (d, 1H, J=7.5 Hz, H1$^D$), 4.32 (bs, 1H, H4$^B$), 4.16 (bs, 1H, H3$^B$), 3.95 (dd, 1H, J=3.4 Hz, and J=12.2 Hz, H6a$^{A or C}$), 3.90-3.72 (m, 6H, incl. H6a$^{C or A}$, H6b$^A$, H6b$^C$ at 3.80), 3.69-3.20 (m, incl. CH$_3$OH, H2$^A$ and H2$^B$ at 3.42, C2$^D$ at 3.34, C3$^D$ at 3.38, C4$^D$ and C5$^D$ at 3.55), 1.62-1.40 (m, 4H, two CH$_2$ linker), 1.40-1.20 (m, 2H, CH$_2$ linker).

5-Aminopentyl [(β-D-Glucopyranosyluronate)-(1→4)-O-(2-acetamido-2-deoxy-α-D-glucopyranoside)-(1→4)-O-(2-O-sulfonate-α-L-idopyranosyl-uronate)-(1→4)-O-2-acetamido-2-deoxy-α-D-glucopyranoside Hexasodium salt (180)

Pd/C 10% (9 mg) was added to tetrasaccharide 176 (7.5 mg, 0.0047 mmol) dissolved in CH$_3$OH (0.8 mL) and distilled H$_2$O (0.8 mL). The mixture was stirred under H$_2$ and processed as indicated in the general debenzylation procedure providing tetrasaccharide 180 (4.6 mg, 95%); $^1$H NMR (800 MHz, 28° C., D$_2$O): δ 5.20 (bs, 1H, H1$^B$), 5.10 (d, 1H, J=3.7 Hz, H1$^C$), 4.87 (d, 1H, J=3.6 Hz, H1$^A$), 4.81 (d, 1H, J=2.1 Hz, H5$^B$), 4.50 (d, 1H, J=7.9 Hz, H1$^D$), 4.27 (bt, 1H, H2$^B$), 4.21 (bt, 1H, J~2.9 Hz, H4$^B$), 4.04 (bt, 1H, J 2.4/2.1 Hz, H-3$^B$), 3.93 (dd, 1H, J=3.7 Hz and J=10.7 Hz, H2$^C$], 3.93-3.84 (m, 7H, H2$^A$, H3$^A$, H5$^{A\ or\ C}$, H6a$^A$, H6b$^A$, H6a$^C$, H6b$^C$), 3.83-3.81 (m, 1H, H5$^{C\ or\ A}$), 3.79 (dd, 1H, J=9.0 Hz and J=10.6 Hz, H3$^C$), 3.76-3.68 (m, 4H, H4$^A$, H4$^C$, H5$^D$, OCHH linker), 3.54-3.51 (m, 2H, H2$^D$, H3$^D$), 3.51-3.47 (m, 1H, OCHH linker), 3.39-3.36 (m, 1H, H2$^D$), 3.00 (t, 2H, J=7.5 Hz, CH$_2$N linker), 2.05 and 2.02 (2s, 3H each, two CH$_3$ Ac), 1.70-1.59 (m, 4H, two CH$_2$ linker), 1.49-1.40 (m, 2H, CH$_2$ linker).

5-Aminopentyl [(β-D-Glucopyranosyluronate)-(1-4)-O-(2-sulfoamino-2-deoxy-α-D-glucopyranoside)-(1-4)-O-(2-O-sulfonate-α-L-idopyranosyl-uronate)-(1 4)-O-2-sulfoamino-2-deoxy-α-D-glucopyranoside Trisodium salt (181)

Pd/C 10% (17 mg) was added to tetrasaccharide 177 (14.0 mg, 0.0082 mmol) dissolved in CH$_3$OH (1.5 mL) and distilled H$_2$O (1.5 mL). The mixture was stirred under H$_2$ and processed as indicated in the general debenzylation procedure providing tetrasaccharide 181 (7.1 mg, 77%); $^1$H NMR (800 MHz, 28° C., D$_2$O): δ 5.39 (d, 1H, J=3.5 Hz, H1$^C$), 5.23 (d, 1H, J=3.2 Hz, H1$^B$), 5.11 (d, 1H, J=3.5 Hz, H1$^A$), 4.71 (d, 1H, J=2.8 Hz, H-5$^B$), 4.49 (d, 1H, J=7.9 Hz, H1$^D$), 4.27 (dd, 1H, J=3.2 Hz, and J=5.8 Hz, H2$^B$), 4.19 (dd, 1H, J=3.7 Hz and J=5.8 Hz, H3$^B$), 4.06 (bt, 1H, J=3.2 Hz, H-4$^B$), 3.90-3.84 (m, 5H, H5$^{A\ or\ C}$, H6a$^A$, H6b$^A$, H6a$^C$, H6b), 3.82 (m, 1H, H5C or A), 3.76-3.67 (m, 6H, H3$^A$, H4$^A$, H3$^C$, H4$^C$, H5$^D$, OCHH linker), 3.56-3.46 (m, 3H, H3$^D$, H4$^D$, OCHH linker), 3.37-3.35 (m, 1H, H2$^D$), 3.25-3.22 (m, 2H, H2$^A$, H2$^C$), 3.00 (t, 2H, J=7.3 Hz, CH$_2$N linker), 1.70-1.59 (m, 4H, two CH$_2$ linker), 1.49-1.40 (m, 2H, CH$_2$ linker). Mono-Sulfation of Tetrasaccharide Diol 162 (Scheme 14)

N-(Benzyl)-benzyloxycarbonyl-5-aminopentyl O-[(methyl 2,4-di-O-acetyl-3-O-benzyl-β-D-glucopyranosyluronate)-(1-4)-O-(6-O-acetyl-2-azido-3-O-benzyl-2-deoxy-α-D-glucopyranoside)-(1→4)-O-(methyl 3-O-benzyl-α-L-idopyranosyl-uronate)]-(1→4)-O-2-azido-3-O-benzyl-2-deoxy-6-O-sulfonate-α-D-gluco pyranoside (183)

SO$_3$.Py complex (12.0 mg, 0.076 mmol, 6 equiv.) were added at once into a solution of tetrasaccharide 162 (20.0 mg, 0.0127 mmol) in anhydrous DMF (0.5 mL) as indicated in the general procedure. Purification of the product provided some unreacted starting material and the expected product which was further chromatographed on RP C18 silicagel as indicated providing tetrasaccharide 183 (8.5 mg, 39.5%); $^1$H NMR (500 MHz, CDCl$_3$): 7.42-7.20 (m, 30H, CH aromatics), 5.25 (d, 1H, J=3.5 Hz, H1$^B$), 5.19-5.08 (m, 4H, CH$_2$Cbz, H1$^C$, CHHPh), 5.05 (t, 1H, J=8.4 Hz, H-4$^D$), 4.96 (t, 1H, J=8.6 Hz, H2$^D$), 4.90-4.80 (m, H-1$^A$, OH, four CHHPh), 4.74 (d, 1H, J=8.0 Hz, H-1$^D$), 4.72-4.67 (m, 2H, H5$^B$, CHHPh), 4.66-4.57 (m, 4H, four CHHPh), 4.51 (bs, 2H, NCH$_2$Ph), 4.42 (bd, 1H, J=12.0 Hz, H6a$^A$), 4.34 (m, 2H, H6a$^C$, H6b$^C$), 4.12 (dd, 1H, J=5.3 Hz and J=12.0 Hz, H6b$^A$), 4.06 (d, 1H, J=9.8 Hz, H5$^D$), 3.95-3.88 (m, 4H, incl. H4$^B$ and H3$^D$), 3.86-3.65 (m, 7H), 3.49 and 3.48 (2s, 3H each, two CO$_2$CH$_3$), 3.37-3.22 (m, incl. CH$_3$OH, H-2$^C$: dd, J=3.6 Hz and J=10.0 Hz at 3.36, H2$^A$, OCHH linker, CH$_2$N linker), 1.99, 1.96, 1.94 (3s, 3H each, three CH$_3$Ac), 1.64-1.50 (m, 4H, two CH$_2$ linker), 1.45-1.30 (m, 2H, CH$_2$ linker).

Synthesis of tetrasaccharide 184: Tetrasaccharide 183 (37 mg, 0.221 mmol) was dissolved in THF (1.2 mL) and subject to the saponification and de-O-acetylation according to the general procedure to provide tetrasaccharide 184 as a sodium salt (24.8 mg, 72%); $^1$H NMR (500 MHz, CD$_3$OD): δ 5.24 (bs, 1H, H1$^B$), 5.18-5.11 (m, 4H, H1$^C$, CHHPh, CH$_2$Cbz), 4.97 (d, 1H, J=11.5 Hz, CHHPh), 4.94-4.80 (m, H-1$^A$, H-5$^B$, OH, five CHHPh), 4.71-4.79 (m, 2H, two CHHPh), 4.65 (d, 1H J=10.6 Hz, CHHPh), 4.60 (bd, 1H, H1$^D$), 4.52-4.45 (m, 3H, NCH$_2$Ph, CHHPh), 4.35-4.26 (m, 2H, H4$^B$, H6a$^A$), 4.26-4.19 (bd, 1H, H6b$^A$), 4.00-3.78 (m, 10H), 3.72-3.48 (m, 4H incl. OCHH linker and H2$^C$ at 3.55), 3.45-3.34 (m, 3H, H2$^D$, H3$^D$, OCHH linker), 3.28-3.15 (m, 3H, H2$^A$, CH$_2$N linker), 1.60-1.40 (m, 4H, two CH$_2$ linker), 1.43-1.25 (m, 2H CH$_2$ linker).

Synthesis of tetrasaccharide 185: A 1M solution of PMe$_3$ in THF (0.256 mL, 0.256 mmol) was added to a solution of tetrasaccharide 184 (26 mg, 0.0160 mmol) in THF (1.1 mL) and 0.1 M NaOH (0.960 mL, 0.096 mmol) according to the general procedure, providing tetrasaccharide 185 (20.8 mg, 86%); $^1$H NMR (500 MHz, CD$_3$OD): δ 7.49-7.16 (m, 30H, CH aromatics), 5.23-5.12 (m, 4H, H1$^B$, three CHHPh), 5.20-4.90 (m, 3H, H1$^C$ at 5.00, H5$^B$ at 4.94, CHHPh), 4.90-4.78 (m, OH, four CHHPh), 4.71-4.59 (m, 4H, H1$^A$ at 4.64, three CHHPh), 4.58-4.54 (bd, 1H, H1$^C$), 4.54-4.47 (m, 2H, NCH$_2$Ph), 4.44 (bd, 1H, J=11.9 Hz, CHHPh), 4.33-4.24 (m, 2H, H4$^B$, H6a$^A$), 4.22-4.15 (bd, 1H, J=10.2 Hz, H6b$^A$), 4.00-3.73 (m, 7H, including H3$^B$ at 3.97 and H2$^B$ at 3.87,), 3.68-3.52 (m, 3H, H4$^D$, H5$^D$, OCHH linker), 3.49-3.39 (m, 3H, H3$^A$, H2$^D$, H3$^D$), 3.28-3.17 (3H, OCHH linker, CH$_2$N linker), 2.82 (bd, 1H, J=4.1 Hz, H2$^C$), 2.50 (bs, 1H, H2$^A$), 1.60-1.40 (m, 4H, two CH$_2$ linker), 1.43-1.25 (m, 2H CH$_2$ linker).

Synthesis of tetrasaccharide 186: Tetrasaccharide 185 (10 mg, 0.0063 mmol) was N-acetylated according to the general procedure for N-acetylation (the progress of the reaction was followed by TLC (silicagel, CHCl$_3$/CH$_3$OH 70:30, v/v) providing tetrasaccharide 186 (8.0 mg, 78.5%); $^1$H NMR (500 MHz, CD$_3$OD): 7.43-7.20 (m, 30H, CH aromatics), 5.22 (bs, 1H, H1$^B$), 5.21-5.08 (m, 2H, CH$_2$Cbz), 5.00-4.78 (m, OH, six CHHPh, H5$^B$ at 4.87, H1$^C$ at 4.82), 4.76-4.58 (m, 5H, three CHHPh, H1$^A$ at 4.65, H1$^C$ at 4.60), 4.58-4.50 (m, 3H, NCH$_2$Ph, CHHPh), 4.38-4.17 (m, 3H, incl H6a$^A$ and H6b$^A$), 4.16-4.00 (m, 3H, incl. H2$^A$, H2$^C$), 4.00-3.50 (m, 12H), 3.44-3.36 (m, 2H, H2$^D$, H3$^D$), 3.36-3.20 (m, CH$_3$OH, OCHH linker, CH$_2$N linker), 1.82 (s, 3H, CH$_3$ Ac), 1.72-1.64 (bd, 3H, CH$_3$ Ac), 1.64-1.42 (m, 4H, two CH$_2$ linker), 1.38-1.22 (m, 2H,CH$_2$ linker).

Synthesis of tetrasaccharide 187: SO$_3$.Py (10 mg, 0.063 mmol) was added to the solution of tetrasaccharide 185 (10 mg, 0.0063 mmol) in anhydrous CH$_3$OH (1.2 mL) and Et$_3$N (0.200 mL) at 0° C. as indicated in the general procedure for N-sulfation which provided tetrasaccharide 187 (8.4 mg, 77%); $^1$H NMR (500 MHz, CD$_3$OD): δ 7.52-7.10 (m, 30H, CH aromatics), 5.33 (d, 1H, J=2.9 Hz, H1$^C$), 5.23 (bs, 1H, H1$^B$), 5.20-5.11 (m, 3H, CH$_2$ Cbz, H1$^A$ at 5.15), 5.05-4.95 (m, 2H, CHHPh), 4.93-4.78 (m, OH, three CHHPh), 4.76-4.70 (m, 2H, two CHHPh), 4.67-4.59 (m, 3H, two CHHPh, H1$^C$ at 4.61). 4.50 (bs, 2H, NCH$_2$Ph), 4.28-4.21 (m, 1H, H6a$^A$), 4.21-4.13 (m, 3H, incl. H6b$^A$ and H4$^B$), 4.07 (bs, 1H, H3$^B$), 3.95-3.88 (m, 2H, incl. H-6a$^C$ at 3.93), 3.87-3.56 (m, 8H, inc. H6b$^C$ at 3.81), 3.54-3.35 (m, 6H, incl. H2$^A$ and H2$^B$ at ~3.44, H2$^D$ at 3.39, H3$^D$ at 3.41, OCHH linker), 3.29-3.20 (m, 2H, CH$_2$N linker), 1.68-1.48 (m, 4H, two CH$_2$ linker), 1.39-1.24 (m, 2H, CH$_2$ linker).

5-Aminopentyl [(β-D-Glucopyranosyluronate)-(1-4)-O-(2-acetamido-2-deoxy-α-D-glucopyranoside)-(1-4)-O-α-L-idopyranosyl-uronate-(1→4)-O-2-acet-amido-2-deoxy-6-O-sulfonate-α-D-glucopyranoside tri-sodium salt (188)

Pd/C 10% (10 mg) was added to tetrasaccharide 186 (8.0 mg, 0.0047 mmol) dissolved in $CH_3OH$ (0.8 mL) and distilled $H_2O$ (0.8 mL). The mixture was stirred under $H_2$ and processed as indicated in the general debenzylation procedure providing tetrasaccharide 188 (4.6 mg, 95%); $^1H$ NMR (800 MHz, 28° C., $D_2O$): δ 5.16 (d, 1H, J=3.7 Hz, H1$^C$), 4.97 (d, 1H, J=3.3 Hz, H1$^B$), 4.88 (d, 1H, J=3.76 Hz, H1$^A$), 4.71 (d, 1H, J=2.7 Hz, H5$^B$), 4.51 (d, 1J, J=7.7 Hz, H1$^D$), 4.36 (dd, 1H, J=2.1 Hz and J=11.1 Hz, H6a$^A$), 4.26 (dd, 1H, J=5.6 Hz, and J=11.3 Hz, H6b$^A$), 4.08-4.04 (m, 2H, H3$^B$, H4$^B$), 3.96-3.93 (m, 2H, H2$^A$, H2$^C$), 3.93-3.88 (m, 3H, H3$^B$, H5$^C$, H6a$^C$), 3.86-3.79 (m, 3H, H3$^A$, H3$^C$, H6b$^C$), 3.77-3.74 (m, 1H, H5$^D$), 3.74-3.66 (m, 4H, H-2$^B$, H4$^A$, H4$^C$, OCHH linker), 3.55-3.50 (m, 3H, H3$^D$, H4$^D$, OCHH linker), 3.39-3.36 (m, 1H, H2$^D$), 3.00 (t, 2H, J=7.9 Hz, $CH_2N$ linker), 2.10, 2.00 (2s, 3H each, two $CH_3$ Ac), 1.72-1.58 (m, 4H, two $CH_2$ linker), 1.48-1.41 (m, 2H, $CH_2$ linker).

5-Aminopentyl [(β-D-Glucopyranosyluronate)-(1-4)-O-(2-deoxy-2-sulfamino-α-D-glucopyranoside)-(1-4)-O-α-L-idopyranosyluronate-(1-4)-O-2-deoxy-2-sulfoamino-6-O-sulfonate-α-D-glucopyranoside penta-sodium salt (189)

Pd/C 10% (10 mg) was added to tetrasaccharide 187 (8.4 mg, 0.0049 mmol) dissolved in $CH_3OH$ (0.8 mL) and distilled $H_2O$ (0.8 mL). The mixture was stirred under $H_2$ and processed as indicated in the general debenzylation procedure providing tetrasaccharide 189 (4.4 mg, 93%); $^1H$ NMR (800 MHz, 25° C., $D_2O$): δ 5.32 (d, 1H, J=3.6 Hz, H1$^C$), 5.12 (d, 1H, J=3.6 Hz, H1$^A$), 4.90 (bs, 1H, H1$^B$), 4.71 (d, 1H, J=2.1 Hz, H5$^B$), 4.50 (d, 1H, J=7.8 Hz, H1$^D$), 4.32 (dd, 1H, J=2.0 Hz and J=11.2 Hz, H6a$^A$), 4.24 (dd, 1H, J=5.2 Hz and J=11.1 Hz, H6b$^A$), 4.10 (bt, 1H, J=3.8/4.1 Hz, H3$^B$), 4.06-4.00 (m, 2H, H4$^B$, H5$^A$), 3.89 (dd, 1H, J=3.0 Hz and J=12.2 Hz, H6a$^C$), 3.86 (m, 1H, H5$^C$), 3.82 (dd, 1H, J=1.6 Hz and J=12.2 Hz, H6b$^C$), 3.77-3.65 (m, 7H, H2$^B$, H3$^A$, H4$^A$, H3$^C$, H4$^C$, H5$^D$, OCHH linker), 3.57-3.53 (m, 1H, OCHH linker), 3.53-3.49 (m, 2H, H3$^D$, H4$^D$), 3.39-3.37 (m, 1H, H-2$^D$), 3.27 (dd, 1H, J=3.6 Hz and J=10.6 Hz, H2$^A$), 3.22 (dd, 1H, J=3.6 Hz and J=10.6 Hz, H2$^C$), 3.00 (t, 2H, J=7.4 Hz, $CH_2N$ linker), 1.72-1.58 (m, 4H, two $CH_2$ linker), 1.48-1.41 (m, 2H, $CH_2$ linker).

The preceding detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims. It is to be understood that the particular examples, materials, amounts, and procedures are to be interpreted broadly in accordance with the scope and spirit of the invention as set forth herein.

The complete disclosures of all patents, patent applications including provisional patent applications, and publications, and electronically available material (e.g., GenBank amino acid and nucleotide sequence submissions) cited herein are incorporated by reference. Additionally, this patent application incorporates by reference U.S. Patent Publications 20090041836 A1, entitled "Glycopeptide and Uses Thereof," published Feb. 12, 2009 and 20090196916 A1, entitled "Liposome-Mediated Ligation," published Aug. 6, 2009; and International Patent Publications WO 2007/079448, entitled "Three Component Carbohydrate Vaccine," published Jul. 12, 2007; WO 2007/146070, entitled "Liposome-Mediated Native Chemical Ligation," published Dec. 21, 2007; and WO 2009/003944, entitled "Glycopeptide and Uses Thereof," published Jan. 7, 2010.

What is claimed is:

1. A library of disaccharides comprising compounds 41, 42, 43, and 44 as follows:

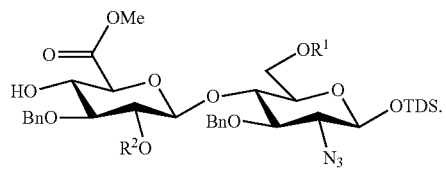

41. $R^1 = R^2 = Ac$
42. $R^1 = Ac, R^2 = Lev$
43. $R^1 = Lev, R^2 = Ac$
44. $R^1 = R^2 = Lev$

2. A library of disaccharides comprising compounds 41a 42a, 43a, and 44a as follows:

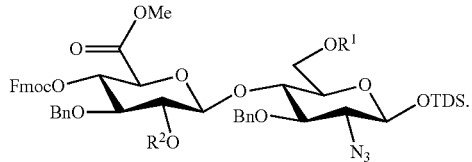

41a. $R^1 = R^2 = Ac$
42a. $R^1 = Ac, R^2 = Lev$
43a. $R^1 = Lev, R^2 = Ac$
44a. $R^1 = R^2 = Lev$

3. A library of disaccharides comprising compounds 53, 54, 55 and 56 as follows:

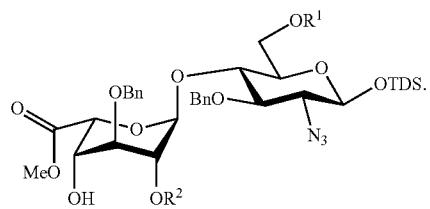

53. $R^1 = R^2 = Ac$
54. $R^1 = Ac, R^2 = Lev$
55. $R^1 = Lev, R^2 = Ac$
56. $R^1 = R^2 = Lev$

4. A library of disaccharides comprising compounds 53a, 54a, 55a and 56a as follows:
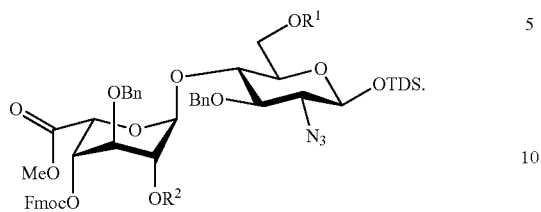
53a. $R^1 = R^2 = Ac$
54a. $R^1 = Ac, R^2 = Lev$
55a. $R^1 = Lev, R^2 = Ac$
56a. $R^1 = R^2 = Lev$
* * * * *